US011905523B2

(12) United States Patent
McCoy et al.

(10) Patent No.: US 11,905,523 B2
(45) Date of Patent: *Feb. 20, 2024

(54) ADENO-ASSOCIATED VIRAL VECTORS FOR TREATMENT OF NIEMANN-PICK DISEASE TYPE-C

(71) Applicant: Ginkgo Bioworks, Inc., Boston, MA (US)

(72) Inventors: Daniel McCoy, Durham, NC (US); Garrett E. Berry, Durham, NC (US); David Dismuke, Cary, NC (US)

(73) Assignee: Ginkgo Bioworks, Inc., Boston, MA (US)

(*) Notice: Subject to any disclaimer, the term of this patent is extended or adjusted under 35 U.S.C. 154(b) by 427 days.

This patent is subject to a terminal disclaimer.

(21) Appl. No.: 17/072,624

(22) Filed: Oct. 16, 2020

(65) Prior Publication Data
US 2021/0115474 A1 Apr. 22, 2021

Related U.S. Application Data

(60) Provisional application No. 63/082,899, filed on Sep. 24, 2020, provisional application No. 63/082,425, filed on Sep. 23, 2020, provisional application No. 62/923,253, filed on Oct. 18, 2019, provisional application No. 62/916,749, filed on Oct. 17, 2019.

(51) Int. Cl.
*C12N 15/861* (2006.01)
*C07K 14/47* (2006.01)
*A61K 48/00* (2006.01)
*C12N 15/86* (2006.01)
*A61P 3/00* (2006.01)
*C07K 14/005* (2006.01)
*C12N 7/00* (2006.01)
*A61K 38/00* (2006.01)

(52) U.S. Cl.
CPC .............. *C12N 15/86* (2013.01); *A61P 3/00* (2018.01); *C07K 14/005* (2013.01); *C07K 14/47* (2013.01); *C12N 7/00* (2013.01); *A61K 38/00* (2013.01); *C12N 2750/14122* (2013.01); *C12N 2750/14143* (2013.01); *C12N 2830/50* (2013.01)

(58) Field of Classification Search
CPC ......... C07K 14/47; C12N 15/86; A61K 38/00
See application file for complete search history.

(56) References Cited

U.S. PATENT DOCUMENTS

| | | | |
|---|---|---|---|
| 4,039,388 A | 8/1977 | Gal et al. | |
| 4,501,729 A | 2/1985 | Boucher et al. | |
| 4,968,603 A | 11/1990 | Slamon et al. | |
| 5,139,941 A | 8/1992 | Muzyczka et al. | |
| 5,328,470 A | 7/1994 | Nabel et al. | |
| 5,399,346 A | 3/1995 | Anderson et al. | |
| 5,478,745 A | 12/1995 | Samulski et al. | |
| 5,658,776 A | 8/1997 | Flotte et al. | |
| 5,686,240 A | 11/1997 | Schuchman et al. | |
| 5,863,541 A | 1/1999 | Samulski et al. | |
| 5,869,248 A | 2/1999 | Yuan et al. | |
| 5,877,022 A | 3/1999 | Stinchcomb et al. | |
| 5,882,652 A | 3/1999 | Valdes et al. | |
| 5,905,040 A | 5/1999 | Mazzara et al. | |
| 5,916,563 A | 6/1999 | Young et al. | |
| 5,962,313 A | 10/1999 | Podsakoff | |
| 6,013,487 A | 1/2000 | Mitchell | |
| 6,040,183 A | 3/2000 | Ferrari et al. | |
| 6,083,702 A | 7/2000 | Mitchell et al. | |
| 6,093,570 A | 7/2000 | Ferrari et al. | |
| 6,156,303 A | 12/2000 | Russell et al. | |
| 6,180,613 B1 | 1/2001 | Kaplitt et al. | |
| 6,387,368 B1 * | 5/2002 | Wilson ................. | C12N 15/86 435/235.1 |
| 6,426,198 B1 | 7/2002 | Carstea et al. | |
| 6,468,524 B1 | 10/2002 | Chiorini et al. | |
| 6,468,798 B1 | 10/2002 | Debs et al. | |
| 6,503,888 B1 | 1/2003 | Kaplitt et al. | |
| 6,544,785 B1 | 4/2003 | Palese et al. | |
| 6,562,958 B1 | 5/2003 | Breton et al. | |
| 6,733,757 B2 | 5/2004 | Patel et al. | |
| 6,822,071 B1 | 11/2004 | Stephens et al. | |
| 6,962,815 B2 | 11/2005 | Bartlett | |
| 6,984,517 B1 | 1/2006 | Chiorini et al. | |
| 7,045,675 B2 | 5/2006 | Carstea et al. | |
| 7,071,172 B2 | 7/2006 | McCown et al. | |

(Continued)

FOREIGN PATENT DOCUMENTS

EP 1033405 A2 9/2000
EP 1777296 A2 4/2007

(Continued)

OTHER PUBLICATIONS

Adachi et al., "Drawing a High-Resolution Functional Map of Adeno-Associated Virus Capsid by Massively Parallel Sequencing," Nature Communications 5(1):14 pages (2013).

Altschul et al., "Gapped BLAST and PSI-BLAST: a new generation of protein database search programs," Nucleic Acids Research 25(17):3389-3402 (1997).

Arrunda et al., "Regional intravascular delivery of AAV-2-F.IX to skeletal muscle achieves long-term correction of hemophilia B in a large animal model," Blood 105:3458-3464 (2005).

(Continued)

Primary Examiner — David Steadman
(74) Attorney, Agent, or Firm — Foley Hoag LLP; Brendan T. Jones

(57) ABSTRACT

Provided herein are gene therapy compositions and methods for treating, preventing, and/or curing NPC1. More specifically, the disclosure provides Adeno-associated virus (AAV) vectors for delivery of nucleic acids and nucleic acids (including AAV transfer cassettes) for treating, preventing, and/or curing NPC1.

20 Claims, 13 Drawing Sheets
Specification includes a Sequence Listing.

(56) References Cited

U.S. PATENT DOCUMENTS

| | | | |
|---|---|---|---|
| 7,105,345 B2 | 9/2006 | Wilson et al. |
| 7,198,951 B2 | 4/2007 | Gao et al. |
| 7,201,898 B2 | 4/2007 | Monahan et al. |
| 7,214,786 B2 | 5/2007 | Kovalic et al. |
| 7,252,997 B1 | 8/2007 | Hallek et al. |
| 7,259,151 B2 | 8/2007 | Arbetman et al. |
| 7,282,199 B2 | 10/2007 | Gao et al. |
| 7,314,912 B1 | 1/2008 | Hallek et al. |
| 7,473,531 B1 | 1/2009 | Dornon |
| 7,588,772 B2 | 9/2009 | Kay et al. |
| 7,712,893 B2 | 5/2010 | Dobashi |
| 7,718,424 B2 | 5/2010 | Chiorini et al. |
| 7,749,492 B2 | 7/2010 | Bartlett et al. |
| 7,777,097 B2 | 8/2010 | Glazebrook et al. |
| 7,790,449 B2 | 9/2010 | Gao et al. |
| 7,867,484 B2 | 1/2011 | Samulski et al. |
| 7,892,809 B2 | 2/2011 | Bowles et al. |
| 7,906,111 B2 | 3/2011 | Wilson et al. |
| 8,067,014 B2 | 11/2011 | Kay et al. |
| 8,299,321 B2 | 10/2012 | Cao |
| 8,318,480 B2 | 11/2012 | Gao et al. |
| 8,343,764 B2 | 1/2013 | Abad et al. |
| 8,445,267 B2 | 5/2013 | Zhong et al. |
| 8,628,966 B2 | 1/2014 | Chatterjee et al. |
| 8,664,475 B2 | 3/2014 | Puzio et al. |
| 8,679,837 B2 | 3/2014 | Zolotukhin et al. |
| 8,734,809 B2 | 5/2014 | Gao et al. |
| 8,802,440 B2 | 8/2014 | Zhong et al. |
| 8,889,641 B2 | 11/2014 | Asokan et al. |
| 8,906,387 B2 | 12/2014 | Kay et al. |
| 8,906,675 B2 | 12/2014 | Gao et al. |
| 8,927,514 B2 | 1/2015 | Chatterjee et al. |
| 8,952,217 B2 | 2/2015 | Puzio et al. |
| 8,962,332 B2 | 2/2015 | Gao et al. |
| 9,012,224 B2 | 4/2015 | Bowles et al. |
| 9,066,966 B2 | 6/2015 | Puccio et al. |
| 9,157,098 B2 | 10/2015 | Zhong et al. |
| 9,409,953 B2 | 8/2016 | Asokan et al. |
| 9,441,244 B2 | 9/2016 | Schaffer et al. |
| 9,453,241 B2 * | 9/2016 | Pan ............... C12N 15/8616 |
| 9,475,845 B2 | 10/2016 | Asokan et al. |
| 9,567,376 B2 | 2/2017 | Cronin et al. |
| 9,585,971 B2 | 3/2017 | Deverman et al. |
| 9,587,250 B2 | 3/2017 | Gao et al. |
| 9,598,468 B2 | 3/2017 | Weigel-Van Aken et al. |
| 9,611,302 B2 | 4/2017 | Srivastava et al. |
| 9,623,120 B2 | 4/2017 | Chatterjee et al. |
| 9,677,088 B2 | 6/2017 | Nakai et al. |
| 9,677,089 B2 | 6/2017 | Gao et al. |
| 9,683,268 B2 | 6/2017 | Barouch et al. |
| 9,695,220 B2 | 7/2017 | Vandenberghe et al. |
| 9,719,070 B2 | 8/2017 | Vandenberghe et al. |
| 9,725,485 B2 | 8/2017 | Srivastava et al. |
| 9,737,618 B2 | 8/2017 | Wilson et al. |
| 9,737,619 B2 | 8/2017 | Ansell et al. |
| 9,775,918 B2 | 10/2017 | Zhong et al. |
| 9,777,291 B2 | 10/2017 | Chatterjee et al. |
| 9,783,825 B2 | 10/2017 | Chatterjee et al. |
| 9,790,472 B2 | 10/2017 | Gao et al. |
| 9,803,218 B2 | 10/2017 | Chatterjee et al. |
| 9,834,789 B2 | 12/2017 | Chatterjee et al. |
| 9,839,696 B2 | 12/2017 | Chatterjee et al. |
| 9,879,275 B2 | 1/2018 | Nadzan et al. |
| 9,890,396 B2 | 2/2018 | Chatterjee et al. |
| 9,909,142 B2 | 3/2018 | Yazicioglu et al. |
| 9,920,097 B2 | 3/2018 | Zhong et al. |
| 9,944,908 B2 | 4/2018 | Vaten et al. |
| 9,976,157 B2 | 5/2018 | Poraty-Gavra et al. |
| 10,011,640 B2 | 7/2018 | Srivastava et al. |
| 10,072,251 B2 | 9/2018 | Gao et al. |
| 10,077,291 B2 | 9/2018 | Asokan et al. |
| 10,081,659 B2 | 9/2018 | Chiorini et al. |
| 10,119,125 B2 | 11/2018 | Vandenberghe et al. |
| 10,214,566 B2 | 2/2019 | Schaffer et al. |
| 10,337,027 B2 | 7/2019 | Puccio et al. |
| 10,369,193 B2 | 8/2019 | Passini et al. |
| 10,385,320 B2 | 8/2019 | Kay et al. |
| 10,392,632 B2 | 8/2019 | Wright et al. |
| 10,406,244 B2 | 9/2019 | Kay et al. |
| 10,414,803 B2 | 9/2019 | Nathwani et al. |
| 10,426,844 B2 | 10/2019 | Agbandje-McKenna et al. |
| 10,526,627 B2 | 1/2020 | Skuratowicz et al. |
| 10,668,094 B2 | 6/2020 | Karlish |
| 10,745,447 B2 | 8/2020 | Asokan et al. |
| 10,907,176 B2 | 2/2021 | Asokan et al. |
| 11,077,128 B2 | 8/2021 | Karlish |
| 11,208,438 B2 | 12/2021 | Asokan et al. |
| 2002/0192189 A1 | 12/2002 | Xiao et al. |
| 2003/0017131 A1 | 1/2003 | Park et al. |
| 2003/0053990 A1 | 3/2003 | Rabinowitz et al. |
| 2003/0225017 A1 | 12/2003 | Murdin et al. |
| 2004/0013645 A1 | 1/2004 | Monahan et al. |
| 2004/0031072 A1 | 2/2004 | La Rosa et al. |
| 2004/0071659 A1 | 4/2004 | Chang et al. |
| 2004/0166519 A1 | 8/2004 | Cargill et al. |
| 2004/0214272 A1 | 10/2004 | La Rosa et al. |
| 2005/0287122 A1 | 12/2005 | Bartlett et al. |
| 2006/0107345 A1 | 5/2006 | Alexandrov et al. |
| 2006/0123505 A1 | 6/2006 | Kikuchi et al. |
| 2006/0171926 A1 | 8/2006 | Passini et al. |
| 2006/0236419 A1 | 10/2006 | La Rosa et al. |
| 2007/0015238 A1 | 1/2007 | Snyder et al. |
| 2007/0124833 A1 | 5/2007 | Abad et al. |
| 2007/0196338 A1 | 8/2007 | Samulski et al. |
| 2007/0243526 A1 | 10/2007 | Kay et al. |
| 2008/0229439 A1 | 9/2008 | La Rosa et al. |
| 2009/0215879 A1 | 8/2009 | Diprimio et al. |
| 2009/0221620 A1 | 9/2009 | Luke et al. |
| 2009/0275107 A1 | 11/2009 | Lock et al. |
| 2009/0317417 A1 | 12/2009 | Vandenberghe et al. |
| 2010/0037352 A1 | 2/2010 | Alexandrov et al. |
| 2010/0047174 A1 | 2/2010 | Kay et al. |
| 2010/0095387 A1 | 4/2010 | Smith et al. |
| 2011/0061124 A1 | 3/2011 | Nadzan et al. |
| 2011/0067143 A2 | 3/2011 | La et al. |
| 2011/0124048 A1 | 5/2011 | Yun |
| 2011/0131679 A2 | 6/2011 | La et al. |
| 2011/0209246 A1 | 8/2011 | Kovalic et al. |
| 2011/0214206 A1 | 9/2011 | La Rosa et al. |
| 2011/0236353 A1 | 9/2011 | Wilson et al. |
| 2011/0294218 A1 | 12/2011 | Chatterjee et al. |
| 2012/0009268 A1 | 1/2012 | Asokan et al. |
| 2012/0137379 A1 | 5/2012 | Gao et al. |
| 2012/0216318 A1 | 8/2012 | La Rosa et al. |
| 2012/0255046 A1 | 10/2012 | Kay et al. |
| 2012/0322861 A1 | 12/2012 | Byrne et al. |
| 2013/0096182 A1 | 4/2013 | Chatterjee et al. |
| 2013/0152224 A1 | 6/2013 | Abad et al. |
| 2013/0185831 A1 | 7/2013 | Kovalic et al. |
| 2013/0195801 A1 | 8/2013 | Gao et al. |
| 2013/0203841 A1 | 8/2013 | Zhong et al. |
| 2013/0216501 A1 | 8/2013 | Zhong et al. |
| 2013/0224836 A1 | 8/2013 | Muramatsu |
| 2013/0225666 A1 | 8/2013 | Kaspar et al. |
| 2013/0326723 A1 | 12/2013 | La Rosa et al. |
| 2014/0017212 A1 | 1/2014 | Rebar |
| 2014/0037585 A1 | 2/2014 | Wright et al. |
| 2014/0050701 A1 | 2/2014 | Zhong et al. |
| 2014/0056854 A1 | 2/2014 | Asokan et al. |
| 2014/0057969 A1 | 2/2014 | Frost et al. |
| 2014/0130203 A1 | 5/2014 | La Rosa et al. |
| 2014/0162319 A2 | 6/2014 | Hareendran et al. |
| 2014/0199313 A1 | 7/2014 | Plesch et al. |
| 2014/0223605 A1 | 8/2014 | Puzio et al. |
| 2014/0259218 A1 | 9/2014 | Kovalic et al. |
| 2014/0296486 A1 | 10/2014 | Gao et al. |
| 2014/0335054 A1 | 11/2014 | Gao et al. |
| 2014/0341852 A1 | 11/2014 | Srivastava et al. |
| 2015/0050302 A1 | 2/2015 | Thess |
| 2015/0079038 A1 | 3/2015 | Deverman et al. |
| 2015/0082481 A1 | 3/2015 | La Rosa et al. |
| 2015/0126588 A1 | 5/2015 | Nakai et al. |
| 2015/0133530 A1 | 5/2015 | Srivastava et al. |
| 2015/0184189 A1 | 7/2015 | Abad et al. |

(56) References Cited

U.S. PATENT DOCUMENTS

| | | |
|---|---|---|
| 2015/0191739 A1 | 7/2015 | La Rosa et al. |
| 2015/0197763 A1 | 7/2015 | La Rosa et al. |
| 2015/0238550 A1 | 8/2015 | McCown |
| 2015/0344911 A1 | 12/2015 | Chatterjee et al. |
| 2016/0017295 A1 | 1/2016 | Schaffer et al. |
| 2016/0025657 A1 | 1/2016 | Shahbazmohamadi et al. |
| 2016/0106865 A1 | 4/2016 | Zhong et al. |
| 2016/0215024 A1 | 7/2016 | Vandenberghe et al. |
| 2016/0222067 A1 | 8/2016 | Gao et al. |
| 2016/0256571 A1 | 9/2016 | Corral-Debrinski et al. |
| 2016/0264984 A1 | 9/2016 | La Rosa et al. |
| 2016/0289275 A1 | 10/2016 | Chiorini et al. |
| 2016/0319294 A1 | 11/2016 | Kovalic et al. |
| 2016/0333372 A1 | 11/2016 | Srivastava et al. |
| 2016/0361439 A1 | 12/2016 | Agbandje-Mckenna et al. |
| 2016/0369299 A1 | 12/2016 | Boye et al. |
| 2017/0007720 A1 | 1/2017 | Boye et al. |
| 2017/0028082 A1 | 2/2017 | Wilson et al. |
| 2017/0049910 A1 | 2/2017 | Cronin et al. |
| 2017/0067908 A1 | 3/2017 | Nakai et al. |
| 2017/0088852 A1 | 3/2017 | Dangoor et al. |
| 2017/0088858 A1 | 3/2017 | Gao et al. |
| 2017/0096683 A1 | 4/2017 | Scaria et al. |
| 2017/0130245 A1 | 5/2017 | Kotin et al. |
| 2017/0159027 A1 | 6/2017 | Wilson et al. |
| 2017/0166926 A1 | 6/2017 | Deverman et al. |
| 2017/0204144 A1 | 7/2017 | Deverman et al. |
| 2017/0211092 A1 | 7/2017 | Chatterjee et al. |
| 2017/0211093 A1 | 7/2017 | Chatterjee et al. |
| 2017/0211094 A1 | 7/2017 | Chatterjee et al. |
| 2017/0211095 A1 | 7/2017 | Chatterjee et al. |
| 2017/0240885 A1 | 8/2017 | Deverman et al. |
| 2017/0275337 A1 | 9/2017 | Srivastava et al. |
| 2017/0298323 A1 | 10/2017 | Vandenberghe et al. |
| 2017/0349911 A1 | 12/2017 | Gao et al. |
| 2018/0002722 A1 | 1/2018 | Asokan et al. |
| 2018/0030096 A1 | 2/2018 | Aslanidi et al. |
| 2018/0030479 A1 | 2/2018 | Gao et al. |
| 2018/0036428 A1 | 2/2018 | Zhong et al. |
| 2018/0066022 A1 | 3/2018 | Chalberg et al. |
| 2018/0066285 A1 | 3/2018 | Ojala et al. |
| 2018/0104289 A1 | 4/2018 | Venditti et al. |
| 2018/0105559 A1 | 4/2018 | Srivastava et al. |
| 2018/0112229 A1 | 4/2018 | Nadzan et al. |
| 2018/0119167 A1 | 5/2018 | Abad et al. |
| 2018/0135074 A1 | 5/2018 | Srivastava et al. |
| 2018/0135076 A1 | 5/2018 | Linden |
| 2018/0163227 A1 | 6/2018 | Chatterjee et al. |
| 2018/0214576 A1 | 8/2018 | Fitzgerald et al. |
| 2018/0244727 A1 | 8/2018 | Zhong et al. |
| 2018/0265863 A1 | 9/2018 | Esteves et al. |
| 2018/0355376 A1 | 12/2018 | Chiorini et al. |
| 2018/0362592 A1 | 12/2018 | Gao et al. |
| 2018/0371024 A1 | 12/2018 | Asokan et al. |
| 2019/0048041 A1 | 2/2019 | Asokan et al. |
| 2019/0055524 A1 | 2/2019 | Vandenberghe et al. |
| 2019/0085301 A1 | 3/2019 | Gao et al. |
| 2019/0100560 A1 | 4/2019 | Vandenberghe et al. |
| 2019/0249195 A1 | 8/2019 | Marsic et al. |
| 2019/0255192 A1 | 8/2019 | Kirn et al. |
| 2019/0262373 A1 | 8/2019 | Woodard et al. |
| 2019/0284576 A1 | 9/2019 | Qu et al. |
| 2019/0292561 A1 | 9/2019 | Qu et al. |
| 2019/0367562 A1 | 12/2019 | Asokan et al. |
| 2020/0109418 A1 | 4/2020 | Li et al. |
| 2020/0399321 A1 | 12/2020 | Asokan et al. |
| 2021/0128652 A1 | 5/2021 | Dismuke |
| 2021/0324418 A1 | 10/2021 | Thomas et al. |
| 2021/0363191 A1 | 11/2021 | McCoy |
| 2021/0371469 A1 | 12/2021 | McCoy |
| 2021/0371471 A1 | 12/2021 | McCoy |
| 2022/0056478 A1 | 2/2022 | O'Banion |
| 2022/0064675 A1 | 3/2022 | McCoy et al. |
| 2022/0088152 A1 | 3/2022 | Mikati |
| 2022/0089651 A1 | 3/2022 | Asokan et al. |

FOREIGN PATENT DOCUMENTS

| | | |
|---|---|---|
| EP | 1887081 A2 | 2/2008 |
| EP | 2194140 A2 | 6/2010 |
| EP | 2359869 A2 | 8/2011 |
| EP | 2492347 A1 | 8/2012 |
| EP | 2660325 A2 | 11/2013 |
| EP | 2315833 B1 | 4/2015 |
| EP | 1453547 B1 | 9/2016 |
| EP | 2007795 B1 | 11/2016 |
| EP | 2675484 B1 | 5/2018 |
| EP | 2263692 B1 | 9/2018 |
| EP | 2206728 B9 | 10/2018 |
| EP | 3244931 B1 | 10/2018 |
| EP | 1633767 B1 | 11/2018 |
| EP | 3060575 B1 | 12/2018 |
| EP | 3250239 B1 | 12/2018 |
| EP | 3459965 A1 | 3/2019 |
| EP | 3511021 A1 | 7/2019 |
| EP | 3108000 B1 | 8/2019 |
| JP | 2014534245 A | 12/2014 |
| RU | 2457252 C2 | 7/2012 |
| WO | WO-9005142 A1 | 5/1990 |
| WO | WO 98/11244 A2 | 3/1998 |
| WO | WO-9901555 A1 | 1/1999 |
| WO | WO 99/61601 A2 | 12/1999 |
| WO | WO 00/028061 A1 | 1/2000 |
| WO | WO 00/17377 A2 | 3/2000 |
| WO | WO-0023477 A2 | 4/2000 |
| WO | WO 00/28004 A1 | 5/2000 |
| WO | WO-0028061 A2 | 5/2000 |
| WO | WO-0111034 A2 | 2/2001 |
| WO | WO-0181581 A2 | 11/2001 |
| WO | WO 01/92551 A2 | 12/2001 |
| WO | WO-0210210 A2 | 2/2002 |
| WO | WO-03000906 A2 | 1/2003 |
| WO | WO-03008540 A2 | 1/2003 |
| WO | WO-03033515 A1 | 4/2003 |
| WO | WO-03042361 A2 | 5/2003 |
| WO | WO-03052051 A2 | 6/2003 |
| WO | WO 03/095647 A2 | 11/2003 |
| WO | WO-2004027019 A2 | 4/2004 |
| WO | WO-2005/033321 A2 | 4/2005 |
| WO | WO 2006/021724 A2 | 3/2006 |
| WO | WO 2006/029319 A2 | 3/2006 |
| WO | WO 2006/066066 A2 | 6/2006 |
| WO | WO 2006/073052 A1 | 7/2006 |
| WO | WO 2006/119432 A2 | 11/2006 |
| WO | WO-2006119137 A1 | 11/2006 |
| WO | WO-2007084773 A2 | 7/2007 |
| WO | WO-2007089632 A2 | 8/2007 |
| WO | WO-2007092563 A2 | 8/2007 |
| WO | WO 2007/100465 A2 | 9/2007 |
| WO | WO-2007120542 A2 | 10/2007 |
| WO | WO-2007127264 A2 | 11/2007 |
| WO | WO 2008/088895 A2 | 7/2008 |
| WO | WO-2009037279 A1 | 3/2009 |
| WO | WO-2009043936 A1 | 4/2009 |
| WO | WO-2009105612 A2 | 8/2009 |
| WO | WO-2009108274 A2 | 9/2009 |
| WO | WO 2010/093784 | 8/2010 |
| WO | WO-2010129021 A1 | 11/2010 |
| WO | WO-2010138263 A2 | 12/2010 |
| WO | WO-2011020118 A1 | 2/2011 |
| WO | WO-2011020710 A2 | 2/2011 |
| WO | WO-2011122950 A1 | 10/2011 |
| WO | WO-2011133890 A1 | 10/2011 |
| WO | WO-2012061744 A2 | 5/2012 |
| WO | WO-2012064960 A2 | 5/2012 |
| WO | WO-2012112578 A2 | 8/2012 |
| WO | WO-2012178173 A1 | 12/2012 |
| WO | WO-2013016315 A1 | 1/2013 |
| WO | WO-2013027223 A2 | 2/2013 |
| WO | WO-2013158879 A1 | 10/2013 |
| WO | WO-2013170078 A1 | 11/2013 |
| WO | WO-2013173512 A2 | 11/2013 |
| WO | WO-2013190059 A1 | 12/2013 |
| WO | WO-2014007858 A1 | 1/2014 |
| WO | WO-2014045674 A1 | 3/2014 |

(56) References Cited

FOREIGN PATENT DOCUMENTS

| | | |
|---|---|---|
| WO | WO-2014124282 A1 | 8/2014 |
| WO | WO 2014/144229 | 9/2014 |
| WO | WO-2014153083 A1 | 9/2014 |
| WO | WO-2014193716 A2 | 12/2014 |
| WO | WO-2014194132 A1 | 12/2014 |
| WO | WO-2015013313 A2 | 1/2015 |
| WO | WO-2015038958 A1 | 3/2015 |
| WO | WO-2015054653 A2 | 4/2015 |
| WO | WO-2015121501 A1 | 8/2015 |
| WO | WO-2015164757 A1 | 10/2015 |
| WO | WO-2015168666 A2 | 11/2015 |
| WO | WO-2015181823 A1 | 12/2015 |
| WO | WO-2015191508 A1 | 12/2015 |
| WO | WO-2016054557 A1 | 4/2016 |
| WO | WO-2016065001 A1 | 4/2016 |
| WO | WO-2016081811 A1 | 5/2016 |
| WO | WO-2016115382 A1 | 7/2016 |
| WO | WO-2016115503 A1 | 7/2016 |
| WO | WO-2016128558 A1 | 8/2016 |
| WO | WO-2016128559 A1 | 8/2016 |
| WO | WO-2016134338 A1 | 8/2016 |
| WO | WO-2016150964 A1 | 9/2016 |
| WO | WO-2016164642 A1 | 10/2016 |
| WO | WO-2016172008 A1 | 10/2016 |
| WO | WO-2016172155 A1 | 10/2016 |
| WO | WO-2016179644 A1 | 11/2016 |
| WO | WO-2017015102 A1 | 1/2017 |
| WO | WO 2017/058892 A2 | 4/2017 |
| WO | WO 2017/058892 A3 | 4/2017 |
| WO | WO-2017066764 A2 | 4/2017 |
| WO | WO-2017070516 A1 | 4/2017 |
| WO | WO-2017/077451 A1 | 5/2017 |
| WO | WO-2017096164 A1 | 6/2017 |
| WO | WO-2017106236 A1 | 6/2017 |
| WO | WO 2017/143100 A1 | 8/2017 |
| WO | WO-2017139643 A1 | 8/2017 |
| WO | WO-2017147123 A1 | 8/2017 |
| WO | WO-2017180854 A1 | 10/2017 |
| WO | WO-2017192750 A1 | 11/2017 |
| WO | WO-2017201248 A1 | 11/2017 |
| WO | WO-2018022608 A2 | 2/2018 |
| WO | WO-2018035213 A1 | 2/2018 |
| WO | WO-2018049226 A1 | 3/2018 |
| WO | WO-2018064624 A1 | 4/2018 |
| WO | WO-2018075798 A1 | 4/2018 |
| WO | WO-2018119330 A2 | 6/2018 |
| WO | WO-2018152333 A1 | 8/2018 |
| WO | WO-2018160582 A1 | 9/2018 |
| WO | WO-2018170310 A1 | 9/2018 |
| WO | WO-2018/204764 A1 | 11/2018 |
| WO | WO-2018203092 A1 * | 11/2018 ........... A61K 35/761 |
| WO | WO-2018209154 A1 | 11/2018 |
| WO | WO-2018226785 A1 | 12/2018 |
| WO | WO-2018237066 A1 | 12/2018 |
| WO | WO-2019006418 A2 | 1/2019 |
| WO | WO-2019025984 A1 | 2/2019 |
| WO | WO-2019141765 A1 | 7/2019 |
| WO | WO-2019168961 A1 | 9/2019 |
| WO | WO-2019169004 A1 | 9/2019 |
| WO | WO-2019169132 A1 | 9/2019 |
| WO | WO-2019173434 A1 | 9/2019 |
| WO | WO-2019173538 A1 | 9/2019 |
| WO | WO-2019178412 A1 | 9/2019 |
| WO | WO 2019/195444 A1 | 10/2019 |
| WO | WO-2019195423 A1 | 10/2019 |
| WO | WO-2019195449 A1 | 10/2019 |
| WO | WO-2019222444 A2 | 11/2019 |
| WO | WO-2020016318 A1 | 1/2020 |
| WO | WO-2020142653 A1 | 7/2020 |
| WO | WO 2020/191300 | 9/2020 |
| WO | WO-2020232297 A1 | 11/2020 |

OTHER PUBLICATIONS

Chao et al. "Several Log Increase in Therapeutic Transgene Delivery by Distinct Adeno-Associated Viral Serotype Vectors" Molecular Therapy 2(6):619-623 (2000).

Chiorini et al. "Cloning and Characterization of adeno-Associated Virus Type 5" Journal of Virology 73(2):1309-1319 (1999).

Chiorini et al. "Cloning of adeno-Associated Virus Type 4 (AAV4). and Generation of Recombinant AAV4 Particles" Journal of Virology 71(9):6823-6833 (1997).

Chipman et al. "Cryo-electron microscopy studies of empty capsids of human parvovirus 819 complexed with its cellular receptor" Proceedings of the National Academy of Sciences 93:7502-7506 (1996).

Chirmule et al., "Humoral Immunity to Adeno-Associated Virus Type 2 Vectors Following Administration to Murine and Nonhuman Primate Muscle," Journal of Virology, The American Society for Microbiology 74(5):2420-2425 (2000).

Cleves, "Protein transport: The nonclassical ins and outs" Current Biology 7:R318-R320 (1997).

Dimattia et al. "Structural Insight into the Unique Properties of adeno-Associated Virus Serotype 9," Journal of Virology, 86(12):6947-6958 (2012).

Fang et al., "Stable antibody expression at therapeutic levels using the 2A peptide," Nature Biotechnology 23:584-590 (2005).

Gao et al. "Novel adeno-associated viruses from Rhesus Monkeys as Vectors for human gene therapy," Proceedings of the National Academy of Sciences 99(18):11854-11859 (2002).

Genbank Accession No. DQ813647, Adeno-Associated Virus 12 Rep 78 and VP1 genes, complete cds., dated Feb. 20, 2008, 3 pages.

Genbank Accession No. AF085716, Adeno-associated virus 5 DNA binding trs helicase (Rep22) and capsid protein (VP1) genes, complete cds., dated Feb. 9, 1999, 3 pages.

Genbank Accession No. AY243001, Non-Human Primate Adeno-associated Virus Isolate AAVrh.34 capsid protein (VP1) gene, complete cds., dated May 14, 2003, 2 pages.

Genbank Accession No. AY243002, Non-Human Primate Adeno-associated Virus Isolate AAVrh.33 capsid protein (VP1) gene, complete cds. dated May 14, 2003, 2 pages.

Genbank Accession No. AY243003, Non-Human Primate Adeno-associated Virus Isolate AAVrh.32 cpsid protein (VP1) gene, complete cds, dated May 14, 2003, 2 pages.

Genbank Accession No. AAR26465, Bovine Adeno-Associated Virus, dated May 25, 2004, 2 pages.

Genbank Accession No. AAT46339, capsid protein [Adeno-associated virus 11], dated Nov. 30, 2004, 2 pages.

Genbank Accession No. ABI16639, VP1 [Adeno-associated virus 12, dated Feb. 20, 2008, 2 pages.

Genbank Accession No. AF063497, Adeno-associated virus 1, complete genome, dated Apr. 27, 1999, 3 pages.

Genbank Accession No. AY186198, Avian adeno-associated virus Atcc VR-865, complete genome, dated Jun. 5, 2003, 3 pages.

Genbank Accession No. AY242997, Non-Human primate Adeno-associated virus isolate AAVrh.8 capsid protein (VP1) gene, complete cds, dated May 14, 2003, 2 pages.

Genbank Accession No. AY242998, Non-Human primate Adeno-associated virus isolate AAVrh.37 capsid protein (VP1) gene, complete cds, dated May 14, 2003, 2 pages.

Genbank Accession No. AY242999, Non-Human primate Adeno-associated virus isolate AAVrh.36 capsid protein (VP1) gene, complete cds, dated May 14, 2003, 2 pages.

Genbank Accession No. AY243000, Non-Human primate Adeno-associated virus isolate AAVrh.35 capsid protein (VP1) gene, complete cds, dated May 14, 2003, 2 pages.

Genbank Accession No. AY243007, Non-Human Primate Adeno-associated Virus Isolate AAVrh.2 capsid protein (VP1) gene, complete cds, dated May 14, 2003, 2 pages.

Genbank Accession No. AY243013, Non-Human primate Adeno-associated virus isolate AAVrh.13 capsid protein (VP1) gene, complete cds, dated May 14, 2003, 2 pages.

Genbank Accession No. AY243015, Non-Human primate Adeno-associated virus isolate AAVrh.10 capsid protein (VP1) gene, complete cds, dated May 14, 2003, 2 pages.

(56) References Cited

OTHER PUBLICATIONS

Genbank Accession No. AY243016, Non-Human primate Adeno-associated virus isolate AAVcy.6 capsid protein (VP1) gene, complete cds, dated May 14, 2003, 2 pages.
Genbank Accession No. AY243017, Non-Human primate Adeno-associated virus isolate AAVcy.5 capsid protein (VP1) gene, complete cds, dated May 14, 2003, 2 pages.
Genbank Accession No. AY243018, Non-Human primate Adeno-associated virus isolate AAVcy.4 capsid protein (VP1) gene, complete cds, dated May 14, 2003, 2 pages.
Genbank Accession No. AY243019, Non-Human primate Adeno-associated virus isolate AAVcy.3 capsid protein (VP1) gene, complete cds, dated May 14, 2003, 2 pages.
Genbank Accession No. AY243020, Non-Human primate Adeno-associated virus isolate AAVcy.2 capsid protein (VP1) gene, complete cds, dated May 14, 2003, 2 pages.
Genbank Accession No. AY243021, Non-Human primate Adeno-associated virus isolate AAVch.5 capsid protein (VP1) gene, complete cds, dated May 14, 2003, 2 pages.
Genbank Accession No. AY243022, Non-Human primate Adeno-associated virus isolate AAVbb.2 capsid protein (VP1) gene, complete cds, dated May 14, 2003, 2 pages.
Genbank Accession No. AY243023, Non-Human primate Adeno-associated virus isolate AAVbb.1 capsid protein (VP1) gene, complete cds, dated May 14, 2003, 2 pages.
Genbank Accession No. AY388617, Bovine adeno-associated virus, complete genome, dated May 25, 2004, 3 pages.
Genbank Accession No. AY530553, Adeno-associated virus isolate pi.1 capsid protein VP1 9cap) gene, complete cds, dated Jun. 24, 2004, 2 pages.
Genbank Accession No. AY530554, Adeno-associated virus isolate pi.2 capsid protein VP1 9cap) gene, complete cds, dated Jun. 24, 2004, 2 pages.
Genbank Accession No. AY530555, Adeno-associated virus isolate pi.3 capsid protein VP1 9cap) gene, complete cds, dated Jun. 24, 2004, 2 pages.
Genbank Accession No. AY530556, Adeno-associated virus isolate rh.1 capsid protein VP1 9cap) gene, complete cds, dated Jun. 24, 2004, 2 pages.
Genbank Accession No. AY530557, Adeno-associated virus isolate rh.25 capsid protein VP1 9cap) gene, complete cds, dated Jun. 24, 2004, 2 pages.
Genbank Accession No. AY530558, Adeno-associated virus isolate rh.38 capsid protein VP1 (cap) gene, complete cds, dated Jun. 24, 2004, 2 pages.
Genbank Accession No. AY530559, Adeno-associated virus isolate rh.40 capsid protein VP1 (cap) gene, complete cds, dated Jun. 24, 2004, 2 pages.
Genbank Accession No. AY530560, Adeno-associated virus isolate rh.43 capsid protein VP1 (cap) gene, complete cds, dated Jun. 24, 2004, 2 pages.
Genbank Accession No. AY530561, Genbank Accession No. AY530560, Adeno-associated virus isolate rh.48 capsid protein VP1 (cap) gene, complete cds, dated Jun. 24, 2004, 2 pages.
Genbank Accession No. AY530562, Adeno-associated virus isolate rh.49 capsid protein VP1 (cap) gene, complete cds, dated Jun. 24, 2004, 2 pages.
Genbank Accession No. AY530563, Adeno-associated virus isolate rh.50 capsid protein VP1 (cap) gene, complete cds, dated Jun. 24, 2004, 2 pages.
Genbank Accession No. AY530564, Adeno-associated virus isolate rh.51 capsid protein VP1 (cap) gene, complete cds, dated Jun. 24, 2004, 2 pages.
Genbank Accession No. AY530565, Adeno-associated virus isolate rh.52 capsid protein VP1 (cap) gene, complete cds, dated Jun. 24, 2004, 2 pages.
Genbank Accession No. AY530566, Adeno-associated virus isolate rh.53 capsid protein VP1 (cap) gene, complete cds, dated Jun. 24, 2004, 2 pages.
Genbank Accession No. AY530567, Adeno-associated virus isolate rh.54 capsid protein VP1 (cap) gene, complete cds, dated Jun. 24, 2004, 2 pages.
Genbank Accession No. AY530568, Adeno-associated virus isolate rh.55 capsid protein VP1 (cap) gene, complete cds, dated Jun. 24, 2004, 2 pages.
Genbank Accession No. AY530569, Adeno-associated virus isolate rh.57 capsid protein VP1 (cap) gene, complete cds, dated Jun. 24, 2004, 2 pages.
Genbank Accession No. AY530570, Adeno-associated virus isolate rh.58 capsid protein VP1 (cap) gene, complete cds, dated Jun. 24, 2004, 2 pages.
Genbank Accession No. AY530572, Adeno-associated virus isolate rh.61 capsid protein VP1 (cap) gene, complete cds, dated Jun. 24, 2004, 2 pages.
Genbank Accession No. AY530573, Adeno-associated virus isolate rh.62 capsid protein VP1 (cap) gene, complete cds, dated Jun. 24, 2004, 2 pages.
Genbank Accession No. AY530574, Adeno-associated virus isolate rh.64 capsid protein VP1 (cap) gene, complete cds, dated Jun. 24, 2004, 2 pages.
Genbank Accession No. AY530575, Adeno-associated virus isolate hu.1 capsid protein VP1 (cap) gene, complete cds, dated Jun. 24, 2004, 2 pages.
Genbank Accession No. AY530576, Adeno-associated virus isolate hu.10 capsid protein VP1 (cap) gene, complete cds, dated Jun. 24, 2004, 2 pages.
Genbank Accession No. AY530577, Adeno-associated virus isolate hu.11 capsid protein VP1 (cap) gene, complete cds, dated Jun. 24, 2004, 2 pages.
Genbank Accession No. AY530578, Adeno-associated virus isolate hu.13 capsid protein VP1 (cap) gene, complete cds, dated Jun. 24, 2004, 2 pages.
Genbank Accession No. AY530579, Adeno-associated virus isolate hu.14 capsid protein VP1 (cap) gene, complete cds, dated Jun. 24, 2004, 2 pages.
Genbank Accession No. AY530580, Adeno-associated virus isolate hu.15 capsid protein VP1 (cap) gene, complete cds, dated Jun. 24, 2004, 2 pages.
Genbank Accession No. AY530581, Adeno-associated virus isolate hu.16 capsid protein VP1 (cap) gene, complete cds, dated Jun. 24, 2004, 2 pages.
Genbank Accession No. AY530582, Adeno-associated virus isolate hu.17 capsid protein VP1 (cap) gene, complete cds, dated Jun. 24, 2004, 2 pages.
Genbank Accession No. AY530583, Adeno-associated virus isolate hu.18 capsid protein VP1 (cap) gene, complete cds, dated Jun. 24, 2004, 2 pages.
Genbank Accession No. AY530584, Adeno-associated virus isolate hu.19 capsid protein VP1 (cap) gene, complete cds, dated Jun. 24, 2004, 2 pages.
Genbank Accession No. AY530585, Adeno-associated virus isolate hu.2 capsid protein VP1 (cap) gene, complete cds, dated Jun. 24, 2004, 2 pages.
Genbank Accession No. AY530586, Adeno-associated virus isolate hu.20 capsid protein VP1 (cap) gene, complete cds, dated Jun. 24, 2004, 2 pages.
Genbank Accession No. AY530587, Adeno-associated virus isolate hu.21 capsid protein VP1 (cap) gene, complete cds, dated Jun. 24, 2004, 2 pages.
Genbank Accession No. AY530588, Adeno-associated virus isolate hu.22 capsid protein VP1 (cap) gene, complete cds, dated Jun. 24, 2004, 2 pages.
Genbank Accession No. AY530589, Adeno-associated virus isolate hu.23 capsid protein VP1 (cap) gene, complete cds, dated Jun. 24, 2004, 2 pages.
Genbank Accession No. AY530590, Adeno-associated virus isolate hu.24 capsid protein VP1 (cap) gene, complete cds, dated Jun. 24, 2004, 2 pages.
Genbank Accession No. AY530591, Adeno-associated virus isolate hu.25 capsid protein VP1 (cap) gene, complete cds, dated Jun. 24, 2004, 2 pages.

(56) References Cited

OTHER PUBLICATIONS

Genbank Accession No. AY530592, Adeno-associated virus isolate hu.27 capsid protein VP1 (cap) gene, complete cds, dated Jun. 24, 2004, 2 pages.
Genbank Accession No. AY530593, Adeno-associated virus isolate hu.28 capsid protein VP1 (cap) gene, complete cds, dated Jun. 24, 2004, 2 pages.
Genbank Accession No. AY530594, Adeno-associated virus isolate hu.29 capsid protein VP1 (cap) gene, complete cds, dated Jun. 24, 2004, 2 pages.
Genbank Accession No. AY530595, Adeno-associated virus isolate hu.3 capsid protein VP1 (cap) gene, complete cds, dated Jun. 24, 2004, 2 pages.
Genbank Accession No. AY530596, Adeno-associated virus isolate hu.31 capsid protein VP1 (cap) gene, complete cds, dated Jun. 24, 2004, 2 pages.
Genbank Accession No. AY530597, Adeno-associated virus isolate hu.32 capsid protein VP1 (cap) gene, complete cds, dated Jun. 24, 2004, 2 pages.
Genbank Accession No. AY530598, Adeno-associated virus isolate hu.34 capsid protein VP1 (cap) gene, complete cds, dated Jun. 24, 2004, 2 pages.
Genbank Accession No. AY530599, Adeno-associated virus isolate hu.35 capsid protein VP1 (cap) gene, complete cds, dated Jun. 24, 2004, 2 pages.
Genbank Accession No. AY530600, Adeno-associated virus isolate hu.37 capsid protein VP1 (cap) gene, complete cds, dated Jun. 24, 2004, 2 pages.
Genbank Accession No. AY530601, Adeno-associated virus isolate hu.39 capsid protein VP1 (cap) gene, complete cds, dated Jun. 24, 2004, 2 pages.
Genbank Accession No. AY530602, Adeno-associated virus isolate hu.4 capsid protein VP1 (cap) gene, complete cds, dated Jun. 24, 2004, 2 pages.
Genbank Accession No. AY530603, Adeno-associated virus isolate hu.40 capsid protein VP1 (cap) gene, complete cds, dated Jun. 24, 2004, 2 pages.
Genbank Accession No. AY530604, Adeno-associated virus isolate hu.41 capsid protein VP1 (cap) gene, complete cds, dated Jun. 24, 2004, 2 pages.
Genbank Accession No. AY530605, Adeno-associated virus isolate hu.42 capsid protein VP1 (cap) gene, complete cds, dated Jun. 24, 2004, 2 pages.
Genbank Accession No. AY530606, Adeno-associated virus isolate hu.43 capsid protein VP1 (cap) gene, complete cds, dated Jun. 24, 2004, 2 pages.
Genbank Accession No. AY530607, Adeno-associated virus isolate hu.44 capsid protein VP1 (cap) gene, complete cds, dated Jun. 24, 2004, 2 pages.
Genbank Accession No. AY530608, Adeno-associated virus isolate hu.45 capsid protein VP1 (cap) gene, complete cds, dated Jun. 24, 2004, 2 pages.
Genbank Accession No. AY530609, Adeno-associated virus isolate hu.46 capsid protein VP1 (cap) gene, complete cds, dated Jun. 24, 2004, 2 pages.
Genbank Accession No. AY530610, Adeno-associated virus isolate hu.47 capsid protein VP1 (cap) gene, complete cds, dated Jun. 24, 2004, 2 pages.
Genbank Accession No. AY530611, Adeno-associated virus isolate hu.48 capsid protein VP1 (cap) gene, complete cds, dated Jun. 24, 2004, 4 pages.
Genbank Accession No. AY530612, Adeno-associated virus isolate hu.49 capsid protein VP1 (cap) gene, complete cds, dated Jun. 24, 2004, 2 pages.
Genbank Accession No. AY530613, Adeno-associated virus isolate hu.51 capsid protein VP1 (cap) gene, complete cds, dated Jun. 24, 2004, 2 pages.
Genbank Accession No. AY530614, Adeno-associated virus isolate hu.52 capsid protein VP1 (cap) gene, complete cds, dated Jun. 24, 2004, 2 pages.
Genbank Accession No. AY530615, Adeno-associated virus isolate hu.53 capsid protein VP1 (cap) gene, complete cds, dated Jun. 24, 2004, 2 pages.
Genbank Accession No. AY530617, Adeno-associated virus isolate hu.55 capsid protein VP1 (cap) gene, complete cds, dated Jun. 24, 2004, 2 pages.
Genbank Accession No. AY530618, Adeno-associated virus isolate hu.56 capsid protein VP1 (cap) gene, complete cds, dated Jun. 24, 2004, 2 pages.
Genbank Accession No. AY530619, Adeno-associated virus isolate hu.57 capsid protein VP1 (cap) gene, complete cds, dated Jun. 24, 2004, 2 pages.
Genbank Accession No. AY530620, Adeno-associated virus isolate hu.58 capsid protein VP1 (cap) gene, complete cds, dated Jun. 24, 2004, 2 pages.
Genbank Accession No. AY530621, Adeno-associated virus isolate hu.6 capsid protein VP1 (cap) gene, complete cds, dated Jun. 24, 2004, 2 pages.
Genbank Accession No. AY530622, Adeno-associated virus isolate hu.60 capsid protein VP1 (cap) gene, complete cds, dated Jun. 24, 2004, 2 pages.
Genbank Accession No. AY530623, Adeno-associated virus isolate hu.61 capsid protein VP1 (cap) gene, complete cds, dated Jun. 24, 2004, 2 pages.
Genbank Accession No. AY530624, Adeno-associated virus isolate hu.63 capsid protein VP1 (cap) gene, complete cds, dated Jun. 24, 2004, 2 pages.
Genbank Accession No. AY530625, Adeno-associated virus isolate hu.64 capsid protein VP1 (cap) gene, complete cds, dated Jun. 24, 2004, 2 pages.
Genbank Accession No. AY530626, Adeno-associated virus isolate hu.66 capsid protein VP1 (cap) gene, complete cds, dated Jun. 24, 2004, 2 pages.
Genbank Accession No. AY530627, Adeno-associated virus isolate hu.67 capsid protein VP1 (cap) gene, complete cds, dated Jun. 24, 2004, 2 pages.
Genbank Accession No. AY530628, Adeno-associated virus isolate hu.7 capsid protein VP1 (cap) gene, complete cds, dated Jun. 24, 2004, 2 pages.
Genbank Accession No. AY530629, Adeno-associated virus isolate hu.9 capsid protein VP1 (cap) gene, complete cds, dated Jun. 24, 2004, 2 pages.
Genbank Accession No. AY629583, Avian adeno-associated virus strain DA-1, complete genome, dated Sep. 10, 2004, 3 pages.
Genbank Accession No. AY631966, Adeno-associated virus 11 nonstructural protein and capsid protein genes, complete cds, dated Nov. 30, 2004, 3 pages.
Genbank Accession No. AY695370, Adeno-associated virus isolate hu.T17 capsid protein VP1 (cap) gene, complete cds, dated Nov. 15, 2005, 3 pages.
Genbank Accession No. AY695371, Adeno-associated virus isolate hu.T32 Rep 78 protein and capsid protein VP1 (cap) genes, complete cds, dated Nov. 15, 2005, 3 pages.
Genbank Accession No. AY695372, Adeno-associated virus isolate hu.T40 Rep 78 protein and capsid protein VP1 (cap) genes, complete cds, dated Nov. 15, 2005, 3 pages.
Genbank Accession No. AY695373, Adeno-associated virus isolate hu.T70 Rep 78 protein and capsid protein VP1 (cap) genes, complete cds, dated Nov. 15, 2005, 3 pages.
Genbank Accession No. AY695374, Adeno-associated virus isolate hu.T32 Rep 71 protein and capsid protein VP1 (cap) genes, complete cds, dated Nov. 15, 2005, 3 pages.
Genbank Accession No. AY695375, Adeno-associated virus isolate hu.T88 Rep 78 protein and capsid protein VP1 (cap) genes, complete cds, dated Nov. 15, 2005, 3 pages.
Genbank Accession No. AY695376, Adeno-associated virus isolate hu.S17 Rep 78 protein and capsid protein VP1 (cap) genes, complete cds, dated Nov. 15, 2005, 3 pages.
Genbank Accession No. AY695377, Adeno-associated virus isolate hu.LG15 capsid protein VP1 (cap) gene, complete cds, dated Nov. 15, 2005, 3 pages.

(56) References Cited

OTHER PUBLICATIONS

Genbank Accession No. AY695378, Adeno-associated virus isolate hu.T41 capsid protein VP1 (cap) gene, complete cds, dated Nov. 15, 2005, 2 pages.
Genbank Accession No. MI332400.1, Sequence 20 from U.S. Pat. No. 9,839,696, dated Feb. 12, 2018, 2 pages.
Genbank Accession No. MI332401.1, Sequence 21 from U.S. Pat. No. 9,839,696, dated Feb. 12, 2018, 2 pages.
Genbank Accession No. MI332402.1, Sequence 22 from U.S. Pat. No. 9,839,696, dated Feb. 12, 2018, 2 pages.
Genbank Accession No. MI332403.1, Sequence 23 from U.S. Pat. No. 9,839,696, dated Feb. 12, 2018, 2 pages.
Genbank Accession No. MI332404.1, Sequence 24 from U.S. Pat. No. 9,839,696, dated Feb. 12, 2018, 2 pages.
Genbank Accession No. MI332405.1, Sequence 25 from U.S. Pat. No. 9,839,696, dated Feb. 12, 2018, 2 pages.
Genbank Accession No. MI332406.1, Sequence 26 from U.S. Pat. No. 9,839,696, dated Feb. 12, 2018, 2 pages.
Genbank Accession No. MI332407.1, Sequence 27 from U.S. Pat. No. 9,839,696, dated Feb. 12, 2018, 2 pages.
Genbank Accession No. MI332408.1, Sequence 28 from U.S. Pat. No. 9,839,696, dated Feb. 12, 2018, 2 pages.
Genbank Accession No. MI332409.1, Sequence 29 from U.S. Pat. No. 9,839,696, dated Feb. 12, 2018, 2 pages.
Genbank Accession No. MI332410.1, Sequence 30 from U.S. Pat. No. 9,839,696, dated Feb. 12, 2018, 2 pages.
Genbank Accession No. MI332411.1, Sequence 31 from U.S. Pat. No. 9,839,696, dated Feb. 12, 2018, 2 pages.
Genbank Accession No. MI332412.1, Sequence 32 from U.S. Pat. No. 9,839,696, dated Feb. 12, 2018, 2 pages.
Genbank Accession No. MI332413.1, Sequence 33 from U.S. Pat. No. 9,839,696, dated Feb. 12, 2018, 2 pages.
Genbank Accession No. MI332414.1, Sequence 34 from U.S. Pat. No. 9,839,696, dated Feb. 12, 2018, 2 pages.
Genbank Accession No. MI332415.1, Sequence 35 from U.S. Pat. No. 9,839,696, dated Feb. 12, 2018, 2 pages.
Genbank Accession No. NC_001729, Adeno-associated virus-3, complete genome, dated Aug. 13, 2018, 3 pages.
Genbank Accession No. NC_001829, Adeno-associated virus-4, complete genome, dated Aug. 13, 2018, 3 pages.
Genbank Accession No. NC_001862, Adeno-associated virus-6, complete genome, dated Jan. 12, 2004, 4 pages.
Genbank Accession No. NC_001863, Adeno-associated virus 3B, complete genome, dated Jan. 12, 2004, 4 pages.
Genbank Accession No. NC_004828, Avian adeno-associated virus ATCC VR-865, complete genome, dated Aug. 13, 2018, 3 pages.
Genbank Accession No. NC_005889, Bovine adeno-associated virus, complete genome, dated Aug. 13, 2018, 3 pages.
Genbank Accession No. NC_006148.1, Snake parvovirus 1, complete genome, dated Aug. 13, 2018, 3 pages.
Genbank Accession No. NC_006263, Avian adeno-associated virus strain DA-1, complete genome, dated Aug. 13, 2018, 3 pages.
Genbank Accession No. Y18065, adeno-associated virus type 5 partial genome (cap and rep genes complete), dated Jan. 15, 1999, 3 pages.
Genbank Accession No. NC_001401, Adeono-associated virus-2, complete genome, dated Aug. 13, 2018, 6 pages.
Genbank Accession No. NC_002077, Adeno-associated virus-1, dated Aug. 13, 2018, 3 pages.
GenBank Accession No. AF028704 "adeno-associated Virus 6, complete genome" NCBI (2 pages). (Jan. 12, 1998).
GenBank Accession No. AF028705 "adeno-associated Virus 3B, complete genome" NCBI (2 pages). (Jan. 12, 1998).
GenBank Accession No. AF043303 "adeno-Associated Virus 2, complete genome" NCBJ (4 pages). (May 20, 2010).
GenBank Accession No. AF063497 "adeno-associated Virus 1, complete genome" NCBI (2 pages). (Apr. 27, 1999).
GenBank Accession No. AF288061 "Hamster parvoVirus 5' terminal hairpin gene sequence" NCBI (1 page). (Apr. 13, 2001), replaced by AH009962.

GenBank Accession No. AF513851 "adeno-associated Virus 7 nonstructural protein and capsid protein genes, complete eds." NCBI (2 pages). (Sep. 5, 2002).
GenBank Accession No. AF513852 "adeno-associated Virus 8 nonstructural protein and capsid protein genes, complete eds" NCBI (2 pages). (Sep. 5, 2002).
GenBank Accession No. AH009962 "Hamster parvovir" NCBI (1 page). (Aug. 25, 2016), replaced AF288061.
GenBank Accession No. AY028223 "B19 Virus isolate patient_A. 1.1 genomic sequence" NCB/ (1 page). (Apr. 16, 2001).
GenBank Accession No. AY028226 "819 Virus isolate patient_A. 2.1 genomic sequence" NCB/ (1 page). (Apr. 16, 2001).
GenBank Accession No. AY530579 "adeno-associated Virus 9 isolate hu.14 capsid protein VP1 (cap). gene, complete eds" NCBI (2 pages). (Jun. 24, 2004).
GenBank Accession No. J00306 "Human somatostatin I gene and flanks" NCBJ (2 pages). (Jan. 13, 1995).
GenBank Accession No. J01901 "adeno-associated Virus 2, complete genome" NCBJ (3 pages). (Apr. 27, 1993).
GenBank Accession No. J02275 "Minute Virus of mice, complete genome" NCBJ (4 pages). (May 22, 1995).
GenBank Accession No. NC_000883 "Human parvoVirus 819, complete genome" NCBI (4 pages). (Feb. 10, 2015).
GenBank Accession No. NC_001358 "ParvoVirus H1, complete genome" NCBI (3 pages). (Feb. 10, 2015).
GenBank Accession No. NC_001401 "adeno-associated Virus-2, complete genome" NCBI (5 pages). (Dec. 2, 2014).
GenBank Accession No. NC_001510 "Minute Virus of mice, complete genome" NCBI (5 pages). (Mar. 28, 2016).
GenBank Accession No. NC_001701 "Goose parvovir, complete genome" NCBI (4 pages). (Jan. 28, 2010).
GenBank Accession No. NC_001729 "adeno-associated virus-3, complete genome" NCBI (3 pages). (Jun. 28, 2010).
GenBank Accession No. NC_001829 "adeno-associated Virus-4, complete genome" NCBI (3 pages). (Jan. 28, 2010).
GenBank Accession No. NC_001862 "adeno-associated Virus 6, complete genome" NCBJ (3 pages). (Jan. 12, 2004).
GenBank Accession No. NC_001863 "adeno-associated Virus 38, complete genome" NCB/ (3 pages). (Jan. 12, 2014).
GenBank Accession No. NC_002077 "adeno-associated Virus-1, complete genome" NCBI (3 pages). (Mar. 11, 2010).
GenBank Accession No. NC_006152 "adeno-associated Virus 5, complete genome" NCBI (3 pages). (Dec. 8, 2008).
GenBank Accession No. P01166 "Somatostatin precursor [Contains:Somatostatin 28; Somatostatin-14]" NCBI (2 pages). (Sep. 15, 2003).
GenBank Accession No. X01457 "ParvoVirus h-1, complete genome" NCBI (3 pages). (Apr. 18, 2005).
GenBank Accession No. NC_006261 "adeno-associated Virus-8, complete genome" NCBI (3 pages). (Mar. 11, 2010).
GenBank Accession No. NC_001540 "Bovine parvovir, complete genome" NCBI (4 pages). (Nov. 30, 2009).
Govindasamy et al., "Structurally mapping the diverse phenotype of adeno-associated virus serotype 4," J. Virology 80:11556-11570 (2006).
Govindasamy et al., "Structural Insights into Adeno-Associated Virus Serotype 5," J. Virology 87:11187-11199 (2013).
Gregorevic et al. "Systemic Microdystrophin Gene Delivery Improves Skeletal Muscle Structure and Function in Old Dystrophic mdx Mice," Molecular Therapy 16(4):657-664 (2008).
Grifman et al. "Incorporation of Tumor-Targeting Peptides into Recombinant Adeno-Associated Virus Capsids" Molecular Therapy 3(6):964-975 (2001).
Gurda et al., "Mapping a Neutralizing Epitope onto the Capsid of Adeno-Associated Virus Serotype 8," Journal of Virology 86(15): 7739-7751 (2012).
Hajitou et al., "Vascular targeting: recent advances and therapeutic perspectives," TCM 16:80-88 (2006).
Hauck et al. "Characterization of Tissue Tropism Determinants of Adeno-Associated Virus Type 1" Journal of Virology 77(4):2768-2774 (2003).
Huang et al. "ParvoVirus glycan interactions" Current Opinion in Virology 7:108-118 (2014).

(56) References Cited

OTHER PUBLICATIONS

Kailasan et al., "Structure of an enteric pathogen, bovine parvovirus," Virology 89:2603-2614 (2015).
Karlin et al. "Applications and statistics for multiple high-scoring segments in molecular sequences" Proceedings of National Academy of Sciences 90:5873-5877 (1993).
Kawakami et al. "Cloning of the gene coding for a shared human melanoma antigen recognized by autologous T cells infiltrating into tumor," Proceedings of the National Academy of Sciences 91:3515-3519 (1994).
Kawakami et al. "Identification of the Immunodominant Peptides of the MART-1 Human Melanoma Antigen Recognized by the Majority of HLA-A2-restricted Tumor Infiltrating Lymphocytes" The Journal of Experimental Medicine 180:347-352 (1994).
Koivunen et al., "Identification of Receptor Ligands with Phase Display Peptide Libraries," J. Nucl. Med. 40:883-888 (1999).
Lerch et al, "The structure of adeno-associated virus serotype 3B (AAV-3B): insights into receptor binding and immune evasion," Virology 403(1):26-36 (2010).
Li et al. "Construction of phospholamban antisense RNA recombinant adeno-associated Virus vector and its effects in rat cardiomyocytes" Acta Pharmalogica Sinica 26(1).51-55 (2005).
McCarty et al., "Self-complementary recombinant adeno-associated virus (scAAV) vectors promote efficient transduction independently of DNA synthesis," Gene Therapy 8:1248-1254 (2001).
Mingozzi et al., "Overcoming the Host Immune Response to Adeno-Associated Virus Gene Delivery Vectors: The Race Between Clearance, Tolerance, Neutralization, and Escape," Annual Review of Virology 1(1):511-534 (2017).
Miyamura et al., "ParvoVirus particles at platforms for protein presentation" Proceedings of National Academy of Sciences 91:8507-8511 (1995).
Mori et al. "Two novel adeno-associated vires from cynomolgus monkey:pseudotyping characterization of capsid protein," Virology 330:375-383 (2004).
Muramatsu et al. "Nucleotide Sequencing and Generation of an Infectious Clone of Adeno-Associated Virus 3," Virology 22(0367):208-217 (1996).
Nam et al. "Structure of Adeno-Associated Virus Serotype 8, a Gene Therapy Vector" Journal of Virology, 81 (22):12260-12271 (2007).
Ng et al. "Structural Characterization of the Dual Glycan Binding adeno-Associated Virus Serotype 6" Journal of Virology, 84(24):12945-12957 (2010).
Robbins et al., "Recognition of tyrosinase by tumor-infiltrating lymphocytes from a patient responding to immunotherapy," Cancer Res. 54:3124-3126 (1994).
Selot et al., "Developing Immunologically Inert Adeno-Associated Virus (AAV). Vectors for Gene Therapy: Possibilities and Limitations," Current Pharmaceutical Biotechnology, Bentham Science Publishers, NL 14(12).1072-1082 (2013).
Shade et al. "Nucleotide Sequence and Genome Organization of Human ParvoVirus B19 Isolated from the Serum of a Child during Aplastic Crisis" Journal of Virology 28(3):921-936 (1986).
Smith et al., "Structural Mapping of AAV9 Antigenic Sites and the Engineering of Immune Escape Variants," Molecular Therapy; 20th Annual Meeting of the American Society of Gene and Cell Therapy (ASGCT).; Washington, DC, A; May 10-13, 2017, Nature Publishing Group, GB vol. 25, No. 5, Suppl 1 (2017).
Srivastava et al. "Nucleotide Sequence and Organization of the adeno-Associated Virus 2 Genome" Journal of Virology 45(2):555-564 (1983).
Tsao et al. The Three-Dimensional Structure of Canine ParvoVirus and Its Functional Implications Science 251(5000):1456-1464 (1991).
Tse et al., "Structure-guided evolution of antigenically distinct adeno-associated Virus variants for immune evasion", Proceedings of the National Academy of Sciences of The United States of America 114(24):E4812-E4821 (2017).
UniProt Accession No. O15118, dated May 30, 2000, 21 pages.
Wang et al. "Adeno-associated Virus vector carrying human minidystrophin genes effectively ameliorates muscular dystrophy in mdx mouse model" Proceedings of the National Academy of Sciences 97(25):13714-13719 (2000).
Work et al., "Vascular bed-targeted in vivo gene delivery using tropism-modified adeno-associated viruses," Molecular Therapy 13(4):683-693 (2006).
Xiao et al. "Gene Therapy Vectors Based on adeno-Associated Virus Type 1" Journal of Virology 73(5):3994-4003 (1999).
Xie, J. et al., "Short DNA Hairpins Compromise Recombinant Adeno-Associated Virus Genome Homogeneity," Mol. Ther., 25(6): 1363-1374 (2017).
Xie et al. "The atomic structure of adeno-associated Virus (AAV-2)., a vector for human gene therapy" Proceeding of the National Academy of Sciences 99(16):10405-10410 (2002).
Zhang et al. "Recombinant Adenovirus expressing adeno-associated Virus cap and rep proteins supports production of high-titer recombinant adeno-associated virus" Gene Therapy 8:704-712 (2001).
ACS on STN, BD Registry, 1182714-10-8 [online] [retrieved on Apr. 4, 2019], 2009215879, Aug. 27, 2009, SEQ ID No. 7, 1 page.
ACS on STN, BD Registry, 1182714-97-1 [online] [retrieved on Apr. 30, 2019], 2009215879, Aug. 27, 2009, SEQ ID No. 210, 1 page.
Agbandje et al. "The Structure of Human Parvovirus B19 at 8 A; Resolution" Virology 203(1):106-115 (1994).
Agbandje-McKenna et al. "AAV Capsid Structure and Cell Interactions" Methods in Molecular Biology, 807:47-92 (2011).
Albright et al., "Mapping the Structural Determinants Required for AAVrh.10 Transport across the Blood-Brain Barrier," Molecular Therapy 26(2), p. 1-14 (2017).
Albright, "Modulation of Sialic Acid Dependence Influences the Central Nervous System Transduction Profile of Adeno-associated Viruses," Journal of Virology 93(11), pp. 1-15 (2019).
Altschul et al. "Basic Local Alignment Search Tool" Journal of Molecular Biology 215:403-410 (1990).
Altschul et al. "Local Alignment Statistics" Methods in Enzymology 266:460-480 (1996).
Altschul, SF et al., 'Issues in searching molecular sequence databases,' Nat. Genet., vol. 6, pp. 119-129, (Feb. 1994).
Andino et al. "AAV-mediated knockdown of phospholamban leads to improved contractility and calcium handling in cardiomyocytes" The Journal of Gene Medicine 10:132-142 (2008).
Arnold et al., "A calcium responsive element that regulates expression of two calcium binding proteins in Purkinje cells," Proc Natl Acad Sci USA 94(16):8842-8847 (1997).
Askoan et al. "Adeno-Associated Virus Type 2 Contains an Integrin a5 1 Binding Domain Essential for Viral Cell Entry" Journal of Virology, 80(18):8961-8969 (2006).
Asokan, et al., "Reengineering a receptor footprint of adeno-associated virus enables selective and systemic gene transfer to muscle", Nat Biotechnol, (Jan. 2010); 28(1): 79-82.
Asuri et al., Directed Evolution of adeno-associated Virus for Enhanced Gene Delivery and Gene Targeting in Human Pluripotent Stem Cells, Molecular Therapy, Nature Publishing Group GB 20(2):329-338 (2013).
Ballabh et al. "The blood-brain barrier: an overview: structure, regulation, and clinical implications" Neurobiology of Disease, 16:1-13 (2004).
Bantel-Schaal et al., "Adeno-associated virus type 5 exploits two different entry pathways in human embryo fibroblast," J Virology 73:939 (1999).
Bartlett, JS et al., 'Selective and Rapid Uptake of Adeno-Associated Virus Type 2 in Brain,' Hum. Gene Ther., 9(8):1181-1186, (May 1998).
Bell et al. "Identification of the Galactose Binding Domain of the Adeno-Associated Virus Serotype 9 Capsid" Journal of Virology, 86(13):7326-7333 (2012).
Bleker et al. "Mutational Analysis of Narrow Pores at the Fivefold Symmetry Axes of Adeno-Associated Virus Type 2 Capsids Reveals a Dual Role in Genome Packaging and Activation of Phospholipase A2 Activity" Journal of Virology, 79(4):2528-2540 (2005).
Bordoli et al. "Protein structure homology modeling using SWISS-MODEL workspace" Nature Protocols, 4(1):1-13 (2008).

(56) References Cited

OTHER PUBLICATIONS

Bowie, et al., "Deciphering the Message in Protein Sequences: Tolerance to Amino Acid Substitutions." Science (1990); 247: 1306-1310.
Bowles et al. "Phase 1 Gene Therapy for Duchenne Muscular Dystrophy Using a Translational Optimized AAV Vector" Molecular Therapy, 20(2):443-455 (2012).
Brichard et al. "The Tyrosinase Gene Codes for an Antigen Recognized by Autologous Cytolytic T Lymphocytes on HLA-AZ Melanomas" Journal of Experimental Medicine 178:489-495 (1993).
Brown et al. "Chimeric Parvovirus 19 Capsids for the Presentation of Foreign Epitopes" Virology 198(2):477-488 (1994).
Brown et al. "Erythrocyte P Antigen: Cellular Receptor for B19 Parvovirus" Science 262(5130):114-117 (1993).
Carrillo-Tripp et al. "VIPERdb2: an enhanced and web API enabled relational database for structural virology" Nucleic Acids Research, 37:D436-D442 (2009).
Carstea, ED et al. 'Niemann-Pick C1 Disease Gene: Homology to Mediators of Cholesterol Homeostasis,' Science, 277(5323): 228-231 (Jul. 1997).
Cearley, C.N. et al. (2008). "Expanded repertoire of AAV vector serotypes mediate unique patterns of transduction in mouse brain," Mol. Ther.16:1710-1718.
Cearley et al. "Transduction Characteristics of Adeno-associated Virus Vectors Expressing Cap Serotypes 7, 8, 9, and Rh10 in the Mouse Brain" Molecular Therapy, 13(3):528-537 (2006).
Chandler et al., "Systemic AAV9 gene therapy improves the lifespan of mice with Niemann-Pick disease, type C1," Human Molecular Genetics 26(1):52-64 (2017).
Chapman et al. "Structure, Sequence, and Function Correlations among Parvoviruses" Virology 194(2):491-508 (1993).
Chen et al. "Efficient Transduction of Vascular Endothelial Cells with Recombinant Adeno-Associated Virus Serotype 1 and 5 Vectors" Human Gene Therapy, 16(2):235-247 (2005).
Chen, SH et al., 'Gene therapy for brain tumors: Regression of experimental gliomas by adenovirus-mediated gene transfer in vivo,' Proc. Natl Acad. Sci. USA, vol. 91, pp. 3054-3057, (Apr. 1994).
Choi et al., "Optimization of AAV expression cassettes to improve packaging capacity and transgene expression in neurons," Molecular Brain, Biomed Central Ltd, London UK, 7(1):17 pp. 1-10 (2014).
Clark, KR et al., 'Highly Purified Recombinant Adeno-Associated Virus Vectors Are Biologically Active and Free of Detectable Helper and Wild-Type Viruses,' Hum. Gene Ther., 10(6):1031-1039, (Apr. 1999).
Corpet, F et al., 'Multiple sequence alignment with hierarchical clustering,' vol. 16 No. 22, pp. 10881-10890, (Oct. 1988).
Cotmore et al.,"The Family Parvoviridae," Archives of Virology 159:1239-1247 (2014).
DataBase GenBank: ABS91093.1, Oct. 8, 2007, [online] [retrieved on Feb. 14, 2020] Retrieved from Internet:https://www.ncbi.nlm.nih.gov/protein/ABS91093.1.
DataBase GenBank: ACW56705.1, Sep. 24, 2009, [online] [retrieved on Jul. 5, 2019] Retrieved from Internet:https://www.ncbi.nlm.nih.gov/protein/ACW56705.1?report=genbank&log$=prottop&blast_rank= 1&RID=D2CZ8TP9O14, 1 page.
De Jesus et al., "Telomerase gene therapy in adult and old mice delays aging and increases longevity without increasing cancer," EMBO Mol. Med. 4(8): 691-704 (2012).
Devereux et al. "A comprehensive set of sequence analysis programs for the VAX" Nucleic Acids Research 12(1):387-395 (1984).
Deverman, BE, Cre-dependent selection yields AAV variants for widespread gene transfer to the adult brain, Nat. Biotechnol., 34(2) :204-209. doi: 10.1038/nbt.3440. PubMed PMID:26829320 (Epub Feb. 1, 2016).
Dipasquale et al. "Identification of PDGFR as a receptor for MV-5 transduction" Nature Medicine, 9:1306-1312 (2003). (Abstract only).

Diprimo, et al., "Surface loop dynamics in adeno-associated virus capsid assembly", Journal of Virology (2008); vol. 82, No. 11, pp. 5178-5189.
Emsley et al. "Features and development of Coot" Acta Crystallographica Section D: Biological Crystallography, D66:486-501 (2010).
European Search Report for European Application No. EP19760157.8 dated Nov. 8, 2021, 6 pages.
Extended European Search Report corresponding to European Patent Application No. 16737901.5 (6 pages). (dated May 15, 2018).
Extended European Search Report corresponding to European Patent Application No. 20212583.7, dated May 3, 2021, 10 pages.
Extended European Search Report issued by the European Patent Office for Application No. 16852471.8, dated Jul. 29, 2019, 13 pages.
Extended European Search Report issued by the European Patent Office for Application No. 18754551, dated Jun. 4, 2021, 11 pages.
Felsenstein, Joseph "Confidence Limits on Phylogenies: An Approach Using the Bootstrap" Evolution, 39 (4):783-791 (1985).
Ferrari et al. "New developments in the generation of Ad-free high-titer rAAV gene therapy vectors" Nature Medicine 3(11):1295-1297 (1997).
Fisher, KJ et al., 'Transduction with Recombinant Adeno-Associated Virus for Gene Therapy Is Limited by Leading-Strand Synthesis,' J. Virol., 70(1):520-532 (LFU assay) (Jan. 1996).
Foster et al., "Emerging Immunotherapies for Autoimmune Kidney Disease," Hyman Vaccines & Immunotherapeutics 15(4):876-890 (2019).
Foust et al. "Intravascular AAV9 preferentially targets neonatal neurons and adult astrocytes" Nature Biotechnology, 27(1):59-65 (2009).
Gao et al. "Adeno-associated viruses undergo substantial evolution in primates during natural infections" Proceedings of the National Academy of Sciences, 100(10):6081-6086 (2003).
Gao et al. "Clades of adeno-Associated Viruses are Widely Disseminated in Human Tissues" Journal of Virology 78(12):6381-6388 (2004).
GenBank Accession No. AF258783.1 'Felis catus Niemann-Pick type C1 disease protein (NPC1) mRNA, complete eds' (2000).
GenBank Accession No. BC045895 'Dania rerio Niemann-Pick disease, type C2, mRNA (cDNA clone MGC:56070 Image:5409780), complete eds' (2003).
GenBank Accession No. BC054539 'Mus musculus Niemann Pick type C1, mRNA (cDNA clone MGC:62352 Image:6405214), complete eds' (2006).
GenBank Accession No. BC090541 'Dania rerio Niemann-Pick disease, type C1, mRNA (cDNA clone Image:7149020), partial eds' (2016).
GenBank Accession No. BC102504 'Bos taurus Niemann-Pick disease, type C2, mRNA (cDNA clone MGC:127986 Image:7954223), complete eds' (2007).
GenBank Accession No. BC117178 '*Homo sapiens* NPC1 (Niemann-Pick disease, type C1, gene)-like 1, mRNA (cDNA clone MGC:150787 Image:40125729), complete eds' (2006).
GenBank Accession No. BC143756 '*Homo sapiens* NPC1 (Niemann-Pick disease, type C1, gene)-like 1, mRNA (cDNA clone MGC:177287 Image:9052270), complete eds' (2009).
GenBank Accession No. BC151276 'Bos taurus Niemann-Pick disease, type C1, mRNA (cDNA clone MGC: 152602 Image:8433293), complete eds' (2007).
GenBank Accession No. KJ893081 'Synthetic construct *Homo sapiens* clone ccsb BroadEn_02475 NPC2 qene, encodes complete protein' (2015).
GenBank Accession No. NM 000271.4 '*Homo sapiens* cholesterol transporter 1 (NPC1), mRNA' (2017).
GenBank Accession No. NM 008720.2 'Mus musculus cholesterol transporter 1 (Npc1), mRNA' (2017).
GenBank Accession No. NM 023409.4 'Mus musculus NPC intracellular cholesterol transporter 2 (Npc2 mRNA' (2017).
GenBank Accession No. NM 173918 Bos taurus NPC intracellular cholesterol transporter 2 (NPC2), mRNA-;-(2017).
GenBank Accession No. NM_006432.3 '*Homo sapiens* NPC intracellular cholesterol transporter 2 (NPC2), mRNA' (2017).

(56) References Cited

OTHER PUBLICATIONS

GenBank Accession No. NM_214206 "Sus scrofa NPC intracellular cholesterol transporter 2 (NPC2), mRNA," dated Jun. 20, 2021, 2 pages.
GenBank Accession No. NP_044927 "capsid [Adeno-associated Virus-4]" NCBI (2 pages). (Jan. 28, 2010).
GenBank Accession No. P61278 "Somatostatin precursor [Contains: Somatostatin 28; Somatostatin-14]" NCBI (2 pages). (Nov. 13, 2019).
GenBankAccession No. BC002532 'Homo sapiens Niemann-Pick disease, type C2, mRNA (cDNA clone MGC:1333 Image:3140870), complete eds' (2006).
Gonzales, "Cross-Species Evolution of Synthetic AAV Strains for clinical Translation," ASGCT, 23 pages. (2020).
Gorman et al. "Stable alteration of pre-mRNA splicing patterns by modified U7 small nuclear RNAs" Proceedings of the National Academy of Sciences 95:4929:4934 (1998).
Gray et al. "Preclinical Differences of Intravascular MV9 Delivery to Neurons and Glia: A Comparative Study of Adult Mice and Nonhuman Primates" Molecular Therapy, 19(6):1058-1069 (2011).
Grieger, et al., "Separate Basic Region Motifs within the Adeno-Associated Virus Capsid Proteins Are Essential for infectivity and Assembly." J. Virol. (2006), 80(11): 5199-5210.
Grimm D., et al., "In Vitro and in Vivo Gene Therapy Vector Evolution Via Multispecies Interbreeding and Retargeting of Adeno-Associated Viruses," Journal of Virology, Jun. 2008, vol. 82(12), pp. 5887-5911, XP002610286.
Gurda et al. "Capsid Antibodies to Different adeno-Associated Virus Serotypes Bind Common Regions" Journal of Virology, 87(16):9111-9124 (2013).
Hadaczek et al. "Transduction of Nonhuman Primate Brain with Adeno-Associated Virus Serotype 1: Vector Trafficking and Immune Response" Human Gene Therapy, 20(3):225-237 (2009).
Havlik, Engineering a Humanized AAV8 Capsid Through Iterative Structure-Guided Evolution ASGCT, 24 pages. (2019).
Higgins, Desmond G., and Sharp, Paul M. "CLUSTAL: a package for performing multiple sequence alignment on a microcomputer." Gene (1988); 73.1: 237-244.
Higgins, DG et al., 'Fast and sensitive multiple sequence alignments on a microcomputer,' Comput Appl Biosci., 5(2):151-3, (Apr. 1989).
Hoshijima et al. "Chronic suppression of heart-failure progression by a pseudo phosphorylated mutant of phospholamban via in vivo cardiac rAAV gene delivery" Nature Medicine 8:864-871 (2002).
Huang et al. "Characterization of the adeno-Associated Virus 1 and 6 Sialic Acid Binding Site" Journal of Virology, 9 (11):5219-5230 (2016).
Huang, X et al., 'Dynamic programming algorithms for restriction map comparison,' Cabios, vol. 8, No. 5., pp. 511-520, (1992).
Hughes et al., "AAV9 intracerebroventricular gene therapy improves lifespan, locomotor function and pathology in a mouse model of Niemann-Pick type C1 disease," Human Molecular Genetics 27(17)3079-3098 (2018).
International Search Report and the Written Opinion of the International Searching Authority corresponding to International Patent Application No. PCT/2018/018381 (14 pages) (dated Jul. 5, 2018).
International Search Report and the Written Opinion of the International Searching Authority corresponding to International Patent Application No. PCT/US2019/020053 (10 pages) (dated Jun. 6, 2019).
International Search Report and Written Opinion issued by the International Searching Authority for Application No. PCT/2016/013460, dated May 12, 2016, 11 pages.
International Search Report and Written Opinion issued by the International Searching Authority for Application No. PCT/2016/054143, dated Mar. 23, 2017, 33 pages.
International Search Report and Written Opinion issued by the International Searching Authority for Application No. PCT/2020/023877, dated Aug. 3, 2020, 21 pages.
International Search Report and Written Opinion issued by the International Searching Authority for Application No. PCT/US20/15386, dated Apr. 27, 2020, 14 pages.
International Search Report and Written Opinion issued by the International Searching Authority for Application No. PCT/US2016/026524, dated Jan. 9, 2016, 10 pages.
International Search Report and Written Opinion issued by the International Searching Authority for Application No. PCT/US2018/038584 dated Aug. 24, 2018, 11 pages.
International Search Report and Written Opinion issued by the International Searching Authority for Application No. PCT/US2019/062531, dated Apr. 1, 2020, 12 pages.
International Search Report and Written Opinion issued by the International Searching Authority for Application No. PCT/US2020/032978, dated Oct. 15, 2020, 14 pages.
International Search Report and Written Opinion issued by the International Searching Authority for Application No. PCT/US2020/056015, dated Feb. 12, 2021, 17 pages.
International Search Report and Written Opinion issued by the International Searching Authority for Application No. PCT/US2020/056031, dated Feb. 15, 2021, 18 pages.
International Search Report and Written Opinion issued by the International Searching Authority for Application No. PCT/US2021/030937, dated Oct. 29, 2021, 14 pages.
International Search Report of International PCT/US2016/026524, dated Sep. 1, 2016.
Invitation to Pay issued by the International Searching Authority for Application No. PCT/US21/30937, dated Aug. 16, 2021, 3 pages.
Invitation to Pay issued by the International Searching Authority for Application No. PCT/US2019/062531, dated Feb. 3, 2020, 2 pages.
Janson, C. et al., 'Clinical protocol. Gene therapy of Canavan disease: AAV-2 vector for neurosurgical delivery of aspartoacylase gene (ASPA) to the human brain,' Hum. Gene Ther., 13(11):1391-1412 (Jul. 2002).
Kaplitt, M.G. et al. (1994). "Long-term gene expression and phenotypic correction using adeno- associated virus vectors in the mammalian brain," Nature Genetics 6:148-154.
Kashiwakura et al. "Hepatocyte Growth Factor Receptor Is a Coreceptor for Adeno-Associated Virus Type 2 Infection" Journal of Virology, 79(1).609-614 (2005).
Kauffman et al., "Mechanism Matters: A Taxonomy of Cell Penetrating Peptides," Trends in Biochemical Sciences, Elsevier, Amsterdam, NL 40(12):749-764 (2015).
Krissinel et al. "Secondary-structure matching (SSM)., a new tool for fast protein structure alignment in three dimensions" Acta Crystallographica Section D: Biological Crystallography, D60:2256-2268 (2004).
Kumar et al. "MEGA7: Molecular Evolutionary Genetics Analysis Version 7.0 for Bigger Datasets" Molecular Biology and Evolution, 33(7):1870-1874 (2016).
Lein et al. "Genome-wide atlas of gene expression in the adult mouse brain" Nature, 445(7124):168-176 (2007). (Abstract only).
Levine et al. "The Tumor Suppressor Genes" Annual Review of Biochemistry 62:623-651 (1993).
Li et al. "Development of Patient-specific AAV Vectors After Neutralizing Antibody Selection for Enhanced Muscle Gene Transfer" Molecular Therapy, 24(1):53-65 (2016).
Li et al. "Engineering and Selection of Shuffled AAV Genomes: A New Strategy for Producing Targeted Biological Nanoparticles" Molecular Therapy, 16(7):1252-1260 (2008).
Li et al. "Single Amino Acid Modification of adeno-Associated Virus Capsid Changes Transduction and Humeral Immune Profiles" Journal of Virology, 86(15):7752-7759 (2012).
Lisowski L., et al., "Selection and Evaluation of Clinically Relevant AAV Variants in a Xenograft Liver Model," Nature, Feb. 2014, vol. 506 (7488), pp. 382-386, XP055573596.
Loftus, SK et al., 'Murine Model of Niemann-Pick C Disease: Mutation in a Cholesterol Homeostasis Gene,' Science, 277(5323):232-235 (Jul. 1997).
Madigan et al. "Engineering AAV receptor footprints for gene therapy" Current Opinion in Virology, 18:89-96 (2016).

(56) References Cited

OTHER PUBLICATIONS

Mauro et al., "A critical analysis of codon optimization in human therapeutics," Trends in Molecular Medicine, Nov. 2014, vol. 20, No. 11, pp. 604-613.
McLaughlin et al., "Adeno-associated virus general transduction vectors: analysis of proviral structures," J. Virol., (1988) 62:1963-1973.
Miller et al. "Production, purification and preliminary X-ray crystallographic studies of adeno-associated virus serotype 1" Acta Crystallographica Section F: Structural Biology and Crystallization Communications, 62(Pt 12):1271-1274 (2006).
Mingozzi et al. "Immune responses to AAV vectors: overcoming barriers to successful gene therapy" Blood, 122 (1):23-36 (2013).
Mller et al. "Random peptide libraries displayed on adeno-associated virus to select for targeted gene therapy vectors", Nat Biotechnol, Sep. 2003; 21(9):1040-6. Epub Aug. 3, 2003.
Murlidharan et al. "265. Polysialic Acid as a Novel Regulator of AAV Tropism in the Developing Brain" Molecular Therapy 23(Supplement 1):S106 (2015), 1 page.
Murlidharan et al. "Biology of adeno-associated viral vectors in the central nervous system" Frontiers in Molecular Neuroscience, 7(76):1-9 (2014).
Murlidharan et al. "CNS-restricted Transduction and CRISPR/Cas9-mediated Gene Deletion with an Engineered AAV Vector" Molecular Therapy: Nucleic Acids, 5:e338 (2016).
Murlidharan et al. "Glymphatic fluid transport controls paravascular clearance of MV vectors from the brain" JCI Insight, 1(14):e88034 (2016).
Murlidharan et al. "Unique Glycan Signatures Regulate adeno-Associated Virus Tropism in the Developing Brain" Journal of Virology 89(7):3976-3987 (2015).
Muzyczka, N. "Use of adeno-Associated Virus as a General Transduction Vector for Mammalian Cells," Current Topics in Microbiology and Immunology 158:97-129 (1992).
Nathwani et al. "Long-Term Safety and Efficacy of Factor IX Gene Therapy in Hemophilia B" The New England Journal of Medicine, 371(21):1994-2004 (2014).
Needleman and Wunsch, "A general method applicable to the search for similarities in the amino acid sequence of two proteins." J Mol Biol. (1970); 48(3): 443-453.
Newton & Deutscher, Phage Peptide Display in Handbook of Experimental Pharmacology, pp. 145-163, Springer-Verlag, Berlin (2008).
Nguyen Vu et al., "Cerebellar Purkinje cell activity drives motor learning", Nature Neuroscience 16(12):1734-1736 (2013).
Padron et al. "Structure of adeno-Associated Virus Type 4" Journal of Virology 79(8):5047-5058 (2005).
Palombo et al. "Site-Specific Integration in Mammalian Cells Mediated by a New Hybrid Baculoviru-Adeno-Associated Virus Vector" Journal of Virology72(6):5025-5034 (1998).
Papadakis, ED et al., 'Promoters and Control Elements: Designing Expression Cassettes for Gene Therapy,' Curr. Gene Therapy, vol. 4, No. 1, pp. 89-113, (Mar. 2004).
Partial Supplementary European Search Report issued by the European Patent Office for Application No. 16852471.8, dated Apr. 24, 2019, 17 pages.
Passini, MA et al., 'Distribution of a Lysosomal Enzyme in the Adult Brain by Axonal Transport and by Cells of the Rostral Migratory Stream,' J. Neuroscience, 22(15):6437-6446 (Aug. 2002).
Paul, CA et al., 'Adenovirus Expressing an NPCI-GFP Fusion Gene Corrects Neuronal and Nonneuronal Defects Associated With Niemann Pick Type C Disease,' J. Neurosci. Res., vol. 81, No. 5, pp. 706-719 (Sep. 2005).
Pillay et al. "An essential receptor for adeno-associated virus infection" Nature, 530(7588):108-112 (2016).
Pulicherla et al. "Engineering Liver-detargeted AAV9 Vectors for Cardiac and Musculoskeletal Gene Transfer" Molecular Therapy, 19(6):1070-1078 (2011).
Puttaraju et al. "Spliceosome-mediated RNA trans-splicing as a tool for gene therapy" Nature Biotechnology 17:246-252 (1999).
Rosenberg et al. "A New Era for Cancer Immunotherapy Based on the Genes that Encode Cancer Antigens" Immunity 10:281-287 (1999).
Rosenberg et al. "Comparative Efficacy and Safety of Multiple Routes of Direct CNS Administration of Adeno-Associated Virus Gene Transfer Vector Serotype rh. 10 Expressing the Human Arylsulfatase A cDNA to Nonhuman Primates" Human Gene Therapy Clinical Development, 25(3):164-177 (2014).
Rosenberg "The Immunotherapy of Solid Cancers Based on Cloning the Genes Encoding Tumor-Rejection Antigens" Annual Review of Medicine 47:481-491 (1996).
Saitou, N. et al. (1987). "The neighbor-joining method: A new method for reconstructing phylogenetic trees," Mol. Biol. Evol. 4:406-425.
Salinas et al. "A hitchhiker's guide to the nervous system: the complex journey of viruses and toxins" Nature Reviews Microbiology, 8(9):645-655 (2010). (Abstract only).
Sharp et al. "RNA Interference" Science 287(5462):2431-2433 (2000).
Shen et al. "Engraftment of a Galactose Receptor Footprint onto adeno-associated Viral Capsids Improves Transduction Efficiency" The Journal of Biological Chemistry, 288(40):28814-28823 (2013).
Shen et al., Multiple Roles for Sialylated Glycans in Determining the Cardiopulmonary Tropism of Adeno-Associated Virus 4, Journal of Virology 87(24):13206-13213 (2013).
Shi et al. "Insertional Mutagenesis at Positions 520 and 584 of adeno-Associated Virus Type 2 (AAV2). Capsid Gene and Generation of AAV2 Vectors with Eliminated Heparin-Binding Ability and Introduced Novel Tropism" Human Gene Therapy 17:353-361 (2006).
Sirin S, Apgar JR, Bennett EM, Keating AE. AB-Bind: Antibody binding mutational database for computational affinity predictions. Protein Sci. Feb. 2016;25(2):393-409. Epub Nov. 6, 2015.
Smith et al, "Comparison of Biosequences", Advanced in Applied Mathematics, vol. 2, Issue 4, Dec. 1981, pp. 482-489.
Smith, TF et al., 'Identification of Common Molecular Subsequences,' Journal of Molecular Biology, 147:195-197, PMID 7265238. doi: 10.1016/0022-2836(81)90087-5, (1981).
Sonntag et al. "Adeno-Associated Virus Type 2 Capsids with Externalized VP1NP2 Trafficking Domains Are Generated prior to Passage through the Cytoplasm and Are Maintained until Uncoating Occurs in the Nucleus" Journal of Virology, 80(22):11040-11054 (2006).
Summerford et al. "Membrane-Associated Heparan Sulfate Proteoglycan Is a Receptor for adeno-Associated Virus Type 2 Virions" Journal of Virology, 72(2):1438-1445 (1998).
Tellez et al. "Characterization of Naturally-Occurring Humoral Immunity to AAV in Sheep" PLoS ONE, 8(9):e75142 (2013).
Tinsley et al. "Amelioration of the dystrophic phenotype of mdx mice using a truncated utrophin transgene" Nature 384(6607):349-353 (1996).
Titeux et al., "SIN Retroviral Vectors Expressing COL7A1 Under Human Promoters for Ex Vivo Gene Therapy of Recessive Dystrophic Epidermolysis Bullosa," Mol. Ther., 2010 18:1509-1518.
Tse et al., "Strategies to Circumvent Humoral Immunity to Adeno-Associated Viral Vectors," Expert Opinion on Biological Therapy 15(6):845-855 (2015).
Tseng et al. "Adeno-Associated Virus Serotype 1 (AAV1).- and AAV5-Antibody Complex Structures Reveal Evolutionary Commonalities in Parvovirus Antigenic Reactivity" Journal of Virology, 89(3):1794-1808 (2015).
Tseng et al. "Generation and characterization of anti-adeno-associated Virus serotype 8 (AAV8). and anti-AAV9 monoclonal antibodies" Journal of Virological Methods, 236:105-110 (2016).
Tseng et al. "Mapping the AAV capsid host antibody response toward the development of second generation gene delivery vectors" Frontiers in Immunology, 5(9):1-11 (2014).
Urabe et al. "Insect Cells as a Factory to Produce adeno-Associated Virus Type 2 Vectors" Human Gene Therapy 13:1935-1943 (2002).
Various: Abstracts , 20th Annual Meeting of the American-Society-of-Gene-and-Cell-Therapy (ASGCT); Washington, DC, USA; May 10-13, 2017 , Molecular Therapy : The Journal of the American Society of Gene Therapy 25:1-363 (2017).

(56) References Cited

OTHER PUBLICATIONS

Veldwijk, MR et al., 'Development and optimization of a real-time quantitative PCR-based method for the titration of AAV-2 vector stocks,' Mal. Ther., 6(2):272-8 (Aug. 2002).
Vincent et al. "Long-term correction of mouse dystrophic degeneration by adenovirus-mediated transfer of a minidystrophin gene" Nature Genetics 5:130-134 (1993).
Walters et al. "Structure of adeno-Associated Virus Serotype 5" Journal of Virology 78(7):3361-3371 (2004).
Wang et al., "Selection of neutralizing antibody-resistant AAV8 variants with structure-guided site-specific saturated mutagenesis," Molecular Therapy, 2011, vol. 19 Suppl. 1, S129.
Wang et al. "Expanding the genetic code" Annual Review of Biophysics and Biomolecular Structure 35:225-249 (2006).
Wassif, CA et al., 'High Incidence of Unrecognized Visceral/Neurological Late onset Niemann-Pick Disease, type C1 Predicted by Analysis of Massively Parallel Sequencinq Data Sets,' Genet Med., 18(1):41-48 (Jan. 2016).
Weller et al. "Epidermal growth factor receptor is a co-receptor for adeno-associated virus serotype 6" Nature Medicine, 16(6):662-664 (2010).
Williams et al. "Monocyte maturation, HIV susceptibility, and transmigration across the blood brain barrier are critical in HIV neuropathogenesis" Journal of Leukocyte Biology, 91(3):401-415 (2012).
Winkler et al., "Changing the Antigen Binding Specificity by Single Point Mutations of an Anti-p24 (HIV-1) Antibody", The Journal of Immunology, 165: 4505-4514 (2000).
Wu et al. "alpha2,3 and alpha2,6 N-Linked Sialic Acids Facilitate Efficient Binding and Transduction by Adeno-Associated Virus Types 1 and 6" Journal of Virology, 80(18):9093-9103 (2006).
Asokan et al., "The AVV Vector Toolkit: Poised at the Clinical Crossroads," Molecular Therapy 20(4):699-708 (2012).
Bennett et al. "AAV6 K531 serves a dual function in selective receptor and antibody ADK6 recognition" Virology, 18:369-376 (2018).
Clapcote et al., "Mutation I810N in the alpha3 isoform of Na+, K+-ATPase causes impairments in the sodium pump and hyperexcitability in the CNS," Proc Natl Acad Sci USA. 106(33):14085-14090 (2009).
Conway et al. "High-titer recombinant adeno-associated virus production utilizing a recombinant herpes simplex virus type 1 vector expressing AAV-2 Rep and Cap" Gene Therapy 6:986-993 (1999).
Extended European Search Report issued by the European Patent Office for Application No. 19887003.2, dated Jul. 12, 2022, 10 pages.
Frankel, A.E. et al. (2000). Characterization of diphtheria fusion proteins targeted to the human int+A893erleukin-3 receptor, Protein Engineering 13:575-581.
Piguet Françoise et al., "Rapid and Complete Reversal of Sensory Ataxia by Gene Therapy in a Novel Model of Friedreich Ataxia", Molecular Therapy, Nature Publishing Group, GB 26(8), pp. 1-13 (2018).
Ghusayni, R. et al., "Magnetic resonance imaging volumetric analysis in patients with Alternating hemiplegia of childhood: A pilot study," Eur J Paediatr Neurol. 26:15-19 (2020).
Heinzen EL, et al., "De nova mutations in ATP1A3 cause alternating hemiplegia of childhood," Nat Genet. 44 (9):1030-1034 (2012).
Helseth AR, et al., "Novel E815K knock-in mouse model of alternating hemiplegia of childhood," Neurobiol Dis. 119:100-112 (2018).
Holm R, et al., "B. Neurological disease mutations of a3 Na+, K+-ATPase: Structural and functional perspectives and rescue of compromised function," Biochim Biophys Acta. 1857(11):1807-1828 (2016).
Hunanyan AS, et al., Knock-in mouse model of alternating hemiplegia of childhood: behavioral and electrophysiologic characterization. Epilepsia. 56(1):82-93 (2015).
Hunanyan AS, et al., "Mechanisms of increased hippocampal excitability in the Mashl+/- mouse model of Na+ /K+ -ATPase dysfunction," Epilepsia 59(7):1455-1468 (2018).
Ikeda K, et al., "Knockout of sodium pump a3 subunit gene(Atp1a3-/-) results in perinatal seizure and defective respiratory rhythm generation," Brain Res. 1666:27-37 (2017).
International Search Report and Written Opinion for International Application No. PCT/US2021/046699 dated Jan. 12, 2022, 17 pages.
International Search Report and Written Opinion issued by the International Searching Authority for Application No. PCT/US2022/012542, dated Jun. 3, 2022, 10 pages.
Isaksen TJ, et al., "Hypothermia-induced dystonia and abnormal cerebellar activity in a mouse model with a single disease-mutation in the sodium-potassium pump," PLoS Genet. 13(5):e1006763, pp. 1-23 (2017).
Kells, A.P., et al., "AAV-Mediated Gene Delivery of BDNF or GDNF is Neuroprotective in a Model of Huntington Disease," Molecular Therapy, May 2004, vol. 9(5), pp. 682-688.
Kirshenbaum GS, et al., "Alternating hemiplegia of childhood-related neural and behavioural phenotypes in Na +, K+-ATPase a3 missense mutant mice," PLoS One. 8(3):e60141, pp. 1-15 (2013).
Kuck et al. "Development of AAV serotype-specific ELISAs using novel monoclonal antibodies" Journal of Virological Methods, 140(1-2):17-24 (2007) (Abstract only).
Lux et al. "Green Fluorescent Protein-Tagged Adeno-Associated Virus Particles Allow the Study of Cytosolic and Nuclear Trafficking" Journal of Virology, 79{18):11776-11787 (2005).
Margolskee, R. F. "Epstein-Barr Virus Based Expression Vectors" Current Topics in Microbiology and Immunology 158:67-95 (1992).
Masoud M, et al., "Diagnosis and Treatment of Alternating Hemiplegia of Childhood," Curr Treat Options Neurol. 19(2):8 (2017).
McCraw et al. "structurE of adeno-associated virus-2 in Complex with Neutralizing Monoclonal antibodY A20" Virology, 431(1-2):40-49 (2012).
Mikati MA, et al., "Alternating hemiplegia of childhood: clinical manifestations and long-term outcome," Pediatr Neurol. 23(2):134-141 (2000).
Pakula A.A., et al., "Genetic Analysis of Protein Stability and Function," Annual Review of Genetics, 1989, vol. 23, pp. 289-310.
Powell et al. Characterization of a Novel Adena-Associated Viral Vector with Preferential Oligodendrocyte Tropism. Gene Therapy, 2016. 23:807-814.
Severino M, et al., "White matter and cerebellar involvement in alternating hemiplegia of childhood," J Neurol. 267 (5):1300-1311 (2020).
Veron et al. "Humeral and Cellular Capsid-Specific Immune Responses to Adena-Associated Virus Type 1 in andomized Healthy Donors" The Journal of Immunology, 188:6418-6424 (2012).
Wang; Q. et al., "Identification of an adeno-associated Virus binding epitope for AVB sepharose affinity resin," Molecular Therapy—Methods & Clinical Development vol. 2, pp. 1-6 (2015).
Wobus et al. "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection," J. of Virology, 74(19):9281-9293 (2000).
Ye Q, et al., "The AAA+ ATPase TRIP13 remodels HORMA domains through N-terminal engagement and unfolding," EMBO J. 36(16):2419-2434 (2017).
Zhong et al. "Next generation of adeno-associated virus 2 vectors: Point mutations in tyrosines lead to high-efficienc ransduction at lower doses" Proceedings of the National Academy of Sciences USA, 105(22):7827-7832 (2008).
Zhong et al. "Tyrosine-phosphorylation of AAV2 vectors and its consequences on viral intracellular trafficking and transgene expression" Virology, 381(2):194-202 (2008).
Zolotukhin et al. "Production and purification of serotype 1, 2, and 5 recombinant adeno-associated viral vectors" Methods, 28(2):158-167 (2002) {Abstract only).
Bantel-Schaal et al. "Human adeno-Associated Virus Type 5 Is Only Distantly Related to Other Known Primate Helper-Dependent Parvovirus" Journal of Virology 73(2):939-947 (1999).

(56) References Cited

OTHER PUBLICATIONS

Genbank Accession No. AY530616, Adeno-associated virus isolate hu.54 capsid protein VP1 (cap) gene, complete cds, dated Jun. 24, 2004, 2 pages.
GenBank Accession No. U89790 "Adeno-associated Virus 4, complete genome" NCBI (2 pages). (Aug. 21, 1997).
Wu et al. "Single Amino Acid Changes Can Influence Titer, Heparin Binding, and Tissue Tropism in Different adeno-Associated Virus Serotypes" Journal of Virology, 80(22):11393-11397 (2006).
Xiao et al., "Gene transfer by adeno-associated virus vectors into the central nervous system," Exp. Neurobiol., (1997) 144:113-124.
Xiao et al. "Interpretation of Electron Density with Stereographic Roadmap Projections" Journal of Structural Biology, 158(2):182-187 (2007).
Xie et al. "Canine Parvovirus Capsid Structure, Analyzed at 2.9 A Resolution" Journal of Molecular Biology 264(3):497-420 (1996).
Yang et al. "Global CNS Transduction of Adult Mice by Intravenously Delivered rAAVrh.8 and rAAVrh. 10 and Nonhuman Primates by rAAVrh.1O" Molecular Therapy, 22(7):1299-1309 (2014).
Zhang, "Endocytic mechanisms and drug discovery in neurodegenerative diseases," Frontiers in Bioscience 13:6086-6105 (2008).
Zhang et al. "Several rAAV Vectors Efficiently Cross the Blood-brain Barrier and Transduce Neurons and Astrocytes in the Neonatal Mouse Central Nervous System" Molecular Therapy, 19(8):1440-1448 (2011).
Zinn, E. et al., "In Silico Reconstruction of the Viral Evolutionary Lineage Yields a Potent Gene Therapy Vector," Cell Reports, Aug. 2015; 12:1056-1068.
Zolotukhin, et al., "Recombinant adeno-associated virus purification using novel methods improves infectious titer and yield." Gene Therapy (1999); vol. 6, pp. 973-985.

\* cited by examiner

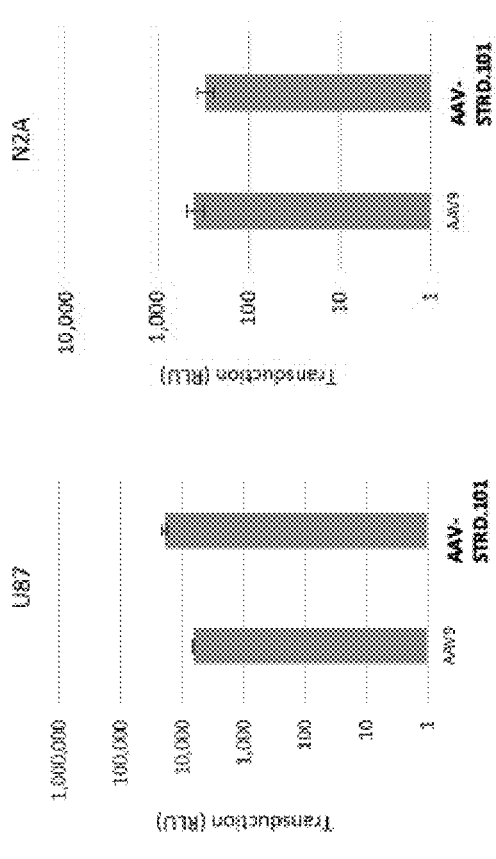
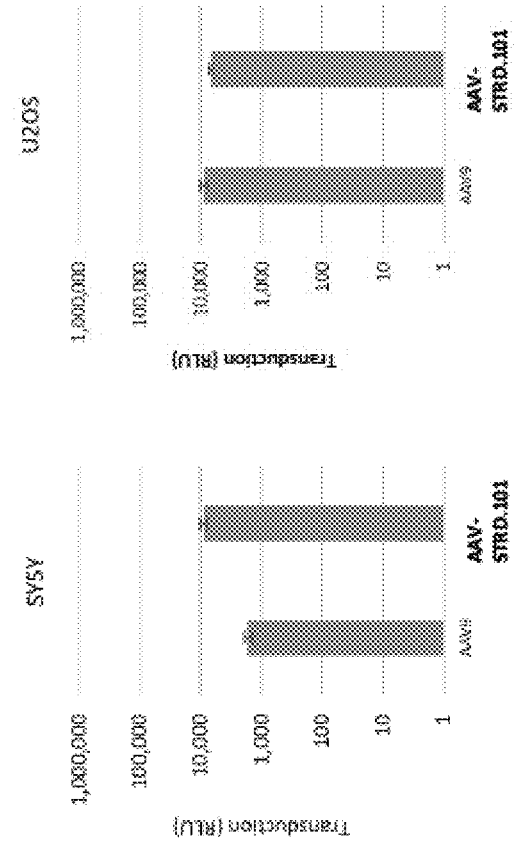
FIG. 4A FIG. 4B FIG. 4C FIG. 4D

ADENO-ASSOCIATED VIRAL VECTORS FOR TREATMENT OF NIEMANN-PICK DISEASE TYPE-C

CROSS-REFERENCE TO RELATED APPLICATIONS

This application claims priority to U.S. Provisional Application No. 63/082,899, filed on Sep. 24, 2020, U.S. Provisional Application No. 63/082,425, filed on Sep. 23, 2020, U.S. Provisional Application No. 62/923,253, filed on Oct. 18, 2019, and U.S. Provisional Application No. 62/916,749, filed on Oct. 17, 2019, each of which is incorporated by reference herein in its entirety.

DESCRIPTION OF THE TEXT FILE SUBMITTED ELECTRONICALLY

The contents of the text file submitted electronically herewith are incorporated by reference in their entirety: a computer readable format copy of the Sequence Listing (filename: STRD_021_02US_SeqList_ST25.txt, date recorded Oct. 14, 2020, file size of 435,696 bytes).

TECHNICAL FIELD

This application relates to recombinant adeno-associated virus (AAV) vectors. In some embodiments, the recombinant AAV vectors evade neutralizing antibodies without decreased transduction efficiency.

BACKGROUND

Niemann-Pick Disease, type C1 (NPC1) is a neurodegenerative disorder characterized by cholesterol accumulation in endolysosomal compartments. It is caused by mutations in the gene encoding NPC1, an endolysosomal protein mediating intracellular cholesterol trafficking.

NPC1 can present in infants, children, or adults. Neonates can present with ascites and severe liver disease from infiltration of the liver and/or respiratory failure from infiltration of the lungs. Other infants, without liver or pulmonary disease, have hypotonia and developmental delay. The classic presentation occurs in mid-to-late childhood with the insidious onset of ataxia, vertical supranuclear gaze palsy (VSGP), and dementia.

Dystonia and seizures are common. Dysarthria and dysphagia eventually become disabling, making oral feeding impossible; death usually occurs in the late second or third decade from aspiration pneumonia. Adults are more likely to present with dementia or psychiatric symptoms.

2-hydroxypropyl-ß-cyclodextrin (HPBCD) has been shown to reduce the cholesterol and lipid accumulation and prolongs survival in NPC1 animal models. However, there are no therapies for NPC1 approved by the Food and Drug Administration (FDA). Accordingly, there is an urgent need for compositions and methods for treating, curing, and/or preventing NPC1.

BRIEF SUMMARY

Provided herein are gene therapy compositions and methods for treating, preventing, and/or curing NPC1. More specifically, the disclosure provides Adeno-associated virus (AAV) vectors and nucleic acids (including nucleic acids comprising AAV transfer cassettes) for treating, preventing, and/or curing NPC1.

In some embodiments, an adeno-associated virus (AAV) vector comprises: (i) a protein capsid comprising a capsid protein subunit comprising the sequence of SEQ ID NO: 180; and (ii) a nucleic acid encapsidated by the protein capsid; wherein the nucleic acid comprises a transfer cassette; wherein the transfer cassette comprises, from 5' to 3': a 5' inverted terminal repeat (ITR); a promoter; a transgene that encodes the NPC1 protein; a polyadenylation signal; and a 3' ITR.

In some embodiments, an adeno-associated virus (AAV) vector comprises: (i) a protein capsid comprising a capsid protein subunit comprising the sequence of SEQ ID NO: 180, or a sequence comprising about 1 to about 25 amino acid mutations relative to SEQ ID NO: 180; and (ii) a nucleic acid encapsidated by the protein capsid; wherein the nucleic acid comprises a transfer cassette; wherein the transfer cassette comprises from 5' to 3': a 5' inverted terminal repeat (ITR); a promoter; a transgene which encodes the NPC1 protein; a polyadenylation signal; and a 3' ITR.

In some embodiments, the transfer cassette comprises an intronic sequence. In some embodiments, the intronic sequence comprises the sequence of SEQ ID NO: 10. In some embodiments, the intronic sequence may be located between the promoter and the transgene.

In some embodiments, the 5' ITR comprises the sequence of SEQ ID NO: 3003. In some embodiments, the 3' ITR comprises the sequence of SEQ ID NO: 3004.

In some embodiments, the promoter is the CBA promoter. In some embodiments, the promoter comprises the sequence of SEQ ID NO: 3005.

In some embodiments, the NPC1 protein is the human NPC1 protein. In some embodiments, the NPC1 protein comprises the sequence of SEQ ID NO: 3001. In some embodiments, the transgene comprises the sequence of SEQ ID NO: 3002.

In some embodiments, the polyadenylation signal is the SV40 polyadenylation signal. In some embodiments, the polyadenylation signal comprises the sequence of SEQ ID NO: 3012.

In some embodiments, the transfer cassette comprises an enhancer.

In some embodiments, the transfer cassette comprises the sequence of SEQ ID NO: 3014. In some embodiments, the transfer cassette comprises the sequence of any one of SEQ ID NO: 3015-3019.

Also provided herein are compositions comprising an AAV vector of the disclosure. Also provided herein are cells comprising an AAV vector of the disclosure.

Also provided here in are methods for treating a subject in need thereof comprising administering to the subject an effective amount of an AAV vector, a nucleic acid, a composition, or a cell of the disclosure. In some embodiments, the subject has Niemann-Pick Disease Type C. In some embodiments, the subject is a human subject These and other embodiments are described in more detail below.

BRIEF DESCRIPTION OF THE DRAWINGS

FIG. 1A-1C. Bubble plots showing analysis of library diversity, directed evolution and enrichment of novel antigenic footprints. Parental (FIG. 1A) and evolved libraries from a first round (FIG. 1B) and a second round (FIG. 1C) of evolution were subjected to high-throughput sequencing using the Illumina MiSeq platform. Following analysis with a custom Perl script, enriched amino acid sequences were plotted. Each bubble represents a distinct capsid protein subunit amino acid sequence with the radius of the bubble proportional to the number of reads for that variant in the respective library. The y-axis represents the percentage of total reads from the sequencing run. Data are spread along the x-axis for ease of visualization. The percent reduction in unique clones (96.5%) directly demonstrates that numerous "un-fit" sequences were removed after a first and second round of evolution. Dominant isolates were selected for further analysis.

FIG. 4A-4D. Transduction of U87 cells (FIG. 4A), N2A cells (FIG. 4B), Sy5Y cells (FIG. 4C), and U2OS cells (FIG. 4D) by recombinant AAV vectors comprising the STRD.101 capsid protein subunit and packaging a luciferase transgene, as compared to wildtype AAV9 vectors similarly packaging a luciferase sequence. Error bars represent standard error.

DETAILED DESCRIPTION

Figure 1A:
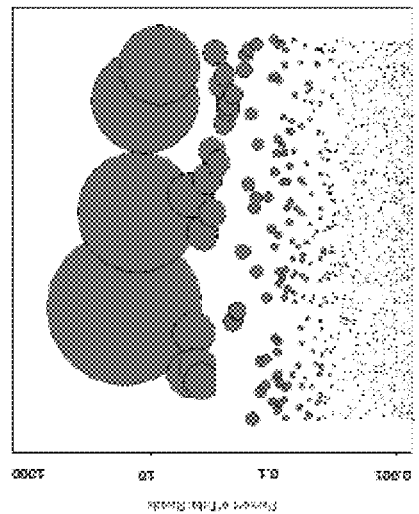
Figure 1B:
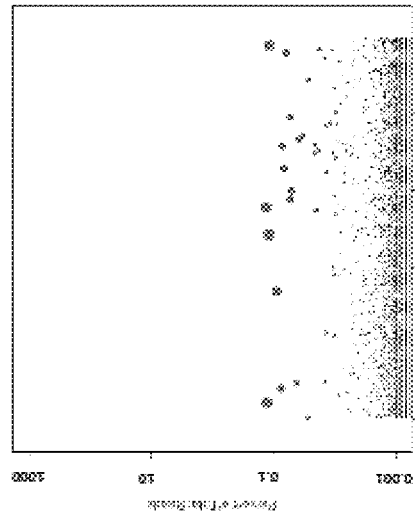
Figure 2:
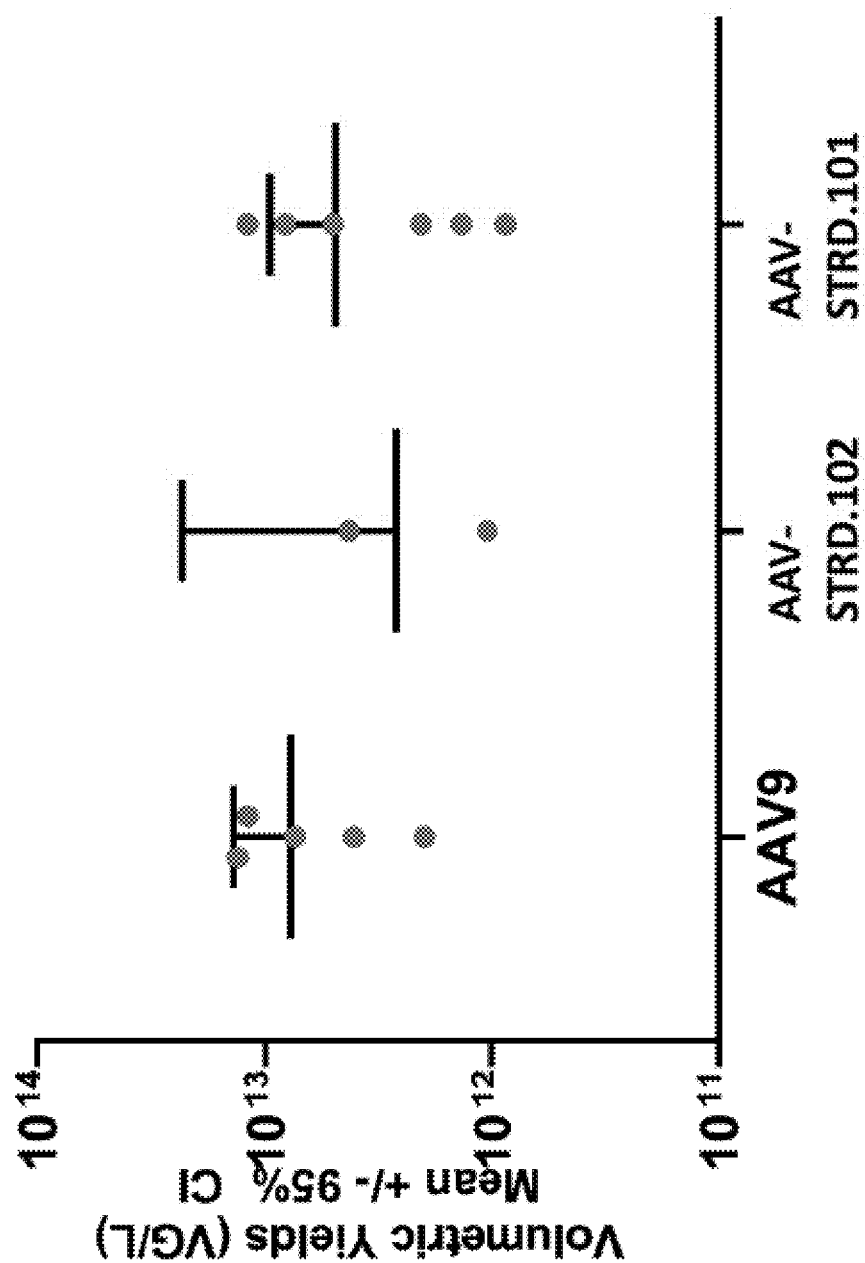
FIG. 2. Volumetric yield of AAV vectors comprising protein capsids comprising capsid protein subunit variants STRD.101 and STRD.102, as compared to wildtype AAV9. Bars represent mean +/−95% confidence interval.

Provided herein are recombinant AAV vectors which evade antibody recognition and/or selectively target tissues of the CNS. These AAV vectors may be useful for treating, preventing, and/or curing diseases such as NPC1.

AAVs are useful as gene delivery agents, and are powerful tools for human gene therapy. Using AAVs, high-frequency DNA delivery and stable expression may be achieved in a variety of cells, both in vivo and in vitro. Unlike some other viral vector systems, AAV does not require active cell division for stable integration in target cells.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank or other accession numbers and other references mentioned herein are incorporated by reference in their entirety for all purposes.

The designation of amino acid positions in the AAV capsid protein subunits in the disclosure and the appended claims is with respect to VP1 numbering. It will be understood by those skilled in the art that the modifications described herein if inserted into the AAV cap gene may result in modifications in the VP1, VP2 and/or VP3 regions. Alternatively, the VP1, VP2, and/or VP3 can be expressed independently to achieve modification in only one or two of these regions (VP1, VP2, VP3, VP1+VP2, VP1+VP3, or VP2+VP3).

Definitions

The following terms are used in the description herein and the appended claims.

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features described herein can be used in any combination. Moreover, in some embodiments, any feature or combination of features set forth herein can be excluded or omitted. To illustrate further, if, for example, the specification indicates that a particular amino acid can be selected from A, G, I, L and/or V, this language also indicates that the amino acid can be selected from any subset of these amino acid(s) for example A, G, 1 or L; A, G, I or V; A or G; only L; etc., as if each such subcombination is expressly set forth herein. Moreover, such language also indicates that one or more of the specified amino acids can be disclaimed. For example, in some embodiments the amino acid is not A, G or I; is not A; is not G or V; etc., as if each such possible disclaimer is expressly set forth herein.

As used herein, the terms "reduce," "reduces," "reduction" and similar terms mean a decrease of at least about 10%, about 15%, about 20%, about 25%, about 35%, about 50%, about 75%, about 80%, about 85%, about 90%, about 95%, about 97% or more.

As used herein, the terms "increase," "improve," "enhance," "enhances," "enhancement" and similar terms indicate an increase of at least about 10%, about 15%, about 20%, about 25%, about 50%, about 75%, about 100%, about 150%, about 200%, about 300%, about 400%, about 500% or more.

The term "parvovirus" as used herein encompasses the family Parvoviridae, including autonomously replicating parvoviruses and dependoviruses. The autonomous parvoviruses include members of the genera Protoparvovirus, Erythroparvovirus, Bocaparvovirus, and Densovirus subfamily. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al, VIROLOGY, volume 2, chapter 69 (4th ed., Lippincott-Raven Publishers; Cotmore et al. Archives of Virology DOI 10.1007/s00705-013-1914-1).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV2i8, AAV2g9, AAV-LK03, AAV7m8, AAV Anc80, AAV PHP.B, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al, (2004) J. Virology 78:6381-6388; Moris et al, (2004) Virology 33-:375-383; and Table 2). Exemplary AAV capsid protein subunit sequences for AAV1-9, AAVrh.10 and AAV11 are provided in SEQ ID NO: 1-11.

As used herein, the term "chimeric AAV" refers to an AAV comprising a protein capsid comprising capsid protein subunits with regions, domains, individual amino acids that are derived from two or more different serotypes of AAV. In some embodiments, a chimeric AAV comprises a capsid protein subunit comprised of a first region that is derived from a first AAV serotype and a second region that is derived from a second AAV serotype. In some embodiments, a chimeric AAV comprises a capsid protein subunit comprised of a first region that is derived from a first AAV serotype, a second region that is derived from a second AAV serotype, and a third region that is derived from a third AAV serotype. In some embodiments, the chimeric AAV may comprise regions, domains, individual amino acids derived from AAV1, AAV2, AAV3, AAV4, AAV5, AAV6, AAV7, AAV8, AAV9, AAV10, AAV11, and/or AAV12. For example, the chimeric AAV may include regions, domains, and/or individual amino acids from a first and a second AAV serotype as shown below (Table 1), wherein AAVX+Y indicates a chimeric AAV including sequences derived from AAVX and AAVY:

TABLE 1

Chimeric AAVs

| | | Second AAV Serotype | | | | | | |
|---|---|---|---|---|---|---|---|---|
| | | AAV1 | AAV2 | AAV3 | AAV4 | AAV5 | AAV6 | AAV7 |
| First AAV Sertoype | AAV1 | X | AAV1 + 2 | AAV1 + 3 | AAV1 + 4 | AAV1 + 5 | AAV1 + 6 | AAV1 + 7 |
| | AAV2 | AAV2 + 1 | X | AAV2 + 3 | AAV2 + 4 | AAV2 + 5 | AAV2 + 6 | AAV2 + 7 |
| | AAV3 | AAV3 + 1 | AAV3 + 2 | X | AAV3 + 4 | AAV3 + 5 | AAV3 + 6 | AAV3 + 7 |
| | AAV4 | AAV4 + 1 | AAV4 + 2 | AAV4 + 3 | X | AAV4 + 5 | AAV4 + 6 | AAV4 + 7 |
| | AAV5 | AAV5 + 1 | AAV5 + 2 | AAV5 + 3 | AAV5 + 4 | X | AAV5 + 6 | AAV5 + 7 |
| | AAV6 | AAV6 + 1 | AAV6 + 2 | AAV6 + 3 | AAV6 + 4 | AAV6 + 5 | X | AAV6 + 7 |
| | AAV7 | AAV7 + 1 | AAV7 + 2 | AAV7 + 3 | AAV7 + 4 | AAV7 + 5 | AAV7 + 6 | X |
| | AAV8 | AAV8 + 1 | AAV8 + 2 | AAV8 + 3 | AAV8 + 4 | AAV8 + 5 | AAV8 + 6 | AAV8 + 7 |
| | AAV9 | AAV9 + 1 | AAV9 + 2 | AAV9 + 3 | AAV9 + 4 | AAV9 + 5 | AAV9 + 6 | AAV9 + 7 |
| | AAV10 | AAV10 + 1 | AAV10 + 2 | AAV10 + 3 | AAV10 + 4 | AAV10 + 5 | AAV10 + 6 | AAV10 + 7 |
| | AAV11 | AAV11 + 1 | AAV11 + 2 | AAV11 + 3 | AAV11 + 4 | AAV11 + 5 | AAV11 + 6 | AAV11 + 7 |
| | AAV12 | AAV12 + 1 | AAV12 + 2 | AAV12 + 3 | AAV12 + 4 | AAV12 + 5 | AAV12 + 6 | AAV12 + 7 |

| | | Second AAV Serotype | | | | |
|---|---|---|---|---|---|---|
| | | AAV8 | AAV9 | AAV10 | AAV11 | AAV12 |
| First AAV Sertoype | AAV1 | AAV1 + 8 | AAV1 + 9 | AAV1 + 10 | AAV1 + 11 | AAV1 + 12 |
| | AAV2 | AAV2 + 8 | AAV2 + 9 | AAV2 + 10 | AAV2 + 11 | AAV2 + 12 |
| | AAV3 | AAV3 + 8 | AAV3 + 9 | AAV3 + 10 | AAV3 + 11 | AAV3 + 12 |
| | AAV4 | AAV4 + 8 | AAV4 + 9 | AAV4 + 10 | AAV4 + 11 | AAV4 + 12 |
| | AAV5 | AAV5 + 8 | AAV5 + 9 | AAV5 + 10 | AAV5 + 11 | AAV5 + 12 |
| | AAV6 | AAV6 + 8 | AAV6 + 9 | AAV6 + 10 | AAV6 + 11 | AAV6 + 12 |
| | AAV7 | AAV7 + 8 | AAV7 + 9 | AAV7 + 10 | AAV7 + 11 | AAV7 + 12 |
| | AAV8 | X | AAV8 + 9 | AAV8 + 10 | AAV8 + 11 | AAV8 + 12 |

TABLE 1-continued

Chimeric AAVs

| | | | | | |
|---|---|---|---|---|---|
| AAV9 | AAV9 + 8 | X | AAV9 + 10 | AAV9 + 11 | AAV9 + 12 |
| AAV10 | AAV10 + 8 | AAV10 + 9 | X | AAV10 + 11 | AAV10 + 12 |
| AAV11 | AAV11 + 8 | AAV11 + 9 | AAV11 + 10 | X | AAV11 + 12 |
| AAV12 | AAV12 + 8 | AAV12 + 9 | AAV12 + 10 | AAV12 + 11 | X |

By including individual amino acids or regions from multiple AAV serotypes in one capsid protein subunit, capsid protein subunits that have multiple desired properties that are separately derived from the multiple AAV serotypes may be obtained.

The genomic sequences of various serotypes of AAV and the autonomous parvoviruses, as well as the sequences of the native terminal repeats (TRs), Rep proteins, and capsid protein subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) J. Virology 45:555; Chiorini et al, (1998) J Virology 71:6823; Chiorini et al., (1999) J. Virology 73: 1309; Bantel-Schaal et al., (1999) J Virology 73:939; Xiao et al, (1999) J Virology 73:3994; Muramatsu et al., (1996) Virology 221:208; Shade et al, (1986) J. Virol. 58:921; Gao et al, (2002) Proc. Nat. Acad. Sci. USA 99:11854; Moris et al, (2004) Virology 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 2. The protein capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) Proc. Nat. Acad. Sci. 99: 10405-10), AAV9 (DiMattia et al., (2012) J. Virol. 86:6947-6958), AAV8 (Nam et al, (2007) J. Virol. 81: 12260-12271), AAV6 (Ng et al., (2010) J. Virol. 84:12945-12957), AAV5 (Govindasamy et al. (2013) J. Virol. 87, 11187-11199), AAV4 (Govindasamy et al. (2006) J. Virol. 80:11556-11570), AAV3B (Lerch et al., (2010) Virology 403:26-36), BPV (Kailasan et al., (2015) J. Virol. 89:2603-2614) and CPV (Xie et al, (1996) J. Mol. Biol. 6:497-520 and Tsao et al, (1991) Science 251:1456-64).

TABLE 2

AAV Serotypes and Clades

| | GenBank Accession Number | | GenBank Accession Number | | GenBank Accession Number |
|---|---|---|---|---|---|
| Complete Genomes | | Clade C | | Rh57 | AY530569 |
| Adeno-associated virus 1 | NC_002077, AF063497 | Hu9 | AY530629 | Rh50 | AY530563 |
| Adeno-associated virus 2 | NC_001401 | Hu10 | AY530576 | Rh49 | AY530562 |
| Adeno-associated virus 3 | NC_001729 | Hu11 | AY530577 | Hu39 | AY530601 |
| Adeno-associated virus 3B | NC_001863 | Hu53 | AY530615 | Rh58 | AY530570 |
| Adeno-associated virus 4 | NC_001829 | Hu55 | AY530617 | Rh61 | AY530572 |
| Adeno-associated virus 5 | Y18065, AF085716 | Hu54 | AY530616 | Rh52 | AY530565 |
| Adeno-associated virus 6 | NC_001862 | Hu7 | AY530628 | Rh53 | AY530566 |
| Avian AAV ATCC VR-865 | AY186198, AY629583, NC_004828 | Hu18 | AY530583 | Rh51 | AY530564 |
| Avian AAV strain DA-1 | NC_006263, AY629583 | Hu15 | AY530580 | Rh64 | AY530574 |
| Bovine AAV | NC_005889, AY388617, AAR26465 | Hu16 | AY530581 | Rh43 | AY530560 |
| AAV11 | AAT46339, AY631966 | Hu25 | AY530591 | AAV8 | AF513852 |
| AAV12 | AB116639, DQ813647 | Hu60 | AY530622 | Rh8 | AY242997 |
| Clade A | | Ch5 | AY243021 | Rh1 | AY530556 |
| AAV1 | NC_002077, AF063497 | Hu3 | AY530595 | Clade F | |
| AAV6 | NC_001862 | Hu1 | AY530575 | Hu14 (AAV9) | AY530579 |
| Hu.48 | AY530611 | Hu4 | AY530602 | Hu31 | AY530596 |
| Hu 43 | AY530606 | Hu2 | AY530585 | Hu32 | AY530597 |
| Hu 44 | AY530607 | Hu61 | AY530623 | HSC1 | MI332400.1 |
| Hu 46 | AY530609 | Clade D | | HSC2 | MI332401.1 |
| Clade B | | Rh62 | AY530573 | HSC3 | MI332402.1 |
| Hu. 19 | AY530584 | Rh48 | AY530561 | HSC4 | MI332403.1 |
| Hu. 20 | AY530586 | Rh54 | AY530567 | HSC5 | MI332405.1 |
| Hu 23 | AY530589 | Rh55 | AY530568 | HSC6 | MI332404.1 |
| Hu22 | AY530588 | Cy2 | AY243020 | HSC7 | MI332407.1 |
| Hu24 | AY530590 | AAV7 | AF513851 | HSC8 | MI332408.1 |
| Hu21 | AY530587 | Rh35 | AY243000 | HSC9 | MI332409.1 |
| Hu27 | AY530592 | Rh37 | AY242998 | HSC11 | MI332406.1 |
| Hu28 | AY530593 | Rh36 | AY242999 | HSC12 | MI332410.1 |
| Hu 29 | AY530594 | Cy6 | AY243016 | HSC13 | MI332411.1 |
| Hu63 | AY530624 | Cy4 | AY243018 | HSC14 | MI332412.1 |
| Hu64 | AY530625 | Cy3 | AY243019 | HSC15 | MI332413.1 |
| Hu13 | AY530578 | Cy5 | AY243017 | HSC16 | MI332414.1 |
| Hu56 | AY530618 | Rh13 | AY243013 | HSC17 | MI332415.1 |
| Hu57 | AY530619 | Clade E | | Hu68 | |
| Hu49 | AY530612 | Rh38 | AY530558 | Clonal Isolate | |
| Hu58 | AY530620 | Hu66 | AY530626 | AAV5 | Y18065, AF085716 |
| Hu34 | AY530598 | Hu42 | AY530605 | AAV 3 | NC_001729 |
| Hu35 | AY530599 | Hu67 | AY530627 | AAV 3B | NC_001863 |
| AAV2 | NC_001401 | Hu40 | AY530603 | AAV4 | NC_001829 |

TABLE 2-continued

AAV Serotypes and Clades

| | GenBank Accession Number | | GenBank Accession Number | | GenBank Accession Number |
|---|---|---|---|---|---|
| Hu45 | AY530608 | Hu41 | AY530604 | Rh34 | AY243001 |
| Hu47 | AY530610 | Hu37 | AY530600 | Rh33 | AY243002 |
| Hu51 | AY530613 | Hu40 | AY530559 | Rh32 | AY243003 |
| Hu52 | AY530614 | Rh2 | AY243007 | Others | |
| Hu T41 | AY695378 | Bb1 | AY243023 | Rh74 | |
| Hu S17 | AY695376 | Bb2 | AY243022 | Bearded Dragon AAV | |
| Hu T88 | AY695375 | Rh10 | AY243015 | Snake AAV | NC_006148.1 |
| Hu T71 | AY695374 | Hu17 | AY530582 | | |
| Hu T70 | AY695373 | Hu6 | AY530621 | | |
| Hu T40 | AY695372 | Rh25 | AY530557 | | |
| Hu T32 | AY695371 | Pi2 | AY530554 | | |
| Hu T17 | AY695370 | Pi1 | AY530553 | | |
| Hu LG15 | AY695377 | Pi3 | AY530555 | | |

Recombinant AAV (rAAV) vectors can be produced in culture using viral production cell lines. The terms "viral production cell", "viral production cell line," or "viral producer cell" refer to cells used to produce viral vectors. HEK293 and 239T cells are common viral production cell lines. Table 3, below, lists exemplary viral production cell lines for various viral vectors. Production of rAAVs typically requires the presence of three elements in the cells: 1) a transgene flanked by AAV inverted terminal repeat (ITR) sequences, 2) AAV rep and cap genes, and 3) helper virus protein sequences. These three elements may be provided on one or more plasmids, and transfected or transduced into the cells.

TABLE 3

Exemplary viral production cell lines

| Virus Vector | Exemplary Viral Production Cell Line(s) |
|---|---|
| Adenovirus | HEK293, 911, pTG6559, PER.C6, GH329, N52.E6, HeLa-E1, UR, VLI-293 |
| Adeno-Associated Virus (AAV) | HEK293, Sf9 |
| Retrovirus | HEK293 |
| Lentivirus | 293T |

"HEK293" refers to a cell line originally derived from human embryonic kidney cells grown in tissue culture. The HEK293 cell line grows readily in culture, and is commonly used for viral production. As used herein, "HEK293" may also refer to one or more variant HEK293 cell lines, i.e., cell lines derived from the original HEK293 cell line that additionally comprise one or more genetic alterations. Many variant HEK293 lines have been developed and optimized for one or more particular applications. For example, the 293T cell line contains the SV40 large T-antigen that allows for episomal replication of transfected plasmids containing the SV40 origin of replication, leading to increased expression of desired gene products.

"Sf9" refers to an insect cell line that is a clonal isolate derived from the parental *Spodoptera frugiperda* cell line IPLB-Sf-21-AE. Sf9 cells can be grown in the absence of serum and can be cultured attached or in suspension.

A "transfection reagent" means a composition that enhances the transfer of nucleic acid into cells. Some transfection reagents commonly used in the art include one or more lipids that bind to nucleic acids and to the cell surface (e.g., Lipofectamine™).

As used herein, the term "multiplicity of infection" or "MOI" refers to number of virions contacted with a cell. For example, cultured cells may be contacted with AAVs at an MOI in the range of $1 \times 10^2$ to $1 \times 10^5$ virions per cell.

The term "self-complimentary AAV" or "scAAV" refers to a recombinant AAV vector comprising a nucleic acid (i.e., a DNA) which forms a dimeric inverted repeat molecule that spontaneously anneals, resulting in earlier and more robust transgene expression compared with conventional single-strand (ss) AAV genomes. See, e.g., McCarty, D. M., et al., Gene Therapy 8, 1248-1254 (2001). Unlike conventional ssAAV, scAAV can bypass second-strand synthesis, the rate-limiting step for gene expression. Moreover, double-stranded scAAV is less prone to DNA degradation after viral transduction, thereby increasing the number of copies of stable episomes. Notably, scAAV can typically only hold a genome that is about 2.4 kb, half the size of a conventional AAV vector. In some embodiments, the AAV vectors described herein are self-complementary AAVs.

As used herein, the term "peptide" refers to a short amino acid sequence. The term peptide may be used to refer to portion or region of an AAV capsid protein subunit amino acid sequence. The peptide may be a peptide that naturally occurs in a native AAV capsid protein, or a peptide that does not naturally occur in a native AAV capsid protein. Naturally occurring AAV peptides in an AAV capsid protein may be substituted by non-naturally occurring peptides. For example, a non-naturally occurring peptide may be substituted into an AAV capsid protein to provide a modified capsid protein, such that the naturally-occurring peptide is replaced by the non-naturally occurring peptide.

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a transgene of interest.

As used here, "systemic tropism" and "systemic transduction" (and equivalent terms) indicate that the virus vector or a virus-like particle as described herein exhibits tropism for or transduces, respectively, tissues throughout the body (e.g., brain, lung, skeletal muscle, heart, liver, kidney and/or pancreas). In some embodiments, systemic transduction of muscle tissues (e.g., skeletal muscle, diaphragm and cardiac muscle) is achieved. In some embodiments, systemic transduction of skeletal muscle tissues is achieved. For example, in some embodiments, essentially all skeletal muscles throughout the body are transduced (although the efficiency of transduction may vary by muscle type). In some embodiments, systemic transduction of limb muscles, cardiac muscle and diaphragm muscle is achieved. Optionally, the virus vector or virus-like particle is administered via a systemic route (e.g., systemic route such as intravenously, intra-articularly or intra-lymphatically).

Alternatively, in some embodiments, the virus vector or virus-like particle is delivered locally (e.g., to the footpad, intramuscularly, intradermally, subcutaneously, topically). In some embodiments, the virus vector or virus-like particle is delivered locally to a tissue of the central nervous system (CNS), such as the brain or the spinal cord. In some embodiments, the virus vector or virus-like particle is administered by intrathecal, intracerebral or intracerebroventricular injection.

Unless indicated otherwise, "efficient transduction" or "efficient tropism," or similar terms, can be determined by reference to a suitable control (e.g., at least about 50%, about 60%, about 70%, about 80%, about 85%, about 90%, about 95% or more of the transduction or tropism, respectively, of the control). In some embodiments, the virus vector (e.g., the AVV vector) efficiently transduces or has efficient tropism for skeletal muscle, cardiac muscle, diaphragm muscle, pancreas (including β-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, viral vectors can be identified that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable virus vector may represent some tradeoffs. To illustrate, a virus vector may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In some embodiments, the virus vector does not efficiently transduce (i.e., does not have efficient tropism) for liver, kidney, gonads and/or germ cells. In some embodiments, undesirable transduction of tissue(s) (e.g., liver) is about 20% or less, about 10% or less, about 5% or less, about 1% or less, about 0.1% or less of the level of transduction of the desired target tissue(s) (e.g., skeletal muscle, diaphragm muscle, cardiac muscle and/or cells of the central nervous system).

As used herein in connection with an AAV vector (or a protein capsid, capsid protein subunit, or peptide thereof), the terms "selectively binds," "selective binding" and similar terms, refer to binding of the AAV vector (or a protein capsid, capsid protein subunit, or peptide thereof) to a target in a manner dependent upon the presence of a particular molecular structure. In some embodiments, selective binding refers to binding of the AAV predominantly to a specific target, without substantial or significant binding to other targets. In some embodiments, an AAV vector (or a protein capsid, capsid protein subunit, or peptide thereof) specifically binds to a receptor in a cell or tissue of interest, but does not exhibit substantial or significant binding to other receptors.

A "polynucleotide" is a sequence of nucleotide bases, and may be RNA, DNA or DNA-RNA hybrid sequences (including both naturally occurring and non-naturally occurring nucleotide). In some embodiments, a polynucleotide is either a single or double stranded DNA sequence.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In some embodiments an "isolated" nucleotide is enriched by at least about 10-fold, about 100-fold, about 1000-fold, about 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In some embodiments an "isolated" polypeptide is enriched by at least about 10-fold, about 100-fold, about 1000-fold, about 10,000-fold or more as compared with the starting material.

As used herein, by "isolate" or "purify" (or grammatical equivalents) a virus vector, it is meant that the virus vector is at least partially separated from at least some of the other components in the starting material. In some embodiments an "isolated" or "purified" virus vector is enriched by at least about 10-fold, about 100-fold, about 1000-fold, about 10,000-fold or more as compared with the starting material.

A "therapeutic" polypeptide or protein is one that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the compositions and/or methods described herein. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the compositions and/or methods described herein.

As used herein, an "effective amount" is the amount of an AAV vector, nucleic acid, or other agent provided herein that is effective to treat or prevent a disease or disorder in a subject or to ameliorate a sign or symptom thereof. The "effective amount" may vary depending, for example, on the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or may be capable of determination by routine experimentation.

As used herein, the terms "virus vector," "vector" refer to a virus (e.g., AAV) particle that functions as a nucleic acid delivery vehicle, and which comprises a vector genome (e.g., a nucleic acid comprising a transgene) packaged within a virion or virus-like particle.

An "adeno-associated virus vector" or "AAV vector" typically comprises a protein capsid, and a nucleic acid (e.g., a nucleic acid comprising a transgene) encapsidated by the protein capsid. The "protein capsid" is a near-spherical protein shell that comprises individual "capsid protein subunits" (e.g., about 60 capsid protein subunits) associated and arranged with T=1 icosahedral symmetry. The protein capsids of the AAV vectors described herein comprise a plurality of capsid protein subunits. When an AAV vector is described as comprising an AAV capsid protein subunit, it will be understood that the AAV vector comprises a protein capsid, wherein the protein capsid comprises one or more AAV capsid protein subunits. As used herein, the term "capsid protein" is sometimes used to refer to a capsid protein subunit. The term "viral-like particle" or "virus-like particle" refers to a protein capsid that does not comprise any vector genome or nucleic acid comprising a transfer cassette or transgene.

In some embodiments, an AAV vector may comprise a nucleic acid comprising a "transfer cassette," i.e., a nucleic acid comprising one or more sequences which can be delivered by the AAV to a cell. In some embodiments, the nucleic acid is self-complementary (i.e., double stranded). In some embodiments, the nucleic acid is not self-complimentary (i.e., single stranded).

A "rAAV vector genome" or "rAAV genome" is an AAV genome (i.e., vDNA) that comprises one or more heterologous nucleic acid sequences. rAAV vectors generally require only the inverted terminal repeat(s) (ITR(s)) in cis to promote nucleic acid replication. All other viral sequences are dispensable and may be supplied in trans (Muzyczka, (1992) Curr. Topics Microbiol. Immunol. 158:97). Typically, the rAAV vector genome will only retain the one or two ITR sequences so as to maximize the size of the transgene that can be efficiently packaged by the AAV vector. The structural and non-structural protein coding sequences may be provided in trans (e.g., from a a plasmid, or by stably integrating the sequences into a packaging cell). In some embodiments, the rAAV vector genome comprises at least one ITR sequence (e.g., AAV ITR sequence), optionally two ITRs (e.g., two AAV ITRs), which typically will be at the 5' and 3' ends of the vector genome (i.e., the 5' ITR and the 3' ITR) and flank the heterologous nucleic acid, but need not be contiguous thereto.

The virus vectors described herein can further be "targeted" virus vectors (e.g., having a directed tropism) and/or "hybrid" virus vectors (i.e., in which the viral ITRs and viral protein capsid are from different viruses) as described in international patent publication WO00/28004 and Chao et al, (2000) Molecular Therapy 2:619. In some embodiments, the virus vectors are targeted to a cell and/or tissue of the CNS.

The virus vectors described herein can further be duplexed virus particles as described in international patent publication WO 01/92551 (the disclosure of which is incorporated herein by reference in its entirety). Thus, in some embodiments, double stranded (duplex) genomes can be packaged into the virus protein capsids described herein. Further, the protein capsid, protein capsid subunits, or genomic elements can contain other modifications, including insertions, deletions and/or substitutions.

As used herein, the term "amino acid" encompasses any naturally occurring amino acid, modified forms thereof, and synthetic amino acids. Naturally occurring, levorotatory (L-) amino acids are shown in Table 4.

TABLE 4

Amino acid residues and abbreviations.

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 5) and/or can be an amino acid that is modified by post-translation modification (e.g., acetylation, amidation, formylation, hydroxylation, methylation, phosphorylation or sulfatation). Methods of chemically modifying amino acids are known in the art (see, e.g., Greg T. Hermanson, Bioconjugate Techniques, 1$^{st}$ edition, Academic Press, 1996).

TABLE 5

Modified Amino Acid Residues

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,21-Diaminopimelic acid | Dpm |
| 2,3-Diaminoproprionic acid | Dpi |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | alle |
| Methionine sulfoxide | MSO |
| N-Methylglycine, sarcosine | MeGly |
| N-Methyl isoleucine | MeIle |
| 6-N-Methyllysine | MeLys |
| N-Methylvaline | MeVal |

TABLE 5-continued

Modified Amino Acid Residues

| Modified Amino Acid Residue | Abbreviation |
|---|---|
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid (as described by Wang et al., Annu Rev Biophys Biomol Struct. 35:225-49 (2006)). These unnatural amino acids can advantageously be used to chemically link molecules of interest to the AAV protein capsid or capsid protein subunit.

Modified AAV Protein Capsid Subunits, Protein Capsids, and AAV Vectors Comprising the Same AAV Vectors Additionally provided herein are adeno-associated virus (AAV) vectors comprising (i) a protein capsid comprising recombinant capsid protein subunits and (ii) a transfer cassette encapsidated by the protein capsid. In some embodiments, the recombinant capsid protein subunits (including VP1, VP2 and/or VP3 regions) may comprise a peptide in their amino acid sequence that does not occur in any native AAV capsid protein subunit sequence. Capsid protein subunits comprising the peptides described herein can confer one or more desirable properties to virus vectors including, without limitation, the ability to evade neutralizing antibodies. Thus, AAV vectors described herein address the limitations associated with conventional AAV vectors.

Accordingly, in some embodiments, the present disclosure provides adeno-associated virus (AAV) vectors comprising (i) one or more recombinant capsid proteins and (ii) a transfer cassette encapsidated by the protein capsid; wherein the capsid protein comprises a peptide having the sequence of any one of SEQ ID NO: 12-20. In some embodiments, the transfer cassette comprises 5' and 3' AAV inverted terminal repeats. In some embodiments, the transfer cassette comprises a transgene (e.g., a NPC1 transgene). In some embodiments, the transfer cassette is double stranded. In some embodiments, the transfer cassette is single stranded. In some embodiments, the transgene encodes a therapeutic protein or RNA. In some embodiments, the recombinant capsid protein has at least 90%, at least 95%, at least 96%, at least 97%, at least 98%, or at least 99% sequence identity to the native sequence of the AAV1, AAV2, AAV3, AAV4, AAV5, AAV6, AAV7, AAV8, AAV9, AAV10, AAV11, AAV12, AAVrh.8, AAVrh.10, AAVrh32.33, AAVrh74, bovine AAV or avian AAV capsid protein. In some embodiments, the recombinant capsid protein has at least 90% sequence identity to the native sequence of the AAV9 capsid protein.

In some embodiments, the peptide is located at the amino acid positions corresponding to amino acids 451-458 of the native AAV9 capsid protein subunit, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and the peptide is selected from any one of SEQ ID NO: 12-18. In some embodiments, the peptide is located at the amino acid positions corresponding to amino acids 587-594 of the native AAV9 capsid protein subunit, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV, and the peptide is selected from SEQ ID NO: 19 or 20.

In some embodiments, a recombinant capsid protein subunit comprises a) a first peptide having a sequence of any one of SEQ ID NO: 12-18; and b) a second peptide having a sequence of any one of SEQ ID NO: 19-20. In some embodiments, the first peptide is at amino acid positions 451-458, and the second peptide is at amino acids 587-594, wherein the amino acid numbering is based on the native AAV9 capsid protein subunit, or the equivalent amino acid residues in AAV1, AAV2, AAV3, AAV4, AAV5, AAV6, AAV7, AAV8, AAV10, AAV11, AAV12, AAVrh.8, AAVrh.10, AAVrh32.33, AAVrh74, bovine AAV or avian AAV.

In some embodiments, the peptide inhibits binding of at least one antibody to the protein capsid or a capsid protein subunit thereof. In some embodiments, the peptide inhibits neutralization of infectivity of the AAV vector by the antibody.

In some embodiments, the peptide selectively binds to a receptor expressed on the surface of a cell in the central nervous system (CNS). In some embodiments, the cell is in the premotor cortex, the thalamus, the cerebellar cortex, the dentate nucleus, the spinal cord, or the dorsal root ganglion. In some embodiments, the peptide selectively binds to a receptor expressed on the surface of a cell in the heart.

In some embodiments, an adeno-associated virus (AAV) vector comprises (i) a protein capsid comprising a mutant AAV9 capsid protein subunit and (ii) a transfer cassette encapsidated by the protein capsid, wherein the capsid protein subunit comprises a peptide having the sequence $X^1-X^2-X^3-X^4-X^5-X^6-X^7-X^8$ (SEQ ID NO: 158) at amino acids 451-458 of the native AAV9 capsid protein subunit sequence, wherein the peptide does not occur in the native AAV9 capsid protein subunit sequence. In some embodiments, $X^1$ is not I, $X^2$ is not N, $X^3$ is not G, $X^4$ is not S, $X^5$ is not G, $X^6$ is not Q, $X^7$ is not N, and/or $X^8$ is not Q. In some embodiments, $X^1$ is S, F, Q, G, K, or R. In some embodiments, $X^2$ is C, G, R, D, T, or Q. In some embodiments, $X^3$ is Q, V, G, Y, R, F, or D. In some embodiments, $X^4$ is P, Q, A, or R. In some embodiments, $X^5$ is T, N, A, P, or I. In some embodiments, $X^6$ is V, Q, A, or I. In some embodiments, $X^7$ is M, P, R, Q, or N. In some embodiments, $X^8$ is N, L, F, E, H, or A. In some embodiments, $X^1$ is S, $X^2$ is C, $X^3$ is Q, $X^4$ is P, $X^5$ is T, $X^6$ is V, $X^7$ is M, and $X^8$ is N. In some embodiments, $X^1$ is F, $X^2$ is G, $X^3$ is V, $X^4$ is P, $X^5$ is N, $X^6$ is Q, $X^7$ is P, and $X^8$ is L. In some embodiments, $X^1$ is Q, $X^2$ is R, $X^3$ is G, $X^4$ is Q, $X^5$ is A, $X^6$ is A, $X^7$ is P, and $X^8$ is F. In some embodiments, $X^1$ is G, $X^2$ is D, $X^3$ is Y, $X^4$ is A, $X^5$ is P, $X^6$ is I, $X^7$ is R, and $X^8$ is E. In some embodiments, $X^1$ is K, $X^2$ is T, $X^3$ is R, $X^4$ is R, $X^5$ is I, $X^6$ is V, $X^7$ is Q, and $X^8$ is H. In some embodiments, $X^1$ is F, $X^2$ is G, $X^3$ is F, $X^4$ is P, $X^5$ is N, $X^6$ is Q, $X^7$ is P, and $X^8$ is L. In some embodiments, $X^1$ is R, $X^2$ is Q, $X^3$ is D, $X^4$ is Q, $X^5$ is P, $X^6$ is I, $X^7$ is N, and $X^8$ is A.

In some embodiments, an adeno-associated virus (AAV) vector comprises (i) a protein capsid comprising a mutant AAV9 capsid protein subunit and (ii) a transfer cassette encapsidated by the protein capsid, wherein the capsid protein subunit comprises a peptide having the sequence $X^1-X^2-X^3-X^4-X^5-X^6-X^7-X^8$ (SEQ ID NO: 158) at amino acids 587-594 of the native AAV9 capsid protein subunit sequence, wherein the peptide does not occur in the native AAV9 capsid protein subunit sequence. In some embodiments, $X^1$ is not A, $X^2$ is not Q, $X^3$ is not A, $X^4$ is not Q, $X^5$ is not A, $X^6$ is not Q, $X^7$ is not T, and/or $X^8$ is not G. In some embodiments, $X^1$ is S. In some embodiments, $X^2$ is K or T. In some embodiments, $X^3$ is V. In some embodiments, $X^4$ is E or D. In some embodiments, $X^5$ is S. In some embodiments, $X^6$ is W or I. In some embodiments, $X^7$ is T or A. In some embodiments, $X^8$ is E or I. In some embodiments, $X^1$ is S, $X^2$ is K, $X^3$ is V, $X^4$ is E, $X^5$ is S, $X^6$ is W, $X^7$ is T, and $X^8$ is E. In some embodiments, $X^1$ is S, $X^2$ is T, $X^3$ is V, $X^4$ is D, $X^5$ is S, $X^6$ is I, $X^7$ is A, and $X^8$ is I.

In some embodiments, an adeno-associated virus (AAV) vector comprises (i) a protein capsid comprising a recombinant capsid protein subunit and (ii) a transfer cassette encapsidated by the protein capsid, wherein the capsid protein subunit comprises an amino acid sequence that is at least 95%, at least 96%, at least 97%, at least 98%, or at least 99% identical to any one of SEQ ID NO: 165-187. In some embodiments, the capsid protein subunit comprises the amino acid sequence of any one of SEQ ID NO: 165-187. In some embodiments, the capsid protein subunit comprises the amino acid sequence of SEQ ID NO: 175. In some embodiments, the capsid protein subunit comprises the amino acid sequence of SEQ ID NO: 180.

In some embodiments, an AAV vector selectively delivers the transfer cassette to a cell or tissue of the central nervous system. In some embodiments, the tissue of the central nervous system is the premotor cortex, the thalamus, the cerebellar cortex, the dentate nucleus, the spinal cord, or the dorsal root ganglion. In some embodiments, the AAV vector delivers the transfer cassette to the brain, but does not deliver the AAV vector to the heart. In some embodiments, the AAV vector delivers the transfer cassette to the brain and to the heart. In some embodiments, delivery of the transfer cassette is greater to the brain than to the heart. In some embodiments, delivery of the transfer cassette is approximately equal in the brain and in the heart.

AAV Capsid Protein Subunits and Protein Capsids Comprising the Same

In some embodiments, the disclosure provides an adeno-associated virus (AAV) capsid protein subunit comprising one or more amino acid modifications (e.g., substitutions and/or deletions) compared to a native AAV capsid protein subunit, wherein the one or more modifications modify one or more antigenic sites on the AAV capsid protein subunit. The modification of the one or more antigenic sites results in reduced recognition by an antibody of the one or more antigenic sites and/or inhibition of neutralization of infectivity of a virus particle comprising the AAV capsid protein subunit. The one or more amino acid modifications (e.g., substitutions and/or deletions) can be in one or more antigenic footprints identified by peptide epitope mapping and/or cryo-electron microscopy studies of AAV-antibody complexes containing AAV capsid protein subunits. In some embodiments, the one or more antigenic sites are common antigenic motifs or CAMs as described in WO 2017/058892, which is incorporated herein by reference in its entirety. In some embodiments, the antigenic sites are in a variable region (VR) of the AAV capsid protein subunit, such as VR-I, VR-II, VR-III, VR-IV, VR-V, VR-VI, VR-VII, VR-VIII, VR-IX. In some embodiments, one or more antigenic sites is in the HI loop of the AAV capsid protein subunit.

In some embodiments, an AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV capsid protein subunit comprises an amino acid modification (e.g., a substitution or deletion) in one or more of the regions identified in Table 6, below.

TABLE 6

Exemplary antigenic or other regions on various AAV capsid protein subunits that may be partially or fully substituted/replaced. Respective VP1 numbering of residues in the native AAV capsid protein subunit sequence is shown.

| | SEQ ID NO |
|---|---|
| AAV1 Sequence (amino acid numbers) | |
| SASTGAS (262-268) | 2591 |
| VFMIPQYGYL (370-379) | 2592 |
| NQSGSAQNK (451-459) | 2593 |
| SV (472-473) | 2594 |
| KTDNNNSN (493-500) | 2595 |
| KDDEDKF (528-534) | 2596 |
| SAGASN (547-552) | 2597 |
| STDPATGDVH (588-597) | 2598 |
| AN (709-710) | 2599 |
| DNNGLYT (716-722) | 2600 |
| AAV2 Sequence (amino acid numbers) | |
| SQSGAS (262-267) | 2601 |
| VFMVPQYGYL (369-378) | 2602 |
| TPSGTTTQS (450-458) | 2603 |
| RD (471-472) | 2604 |
| SADNNNSE (492-499) | 2605 |
| KDDEEKF (527-533) | 2606 |
| GSEKTN (546-551) | 2607 |

TABLE 6-continued

Exemplary antigenic or other regions on various AAV capsid protein subunits that may be partially or fully substituted/replaced. Respective VP1 numbering of residues in the native AAV capsid protein subunit sequence is shown.

| | SEQ ID NO |
|---|---|
| NRQAATADVN (587-596) | 2608 |
| VN (708-709) | 2609 |
| DTNGVYS (715-721) | 2610 |
| AAV3 Sequence (amino acid numbers) | |
| SQSGAS (262-267) | 2611 |
| VFMVPQYGYL (369-378) | 2612 |
| TTSGTTNQS (451-459) | 2613 |
| SL (472-473) | 2614 |
| ANDNNNSN (493-500) | 2615 |
| KDDEEKF (528-534) | 2616 |
| GTTASN (547-552) | 2617 |
| NTAPTTGTVN (588-597) | 2618 |
| VN (709-710) | 2619 |
| DTNGVYS (716-722) | 2620 |
| AAV4 Sequence (amino acid numbers) | |
| RLGESLQS (253-260) | 2621 |
| VFMVPQYGYC (360-369) | 2622 |
| GTTLNAGTA (445-453) | 2623 |
| SN (466-467) | 2624 |
| ANQNYKIPATGS (487-498) | 2625 |
| GPADSKF (527-533) | 2626 |
| QNGNTA (545-560) | 2627 |
| SNLPTVDRLT (583-595) | 2628 |
| NS (707-708) | 2629 |
| DAAGKYT (714-720) | 2630 |
| AAV5 Sequence (amino acid numbers) | |
| EIKSGSVDGS (249-258) | 2631 |
| VFTLPQYGYA (360-369) | 2632 |
| STNNTGGVQ (440-448) | 2633 |
| AN (458-459) | 2634 |
| SGVNRAS (479-485) | 2635 |
| LQGSNTY (515-521) | 2636 |
| ANPGTTAT (534-541) | 2637 |
| TTAPATGTYN (577-586) | 2638 |
| QF (697-698) | 2639 |
| DSTGEYR (704-710) | 2640 |
| AAV6 (amino acid numbers) | |
| SASTGAS (262-268) | 2641 |
| VFMIPQYGYL (370-379) | 2642 |
| NQSGSAQNK (451-459) | 2643 |
| SV (472-473) | 2644 |

TABLE 6-continued

Exemplary antigenic or other regions on various AAV capsid protein subunits that may be partially or fully substituted/replaced. Respective VP1 numbering of residues in the native AAV capsid protein subunit sequence is shown.

| | SEQ ID NO |
|---|---|
| KTDNNNSN (493-500) | 2645 |
| KDDKDKF (528-534) | 2646 |
| SAGASN (547-552) | 2647 |
| STDPATGDVH (588-897) | 2648 |
| AN (709-710) | 2649 |
| DNNGLYT (716-722) | 2650 |
| AAV7 (amino acid numbers) | |
| SETAGST (263-269) | 2651 |
| VFMIPQYGYL (371-380) | 2652 |
| NPGGTAGNR (453-461) | 2653 |
| AN (474-475) | 2654 |
| LDQNNSN (495-502) | 2655 |
| KDDEDRF (530-536) | 2656 |

TABLE 6-continued

Exemplary antigenic or other regions on various AAV capsid protein subunits that may be partially or fully substituted/replaced. Respective VP1 numbering of residues in the native AAV capsid protein subunit sequence is shown.

| | SEQ ID NO |
|---|---|
| QTTGTGGTQ (451-459) | 2683 |
| AN (472-473) | 2684 |
| TNQNNNSN (493-500) | 2685 |
| KDDDDRF (528-534) | 2686 |
| GAGNDG (547-552) | 2687 |
| NTQAQTGLVH (588-597) | 2688 |
| TN (709-710) | 2689 |
| NTEGVYS (716-722) | 2690 |
| AAVrh10 (amino acid numbers) | |
| NGTSGGST (263-270) | 2691 |
| VFMIPQYGYL (372-381) | 2692 |
| STGGTAGTQ (453-461) | 2693 |
| SA (474-475) | 2694 |
| LSQNNNSN (495-502) | 2695 |
| KDDEERF (530-536) | 2696 |
| GAGKDN (549-554) | 2697 |
| NAAPIVGAVN (590-599) | 2698 |
| TN (711-712) | 2699 |
| NTDGTYS (718-724) | 2700 |
| AAV10 (amino acid numbers) | |
| NGTSGGST (263-270) | 2701 |
| VFMIPQYGYL (372-381) | 2702 |
| STGGTQGTQ (453-461) | 2703 |
| SA (474-475) | 2704 |
| LSQNNNSN (495-502) | 2705 |
| KDDEERF (530-536) | 2706 |
| GAGRDN (549-554) | 2707 |
| NTGPIVGNVN (590-599) | 2708 |
| TN (711-712) | 2709 |
| NTEGTYS (718-724) | 2710 |
| AAV11 (amino acid numbers) | |
| RLGTTSSS (253-260) | 2711 |
| VFMVPQYGYC (360-369) | 2712 |
| GETLNQGNA (444-452) | 2713 |
| AF (465-466) | 2714 |
| ASQNYKIPASGG (486-497) | 2715 |
| GPSDGDF (526-532) | 2716 |
| VTGNTT (544-549) | 2717 |
| TTAPITGNVT (585-594) | 2718 |

TABLE 6-continued

Exemplary antigenic or other regions on various AAV capsid protein subunits that may be partially or fully substituted/replaced. Respective VP1 numbering of residues in the native AAV capsid protein subunit sequence is shown.

| | SEQ ID NO |
|---|---|
| SS (706-707) | 2719 |
| DTTGKYT (713-719) | 2720 |
| AAV12 (amino acid numbers) | |
| RIGTTANS (262-269) | 2721 |
| VFMVPQYGYC (369-378) | 2722 |
| GNSLNQGTA (453-461) | 2723 |
| AY (474-475) | 2724 |
| ANQNYKIPASGG (495-506) | 2725 |
| GAGDSDF (535-541) | 2726 |
| PSGNTT (553-558) | 2727 |
| TTAPHIANLD (594-503) | 2728 |
| NS (715-716) | 2729 |
| DNAGNYH (722-728) | 2730 |
| AAVrh32.33 (amino acid numbers) | |
| RLGTTSNS (253-260) | 2731 |
| VFMVPQYGYC (360-369) | 2732 |
| GETLNQGNA (444-452) | 2733 |
| AF (465-466) | 2734 |
| ASQNYKIPASGG (486-497) | 2735 |
| GPSDGDF (526-532) | 2736 |
| VTGNTT (544-549) | 2737 |
| TTAPITGNVT (585-594) | 2738 |
| SS (706-707) | 2739 |
| DTTGKYT (713-719) | 2740 |
| Bovine AAV (amino acid numbers) | |
| RLGSSNAS (255-262) | 2741 |
| VFMVPQYGYC (362-371) | 2742 |
| GGTLNQGNS (447-455) | 2743 |
| SG (468-469) | 2744 |
| ASQNYKIPQGRN (489-500) | 2745 |
| ANDATDF (529-535) | 2746 |
| ITGNTT (547-552) | 2747 |
| TTVPTVDDVD (588-597) | 2748 |
| DS (709-710) | 2749 |
| DNAGAYK (716-722) | 2750 |
| Avian AAV (amino acid numbers) | |
| RIQGPSGG (265-272) | 2751 |
| IYTIPQYGYC (375-384) | 2752 |
| VSQAGSSGR (454-462) | 2753 |
| AA (475-476) | 2754 |
| ASNITKNNVFSV (496-507) | 2755 |

TABLE 6-continued

Exemplary antigenic or other regions on
various AAV capsid protein subunits that may
be partially or fully substituted/replaced.
Respective VP1 numbering of residues in
the native AAV capsid protein subunit
sequence is shown.

| | SEQ ID NO |
|---|---|
| FSGEPDR (533-539) | 2756 |
| VYDQTTAT (552-559) | 2757 |
| VTPGTRA AVN (595-604) | 2758 |
| AD (716-717) | 2759 |
| SDTGSYS (723-729) | 2760 |

In some embodiments, the amino acid substitution replaces any eight amino acids in an AAV capsid protein subunit from any one of the following serotypes: AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV. For example, the amino acid substitution may replace the following amino acids (VP1 numbering): 355-362, 363-370, 371-378, 379-386, 387-394, 395-402, 403-410, 411-418, 419-426, 427-434, 435-442, 443-450, 451-458, 459-466, 467-474, 475-482, 483-490, 491-498, 499-506, 507-514, 515-522, 523-530, 531-538, 539-546, 547-554, 555-562, 563-570, 571-578, 579-586, 587-594, 595-602, 603-610, 611-618, 619-626, 627-634, 635-642, 643-650, 651-658, 659-666, 667-674, 675-682, 683-690, 691-698, 699-706, 707-714, 715-722 in any of the above-listed AAV serotypes.

In some embodiments, the amino acid substitution is selected from any one of SEQ ID NO: 19-20. In some embodiments, the amino acid substitution has at least 95%, at least 96%, at least 97%, at least 98%, or at least 99% sequence identity with any one of SEQ ID NO: 12-18. In some embodiments, the substitution is at the amino acids corresponding to amino acids 587-594 of the wildtype AAV9 capsid protein subunit. In some embodiments, the substitution is at the amino acids corresponding to amino acids 587-594 of the wildtype AAV1 capsid protein subunit. In some embodiments, the substitution is at the amino acids corresponding to amino acids 587-594 of the wildtype AAV6 capsid protein subunit. In some embodiments, the substitution is at the amino acids corresponding to amino acids 589-596 of the wildtype AAV8 capsid protein subunit. In some embodiments, the substitution is at the amino acids corresponding to amino acids 587-594 of the wildtype AAVrh8 capsid protein subunit. In some embodiments, the substitution is at the amino acids corresponding to amino acids 589-596 of the wildtype AAVrh10 capsid protein subunit.

In some embodiments, the amino acid substitution is selected from any one of SEQ ID NO: 18-20. In some embodiments, the amino acid substitution has at least 95%, at least 96%, at least 97%, at least 98%, or at least 99% sequence identity with any one of SEQ ID NO: 18-20. In some embodiments, the substitution is at the amino acids corresponding to amino acids 451-458 of the wildtype AAV9 capsid protein subunit.

In some embodiments, an amino acid deletion comprises a deletion of at least one, at least two, at least three, at least four, at least five, at least six, at least seven, at least eight, at least nine, or at least ten amino acids compared to the wildtype capsid protein subunit.

In some embodiments, an AAV capsid protein subunit comprises one or more amino acid substitutions and one or more amino acid deletions. In some embodiments, a capsid protein subunit comprises at least one amino acid substitution and at least one amino acid deletion. In some embodiments, a capsid protein subunit comprises at least one amino acid substitution and at least one amino acid deletion, wherein the at least one amino acid substitution and the at least one amino acid deletion are immediately adjacent to one another in the capsid protein subunit amino acid sequence.

In some embodiments, the capsid protein subunits are modified to produce an AAV capsid protein subunit that, when present in an AAV virus particle or AAV virus vector, has a phenotype of selectively targeting the CNS (e.g., the brain, the spinal cord). In some embodiments, the capsid protein subunits are modified to produce an AAV capsid protein subunit that, when present in an AAV virus particle or AAV virus vector, has a phenotype of evading neutralizing antibodies. The AAV virus-like particle or AAV vector can also have a phenotype of enhanced or maintained transduction efficiency in addition to the phenotype of evading neutralizing antibodies and/or targeting the CNS.

In some embodiments, the one or more substitutions can introduce one or more sequences from a capsid protein subunit of a first AAV serotype into the capsid protein subunit of a second AAV serotype that is different from the first AAV serotype.

The base AAV capsid protein subunit to which modifications are added can be a capsid protein subunit of an AAV serotype selected from AAV1, AAV2, AAV3, AAV3B, AAV4, AAV5, AAV6, AAV7, AAV8, AAV9, AAV10, AAV11, AAV12, AAVrh.8, AAVrh.10, AAVrh.32.33, AAVrh74, bovine AAV, avian AAV or any other AAV now known or later identified. In some embodiments, the base AAV capsid protein subunit is of the AAV9 serotype. In some embodiments, the base AAV capsid protein subunit is chimeric. In some embodiments, the base AAV capsid protein subunit is an AAV8/9 chimera.

Several examples of a modified AAV capsid protein subunit are provided herein. In the following examples, the capsid protein subunit can comprise the specific substitutions described and, in some embodiments, can comprise fewer or more substitutions than those described. As used herein, "substitution" may refer to a single amino acid substitution, or a substitution of more than one contiguous amino acid. For example in some embodiments, a capsid protein subunit can comprise at least 1, 2, 3, 4, 5, 6, 7, 8, 9, 10, etc., single amino acid substitutions. In some embodiments, a capsid protein subunit can comprise one or more substitutions of multiple contiguous amino acids, such as one or more substitutions of 2, 3, 4, 5, 6, 7, 8, 9, 10, 11, or 12 contiguous amino acids.

Furthermore, in some embodiments described herein wherein an amino acid residue is substituted by any amino acid residue other than the amino acid residue present in the wildtype or native amino acid sequence, the any other amino acid residue can be any natural or non-natural amino acid residue known in the art (see, e.g., Tables 2 and 4). In some embodiments, the substitution can be a conservative substitution and in some embodiments, the substitution can be a nonconservative substitution. In some embodiments, an AAV capsid protein subunit comprises one or more amino acid substitutions, wherein the amino acid substitutions are each individually selected from SEQ ID NO: 12-18 as shown in Table 7.1.

TABLE 7.1

AMINO ACID SUBSTITUTIONS

| Amino Acid Substitution | SEQ ID NO. |
|---|---|
| SCQPTVMN | 12 |
| FGVPNQPL | 13 |
| QRGQAAPF | 14 |
| GDYAPIRE | 15 |
| KTRRIVQH | 16 |
| FGFPNQPL | 17 |
| RQDQPINA | 18 |

In some embodiments, an AAV capsid protein subunit comprises one or more amino acid substitutions, wherein the amino acid substitutions are each selected from SEQ ID NO: 19-20 as shown in Table 7.2.

TABLE 7.2

AMINO ACID SUBSTITUTIONS

| Amino Acid Substitution | SEQ ID NO. |
|---|---|
| SKVESWTE | 19 |
| STVDSIAI | 20 |

In some embodiments, an AAV capsid protein subunit may comprise a first substitution selected from the sequences listed in Table 7.1 and a second substitution selected from the sequences listed in Table 7.2. In some embodiments, an AAV capsid protein subunit may comprise a first substitution, a second substitution as shown in Tables 7.3 and 7.4.

TABLE 7.3

COMBINATIONS OF AMINO ACID SUBSTITUTIONS

| First Substitution (SEQ ID NO) | Second Substitution (SEQ ID NO) |
|---|---|
| 12, 13, 14, 15, 16, 17, or 18 | 19 or 20 |

TABLE 7.4

COMBINATIONS OF AMINO ACID SUBSTITUTIONS

| First Substitution (SEQ ID NO) | Second Substitution (SEQ ID NO) |
|---|---|
| 12 | 19 |
| 12 | 20 |
| 13 | 19 |
| 13 | 20 |
| 14 | 19 |
| 14 | 20 |

TABLE 7.4-continued

COMBINATIONS OF AMINO ACID SUBSTITUTIONS

| First Substitution (SEQ ID NO) | Second Substitution (SEQ ID NO) |
|---|---|
| 15 | 19 |
| 15 | 20 |
| 16 | 19 |
| 16 | 20 |
| 17 | 19 |
| 17 | 20 |
| 18 | 19 |
| 18 | 20 |

In some embodiments, an AAV capsid protein subunit comprises an amino acid modification (e.g., substitution and/or deletion), wherein the amino acid modification modifies one or more surface-exposed regions, such as an antigenic region, on the AAV capsid protein subunit.

In some embodiments, an AAV capsid protein subunit comprises one or more amino acid substitutions, wherein at least one of the amino acid substitutions comprises one of SEQ ID NOs: 19-20. In some embodiments, the substitution replaces the amino acids corresponding to amino acids 587-594 of the wildtype AAV9 capsid protein subunit.

In some embodiments, an AAV capsid protein subunit comprises one or more amino acid substitutions, wherein at least one of the amino acid substitutions comprises one of SEQ ID NOs: 12-18. In some embodiments, the substitution replaces the amino acids corresponding to amino acids 451-458 of the wildtype AAV9 capsid protein subunit.

In some embodiments, an AAV capsid protein subunit comprises a substitution comprising a sequence of eight amino acids ($X^1$-$X^2$-$X^3$-$X^4$-$X^5$-$X^6$-$X^7$-$X^8$) (SEQ ID NO: 158) that does not occur in the native capsid protein subunit sequence. In some embodiments, $X^1$ is not I, $X^2$ is not N, $X^3$ is not G, $X^4$ is not S, $X^5$ is not G, $X^6$ is not Q, $X^7$ is not N, and/or $X^8$ is not Q. In some embodiments, $X^1$ is S, F, Q, G, K, or R. In some embodiments, $X^2$ is C, G, R, D, T, or Q. In some embodiments, $X^3$ is Q, V, G, Y, R, F, or D. In some embodiments, $X^4$ is P, Q, A, or R. In some embodiments, $X^5$ is T, N, A, P, or I. In some embodiments, $X^6$ is V, Q, A, or I. In some embodiments, $X^7$ is M, P, R, Q, or N. In some embodiments, $X^8$ is N, L, F, E, H, or A. In some embodiments, $X^1$ is S, $X^2$ is C, $X^3$ is Q, $X^4$ is P, $X^5$ is T, $X^6$ is V, $X^7$ is M, and $X^8$ is N. In some embodiments, $X^1$ is F, $X^2$ is G, $X^3$ is V, $X^4$ is P, $X^5$ is N, $X^6$ is Q, $X^7$ is P, and $X^8$ is L. In some embodiments, $X^1$ is Q, $X^2$ is R, $X^3$ is G, $X^4$ is Q, $X^5$ is A, $X^6$ is A, $X^7$ is P, and $X^8$ is F. In some embodiments, $X^1$ is G, $X^2$ is D, $X^3$ is Y, $X^4$ is A, $X^5$ is P, $X^6$ is I, $X^7$ is R, and $X^8$ is E. In some embodiments, $X^1$ is K, $X^2$ is T, $X^3$ is R, $X^4$ is R, $X^5$ is I, $X^6$ is V, $X^7$ is Q, and $X^8$ is H. In some embodiments, $X^1$ is F, $X^2$ is G, $X^3$ is F, $X^4$ is P, $X^5$ is N, $X^6$ is Q, $X^7$ is P, and $X^8$ is L. In some embodiments, $X^1$ is R, $X^2$ is Q, $X^3$ is D, $X^4$ is Q, $X^5$ is P, $X^6$ is I, $X^7$ is N, and $X^8$ is A.

In some embodiments, $X^1$ is not A, $X^2$ is not Q, $X^3$ is not A, $X^4$ is not Q, $X^5$ is not A, $X^6$ is not Q, $X^7$ is not T, and/or $X^8$ is not G. In some embodiments, $X^1$ is S. In some embodiments, $X^2$ is K or T. In some embodiments, $X^3$ is V. In some embodiments, $X^4$ is E or D. In some embodiments, $X^5$ is S. In some embodiments, $X^6$ is W or I. In some embodiments, $X^7$ is T or A. In some embodiments, $X^8$ is E or I. In some embodiments, $X^1$ is S, $X^2$ is K, $X^3$ is V, $X^4$ is E, $X^5$ is S, $X^6$ is W, $X^7$ is T, and $X^8$ is E. In some embodiments, $X^1$ is S, $X^2$ is T, $X^3$ is V, $X^4$ is D, $X^5$ is S, $X^6$ is I, $X^7$ is A, and $X^8$ is I.

In some embodiments, an AAV subunit protein comprises one or more amino acid deletions, wherein the amino acid deletion comprises a deletion of at least six or at least eight amino acids compared to the wildtype AAV capsid protein subunit. In some embodiments, an AAV capsid protein subunit comprises a deletion of eight consecutive amino acids compared to the native capsid protein subunit sequence. In some embodiments, an AAV capsid protein subunit comprises a deletion of six consecutive amino acids compared to the native capsid protein subunit sequence.

In some embodiments, an AAV capsid protein subunit comprises the sequence LSKTQTLK (SEQ ID NO: 1374) or the sequence LSKTDPQTLK (SEQ ID NO: 1375). In some embodiments, the AAV capsid protein subunit comprising SEQ ID NO: 1374 or 1375 is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

In some embodiments, an AAV capsid protein subunit comprises a first substitution comprising a sequence selected from SEQ ID NO: 12-18; and a second substitution comprising a sequence selected from SEQ ID NO: 19-20.

In some embodiments, an AAV capsid protein subunit comprises an amino acid deletion and a substitution, wherein the substitution comprises a sequence selected from SEQ ID NO: 12-20.

In some embodiments, a recombinant capsid protein subunit has a sequence that is at least 90%, at least 95%, at least 96%, at least 97%, at least 98%, at least 99% or 100% identical to SEQ ID NO: 9 (AAV9) and comprises one or more of the following amino acid substitutions: I451S, I451F, I451Q, I451G, I451K, I451R, N452C, N452G, N452R, N452D, N452T, N452Q, G453Q, G453V, G453Y, G453R, G453F, G453D, S454P, S454Q, S454A, S454R, G455T, G455N, G455A, G455P, G455I, Q456V, Q456A, Q456I, N457M, N457P, N457R, N457Q, Q458N, Q458L, Q458F, Q458E, Q458H, Q458A, A587S, Q588K, Q588T, A589V, Q590E, Q590D, A591S, Q592W, Q592I, T593A, G594E, G594I.

Any of the AAV capsid protein subunits described herein may further comprise a modification (e.g., a substitution or a deletion) in the HI loop. The HI loop is a prominent domain on the AAV capsid protein subunit surface, between β strands βH and β1, that extends from each viral protein (VP) subunit overlapping the neighboring fivefold VP. In some embodiments, an AAV capsid protein subunit comprises one, two, three, four, five, six, seven, or eight amino acid substitutions in the HI loop. In some embodiments, the AAV capsid protein subunit comprises one or more of the following substitutions in the HI loop: P661R, T662S, Q666G, S667D, wherein the numbering corresponds to the wildtype AAV8 capsid protein subunit (SEQ ID NO: 8). In some embodiments, the AAV capsid protein subunit comprises one or more of the following substitutions in the HI loop: P659R, T660S, A661T, K664G, wherein the numbering corresponds to the wildtype AAV9 capsid protein subunit (SEQ ID NO: 9).

In some embodiments, an AAV capsid protein subunit comprises one, two, three, or four amino acid substitutions, wherein each substitution modifies a different antigenic site on the AAV capsid protein subunit, and wherein at least one of the amino acid substitutions modifies the HI loop of the capsid protein subunit.

In some embodiments, an AAV capsid protein subunit comprises a first, a second, a third, and a fourth amino acid substitution. In some embodiments, at least one of the substitutions modifies the HI Loop of the capsid protein subunit. In some embodiments, the AAV capsid protein subunit comprises one or more of the following substitutions in the HI loop: P661R, T662S, Q666G, S667D, wherein the numbering corresponds to the wildtype AAV8 capsid protein subunit (SEQ ID NO: 8); or P659R, T660S, A661T, K664G, wherein the numbering corresponds to the wildtype AAV9 capsid protein subunit (SEQ ID NO: 9). In some embodiments, an AAV capsid protein subunit comprises the amino acid sequence of any one of SEQ ID NO: 185-187. In some embodiments, an AAV capsid protein subunit comprises an amino acid sequence sharing at least 90%, at least 95%, at least 96%, at least 97%, at least 98%, or at least 99% sequence identity to any one of SEQ ID NO: 165-187.

Also provided herein is a nucleic acid, or a plasmid comprising the same that encodes one or more of the AAV capsid protein subunits described herein. The nucleotide sequence may be a DNA sequence or an RNA sequence. In some embodiments, cell comprises one or more nucleic acids or plasmids described herein.

In some embodiments, an AAV protein capsid comprises an AAV capsid protein subunit as described herein. Further provided herein is a viral vector comprising an AAV protein capsid as well as a composition comprising the AAV protein capsid, AAV capsid protein subunit and/or viral vector in a pharmaceutically acceptable carrier.

In some embodiments, modification of one or more antigenic sites results in reduced binding by an antibody to the one or more antigenic sites. In some embodiments, modification of the one or more antigenic sites results in inhibition of neutralization of infectivity of a virus particle comprising the AAV capsid protein subunit.

As described herein, the nucleic acid and amino acid sequences of the capsid protein subunits from a number of AAV are known in the art. Thus, the amino acids "corresponding" to amino acid positions of the native AAV capsid protein subunits can be readily determined for any other AAV (e.g., by using sequence alignments).

The modified capsid protein subunits can be produced by modifying the capsid protein subunit of any AAV now known or later discovered. Further, the base AAV capsid protein subunit that is to be modified can be a naturally occurring AAV capsid protein subunit (e.g., an AAV2, AAV3a or 3b, AAV4, AAV5, AAV6, AAV7, AAV8, AAV9, AAV10 or AAV11 capsid protein subunit or any of the AAV shown in Table 2) but is not so limited. Those skilled in the art will understand that a variety of manipulations to the AAV capsid protein subunits are known in the art and the disclosure is not limited to modifications of naturally occurring AAV capsid protein subunits. For example, the capsid protein to be modified may already have alterations as compared with naturally occurring AAV (e.g., is derived from a naturally occurring AAV capsid protein subunit, e.g., AAV2, AAV3a, AAV3b, AAV4, AAV5, AAV6, AAV7, AAV8, AAV9, AAV10, AAV11, AAV12 or any other AAV now known or later discovered). In some embodiments, the capsid protein subunit may be a chimeric capsid protein subunit. In some embodiments, the capsid protein subunit may be an engineered AAV, such as AAV2i8, AAV2g9, AAV-LK03, AAV7m8, AAV Anc80, AAV PHP.B.

Thus, in some embodiments, the AAV capsid protein subunit to be modified can be derived from a naturally occurring AAV but further comprises one or more foreign sequences (e.g., that are exogenous to the native virus) that are inserted and/or substituted into the capsid protein subunit and/or has been altered by deletion of one or more amino acids.

Accordingly, when referring herein to a specific AAV capsid protein subunit (e.g., an AAV2, AAV3, AAV4, AAV5, AAV6, AAV7, AAV8, AAV9, AAV10 or AAV11 capsid protein subunit or a capsid protein subunit from any of the AAV shown in Table 2, etc.), it is intended to encompass the native capsid protein subunit as well as capsid protein subunits that have alterations other than the modifications described herein. Such alterations include substitutions, insertions and/or deletions. In some embodiments, the capsid protein subunit comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids inserted therein (other than the insertions described herein) as compared with the native AAV capsid protein subunit sequence. In some embodiments, the capsid protein subunit comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acid substitutions (other than the amino acid substitutions described herein) as compared with the native AAV capsid protein subunit sequence, in some embodiments, the capsid protein subunit comprises a deletion of 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids as compared with the native AAV capsid protein subunit sequence.

In some embodiments, the AAV capsid protein subunit has an amino acid sequence that is at least about 90%, about 95%, about 97%, about 98% or about 99% similar or identical to a native AAV capsid protein subunit sequence.

Methods of determining sequence similarity or identity between two or more amino acid sequences are known in the art. Sequence similarity or identity may be determined for an entire length of a nucleic acid or for an indicated portion of a nucleic acid. Sequence similarity or identity may be determined using standard techniques, including, but not limited to, the local sequence identity algorithm of Smith & Waterman, Adv. Appl. Math. 2, 482 (1981), by the sequence identity alignment algorithm of Needleman & Wunsch, J Mol. Biol. 48, 443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

For purposes of the instant disclosure, unless otherwise indicated, percent identity is calculated using the Basic Local Alignment Search Tool (BLAST) available online at blast.ncbi.nlm.nih.gov/Blast.cgi. The skilled artisan will understand that other algorithms may be substituted as appropriate.

In some embodiments, a protein capsid comprises a modified AAV capsid protein subunit as described herein. In some embodiments, the protein capsid is a parvovirus capsid, which may further be an autonomous parvovirus capsid or a dependovirus capsid. Optionally, the protein capsid is an AAV protein capsid. In some embodiments, the AAV protein capsid is an AAV1, AAV2, AAV3a, AAV3b, AAV4, AAV5, AAV6, AAV7, AAV8, AAV9, AAV10, AAV11, AAV12, AAVrh8, AAVrh10, AAVrh32.33, bovine AAV protein capsid, avian AAV protein capsid or any other AAV now known or later identified. A nonlimiting list of AAV serotypes is shown in Table 2. An AAV protein capsid can be any AAV serotype listed in Table 2 or derived from any of the foregoing by one or more insertions, substitutions and/or deletions. Molecules that can be packaged by the modified virus protein capsid and transferred into a cell include transfer cassettes (e.g., heterologous DNA or RNA), polypeptides, small organic molecules, metals, or combinations of the same.

Heterologous molecules are defined as those that are not naturally found in an AAV infection, e.g., those not encoded by a wild-type AAV genome. Further, therapeutically useful molecules can be associated with the outside of the chimeric protein capsid for transfer of the molecules into host target cells. Such associated molecules can include DNA, RNA, small organic molecules, metals, carbohydrates, lipids and/or polypeptides. In some embodiments the therapeutically useful molecule is covalently linked (i.e., conjugated or chemically coupled) to the protein capsid or a capsid protein thereof. Methods of covalently linking molecules are known by those skilled in the art.

The modified protein capsids also find use in raising antibodies against the novel protein capsid structures. As a further alternative, an exogenous amino acid sequence may be inserted into the modified protein capsid or capsid protein subunit thereof for antigen presentation to a cell, e.g., for administration to a subject to produce an immune response to the exogenous amino acid sequence.

In some embodiments, the protein capsids can be administered to block certain cellular sites prior to and/or concurrently with (e.g., within minutes or hours of each other) administration of a virus vector delivering a nucleic acid encoding a polypeptide or functional RNA of interest. For example, the inventive protein capsids can be delivered to block cellular receptors on liver cells and a delivery vector (e.g., an AAV vector) can be administered subsequently or concurrently, which may reduce transduction of liver cells, and enhance transduction of other targets (e.g., skeletal, cardiac and/or diaphragm muscle).

According to some embodiments, modified protein capsids can be administered to a subject prior to and/or concurrently with a modified virus vector as described herein. Further, the disclosure provides compositions and pharmaceutical formulations comprising the inventive modified protein capsids or capsid protein subunit thereof; optionally, the composition also comprises a modified virus vector as described herein.

In some embodiments, a nucleic acid (optionally, an isolated nucleic acid) encodes the modified protein capsid subunits described herein. Further provided are nucleic acids, and cells (in vivo or in culture) comprising the nucleic acids and/or virus vectors described herein. As one example, a virus vector may comprise: (a) a protein capsid comprising a modified AAV capsid protein subunit as described herein;

and (b) a nucleic acid comprising at least one terminal repeat sequence, wherein the nucleic acid is encapsidated by the AAV protein capsid.

Suitable viral vectors include, for example, adenovirus, AAV, herpesvirus, vaccinia, poxviruses, baculovirus, lentivirus, coronavirus, and the like. Suitable nucleic acids include, but are not limited to, plasmids, phage, YACs, BACs, and the like. Such nucleic acids and cells can be used, for example, as reagents (e.g., helper packaging constructs or packaging cells) for the production of modified virus protein capsids, protein capsid subunits, or virus vectors as described herein.

Protein capsids and capsid protein subunits described herein can be produced using any method known in the art, e.g., by using a baculovirus system (Brown et al., (1994) Virology 198:477-488).

The modifications to the AAV capsid protein subunit as described herein are "selective" modifications. This approach is in contrast to previous work with whole subunit or large domain swaps between AAV serotypes (see, e.g., international patent publication WO 00/28004 and Hauck et al., (2003) J. Virology 77:2768-2774). In some embodiments, a "selective" modification results in the insertion and/or substitution and/or deletion of less than or equal to about 20, 18, 15, 12, 10, 9, 8, 7, 6, 5, 4 or 3 contiguous amino acids.

The modified capsid protein subunits and protein capsids described herein can further comprise any other modification, now known or later identified. For example, the AAV capsid protein subunits and protein capsids can be chimeric in that they can comprise all or a portion of a capsid protein subunit from another virus, optionally another parvovirus or AAV, e.g., as described in international patent publication WO 00/28004.

In some embodiments, the protein capsid or capsid protein subunit can be a targeted protein capsid or capsid protein subunit, comprising a targeting sequence (e.g., substituted or inserted in the protein capsid or capsid protein subunit) that directs the protein capsid or capsid protein subunit to interact with cell-surface molecules present on desired target tissue(s) (see, e.g., International patent publication WO 00/28004 and Hauck et al., (2003) J. Virology 77:2768-2774); Shi et al., Human Gene Therapy 17:353-361 (2006) [describing insertion of the integrin receptor binding motif RGD at positions 520 and/or 584 of the AAV capsid protein subunit]; and U.S. Pat. No. 7,314,912 [describing insertion of the PI peptide containing an RGD motif following amino acid positions 447, 534, 573 and 587 of the AAV2 capsid protein subunit]). Other positions within the AAV capsid protein subunit that tolerate insertions are known in the art (e.g., positions 449 and 588 described by Grifman et al., Molecular Therapy 3:964-975 (2001)).

For example, a protein capsid or capsid protein subunit as described herein may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the protein capsid (or a capsid protein subunit thereof) a desired tropism and, optionally, selective tropism for particular tissue(s). AAV capsid protein subunits, protein capsids and AAV vectors comprising targeting sequences are described, for example in international patent publication WO 00/28004. As another example, one or more non-naturally occurring amino acids as described by Wang et al., Annu Rev Biophys Biomol Struct. 35:225-49 (2006)) can be incorporated into an AAV capsid protein subunit as described herein at an orthogonal site as a means of redirecting a low-transduction vector to desired target tissue(s). These unnatural amino acids can advantageously be used to chemically link molecules of interest to the AAV capsid protein subunit including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like.

In some embodiments, the targeting sequence may be a capsid protein subunit sequence (e.g., an autonomous parvovirus capsid sequence, AAV capsid protein subunit sequence, or any other viral capsid sequence) that directs infection to a particular cell type(s).

As another nonlimiting example, a heparin or heparan sulfate binding domain (e.g., the respiratory syncytial virus heparin binding domain) may be inserted or substituted into a capsid protein subunit that does not typically bind HS receptors (e.g., AAV4, AAV5) to confer heparin and/or heparan sulfate binding to the resulting mutant.

B19 infects primary erythroid progenitor cells using globoside as its receptor (Brown et al, (1993) Science 262: 114). The structure of B19 has been determined to 8 Å resolution (Agbandje-McKenna et al, (1994) Virology 203: 106). The region of the B19 capsid that binds to globoside has been mapped between amino acids 399-406 (Chapman et al, (1993) Virology 194:419), a looped out region between β-barrel structures E and F (Chipman et al, (1996) Proc. Nat. Acad. Sci. USA 93:7502). Accordingly, the globoside receptor binding domain of the B19 capsid may be substituted into an AAV capsid protein subunit to target a protein capsid or virus vector comprising the same to erythroid cells.

In some embodiments, the exogenous targeting sequence may be any amino acid sequence encoding a peptide that alters the tropism of a protein capsid or virus vector comprising the modified AAV capsid protein subunit. In some embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., a, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, alpha-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as alpha-bungarotoxin, and the like) can be substituted into the capsid protein subunit as a targeting sequence. In some embodiments, the AAV capsid protein subunit can be modified by substitution of a "nonclassical" import/export signal peptide (e.g., fibroblast growth factor-1 and -2, interleukin 1, HIV-1 Tat protein, herpes virus VP22 protein, and the like) as described by Cleves (Current Biology 7:R318 (1997)) into the AAV capsid protein subunit. Also encompassed are peptide motifs that direct uptake by specific cells, e.g., a FVFLP (SEQ ID NO: 22) peptide motif triggers uptake by liver cells.

Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC 1 glycoproteins, carbohydrate components found on membrane glycoproteins, including, mannose, N-acetyl-galactosamine, N-acetyl-glucosamine, fucose, galactose, and the like.

In some embodiments, a heparan sulfate (HS) or heparin binding domain is substituted into the capsid protein subunit (for example, in an AAV protein capsid subunit that otherwise does not bind to HS or heparin). It is known in the art that HS/heparin binding is mediated by a "basic patch" that is rich in arginines and/or lysines. In some embodiments, a sequence following the motif BXXB (SEQ ID NO: 23), where "B" is a basic residue and X is neutral and/or hydrophobic residue can be employed. As a nonlimiting example, BXXB can be RGNR (SEQ ID NO: 24). As another nonlimiting example, BXXB is substituted for amino acid positions 262 through 265 in the native AAV2 capsid protein subunit or at the corresponding position(s) in the capsid protein subunit of another AAV serotype.

Table 8 shows other non-limiting examples of suitable targeting sequences.

TABLE 8

TARGETING SEQUENCES

| Sequence | SEQ ID NO | Reference |
| --- | --- | --- |
| NSVRDL(G/S) | 25 | Muller et al., Nature Biotechnology 21: 1040-1046 (2003) |
| PRSVTVP | 26 | Muller et al., Nature Biotechnology 21: 1040-1046 (2003) |
| NSVSSX(S/A) | 27 | Muller et al., Nature Biotechnology 21: 1040-1046 (2003) |
| NGR, NGRAHA | 28 | Grifman et al., Molecular Therapy 3: 964-975 (2001) |
| QPEHSST | 29 | Work et al., Molecular Therapy 13: 683-693 (2006) |
| VNTANST | 30 | Work et al., Molecular Therapy 13: 683-693 (2006) |
| HGPMQS | 31 | Work et al., Molecular Therapy 13: 683-693 (2006) |
| PHKPPLA | 32 | Work et al., Molecular Therapy 13: 683-693 (2006) |
| IKNNEMW | 33 | Work et al., Molecular Therapy 13: 683-693 (2006) |
| RNLDTPM | 34 | Work et al., Molecular Therapy 13: 683-693 (2006) |
| VDSHRQS | 35 | Work et al., Molecular Therapy 13: 683-693 (2006) |
| YDSKTKT | 36 | Work et al., Molecular Therapy 13: 683-693 (2006) |
| SQLPHQK | 37 | Work et al., Molecular Therapy 13: 683-693 (2006) |
| STMQQNT | 38 | Work et al., Molecular Therapy 13: 683-693 (2006) |
| TERYMTQ | 39 | Work et al., Molecular Therapy 13: 683-693 (2006) |
| QPEHSST | 40 | Work et al., Molecular Therapy 13: 683-693 (2006) |
| DASLSTS | 41 | Work et al., Molecular Therapy 13: 683-693 (2006) |
| DLPNKT | 42 | Work et al., Molecular Therapy 13: 683-693 (2006) |
| DLTAARL | 43 | Work et al., Molecular Therapy 13: 683-693 (2006) |
| EPHQFNY | 44 | Work et al., Molecular Therapy 13: 683-693 (2006) |
| EPQSNHT | 45 | Work et al., Molecular Therapy 13: 683-693 (2006) |
| MSSWPSQ | 46 | Work et al., Molecular Therapy 13: 683-693 (2006) |
| NPKHNAT | 47 | Work et al., Molecular Therapy 13: 683-693 (2006) |
| PDGMRTT | 48 | Work et al., Molecular Therapy 13: 683-693 (2006) |
| PNNNKTT | 49 | Work et al., Molecular Therapy 13: 683-693 (2006) |
| QSTTHDS | 50 | Work et al., Molecular Therapy 13: 683-693 (2006) |

TABLE 8-continued

TARGETING SEQUENCES

| Sequence | SEQ ID NO | Reference |
|---|---|---|
| TGSKQKQ | 51 | Work et al., Molecular Therapy 13: 683-693 (2006) |
| SLKHQAL | 52 | Work et al., Molecular Therapy 13: 683-693 (2006) |
| SPIDGEQ | 53 | Work et al., Molecular Therapy 13: 683-693 (2006) |
| WIFPWIQL | 54 | Hajitou et al., TCM 16: 80-88 (2006) |
| CDCRGDCFC | 55 | Hajitou et al., TCM 16: 80-88 (2006) |
| CNGRC | 56 | Hajitou et al., TCM 16: 80-88 (2006) |
| CPRECES | 57 | Hajitou et al., TCM 16: 80-88 (2006) |
| CTTHWGFTLC | 58 | Hajitou et al., TCM 16: 80-88 (2006) |
| CGRRAGGSC | 59 | Hajitou et al., TCM 16: 80-88 (2006) |
| CKGGRAKDC | 60 | Hajitou et al., TCM 16: 80-88 (2006) |
| CVPELGHEC | 61 | Hajitou et al., TCM 16: 80-88 (2006) |
| CRRETAWAK | 62 | Koivunen et al., J. Nucl. Med. 40: 883-888 (1999) |
| VSWFSHRYSPFAVS | 63 | Koivunen et al., J. Nucl. Med. 40: 883-888 (1999) |
| GYRDGYAGPILYN | 64 | Koivunen et al., J. Nucl. Med. 40: 883-888 (1999) |
| XXXY*XXX | 65 | Koivunen et al., J. Nucl. Med. 40: 883-888 (1999) |
| Y*E/MNW | 66 | Koivunen et al., J. Nucl. Med. 40: 883-888 (1999) |
| RPLPPLP | 67 | Koivunen et al., J. Nucl. Med. 40: 883-888 (1999) |
| APPLPPR | 68 | Koivunen et al., J. Nucl. Med. 40: 883-888 (1999) |
| DVFYPYPYASGS | 69 | Koivunen et al., J. Nucl. Med. 40: 883-888 (1999) |
| MYWYPY | 70 | Koivunen et al., J. Nucl. Med. 40: 883-888 (1999) |
| DITWDQLWDLMK | 71 | Koivunen et al., J. Nucl. Med. 40: 883-888 (1999) |
| CWDD(G/L)WLC | 72 | Koivunen et al., J. Nucl. Med. 40: 883-888 (1999) |
| EWCEYLGGYLRCYA | 73 | Koivunen et al., J. Nucl. Med. 40: 883-888 (1999) |
| YXCXXGPXTWXCXP | 74 | Koivunen et al., J. Nucl. Med. 40: 883-888 (1999) |
| IEGPTLRQWLAARA | 75 | Koivunen et al., J. Nucl. Med. 40: 883-888 (1999) |
| LWXX(Y/W/F/H) | 76 | Koivunen et al., J. Nucl. Med. 40: 883-888 (1999) |
| XFXXYLW | 77 | Koivunen et al., J. Nucl. Med. 40: 883-888 (1999) |
| RWGLCD | 78 | Koivunen et al., J. Nucl. Med. 40: 883-888 (1999) |
| MSRPACPPNDKYE | 79 | Koivunen et al., J. Nucl. Med. 40: 883-888 (1999) |
| CLRSGRGC | 80 | Koivunen et al., J. Nucl. Med. 40: 883-888 (1999) |
| CHWMFSPWC | 81 | Koivunen et al., J. Nucl. Med. 40: 883-888 (1999) |
| WXXF | 82 | Koivunen et al., J. Nucl. Med. 40: 883-888 (1999) |
| CSSRLDAC | 83 | Koivunen et al., J. Nucl. Med. 40: 883-888 (1999) |
| CLPVASC | 84 | Koivunen et al., J. Nucl. Med. 40: 883-888 (1999) |
| CGFECVRQCPERC | 85 | Koivunen et al., J. Nucl. Med. 40: 883-888 (1999) |
| CVALCREACGEGC | 86 | Koivunen et al., J. Nucl. Med. 40: 883-888 (1999) |

TABLE 8-continued

TARGETING SEQUENCES

| Sequence | SEQ ID NO | Reference |
|---|---|---|
| SWCEPGWCR | 87 | Koivunen et al., J. Nucl. Med. 40: 883-888 (1999) |
| YSGWGW | 88 | Koivunen et al., J. Nucl. Med. 40: 883-888 (1999) |
| GLSGGRS | 89 | Koivunen et al., J. Nucl. Med. 40: 883-888 (1999) |
| LMLPRAD | 90 | Koivunen et al., J. Nucl. Med. 40: 883-888 (1999) |
| CSCFRDVCC | 91 | Koivunen et al., J. Nucl. Med. 40: 883-888 (1999) |
| CRDVVSVIC | 92 | Koivunen et al., J. Nucl. Med. 40: 883-888 (1999) |
| CNGRC | 93 | Koivunen et al., J. Nucl. Med. 40: 883-888 (1999) |
| MARSGL | 94 | Newton & Deutscher, Phage Peptide Display in Handbook of Experimental Pharmacology, pages 145-163, Springer-Verlag, Berlin (2008) |
| MARAKE | 95 | Newton & Deutscher, Phage Peptide Display in Handbook of Experimental Pharmacology, pages 145-163, Springer-Verlag, Berlin (2008) |
| MSRTMS | 96 | Newton & Deutscher, Phage Peptide Display in Handbook of Experimental Pharmacology, pages 145-163, Springer-Verlag, Berlin (2008) |
| KCCYSL | 97 | Newton & Deutscher, Phage Peptide Display in Handbook of Experimental Pharmacology, pages 145-163, Springer-Verlag, Berlin (2008) |
| MYWGDSHWLQYWYE | 98 | Newton & Deutscher, Phage Peptide Display in Handbook of Experimental Pharmacology, pages 145-163, Springer-Verlag, Berlin (2008) |
| MQLPLAT | 99 | Newton & Deutscher, Phage Peptide Display in Handbook of Experimental Pharmacology, pages 145-163, Springer-Verlag, Berlin (2008) |
| EWLS | 100 | Newton & Deutscher, Phage Peptide Display in Handbook of Experimental Pharmacology, pages 145-163, Springer-Verlag, Berlin (2008) |
| SNEW | 101 | Newton & Deutscher, Phage Peptide Display in Handbook of Experimental Pharmacology, pages 145-163, Springer-Verlag, Berlin (2008) |
| TNYL | 102 | Newton & Deutscher, Phage Peptide Display in Handbook of Experimental Pharmacology, pages 145-163, Springer-Verlag, Berlin (2008) |
| WIFPWIQL | 103 | Newton & Deutscher, Phage Peptide Display in Handbook of Experimental Pharmacology, pages 145-163, Springer-Verlag, Berlin (2008) |
| WDLAWMFRLPVG | 104 | Newton & Deutscher, Phage Peptide Display in Handbook of Experimental Pharmacology, pages 145-163, Springer-Verlag, Berlin (2008) |
| CTVALPGGYVRVC | 105 | Newton & Deutscher, Phage Peptide Display in Handbook of Experimental Pharmacology, pages 145-163, Springer-Verlag, Berlin (2008) |
| CVPELGHEC | 106 | Newton & Deutscher, Phage Peptide Display in Handbook of Experimental Pharmacology, pages 145-163, Springer-Verlag, Berlin (2008) |
| CGRRAGGSC | 107 | Newton & Deutscher, Phage Peptide Display in Handbook of Experimental Pharmacology, pages 145-163, Springer-Verlag, Berlin (2008) |
| CVAYCIEHHCWTC | 108 | Newton & Deutscher, Phage Peptide Display in Handbook of Experimental Pharmacology, pages 145-163, Springer-Verlag, Berlin (2008) |

TABLE 8-continued

TARGETING SEQUENCES

| Sequence | SEQ ID NO | Reference |
|---|---|---|
| CVFAHNYDYLVC | 109 | Newton & Deutscher, Phage Peptide Display in Handbook of Experimental Pharmacology, pages 145-163, Springer-Verlag, Berlin (2008) |
| CVFTSNYAFC | 110 | Newton & Deutscher, Phage Peptide Display in Handbook of Experimental Pharmacology, pages 145-163, Springer-Verlag, Berlin (2008) |
| VHSPNKK | 111 | Newton & Deutscher, Phage Peptide Display in Handbook of Experimental Pharmacology, pages 145-163, Springer-Verlag, Berlin (2008) |
| CDCRGDCFC | 112 | Newton & Deutscher, Phage Peptide Display in Handbook of Experimental Pharmacology, pages 145-163, Springer-Verlag, Berlin (2008) |
| CRGDGWC | 113 | Newton & Deutscher, Phage Peptide Display in Handbook of Experimental Pharmacology, pages 145-163, Springer-Verlag, Berlin (2008) |
| XRGCDX | 114 | Newton & Deutscher, Phage Peptide Display in Handbook of Experimental Pharmacology, pages 145-163, Springer-Verlag, Berlin (2008) |
| PXX(S/T) | 115 | Newton & Deutscher, Phage Peptide Display in Handbook of Experimental Pharmacology, pages 145-163, Springer-Verlag, Berlin (2008) |
| CTTHWGFTLC | 116 | Newton & Deutscher, Phage Peptide Display in Handbook of Experimental Pharmacology, pages 145-163, Springer-Verlag, Berlin (2008) |
| SGKGPRQITAL | 117 | Newton & Deutscher, Phage Peptide Display in Handbook of Experimental Pharmacology, pages 145-163, Springer-Verlag, Berlin (2008) |
| A(A/Q)(N/A)(L/Y)(T/V/M/R)(R/K) | 118 | Newton & Deutscher, Phage Peptide Display in Handbook of Experimental Pharmacology, pages 145-163, Springer-Verlag, Berlin (2008) |
| VYMSPF | 119 | Newton & Deutscher, Phage Peptide Display in Handbook of Experimental Pharmacology, pages 145-163, Springer-Verlag, Berlin (2008) |
| MQLPLAT | 120 | Newton & Deutscher, Phage Peptide Display in Handbook of Experimental Pharmacology, pages 145-163, Springer-Verlag, Berlin (2008) |
| ATWLPPR | 121 | Newton & Deutscher, Phage Peptide Display in Handbook of Experimental Pharmacology, pages 145-163, Springer-Verlag, Berlin (2008) |
| HTMYYHHYQHHL | 122 | Newton & Deutscher, Phage Peptide Display in Handbook of Experimental Pharmacology, pages 145-163, Springer-Verlag, Berlin (2008) |
| SEVGCRAGPLQWLCEKYFG | 123 | Newton & Deutscher, Phage Peptide Display in Handbook of Experimental Pharmacology, pages 145-163, Springer-Verlag, Berlin (2008) |
| CGLLPVGRPDRNVWRWLC | 124 | Newton & Deutscher, Phage Peptide Display in Handbook of Experimental Pharmacology, pages 145-163, Springer-Verlag, Berlin (2008) |
| CKGQCDRFKGLPWEC | 125 | Newton & Deutscher, Phage Peptide Display in Handbook of Experimental Pharmacology, pages 145-163, Springer-Verlag, Berlin (2008) |
| SGRSA | 126 | Newton & Deutscher, Phage Peptide Display in Handbook of Experimental Pharmacology, pages 145-163, Springer-Verlag, Berlin (2008) |
| WGFP | 127 | Newton & Deutscher, Phage Peptide Display in Handbook of Experimental Pharmacology, pages 145-163, Springer-Verlag, Berlin (2008) |

TABLE 8-continued

TARGETING SEQUENCES

| Sequence | SEQ ID NO | Reference |
|---|---|---|
| LWXXAr | 128 | Newton & Deutscher, Phage Peptide Display in Handbook of Experimental Pharmacology, pages 145-163, Springer-Verlag, Berlin (2008) |
| XFXXYLW | 129 | Newton & Deutscher, Phage Peptide Display in Handbook of Experimental Pharmacology, pages 145-163, Springer-Verlag, Berlin (2008) |
| AEPMPHSLNFSQYLWYT | 130 | Newton & Deutscher, Phage Peptide Display in Handbook of Experimental Pharmacology, pages 145-163, Springer-Verlag, Berlin (2008) |
| WAY(W/F)SP | 131 | Newton & Deutscher, Phage Peptide Display in Handbook of Experimental Pharmacology, pages 145-163, Springer-Verlag, Berlin (2008) |
| IELLQAR | 132 | Newton & Deutscher, Phage Peptide Display in Handbook of Experimental Pharmacology, pages 145-163, Springer-Verlag, Berlin (2008) |
| DITWDQLWDLMK | 133 | Newton & Deutscher, Phage Peptide Display in Handbook of Experimental Pharmacology, pages 145-163, Springer-Verlag, Berlin (2008) |
| AYTKCSRQWRTCMTTH | 134 | Newton & Deutscher, Phage Peptide Display in Handbook of Experimental Pharmacology, pages 145-163, Springer-Verlag, Berlin (2008) |
| PQNSKIPGPTFLDPH | 135 | Newton & Deutscher, Phage Peptide Display in Handbook of Experimental Pharmacology, pages 145-163, Springer-Verlag, Berlin (2008) |
| SMEPALPDVVWWKMFK | 136 | Newton & Deutscher, Phage Peptide Display in Handbook of Experimental Pharmacology, pages 145-163, Springer-Verlag, Berlin (2008) |
| ANTPCGPYTHDCPVKR | 137 | Newton & Deutscher, Phage Peptide Display in Handbook of Experimental Pharmacology, pages 145-163, Springer-Verlag, Berlin (2008) |
| TACHQHVRMVRP | 138 | Newton & Deutscher, Phage Peptide Display in Handbook of Experimental Pharmacology, pages 145-163, Springer-Verlag, Berlin (2008) |
| VPWMEPAYQRFL | 139 | Newton & Deutscher, Phage Peptide Display in Handbook of Experimental Pharmacology, pages 145-163, Springer-Verlag, Berlin (2008) |
| DPRATPGS | 140 | Newton & Deutscher, Phage Peptide Display in Handbook of Experimental Pharmacology, pages 145-163, Springer-Verlag, Berlin (2008) |
| FRPNRAQDYNTN | 141 | Newton & Deutscher, Phage Peptide Display in Handbook of Experimental Pharmacology, pages 145-163, Springer-Verlag, Berlin (2008) |
| CTKNSYLMC | 142 | Newton & Deutscher, Phage Peptide Display in Handbook of Experimental Pharmacology, pages 145-163, Springer-Verlag, Berlin (2008) |
| C(R/Q)L/RT(G/N)XXG(A/V)GC | 143 | Newton & Deutscher, Phage Peptide Display in Handbook of Experimental Pharmacology, pages 145-163, Springer-Verlag, Berlin (2008) |
| CPIEDRPMC | 144 | Newton & Deutscher, Phage Peptide Display in Handbook of Experimental Pharmacology, pages 145-163, Springer-Verlag, Berlin (2008) |
| HEWSYLAPYPWF | 145 | Newton & Deutscher, Phage Peptide Display in Handbook of Experimental Pharmacology, pages 145-163, Springer-Verlag, Berlin (2008) |

TABLE 8-continued

TARGETING SEQUENCES

| Sequence | SEQ ID NO | Reference |
|---|---|---|
| MCPKHPLGC | 146 | Newton & Deutscher, Phage Peptide Display in Handbook of Experimental Pharmacology, pages 145-163, Springer-Verlag, Berlin (2008) |
| RMWPSSTVNLSAGRR | 147 | Newton & Deutscher, Phage Peptide Display in Handbook of Experimental Pharmacology, pages 145-163, Springer-Verlag, Berlin (2008) |
| SAKTAVSQRVWLPSHRGGEP | 148 | Newton & Deutscher, Phage Peptide Display in Handbook of Experimental Pharmacology, pages 145-163, Springer-Verlag, Berlin (2008) |
| KSREHVNNSACPSKRITAAL | 149 | Newton & Deutscher, Phage Peptide Display in Handbook of Experimental Pharmacology, pages 145-163, Springer-Verlag, Berlin (2008) |
| EGFR | 150 | Newton & Deutscher, Phage Peptide Display in Handbook of Experimental Pharmacology, pages 145-163, Springer-Verlag, Berlin (2008) |
| AGLGVR | 151 | Newton & Deutscher, Phage Peptide Display in Handbook of Experimental Pharmacology, pages 145-163, Springer-Verlag, Berlin (2008) |
| GTRQGHTMRLGVSDG | 152 | Newton & Deutscher, Phage Peptide Display in Handbook of Experimental Pharmacology, pages 145-163, Springer-Verlag, Berlin (2008) |
| IAGLATPGWSHWLAL | 153 | Newton & Deutscher, Phage Peptide Display in Handbook of Experimental Pharmacology, pages 145-163, Springer-Verlag, Berlin (2008) |
| SMSIARL | 154 | Newton & Deutscher, Phage Peptide Display in Handbook of Experimental Pharmacology, pages 145-163, Springer-Verlag, Berlin (2008) |
| HTFEPGV | 155 | Newton & Deutscher, Phage Peptide Display in Handbook of Experimental Pharmacology, pages 145-163, Springer-Verlag, Berlin (2008) |
| NTSLKRISNKR1RRK | 156 | Newton & Deutscher, Phage Peptide Display in Handbook of Experimental Pharmacology, pages 145-163, Springer-Verlag, Berlin (2008) |
| LRIKRKRRKRKKTRK | 157 | Newton & Deutscher, Phage Peptide Display in Handbook of Experimental Pharmacology, pages 145-163, Springer-Verlag, Berlin (2008) |

Y* is phospho-Tyr

In some embodiments, the targeting sequence may be a peptide that can be used for chemical coupling (e.g., can comprise arginine and/or lysine residues that can be chemically coupled through their R groups) to another molecule that targets entry into a cell.

In some embodiments, the AAV capsid protein subunit or protein capsid can comprise a mutation as described in WO 2006/066066. For example, the capsid protein subunit can comprise a selective amino acid substitution at amino acid position 263, 705, 708 and/or 716 of the native AAV2 capsid protein subunit or a corresponding change(s) in a capsid protein subunit from another AAV serotype.

Additionally, or alternatively, in some embodiments, the capsid protein subunit, protein capsid or viral vector comprises a selective amino acid insertion directly following amino acid position 264 of the AAV2 capsid protein subunit or a corresponding change in the capsid protein subunit from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.).

Furthermore, in some embodiments, the capsid protein subunit, protein capsid or viral vector can comprise amino acid modifications such as described in PCT Publication No. WO 2010/093784 (e.g., 2i8) and/or in PCT Publication No. WO 2014/144229 (e.g., dual glycan).

In some embodiments, the capsid protein subunit, protein capsid or viral vector can have equivalent or enhanced transduction efficiency relative to the transduction efficiency of the AAV serotype from which the capsid protein subunit, protein capsid or viral vector originated. In some embodiments, the capsid protein subunit, protein capsid or viral vector can have reduced transduction efficiency relative to the transduction efficiency of the AAV serotype from which the capsid protein subunit, protein capsid or viral vector originated. In some embodiments, the capsid protein subunit, protein capsid or viral vector can have equivalent or enhanced tropism relative to the tropism of the AAV serotype from which the capsid protein subunit, protein capsid or viral vector originated. In some embodiments, the capsid protein subunit, protein capsid or viral vector can have an altered or different tropism relative to the tropism of the AAV serotype from which the capsid protein subunit, protein capsid or viral vector originated. In some embodiments, the capsid protein subunit, protein capsid or viral vector can have or be engineered to have tropism for brain tissue. In some embodiments, the capsid protein subunit, protein capsid or viral vector can have or be engineered to have tropism for liver tissue.

The AAV vectors described herein can be used to deliver a heterologous nucleic acid to a cell or subject. For example, the modified vector can be used to treat a lysosomal storage disorder such as a mucopolysaccharidosis disorder (e.g., Sly syndrome [β-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome (A [heparan sulfamidase], B [N-acetylglucosam inidase], C [acetyl-CoA:alpha-glucosaminide acetyltransferase], D [N-acetylglucosamine 6-sulfatase]), Morquio Syndrome (A [galactose-6-sulfate sulfatase], B [β-galactosidase]), Maroteaux-Lamy Syndrome [N-acetylgalactosamine-4-sulfatase], etc.), Fabry disease (a-galactosidase), Gaucher's disease (glucocerebrosidase), or a glycogen storage disorder (e.g., Pompe disease; lysosomal acid alpha-glucosidase) as described herein.

Those skilled in the art will appreciate that for some AAV capsid protein subunits, the corresponding modification will be an insertion and/or a substitution, depending on whether the corresponding amino acid positions are partially or completely present in the virus or, alternatively, are completely absent.

In some embodiments, virus vectors comprise the modified capsid protein subunits and protein capsids described herein. In some embodiments, the virus vector is a parvovirus vector (e.g., comprising a parvovirus protein capsid and/or vector genome), for example, an AAV vector (e.g., comprising an AAV protein capsid and/or vector genome). In some embodiments, the virus vector comprises a modified AAV protein capsid comprising a modified capsid protein subunit as described herein and a vector genome.

For example, in some embodiments, the virus vector comprises: (a) a modified protein capsid (e.g., a modified AAV protein capsid) comprising a modified capsid protein subunit described herein; and (b) a nucleic acid comprising a terminal repeat sequence (e.g., an AAV TR), wherein the nucleic acid comprising the terminal repeat sequence is encapsidated by the modified protein capsid. The nucleic acid can optionally comprise two terminal repeats (e.g., two AAV TRs).

In some embodiments, the virus vector is a recombinant virus vector comprising a heterologous nucleic acid encoding a polypeptide or functional RNA of interest. Recombinant virus vectors are described in more detail below.

In some embodiments, the virus vectors (i) have reduced transduction of liver as compared with the level of transduction by a virus vector without the modified capsid protein subunit; (ii) exhibit enhanced systemic transduction by the virus vector in an animal subject as compared with the level observed by a virus vector without the modified capsid protein subunit; (iii) demonstrate enhanced movement across endothelial cells as compared with the level of movement by a virus vector without the modified capsid protein subunit, and/or (iv) exhibit a selective enhancement in transduction of muscle tissue (e.g., skeletal muscle, cardiac muscle and/or diaphragm muscle), (v) exhibit a selective enhancement in transduction of liver tissue, and/or (vi) reduced transduction of brain tissues (e.g., neurons) as compared with the level of transduction by a virus vector without the modified capsid protein subunit. In some embodiments, the virus vector has systemic transduction toward liver.

In some embodiments, an adeno-associated virus (AAV) vector comprises: (i) a protein capsid comprising a capsid protein subunit comprising the sequence of SEQ ID NO: 180 or 175; and (ii) a transfer cassette encapsidated by the protein capsid; wherein the transfer cassette comprises from 5' to 3': a 5' inverted terminal repeat (ITR); a promoter; a transgene which encodes the NPC1 protein; a polyadenylation signal; and a 3' ITR. In some embodiments, the capsid protein subunit comprises the sequence of SEQ ID NO: 180. In some embodiments, the capsid protein subunit comprises the sequence of SEQ ID NO: 175.

In some embodiments, an adeno-associated virus (AAV) vector comprises: (i) a protein capsid comprising a capsid protein subunit comprising the sequence of SEQ ID NO: 180 or 175, or a sequence comprising about 1 to about 25 amino acid mutations relative to SEQ ID NO: 180 or 175; and (ii) a transfer cassette encapsidated by the protein capsid; wherein the transfer cassette comprises from 5' to 3':a 5' inverted terminal repeat (ITR); a promoter; a transgene which encodes the NPC1 protein; a polyadenylation signal; and a 3' ITR. In some embodiments, the capsid protein subunit comprises 1, 2, 3, 4, 5, 6, 7, 8, 9, 10, 11, 12, 13, 14, 15, 16, 17, 18, 19, 20, 21, 22, 23, 24, 25, or more amino acid mutations relative to SEQ ID NO: 180 or 175.

In some embodiments, at least one of the 5' ITR and the 3' ITR is about 110 to about 160 nucleotides in length. In some embodiments, the 5' ITR is the same length as the 3' ITR. In some embodiments the 5' ITR and the 3' ITR have different lengths. In some embodiments, at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, the 5' ITR comprises the sequence of SEQ ID NO: 3003. In some embodiments, the 3' ITR comprises the sequence of SEQ ID NO: 3004.

In some embodiments, the promoter is a constitutive promoter. In some embodiments, the promoter is an inducible promoter. In some embodiments, the promoter is a tissue-specific promoter. In some embodiments, the promoter is selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the dihydrofolate reductase (DHFR) promoter, and the phosphoglycerol kinase (PGK) promoter. In some embodiments, the promoter is selected from the group consisting of the CBA promoter, the GUSB240 promoter, the GUSB379 promoter, and the HSVTK promoter. In some embodiments, the promoter comprises a sequence at least 95% or 100% identical to any one of SEQ ID NO: 3005, SEQ ID NO: 3006, SEQ ID NO: 3007, or SEQ ID NO: 3008.

In some embodiments, the NPC1 protein is the human NPC1 protein. In some embodiments, the NPC1 protein has a sequence that is at least 90% identical to the sequence of the human NPC1 protein. In some embodiments, the NPC1 protein has a sequence that is at least 95% identical to the sequence of the human NPC1 protein. In some embodiments, the NPC1 protein has a sequence that is at least 98% identical to the sequence of the human NPC1 protein. In some embodiments, the NPC1 protein comprises the sequence of SEQ ID NO: 3001.

In some embodiments, the transgene comprises the sequence of SEQ ID NO: 3002.

In some embodiments, the polyadenylation signal is selected from simian virus 40 (SV40), rBG, α-globin, β-globin, human collagen, human growth hormone (hGH), polyoma virus, human growth hormone (hGH) and bovine growth hormone (bGH). In some embodiments, the polyadenylation signal is the SV40 polyadenylation signal. In some embodiments, the polyadenylation signal is the rBG polyadenylation signal.

In some embodiments, the polyadenylation signal comprises the sequence at least 95% or 100% identical to SEQ ID NO: 3012 or to SEQ ID NO: 3013.

In some embodiments, the transfer cassette further comprises an enhancer. In some embodiments, the enhancer is the CMV enhancer. In some embodiments, the enhancer comprises the sequence of SEQ ID NO: 3009, or a sequence at least 95% identical thereto.

In some embodiments, the transfer cassette further comprises an intronic sequence. In some embodiments, the intronic sequence is a chimeric sequence.

In some embodiments, the intronic sequence is a hybrid sequence. In some embodiments, the intronic sequence comprises a sequence isolated or derived from SV40. In some embodiments, the intronic sequence comprises the sequence of any one of SEQ ID NO: 3010-3011. In some embodiments, the AAV transfer cassette comprises the sequence of any one of SEQ ID NO: 3014-3019.

It will be understood by those skilled in the art that the modified capsid protein subunits, protein capsids and virus vectors described herein exclude those capsid protein subunits, protein capsids and virus vectors that have the indicated amino acids at the specified positions in their native state (i.e., are not mutants).

AAV Transfer Cassettes

Described herein are AAV transfer cassettes, nucleic acids and plasmids used in the production of recombinant adeno-associated viral (rAAV) vectors. The disclosed cassettes, nucleic acids and plasmids comprise sequences that may be used to express one or more transgenes having therapeutic efficacy in the amelioration, treatment and/or prevention of one or more diseases or disorders.

In some embodiments, the AAV transfer cassettes comprise a 5' inverted terminal repeat (ITR); a transgene; and a 3' ITR. In some embodiments, the AAV transfer cassettes comprise a 5' ITR, a promoter, a transgene, and a 3' ITR. In some embodiments, the AAV transfer cassettes comprise a 5' ITR, a promoter, a transgene, a polyadenylation sequence and a 3' ITR. In some embodiments, the AAV transfer cassettes comprise a 5' ITR, a promoter, a transgene, a polyadenylation sequence and a 3' ITR; wherein the transfer cassette comprises an intronic sequence. In some embodiments, the AAV transfer cassettes comprise a 5' ITR, a promoter, an intronic sequence, a transgene, a polyadenylation sequence and a 3' ITR. In some embodiments, wherein the transgene encodes the NPC1 protein, or a fragment or variant thereof.

Inverted Terminal Repeat

Inverted Terminal Repeat or ITR sequences are sequences that mediate AAV proviral integration and for packaging of AAV DNA into virions. ITRs are involved in a variety of activities in the AAV life cycle. For example, the ITR sequences, which can form a hairpin structure, play roles in excision from the plasmid after transfection, replication of the vector genome, and integration and rescue from a host cell genome.

The AAV transfer cassettes of the disclosure may comprise a 5' ITR and a 3' ITR. The ITR sequences may be about 110 to about 160 nucleotides in length, for example 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159 or 160 nucleotides in length. In some embodiments, the ITR sequences may be about 141 nucleotides in length. In some embodiments, the 5' ITR is the same length as the 3' ITR. In some embodiments, the 5' ITR and the 3' ITR have different lengths. In some embodiments, the 5' ITR is longer than the 3' ITR, and in other embodiments, the 3' ITR is longer than the 5' ITR.

The ITRs may be isolated or derived from the genome of any AAV, for example the AAVs listed in Table 1. In some embodiments, at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV. In some embodiments, at least one of the 5' ITR and the 3'ITR may be a wildtype or mutated ITR isolated derived from a member of another parvovirus species besides AAV. For example, in some embodiments, an ITR may be a wildtype or mutant ITR isolated or derived from bocavirus or parvovirus B19.

In some embodiments, the ITR comprises a modification to promote production of a scAAV. In some embodiments, the modification to promote production of a scAAV is deletion of the terminal resolution sequence (TRS) from the ITR. In some embodiments, the 5' ITR is a wildtype ITR, and the 3' ITR is a mutated ITR lacking the terminal resolution sequence. In some embodiments, the 3' ITR is a wildtype ITR, and the 5' ITR is a mutated ITR lacking the terminal resolution sequence. In some embodiments, the terminal resolution sequence is absent from both the 5' ITR and the 3'ITR. In other embodiments, the modification to promote production of a scAAV is replacement of an ITR with a different hairpin-forming sequence, such as a shRNA-forming sequence.

In some embodiments, the 5' ITR may comprise the sequence of SEQ ID NO: 3003, or a sequence at least 95% identical thereto. In some embodiments, the 3' ITR may comprise the sequence of SEQ ID NO: 3004, or a sequence at least 95% identical thereto. In some embodiments, the 5' ITR comprises the sequence of SEQ ID NO: 3003, and the 3' ITR comprises the sequence of SEQ ID NO: 3004.

In some embodiments, the AAV transfer cassettes comprise one or more "surrogate" ITRs, i.e., non-ITR sequences that serve the same function as ITRs. See, e.g., Xie, J. et al., Mol. Ther., 25(6): 1363-1374 (2017). In some embodiments, an ITR in an AAV transfer cassette is replaced by a surrogate ITR. In some embodiments, the surrogate ITR comprises a hairpin-forming sequence. In some embodiments, the surrogate ITR is a short hairpin (sh)RNA-forming sequence.

Promoters, Enhancers, Repressors and Other Regulatory Sequences

Gene expression may be controlled by nucleotide sequences called promoters and enhancers that flank the coding region for a given protein.

As used herein, the term "promoter" refers to one or more nucleic acid control sequences that direct transcription of an operably linked nucleic acid. Promoters may include nucleic acid sequences near the start site of transcription, such as a TATA element. Promoters may also include cis-acting polynucleotide sequences that can be bound by transcription factors.

A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

Gene expression may also be controlled by one or more distal "enhancer" or "repressor" elements, which can be located as much as several thousand base pairs from the start site of transcription. Enhancer or repressor elements regulate transcription in an analogous manner to cis-acting elements near the start site of transcription, with the exception that enhancer elements can act from a distance from the start site of transcription.

In some embodiments, the AAV transfer cassettes described herein comprise a promoter. They promoter may be, for example, a constitutive promoter or an inducible promoter. In some embodiments, the promoter is a tissue-specific promoter.

Exemplary promoters that may be used in the AAV transfer cassettes described herein include the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the dihydrofolate reductase (DHFR) promoter, and the phosphoglycerol kinase (PGK) promoter. In some embodiments, the promoter is selected from the group consisting of the chicken β-actin (CBA) promoter the EF-1 alpha promoter, and the EF-1 alpha short promoter. In some embodiments, the promoter comprises a sequence selected from any one of SEQ ID NO: 3005-3008, or a sequence at least 95% identical thereto.

In some embodiments, the AAV transfer cassettes described herein comprise an enhancer. The enhancer may be, for example, the CMV enhancer. In some embodiments, the enhancer comprises the sequence of SEQ ID NO: 3009, or a sequence at least 95% identical thereto.

A non-limiting list of exemplary tissue-specific promoters and enhancers that may be used in the AAV transfer cassettes described herein includes: HMG-COA reductase promoter; sterol regulatory element 1 (SRE-1); phosphoenol pyruvate carboxy kinase (PEPCK) promoter; human C-reactive protein (CRP) promoter; human glucokinase promoter; cholesterol 7-alpha hydroylase (CYP-7) promoter; beta-galactosidase alpha-2,6 sialyltransferase promoter; insulin-like growth factor binding protein (IGFBP-1) promoter; aldolase B promoter; human transferrin promoter; collagen type I promoter; prostatic acid phosphatase (PAP) promoter; prostatic secretory protein of 94 (PSP 94) promoter; prostate specific antigen complex promoter; human glandular kallikrein gene promoter (hgt-1); the myocyte-specific enhancer binding factor MEF-2; muscle creatine kinase promoter; pancreatitis associated protein promoter (PAP); elastase 1 transcriptional enhancer; pancreas specific amylase and elastase enhancer promoter; pancreatic cholesterol esterase gene promoter; uteroglobin promoter; cholesterol side-chain cleavage (SCC) promoter; gamma-gamma enolase (neuron-specific enolase, NSE) promoter; neurofilament heavy chain (NF-H) promoter; human CGL-1/granzyme B promoter; the terminal deoxy transferase (TdT), lambda 5, VpreB, and lck (lymphocyte specific tyrosine protein kinase p561ck) promoter; the humans CD2 promoter and its 3' transcriptional enhancer; the human NK and T cell specific activation (NKGS) promoter; pp60c-src tyrosine kinase promoter; organ-specific neoantigens (OSNs), mw 40 kDa (p40) promoter; colon specific antigen-P promoter; human alpha-lactalbumin promoter; phosphoeholpyruvate carboxykinase (PEPCK) promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, alpha or beta globin promoter, T-cell receptor promoter, the osteocalcin promoter the IL-2 promoter, IL-2 receptor promoter, whey (wap) promoter, and the MHC Class II promoter.

Transgene

The AAV transfer cassettes described herein comprise a transgene for expression in a target cell.

The transgene may be any heterologous nucleic acid sequence(s) of interest. Such nucleic acids may include nucleic acids encoding polypeptides, including therapeutic (e.g., for medical or veterinary uses) or immunogenic (e.g., for vaccines) polypeptides or RNAs. Alternatively, the nucleic acid may encode an antisense nucleic acid, a ribozyme, RNAs that effect spliceosome-mediated/ramsplicing, interfering RNAs (RNAi) including siRNA, shRNA or miRNA that mediate gene silencing, and other non-translated RNAs. In some embodiments, the nucleic acid sequence may direct gene editing. For example, the nucleic acid may encode a gene-editing molecule such as a guide RNA or a nuclease. In some embodiments, the nucleic acid may encode a zinc-finger nuclease, a homing endonuclease, a TALEN (transcription activator-like effector nuclease), a NgAgo (agronaute endonuclease), a SGN (structure-guided endonuclease), or a RGN (RNA-guided nuclease) such as a Cas9 nuclease or a Cpf1 nuclease. In some embodiments, the nucleic acid may share homology with and recombine with a locus on a host chromosome. This approach can be utilized, for example, to correct a genetic defect in the host cell.

The virus vectors according to the present disclosure provide a means for delivering transgenes into a broad range of cells, including dividing and non-dividing cells. The virus vectors can be employed to deliver a transgene to a cell in vitro, e.g., to produce a polypeptide in vitro or for ex vivo gene therapy. The virus vectors are additionally useful in a method of delivering a transgene to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect. As used herein, the term "functional RNA" refers to any non-coding RNA sequence that has one or more functions in a cell, such as those described in the preceding paragraph.

The virus vectors can also be used to deliver nucleic acids for the production of a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present disclosure can be employed to deliver a transgene encoding a polypeptide or functional RNA to treat and/or prevent any disease state for which it is beneficial to deliver a therapeutic polypeptide or functional RNA.

In some embodiments, the transgene is useful for treating NPC1. In some embodiments, the transgene encodes the NPC1 protein. The NPC1 protein may be, for example, the human NPC1 protein. In some embodiments, the NPC1 protein has a sequence that is at least 90% identical, at least 95% identical, or at least 98% identical to the sequence of the human NPC1 protein. In some embodiments, the NPC1 protein comprises one or more of the single nucleotide changes listed in the Table 9 (numbering based on SEQ ID NO: 3001 or 3020). In some embodiments, the NPC1 protein is a truncated form of the human NPC1 protein. In some embodiments, the NPC1 protein comprises the sequence of SEQ ID NO: 3001, or a sequence at least 90% identical, at least 95% identical, at least 96% identical, at least 97% identical, at least 98% identical, or at least 99% identical thereto. In some embodiments, the NPC1 protein comprises the sequence of SEQ ID NO: 3020, or a sequence at least 90% identical, at least 95% identical, at least 96% identical, at least 97% identical, at least 98% identical, or at least 99% identical thereto. In some embodiments, the NPC1 protein comprises the sequence of SEQ ID NO: 3001 or 3020, with one or more of the single nucleotide changes listed in Table 9. In some embodiments, the NPC1 protein (Niemann-Pick intracellular cholesterol transporter 1) has a sequence as shown in UniProt Accession No. 015118, incorporated herein by reference in its entirety.

In some embodiments, the transgene comprises the sequence of SEQ ID NO: 3002, or a sequence at least 90% identical, at least 95% identical, at least 96% identical, at least 97% identical, at least 98% identical, or at least 99% identical thereto. In some embodiments, the transgene comprises the sequence of SEQ ID NO: 3002, or a sequence with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more nucleic acid changes relative thereto. In some embodiments, the transgene encodes the amino acid sequence of SEQ ID NO: 3001. In some embodiments, the transgene encodes the amino acid sequence of SEQ ID NO: 3020.

TABLE 9

NPC1 Variant Sequences
Position numbering based on SEQ ID NO: 3001 or SEQ ID NO: 3020.

| Position | Mutation |
|---|---|
| 63 | C→R |
| 74 | C→Y |
| 92 | Q→R |
| 113 | C→R |
| 137 | T→M |
| 151 | S→G |
| 166 | P→S |
| 177 | C→G |
| 177 | C→Y |
| 215 | H→R |
| 222 | N→S |
| 231 | V→G |
| 237 | P→S |
| 242 | D→H |
| 242 | D→N |
| 247 | C→Y |
| 248 | G→N |

TABLE 9-continued

NPC1 Variant Sequences
Position numbering based on SEQ ID NO: 3001 or SEQ ID NO: 3020.

| Position | Mutation |
|---|---|
| 272 | M→R |
| 333 | G→D |
| 372 | R→W |
| 378 | V→A |
| 380 | L→F |
| 381 | W→C |
| 388 | A→P |
| 389 | R→C |
| 401 | P→T |
| 404 | R→P |
| 404 | R→Q |
| 404 | R→W |
| 433 | P→L |
| 434 | P→L |
| 434 | P→S |
| 451 | E→K |
| 472 | L→P |
| 473 | S→P |
| 474 | P→L |
| 479 | C→Y |
| 509 | Y→S |
| 510 | H→P |
| 511 | T→M |
| 512 | H→R |
| 518 | R→Q |
| 518 | R→W |
| 521 | A→S |
| 537 | F→L |
| 543 | P→L |
| 574 | T→K |
| 576 | K→R |
| 605 | A→N |
| 612 | E→D |
| 615 | R→C |
| 615 | R→L |
| 631 | M→R |
| 640 | G→R |
| 642 | M→I |
| 652 | S→W |
| 660 | G→S |
| 664 | V→M |
| 666 | S→N |
| 670 | C→W |
| 673 | G→N |
| 684 | L→F |
| 691 | P→L |
| 695 | L→N |
| 700 | D→N |
| 703 | F→S |
| 724 | L→P |
| 727 | V→F |
| 734 | S→I |
| 742 | E→K |
| 745 | A→E |
| 754 | M→K |
| 757 | V→A |
| 763 | F→L |
| 767 | A→N |
| 775 | Q→P |
| 789 | R→C |
| 789 | R→G |
| 825 | Y→C |
| 849 | S→I |
| 858 | I→V |
| 862 | Q→L |
| 865 | S→L |
| 871 | Y→C |
| 873 | V→A |
| 874 | D→N |
| 888 | P→S |
| 889 | V→M |
| 890 | Y→C |
| 899 | Y→D |
| 910 | G→S |
| 917 | D→Y |

TABLE 9-continued

NPC1 Variant Sequences
Position numbering based on SEQ ID NO: 3001 or SEQ ID NO: 3020.

| Position | Mutation |
| --- | --- |
| 926 | A→T |
| 927 | A→N |
| 928 | Q→P |
| 929 | L→P |
| 934 | R→Q |
| 940 | S→L |
| 942 | W→C |
| 943 | I→M |
| 944 | D→N |
| 945 | D→N |
| 948 | D→H |
| 948 | D→N |
| 948 | D→Y |
| 950 | V→M |
| 954 | S→L |
| 956 | C→Y |
| 958 | R→L |
| 958 | R→Q |
| 959 | V→E |
| 961-966 | NITDQF→S |
| 961 | N→S |
| 968 | N→S |
| 971 | V→G |
| 976 | C→R |
| 978 | R→C |
| 986 | G→S |
| 992 | G→A |
| 992 | G→R |
| 992 | G→W |
| 996 | M→R |
| 1004 | S→L |
| 1007 | P→A |
| 1012 | G→D |
| 1015 | G→N |
| 1016 | H→R |
| 1023 | V→G |
| 1034 | G→R |
| 1035 | A→N |
| 1036 | T→K |
| 1036 | T→M |
| 1049 | A→N |
| 1054 | A→T |
| 1059 | R→Q |
| 1061 | I→T |
| 1062 | A→N |
| 1066 | T→N |
| 1087 | F→L |
| 1088 | Y→C |
| 1089 | E→K |
| 1094 | I→T |
| 1097 | D→N |
| 1137 | N→I |
| 1140 | G→N |
| 1142 | M→T |
| 1150 | N→K |
| 1156 | N→I |
| 1156 | N→S |
| 1165 | V→M |
| 1167 | F→L |
| 1168 | C→Y |
| 1174 | A→N |
| 1186 | R→H |
| 1189 | E→G |
| 1205 | T→K |
| 1205 | T→R |
| 1212 | V→L |
| 1213 | L→F |
| 1213 | L→N |
| 1216 | A→N |
| 1220 | I→T |
| 1224 | F→L |
| 1236 | G→E |
| 1240 | G→R |
| 1249 | S→G |
| 1266 | R→Q |

Polyadenylation (PolyA) Signal

Polyadenylation signals are nucleotide sequences found in nearly all mammalian genes and control the addition of a string of approximately 200 adenosine residues (the poly(A) tail) to the 3' end of the gene transcript. The poly(A) tail contributes to mRNA stability, and mRNAs lacking the poly(A) tail are rapidly degraded. There is also evidence that the presence of the poly(A) tail positively contributes to the translatability of mRNA by affecting the initiation of translation.

In some embodiments, the AAV transfer cassettes of the disclosure comprise a polyadenylation signal. The polyadenylation signal may be selected from the polyadenylation signal of simian virus 40 (SV40), α-globin, β-globin, human collagen, human growth hormone (hGH), polyoma virus, human growth hormone (hGH) and bovine growth hormone (bGH). In some embodiments, the polyadenylation signal is the SV40 polyadenylation signal. In some embodiments, the polyadenylation signal is the rBG polyadenylation signal. In some embodiments, the polyadenylation signal comprises the sequence of SEQ ID NO: 3012 or SEQ ID NO: 3013. In some embodiments, the polyadenylation signal comprises a sequence at least 90%, at least 95%, at least 96%, at least 97%, at least 98%, or at least 99% identical to the sequence of SEQ ID NO: 3012 or SEQ ID NO: 3013.

Stuffer Sequences

AAV vectors typically accept inserts of DNA having a defined size range which is generally about 4 kb to about 5.2 kb, or slightly more. Thus, for shorter transgene sequences, it may be necessary to include additional nucleic acid in the insert fragment in order to achieve the required length which is acceptable for the AAV vector. Accordingly, in some embodiments, the AAV transfer cassettes of the disclosure may comprise a suffer sequence. The stuffer sequence may be for example, a sequence between 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, to 4,500-5,000 nucleotides in length. The stuffer sequence can be located in the cassette at any desired position such that it does not prevent a function or activity of the vector.

Intronic Sequences

In some embodiments, the AAV transfer cassettes of the disclosure may comprise an intronic sequence. Inclusion of an intronic sequence may enhance expression compared with expression in the absence of the intronic sequence. In some the intronic sequence can increase gene expression without functioning as a binding site for transcription factors. For example, the intronic sequence can increase transcript levels by affecting the rate of transcription, nuclear export, and transcript stability. In some embodiments, the intronic sequence increases the efficiency of mRNA translation.

In some embodiments, the intronic sequence is a hybrid or chimeric sequence. In some embodiments, the intronic sequence is isolated or derived from an intronic sequence of one or more of SV40, β-globin, chicken beta-actin, minute virus of mice (MVM), factor IX, and/or human IgG (heavy or light chain). In some embodiments, the intronic sequence is isolated or derived from SV40. In some embodiments, the intronic sequence is chimeric. In some embodiments, the intronic sequence comprises the sequence of SEQ ID NO: 3010 or SEQ ID NO:3011, or a sequence that is at least 90%, at least 95%, at least 96%, at least 97%, at least 98%, or at least 99% identical thereto.

The intronic sequence may be located anywhere in the transfer cassette where it doesn't interfere with production of the AAV vector. For example, in some embodiments, the intronic sequence may be located between the promoter and the transgene.

Illustrative AAV Transfer Cassettes

In some embodiments, an adeno-associated virus (AAV) transfer cassette comprises a 5' inverted terminal repeat (ITR), a promoter, a transgene, a polyadenylation signal, and a 3' ITR. In some embodiments, an adeno-associated virus (AAV) transfer cassette comprises a 5' inverted terminal repeat (ITR), a promoter, an intronic sequence, a transgene, a polyadenylation signal, and a 3' ITR. In some embodiments, the transgene encodes the NPC1 protein. In some embodiments, the AAV transfer cassette further comprises an enhancer. In some embodiments, the AAV transfer cassette further comprises an intronic sequence.

In some embodiments, the 5' ITR comprises the sequence of SEQ ID NO: 3003 and the 3' ITR comprises the sequence of SEQ ID NO: 3004. In some embodiments, the enhancer comprises the sequence of SEQ ID NO: 3009. In some embodiments, the promoter comprises the sequence of any one of SEQ ID NO: 3005-3008. In some embodiments, the intronic sequence comprises the sequence of SEQ ID NO: 3010 or 3011. In some embodiments, the transgene comprises the sequence of SEQ ID NO: 3002. In some embodiments, the polyA signal comprises the sequence of SEQ ID NO: 3012 or 3013. In some embodiments, the AAV transfer cassette comprises the sequence of any one of SEQ ID NO: 3014-3019.

In some embodiments, an AAV transfer cassette comprises a 5' ITR, a CBA promoter, a SV40 intron, a transgene encoding the NPC1 protein, a SV40 polyadenylation signal, and a 3' ITR. In some embodiments, an AAV transfer cassette comprises a 5' ITR, a GUSB240 promoter, a chimeric intron, a transgene encoding the NPC1 protein, a rBG polyadenylation signal, and a 3' ITR. In some embodiments, an AAV transfer cassette comprises a 5' ITR, a GUSB379 promoter, a SV40 intron, a transgene encoding the NPC1 protein, a rBG polyadenylation signal, and a 3' ITR. In some embodiments, an AAV transfer cassette comprises a 5' ITR, a GUSB240 promoter, a chimeric intron, a transgene encoding the NPC1 protein, a SV40 polyadenylation signal, and a 3' ITR. In some embodiments, an AAV transfer cassette comprises a 5' ITR, a GUSB240 promoter, a SV40 intron, a transgene encoding the NPC1 protein, a SV40 polyadenylation signal, and a 3' ITR. In some embodiments, an AAV transfer cassette comprises a 5' ITR, a CMV enhancer, a HSVTK promoter, a transgene encoding the NPC1 protein, a rBG polyadenylation signal, and a 3' ITR.

In some embodiments, an AAV transfer cassette comprises a 5' ITR comprising the sequence of SEQ ID NO: 3003, a CBA promoter comprising the sequence of SEQ ID NO: 3005, a SV40 intron comprising the sequence of SEQ ID NO: 3010, a transgene encoding the NPC1 protein (SEQ ID NO: 3001), a SV40 polyadenylation signal comprising SEQ ID NO: 3012, and a 3' ITR comprising the sequence of SEQ ID NO: 3004.

In some embodiments, an AAV transfer cassette comprises a 5' ITR comprising the sequence of SEQ ID NO: 3003, a GUSB240 promoter comprising the sequence of SEQ ID NO: 3006, a chimeric intron comprising SEQ ID NO: 3011, a transgene encoding the NPC1 protein (SEQ ID NO: 3001), a rBG polyadenylation signal comprising SEQ ID NO: 3013, and a 3' ITR comprising the sequence of SEQ ID NO: 3004.

In some embodiments, an AAV transfer cassette comprises a 5' ITR comprising the sequence of SEQ ID NO: 3003, a GUSB379 promoter comprising SEQ ID NO: 3006, a SV40 intron comprising the sequence of SEQ ID NO: 3010, a transgene encoding the NPC1 protein (SEQ ID NO: 3001), a rBG polyadenylation signal comprising SEQ ID NO: 3013, and a 3' ITR comprising the sequence of SEQ ID NO: 3004.

In some embodiments, an AAV transfer cassette comprises a 5' ITR comprising the sequence of SEQ ID NO: 3003, a GUSB240 promoter comprising SEQ ID NO: 3007, a chimeric intron comprising the sequence of SEQ ID NO: 3011, a transgene encoding the NPC1 protein (SEQ ID NO: 3001), a SV40 polyadenylation signal comprising SEQ ID NO: 3012, and a 3' ITR comprising the sequence of SEQ ID NO: 3004.

In some embodiments, an AAV transfer cassette comprises a 5' ITR comprising the sequence of SEQ ID NO: 3003, a GUSB240 promoter comprising SEQ ID NO: 3006, a SV40 intron comprising the sequence of SEQ ID NO: 3010, a transgene encoding the NPC1 protein (SEQ ID NO: 3001), a SV40 polyadenylation signal comprising SEQ ID NO: 3012, and a 3' ITR comprising the sequence of SEQ ID NO: 3004.

In some embodiments, an AAV transfer cassette comprises a 5' ITR comprising the sequence of SEQ ID NO: 3003, a CMV enhancer, a HSVTK promoter comprising SEQ ID NO: 3008, a transgene encoding the NPC1 protein (SEQ ID NO: 3001), a rBG polyadenylation signal comprising SEQ ID NO: 3013, and a 3' ITR comprising the sequence of SEQ ID NO: 3004.

In some embodiments, a nucleic acid comprises an AAV transfer cassette. In some embodiments, a nucleic acid comprises a transgene, wherein the transgene encodes the amino acid sequence of SEQ ID NO: 3001. In some embodiments, a nucleic acid comprises a transgene, wherein the transgene encodes the amino acid sequence of SEQ ID NO: 3020. In some embodiments, a nucleic acid comprises, from 5' to 3', a 5' inverted terminal repeat (ITR); a promoter; a transgene; a polyadenylation signal; and a 3' ITR; wherein the transgene encodes the amino acid sequence of SEQ ID NO: 3001 or SEQ ID NO: 3020. In some embodiments, a nucleic acid comprises, from 5' to 3', a 5' inverted terminal repeat (ITR); a promoter; a transgene; a polyadenylation signal; and a 3' ITR; wherein the nucleic acid comprises an intronic sequence; wherein the transgene encodes the amino acid sequence of SEQ ID NO: 3001 or SEQ ID NO: 3020. In some embodiments, a nucleic acid comprises, from 5' to 3', a 5' inverted terminal repeat (ITR); a chicken beta-actin promoter; a transgene; a polyadenylation signal; and a 3' ITR; wherein the transfer cassette comprises an intronic sequence; wherein the transgene encodes the amino acid sequence of SEQ ID NO: 3001 or SEQ ID NO: 3020. In some embodiments, a nucleic acid comprises, from 5' to 3', a 5' inverted terminal repeat (ITR); a promoter; an intronic sequence; a transgene; a polyadenylation signal; and a 3' ITR; wherein the transgene encodes the amino acid sequence of SEQ ID NO: 3001 or SEQ ID NO: 3020. In some embodiments, a nucleic acid comprises, from 5' to 3', a 5' inverted terminal repeat (ITR); a chicken beta-actin promoter; an intronic sequence; a transgene; a polyadenylation signal; and a 3' ITR; wherein the transgene encodes the amino acid sequence of SEQ ID NO: 3001 or SEQ ID NO: 3020. The AAV transfer cassettes described herein may be incorporated into a vector (e.g., a plasmid or a bacmid) using standard molecular biology techniques. The vector (e.g., plasmid or bacmid) may further comprise one or more genetic elements used during production of AAV, including, for example, AAV rep and cap genes, and helper virus protein sequences.

Methods for Producing Virus Vectors

Also provided herein are methods of producing virus vectors. In some embodiments, a method of producing an AAV vector that evades neutralizing antibodies, comprises: a) identifying contact amino acid residues that form a three dimensional antigenic footprint on an AAV capsid protein subunit or protein capsid; b) generating a library of AAV capsid protein subunits comprising amino acid substitutions of the contact amino acid residues identified in (a); c) producing AAV particles comprising capsid protein subunits from the library of AAV capsid protein subunits of (b); d) contacting the AAV particles of (c) with cells under conditions whereby infection and replication can occur; e) selecting AAV particles that can complete at least one infectious cycle and replicate to titers similar to control AAV particles: 1) contacting the AAV particles selected in (e) with neutralizing antibodies and cells under conditions whereby infection and replication can occur; and g) selecting AAV particles that are not neutralized by the neutralizing antibodies of (f). Nonlimiting examples of methods for identifying contact amino acid residues include peptide epitope mapping and/or cryo-electron microscopy.

Resolution and identification of the antibody contact residues within the three dimensional antigenic footprint allows for their subsequent modification through random, rational and/or degenerate mutagenesis to generate antibody-evading AAV protein capsids and/or capsid protein subunits that can be identified through further selection and/or screening.

Thus, in some embodiments, a method of producing an AAV vector that evades neutralizing antibodies comprises: a) identifying contact amino acid residues that form a three dimensional antigenic footprint on an AAV capsid protein subunits and/or protein capsids; b) generating AAV capsid protein subunits comprising amino acid substitutions of the contact amino acid residues identified in (a) by random, rational and/or degenerate mutagenesis; c) producing AAV particles comprising capsid protein subunits from the AAV capsid protein subunits of (b); d) contacting the AAV particles of (c) with cells under conditions whereby infection and replication can occur; e) selecting AAV particles that can complete at least one infectious cycle and replicate to titers similar to control AAV particles; f) contacting the AAV particles selected in (e) with neutralizing antibodies and cells under conditions whereby infection and replication can occur; and g) selecting AAV particles that are not neutralized by the neutralizing antibodies of (f).

Nonlimiting examples of methods for identifying contact amino acid residues include peptide epitope mapping and/or cryo-electron microscopy. Methods of generating AAV capsid protein subunits comprising amino acid substitutions of contact amino acid residues by random, rational and/or degenerate mutagenesis are known in the art.

This comprehensive approach presents a platform technology that can be applied to modifying any AAV protein capsid and/or capsid protein subunit. Application of this platform technology yields AAV antigenic variants derived from the original AAV capsid protein subunit template without loss of transduction efficiency. As one advantage and benefit, application of this technology will expand the cohort of patients eligible for gene therapy with AAV vectors.

In some embodiments, a method of producing a virus vector comprises providing to a cell: (a) a nucleic acid template comprising at least one TR sequence (e.g., AAV TR sequence), and (b) AAV sequences sufficient for replication of the nucleic acid template and encapsidation into AAV protein capsids (e.g., AAV rep sequences and AAV cap sequences encoding the AAV capsid subunits). Optionally, the nucleic acid template further comprises at least one heterologous nucleic acid sequence. In some embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV protein capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In some embodiments, the cell is a mammalian cell. As another option, the cell can be a trans-complementing packaging cell line that provides functions deleted from a replication-defective helper virus, e.g., 293 cells or other Ela trans-complementing cells.

The AAV replication and capsid protein subunit sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the Ela or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) Curr. Top. Microbiol. Immun. 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a plasmid or viral vector. In some embodiments, the nucleic acid template is supplied by a herpesvirus or adenovirus vector (e.g., inserted into the Ela or E3 regions of a deleted adenovirus). As another illustration, Palombo et al., (1998) J. Virology 72:5025, describes a baculovirus vector carrying a reporter gene flanked by the AAV TRs. EBV vectors may also be employed to deliver the template, as described above with respect to the rep/cap genes.

In some embodiments, the nucleic acid template is provided by a replicating rAAV virus. In some embodiments, an AAV provirus comprising the nucleic acid template is stably integrated into the nucleus of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a noninfectious adenovirus miniplasmid that carries all of the helper genes that promote efficient AAV production as described by Ferrari et al., (1997) Nature Med. 3: 1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the AAV replication and capsid protein subunit sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In some embodiments, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In some embodiments, the AAV rep/cap sequences and the adenovirus helper sequences are supplied by a single adenovirus helper vector. According to this embodiment, the rAAV template can be provided as a plasmid template.

In some embodiments, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In some embodiments, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and, if present, the rAAV template are embedded in the adenovirus backbone and are flanked by the 5' and 3' cis sequences, so that these sequences may be packaged into adenovirus protein capsids. As described above, the adenovirus helper sequences and the AAV rep/cap sequences are generally not flanked by ITRs so that these sequences are not packaged into the AAV virions. Zhang et al., ((2001) Gene Ther. 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al., (1999) Gene Therapy 6:986 and WO 00/17377.

As a further alternative, virus vectors can be produced in insect cells using baculovirus vectors to deliver the rep/cap genes and rAAV template as described, for example, by Urabe et al., (2002) Human Gene Therapy 13: 1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) Gene Therapy 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The virus vectors described herein are useful for the delivery of nucleic acids to cells in vitro, ex vivo, and in vivo. In particular, the virus vectors can be advantageously employed to deliver or transfer nucleic acids to animal, including mammalian, cells. Thus, in some embodiments, a nucleic acid may be encapsidated by a protein capsid described herein. In some embodiments, the nucleic acid is a transfer cassette. In some embodiments, the transfer cassette comprises a vector genome (e.g., 5' ITR, transgene, and 3' ITR). In some embodiments, the nucleic acid is an AAV transfer cassette.

The transfer cassette sequence delivered by the virus vectors may be any heterologous nucleic acid sequence(s) of interest. Nucleic acids of interest include nucleic acids encoding polypeptides, including therapeutic (e.g., for medical or veterinary uses) or immunogenic (e.g., for vaccines) polypeptides or RNAs. In some embodiments, the transfer cassette comprises a 5' ITR and a 3' ITR. In some embodiments, the transfer cassette comprises a 5' ITR, a transgene, and a 3'ITR. In some embodiments, the transgene encodes a therapeutic protein or RNA.

Therapeutic polypeptides include, but are not limited to, cystic fibrosis transmembrane regulator protein (CFTR), dystrophin (including mini- and micro-dystrophins, see, e.g., Vincent et al, (1993) Nature Genetics 5: 130; U.S. Patent Publication No. 2003/017131; International publication WO/2008/088895, Wang et al., Proc. Natl. Acad. Sci. USA 97: 1 3714-13719 (2000); and Gregorevic et al., Mol. Ther. 16:657-64 (2008)), myostatin propeptide, follistatin, activin type 11 soluble receptor, IGF-1, apolipoproteins such as apoA (apoA1, apoA2, apoA4, apoA-V), apoB (apoB100, ApoB48), apoC (apoCI, apoCII, apoCIII, apoCIV), apoD, apoE, apoH, apoL, apo(a), anti-inflammatory polypeptides such as the Ikappa B dominant mutant, amyloid beta, tau, sarcospan, utrophin (Tinsley et al, (1996) Nature 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, progranulin, ornithine transcarbamylase, β-globin, α-globin, spectrin, alpha-1-antitrypsin, adenosine deaminase, hypoxanthine guanine phosphoribosyl transferase, β-glucocerebrosidase, battenin, sphingomyelinase, lysosomal hexosaminidase A, branched-chain keto acid dehydrogenase, frataxin, RP65 protein, cytokines (e.g., alpha-interferon, beta-interferon, gamma-interferon, interleukin-2, interleukin-4, alpha synuclein, parkin, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), huntingin, lysosomal acid alpha-glucosidase, iduronate-2-sulfatase, N-sulfoglucosamine sulfohydrolase, alpha-galactosidase A, receptors (e.g., the tumor necrosis growth factor soluble receptor), S100A1, ubiquitin protein ligase E3, parvalbumin, adenylyl cyclase type 6, a molecule that modulates calcium handling (e.g., SERCA$_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172)), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins that enhance or inhibit transcription of host factors (e.g., nuclease-dead Cas9 linked to a transcription enhancer or inhibitor element, zinc-finger proteins linked to a transcription enhancer or inhibitor element, transcription activator-like (TAL) effectors linked to a transcription enhancer or inhibitor element), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al., Nature Biotechnology 23:584-590 (2005)). Heterologous nucleic acid sequences encoding polypeptides include those encoding reporter polypeptides (e.g., an enzyme). Reporter polypeptides are known in the art and include, but are not limited to, Green Fluorescent Protein, β-galactosidase, alkaline phosphatase, luciferase, and chloramphenicol acetyltransferase gene.

Optionally, the heterologous nucleic acid encodes a secreted polypeptide (e.g., a polypeptide that is a secreted polypeptide in its native state or that has been engineered to be secreted, for example, by operable association with a secretory signal sequence as is known in the art).

Alternatively, in some embodiments, the heterologous nucleic acid may encode an antisense nucleic acid, a ribozyme (e.g., as described in U.S. Pat. No. 5,877,022), RNAs that effect spliceosome-mediated/ram-splicing (see, Puttaraju et al, (1999) Nature Biotech. 17:246; U.S. Pat. Nos. 6,013,487; 6,083,702), interfering RNAs (RNAi) including siRNA, shRNA or miRNA that mediate gene silencing (see, Sharp et al, (2000) Science 287:2431), and other non-translated RNAs, such as "guide" RNAs (Gorman et al., (1998) Proc. Nat. Acad. Sci. USA 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al., J. Gene Med. 10: 132-142 (2008) and Li et al., Acta Pharmacol Sin. 26:51-55 (2005)); phospholamban inhibitory or dominant-negative molecules such as phospholamban 516E (e.g., to treat cardiovascular disease, see, e.g., Hoshijima et al. Nat. Med. 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified protein capsid.

In some embodiments, a nucleic acid sequence that directs gene editing can be delivered. For example, the nucleic acid may encode a guide RNA. In some embodiments, the guide RNA is a single guide RNA (sgRNA) comprising a crRNA sequence and a tracrRNA sequence. In some embodiments, the nucleic acid may encode a nuclease. In some embodiments, the nuclease is a zinc-finger nuclease, a homing endonuclease, a TALEN (transcription activator-like effector nuclease), a NgAgo (agronaute endonuclease), a SGN (structure-guided endonuclease), a RGN (RNA-guided nuclease), or modified or truncated variants thereof. In some embodiments, the RNA-guided nuclease is a Cas9 nuclease, a Cas12(a) nuclease (Cpf1), a Cas12b nuclease, a Cas12c nuclease, a TrpB-like nuclease, a Cas13a nuclease (C2c2), a Cas13b nuclease, or modified or truncated variants thereof. In some embodiments, the Cas9 nuclease is isolated or derived from *S. pyogenes* or *S. aureus*.

In some embodiments, a nucleic acid sequence that directs gene knockdown can be delivered. For example, the nucleic acid sequence may encode a siRNA, an shRNA, a microRNA, or an antisense nucleic acid. The virus vector may also comprise a heterologous nucleic acid that shares homology with and recombines with a locus on a host chromosome. This approach can be utilized, for example, to correct a genetic defect in the host cell.

Also provided are virus vectors that express an immunogenic polypeptide, e.g., for vaccination. The nucleic acid may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura el al, (1994) Proc. Nat. Acad. Sci USA 91:8507; U.S. Pat. No. 5,916,563 to Young et al, U.S. Pat. No. 5,905,040 to Mazzara et al, U.S. Pat. Nos. 5,882, 652, 5,863,541 to Samulski et al). The antigen may be presented in the parvovirus capsid.

Alternatively, the antigen may be expressed from a heterologous nucleic acid introduced into a recombinant vector genome. In some embodiments, any immunogen of interest as described herein and/or as is known in the art can be provided by the virus vectors described herein.

An immunogenic polypeptide can be any polypeptide suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP 160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens), a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell.

Exemplary cancer and tumor cell antigens are described in S. A. Rosenberg (Immunity 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al., (1994) Proc. Natl. Acad. Sci. USA 91:3515; Kawakami et al., (1994) J. Exp. Med., 180:347; Kawakami et al., (1994) Cancer Res. 54:3124), MART-1, gp100, MAGE-1, MAGE-2, MAGE-3, CEA, TRP-1, TRP-2, P-15, tyrosinase (Brichard et al., (1993) J Exp. Med. 178:489); HER-2/neu gene product (U.S. Pat. No. 4,968, 603), CA 125, LK26, FB5 (endosialin), TAG 72, AFP, CA 19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine, (1993) Ann. Rev. Biochem. 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition or metastasis thereof now known or later identified (see, e.g., Rosenberg, (1996) Ann. Rev. Med. 47:481-91).

As a further alternative, the heterologous nucleic acid can encode any polypeptide that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid(s) of interest can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In some embodiments, the promoter/enhancer elements can be native to the target cell or subject to be treated. In some embodiments, the promoters/enhancer element can be native to the heterologous nucleic acid sequence. The promoter/enhancer element is generally chosen so that it functions in the target cell(s) of interest. Further, in some embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In some embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors described herein provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the described herein can be employed to deliver a heterologous nucleic acid encoding a polypeptide or functional RNA to treat and/or prevent any disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (β-globin), anemia (erythropoietin) and other blood disorders. Alzheimer's disease (GDF; neprilysin), multiple sclerosis (β-interferon), Parkinson's disease (glial-cell line derived neurotrophic factor [GDNF]), Huntington's disease (RNAi to remove repeats), Canavan's disease, amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., a, β, γ], RNAi against myostatic myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Myotonic dystrophy 1 or 2, facioscapulohumeral muscular dystrophy (FSHD), Gaucher disease (glucocerebrosidase), Hurler's disease (a-L-iduronidase), adenosine deaminase deficiency (adenosine deaminase), glycogen storage diseases (e.g., Fabry disease [a-galactosidase] and Pompe disease [lysosomal acid alpha-glucosidase]) and other metabolic disorders, congenital emphysema (alpha-1-antitrypsin), Lesch-Nyhan Syndrome (hypoxan thine guanine phosphoribosyl transferase), Niemann-Pick disease (sphingomyelinase), Tay-Sachs disease (lysosomal hexosaminidase A), frontotemporal dementia, Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (1-1) and fragments thereof (e.g., IIC), serca2a, zinc finger proteins that regulate the phospholamban gene, Barkct, [32-adrenergic receptor, 2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as I RAP and TNFa soluble receptor), hepatitis (a-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The compositions and methods disclosed herein can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

In some embodiments, the virus vectors described herein can be employed to deliver a heterologous nucleic acid encoding a polypeptide or functional RNA to treat and/or prevent a liver disease or disorder. The liver disease or disorder may be, for example, primary biliary cirrhosis, nonalcoholic fatty liver disease (NAFLD), non-alcoholic steatohepatitis (NASH), autoimmune hepatitis, hepatitis B, hepatitis C, alcoholic liver disease, fibrosis, jaundice, primary sclerosing cholangitis (PSC), Budd-Chiari syndrome, hemochromatosis, Wilson's disease, alcoholic fibrosis, non-alcoholic fibrosis, liver steatosis, Gilbert's syndrome, biliary atresia, alpha-1-antitrypsin deficiency, alagille syndrome, progressive familial intrahepatic cholestasis, Hemophilia B, Hereditary Angioedema (HAE), Homozygous Familial Hypercholesterolemia (HoFH), Heterozygous Familial Hypercholesterolemia (HeFH), Von Gierke's Disease (GSD I), Hemophilia A, Methylmalonic Acidemia, Propionic Acidemia, Homocystinuria, Phenylketonuria (PKU), Tyrosinemia Type 1, Arginase 1 Deficiency, Argininosuccinate Lyase Deficiency, Carbamoyl-phosphate synthetase 1 deficiency, Citrullinemia Type 1, Citrin Deficiency, Crigler-Najjar Syndrome Type 1, Cystinosis, Fabry Disease, Glycogen Storage Disease 1 b, LPL Deficiency, N-Acetylglutamate Synthetase Deficiency, Ornithine Transcarbamylase Deficiency, Ornithine Translocase Deficiency, Primary Hyperoxaluria Type 1, or ADA SCID.

The compositions and methods described herein can also be used to produce induced pluripotent stem cells (iPS). For example, a virus vector described herein can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like.

Nucleic acids encoding factors associated with stem cells are known in the art. Nonlimiting examples of such factors associated with stem cells and pluripotency include Oct-3/4, the SOX family (e.g., SOX 1, SOX2, SOX3 and/or SOX 15), the Klf family (e.g., Klfl, KHZ Klf4 and/or Klf5), the Myc family (e.g., C-myc, L-myc and/or N-myc), NANOG and/or LIN28.

The methods described herein can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [alpha-L-iduronidase], Scheie Syndrome [alpha-L-iduronidase], Hurler-Scheie Syndrome [alpha-L-iduronidase], Hunter's Syndrome [iduronate sulfatase], Sanfilippo Syndrome A [heparan sulfamidase], B [N-acetylglucosaminidase], C [acetyl-CoA:alpha-glucosaminide acetyltransferase], D [N-acetylglucosamine 6-sulfatase], Morquio Syndrome A [galactoses-sulfate sulfatase], B [β-galactosidase], Maroteaux-Lamy Syndrome [N-acetylgalactosamine-4-sulfatase], etc.), Fabry disease (alpha-galactosidase), Gaucher's disease (glucocerebrosidase), or a glycogen storage disorder (e.g., Pompe disease; lysosomal acid alpha-glucosidase).

Gene transfer has substantial use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors as described herein permit the treatment and/or prevention of genetic diseases.

The virus vectors described herein may also be employed to provide a functional RNA to a cell in vitro or in vivo. The functional RNA may be, for example, a non-coding RNA. In some embodiments, expression of the functional RNA in the cell can diminish expression of a particular target protein by the cell. Accordingly, functional RNA can be administered to decrease expression of a particular protein in a subject in need thereof. In some embodiments, expression of the functional RNA in the cell can increase expression of a particular target protein by the cell. Accordingly, functional RNA can be administered to increase expression of a particular protein in a subject in need thereof. In some embodiments, expression of the functional RNA can regulate splicing of a particular target RNA in a cell. Accordingly, functional RNA can be administered to regulate splicing a particular RNA in a subject in need thereof. In some embodiments, expression of the functional RNA in the cell can regulate the function of a particular target protein by the cell. Accordingly, functional RNA can be administered to regulate the function of a particular protein in a subject in need thereof. Functional RNA can also be administered to cells in vitro to regulate gene expression and/or cell physiology, e.g., to optimize cell or tissue culture systems or in screening methods.

In addition, virus vectors as described herein find use in diagnostic and screening methods, whereby a nucleic acid of interest is transiently or stably expressed in a cell culture system, or alternatively, a transgenic animal model.

The virus vectors can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

In some embodiments, the virus vectors may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In some embodiments, the cell is an antigen-presenting cell (e.g., a dendritic cell).

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, Immunophysiology: Cell Function and Cellular Interactions in Antibody Formation, in IMMUNOLOGY: BASIC PROCESSES 117 (Joseph A. Bellanti ed., 1985). Alternatively stated, an active immune response is mounted by the host after exposure to an immunogen by infection or by vaccination. Active immunity can be contrasted with passive immunity, which is acquired through the transfer of preformed substances (antibody, transfer factor, thymic graft, interleukin-2) from an actively immunized host to a non-immune host.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In some embodiments, the virus vector or cell comprising the heterologous nucleic acid can be administered in an immunogenically effective amount, as described below.

In some embodiments, the virus vectors can be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein.

Alternatively, the cancer antigen can be expressed as part of the capsid protein subunit, or be otherwise associated with the protein capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In some embodiments, a method of treating and/or preventing tumor-forming cancers is provided.

The term "tumor" is also understood in the art, for example, as an abnormal mass of undifferentiated cells within a multicellular organism. Tumors can be malignant or benign. In some embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In some embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

In some embodiments, cells may be removed from a subject with cancer and contacted with a virus vector expressing a cancer cell antigen as described herein. The modified cell is then administered to the subject, whereby an immune response against the cancer cell antigen is elicited. This method can be advantageously employed with immunocompromised subjects that cannot mount a sufficient immune response in vivo (i.e., cannot produce enhancing antibodies in sufficient quantities).

It is known in the art that immune responses may be enhanced by immunomodulatory cytokines (e.g., alpha-interferon, beta-interferon, gamma-interferon, omega-interferon, tau-interferon, interleukin-1-alpha, interleukin-1β, interleukin-2, interleukin-3, interleukin-4, interleukin 5, interleukin-6, interleukin-7, interleukin-8, interleukin-9, interleukin-10, interleukin-11, interleukin-12, interleukin-13, interleukin-14, interleukin-18, B cell Growth factor, CD40 Ligand, tumor necrosis factor-alpha, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector. Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and viral-like particles as described herein find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammals" as used herein includes, but is not limited to, humans, non-human primates, bovines, ovines, caprines, equines, felines, canines, lagomorphs, etc. Human subjects include neonates, infants, juveniles, adults and geriatric subjects.

In some embodiments, the subject is "in need" of the methods described herein.

In some embodiments, a pharmaceutical composition is provided comprising a virus vector and/or virus-like particle in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

Also provided herein are method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In some embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendrocytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In some embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In some embodiments, the cells have been removed from a subject, the virus vector is introduced therein, and the cells are then administered back into the subject. Methods of removing cells from the subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In some embodiments, the cells transduced with the virus vector are administered to the subject in an effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the protein capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In some embodiments, the dosage is sufficient to produce a protective immune response (as defined above). The degree of protection conferred need not be complete or permanent, as long as the benefits of administering the immunogenic polypeptide outweigh any disadvantages thereof.

Thus, in some embodiments, a method of administering a nucleic acid to a cell comprises contacting the cell with the virus vector, virus particle and/or composition as described herein.

Also provided herein is a method of administering the virus vector, virus particle and/or virus-like particle as described herein to a subject. In some embodiments, a method of delivering a nucleic acid to a subject comprises administering to the subject a virus particle, virus vector and/or composition as described herein. Administration of the virus vectors, virus particles and/or viral-like particles to a human subject or an animal in need thereof can be by any means known in the art. Optionally, the virus vector, virus particle and/or viral-like particle is delivered in an effective dose in a pharmaceutically acceptable carrier. In some embodiments, an effective amount of the virus vector, virus particle and/or viral-like particle is delivered.

The virus vectors and/or viral-like particles described herein can further be administered to elicit an immunogenic response (e.g., as a vaccine). Typically, immunogenic compositions comprise an immunogenically effective amount of virus vector and/or viral-like particle in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or viral-like particle to be administered to a subject depend upon the mode of administration, the disease or condition to be treated and/or prevented, the individual subject's condition, the particular virus vector or protein capsid, and the nucleic acid to be delivered, and the like, and can be determined in a routine manner. In some embodiments, the dose of recombinant AAV is an effective dose. Exemplary effective doses may be, for example, a dose of at least about $10^5$, about $10^6$, about $10^7$ about $10^8$, about $10^9$ about $10^{10}$, about $10^{11}$, about $10^{12}$, about $10^{13}$, about $10^{14}$, about $10^{15}$ transducing units, optionally about $10^8$ to about $10^{13}$ transducing units. In some embodiments, an effective dose of recombinant AAV is a dose in the range of about $1\times10^{11}$ to about $1\times10^{15}$ vector genomes per kilogram body weight of the subject. For example, the effective dose may be about $1\times10^{11}$, about $5\times10^{11}$, about $1\times10^{12}$, about $5\times10^{12}$, about $1\times10^{13}$, about $5\times10^{13}$, about $1\times10^{14}$, about $5\times10^{14}$, or about $1\times10^{15}$ vector genomes per kilogram (vg/kg) body weight of the subject. In some embodiments, the dose of AAV administered may be $2.8\times10^{13}$ vg/kg or $2.9\times10^{13}$ vg/kg. In some embodiments, the dose may be $2.1\times10^{13}$ vg or $3.0\times10^{13}$ vg.

In some embodiments, more than one administration (e.g., two, three, four or more administrations) may be employed to achieve the desired level of gene expression over a period of various intervals, e.g., daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

Administration to skeletal muscle includes but is not limited to administration to skeletal muscle in the limbs (e.g., upper arm, lower arm, upper leg, and/or lower leg), back, neck, head (e.g., tongue), thorax, abdomen, pelvis/perineum, and/or digits. Suitable skeletal muscles include but are not limited to abductor digiti minimi (in the hand), abductor digiti minimi (in the foot), abductor hallucis, abductor ossis metatarsi quinti, abductor pollicis brevis, abductor pollicis longus, adductor brevis, adductor hallucis, adductor longus, adductor magnus, adductor pollicis, anconeus, anterior scalene, articularis genus, biceps brachii, biceps femoris, brachialis, brachioradialis, buccinator, coracobrachialis, corrugator supercilii, deltoid, depressor anguli oris, depressor labii inferioris, digastric, dorsal interossei (in the hand), dorsal interossei (in the foot), extensor carpi radialis brevis, extensor carpi radialis longus, extensor carpi ulnaris, extensor digiti minimi, extensor digitorum, extensor digitorum brevis, extensor digitorum longus, extensor hallucis brevis, extensor hallucis longus, extensor indicis, extensor pollicis brevis, extensor pollicis longus, flexor carpi radialis, flexor carpi ulnaris, flexor digiti minimi brevis (in the hand), flexor digiti minimi brevis (in the foot), flexor digitorum brevis, flexor digitorum longus, flexor digitorum profundus, flexor digitorum superficial is, flexor hallucis brevis, flexor hallucis longus, flexor pollicis brevis. flexor pollicis longus, frontalis, gastrocnemius, geniohyoid, gluteus maximus, gluteus medius, gluteus minimus, gracilis, iliocostalis cervicis, iliocostalis lumborum, iliocostalis thoracis, illiacus, inferior gemellus, inferior oblique, inferior rectus, infraspinatus, interspinalis, intertransversi, lateral pterygoid, lateral rectus, latissimus dorsi, levator anguli oris, levator labii superioris, levator labii superioris alaeque nasi, levator palpebrae superioris, levator scapulae, long rotators, longissimus capitis, longissimus cervicis, longissimus thoracis, longus capitis, longus colli, lumbricals (in the hand), lumbricals (in the foot), masseter, medial pterygoid, medial rectus, middle scalene, multifidus, mylohyoid, obliquus capitis inferior, obliquus capitis superior, obturator externus, obturator internus, occipitalis, omohyoid, opponens digiti minimi, opponens pollicis, orbicularis oculi, orbicularis oris, palmar interossei, palmaris brevis, palmaris longus, pectineus, pectoralis major, pectoralis minor, peroneus brevis, peroneus longus, peroneus tertius, piriformis, plantar interossei, plantaris, platysma, popliteus, posterior scalene, pronator quadratus, pronator teres, psoas major, quadratus femoris, quadratus plantae, rectus capitis anterior, rectus capitis lateralis, rectus capitis posterior major, rectus capitis posterior minor, rectus femoris, rhomboid major, rhomboid minor, risorius, sartorius, scalenus minimus, semimembranosus, semispinalis capitis, semispinalis cervicis, semispinalis thoracis, semitendinosus, serratus anterior, short rotators, soleus, spinalis capitis, spinalis cervicis, spinalis thoracis, splenius capitis, splenius cervicis, sternocleidomastoid, sternohyoid, sternothyroid, stylohyoid, subclavius, subscapularis, superior gemellus, superior oblique, superior rectus, supinator, supraspinatus, temporalis, tensor fascia lata, teres major, teres minor, thoracis, thyrohyoid, tibialis anterior, tibialis posterior, trapezius, triceps brachii, vastus intermedius, vastus lateralis, vastus medialis, zygomaticus major, and zygomaticus minor, and any other suitable skeletal muscle as known in the art.

The virus vector and/or viral-like particle can be delivered to skeletal muscle by intravenous administration, intra-arterial administration, intraperitoneal administration, limb perfusion, (optionally, isolated limb perfusion of a leg and/or arm; see, e.g. Arruda et al., (2005) Blood 105: 3458-3464), and/or direct intramuscular injection. In some embodiments, the virus vector and/or viral-like particle is administered to a limb (arm and/or leg) of a subject (e.g., a subject with muscular dystrophy such as Duchenne muscular dystrophy (DMD) or limb-girdle muscular dystrophy (LGMD)) by limb perfusion, optionally isolated limb perfusion (e.g., by intravenous or intra-articular administration). In some embodiments, the virus vectors and/or viral-like particles can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In some embodiments, the viral vectors and/or viral-like particles can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome. Administration to cardiac muscle includes administration to the left atrium, right atrium, left ventricle, right ventricle and/or septum. The virus vector and/or viral-like particle can be delivered to cardiac muscle by intravenous administration, intra-arterial administration such as intra-aortic administration, direct cardiac injection (e.g., into left atrium, right atrium, left ventricle, right ventricle), and/or coronary artery perfusion.

Administration to diaphragm muscle can be by any suitable method including intravenous administration, intra-arterial administration, and/or intra-peritoneal administration.

Delivery to a target tissue can also be achieved by delivering a depot comprising the virus vector and/or viral-like particle. As described herein, delivery of a "depot" refers to administration of a sustained-action formulation that allows slow release and/or gradual dissemination of the virus, so that the virus can act for longer periods than is possible with standard injections. In some embodiments, a depot comprising the virus vector and/or viral-like particle is implanted into skeletal, cardiac and/or diaphragm muscle tissue or the tissue can be contacted with a film or other matrix comprising the virus vector and/or viral-like particle. Such implantable matrices or substrates are described in U.S. Pat. No. 7,201,898.

In some embodiments, a virus vector and/or viral-like particle according is administered to skeletal muscle, diaphragm muscle and/or cardiac muscle (e.g., to treat and/or prevent muscular dystrophy, heart disease [for example, PAD or congestive heart failure]).

In some embodiments, the compositions and methods described herein are used to treat and/or prevent diseases or disorders of skeletal, cardiac and/or diaphragm muscle. The diseases or disorders of the muscle may be, for example, muscular dystrophy, myopathy, motor neuron disease, and cardiomyopathy. The diseases or disorders of the muscle may be, for example, dystrophinopathies, Duchenne muscular dystrophy, Becker muscular dystrophy, myotonic dystrophies (e.g., myotonic dystrophy 1 and 2), facioscapulohumeral muscular dystrophy (FDHD), Eimery-Dreifuss muscular dystrophy, limb-girdle disease, facioscapulohumeral muscular dystrophy, oculopharyngeal muscular dystrophy, distal muscular dystrophy, congenital muscular dystrophy, juvenile macular dystrophy, centronuclear myopathy, central core myopathy, and inclusion body myositis.

In some embodiments, a method of treating and/or preventing muscular dystrophy in a subject in need thereof is provided, the method comprising: administering a treatment or prevention effective amount of a virus vector to a mammalian subject, wherein the virus vector comprises a heterologous nucleic acid encoding dystrophin, a mini-dystrophin, a micro-dystrophin, myostatin propeptide, follistatin, activin type II soluble receptor, IGF-1, anti-inflammatory polypeptides such as the Ikappa B dominant mutant, sarcospan, utrophin, a micro-dystrophin, laminin-a2, alpha-sarcoglycan, beta-sarcoglycan, gamma-sarcoglycan, delta-sarcoglycan, IGF-1, an antibody or antibody fragment against myostatin or myostatin propeptide, and/or RNAi against myostatin. In some embodiments, the virus vector can be administered to skeletal, diaphragm and/or cardiac muscle as described elsewhere herein.

Alternatively, methods described herein can be practiced to deliver a nucleic acid to skeletal, cardiac or diaphragm muscle, which is used as a platform for production of a polypeptide (e.g., an enzyme) or functional RNA (e.g., RNAi, micro RNA, antisense RNA) that normally circulates in the blood or for systemic delivery to other tissues to treat and/or prevent a disorder (e.g., a metabolic disorder, such as diabetes [e.g., insulin], hemophilia [e.g., Factor IX or Factor VIII], a mucopolysaccharide disorder [e.g., Sly syndrome, Hurler Syndrome, Scheie Syndrome, Hurler-Scheie Syndrome, Hunter's Syndrome, Sanfilippo Syndrome A, B, C, D, Morquio Syndrome, Maroteaux-Lamy Syndrome, etc.] or a lysosomal storage disorder such as Gaucher's disease [glucocerebrosidase] or Fabry disease [a-galactosidase A] or a glycogen storage disorder such as Pompe disease [lysosomal acid alpha glucosidase]). Other suitable proteins for treating and/or preventing metabolic disorders are described herein. The use of muscle as a platform to express a nucleic acid of interest is described in U.S. Patent publication US 2002/0192189.

In some embodiments, a method of treating and/or preventing a metabolic disorder in a subject in need thereof comprises administering a treatment or prevention effective amount of a virus vector to skeletal muscle of a subject, wherein the virus vector comprises a heterologous nucleic acid encoding a polypeptide, wherein the metabolic disorder is a result of a deficiency and/or defect in the polypeptide. Illustrative metabolic disorders and heterologous nucleic acids encoding polypeptides are described herein. Optionally, the polypeptide is secreted (e.g., a polypeptide that is a secreted polypeptide in its native state or that has been engineered to be secreted, for example, by operable association with a secretory signal sequence as is known in the art). Without being limited by any particular theory, according to this embodiment, administration to the skeletal muscle can result in secretion of the polypeptide into the systemic circulation and delivery to target tissue(s). Methods of delivering virus vectors to skeletal muscle is described in more detail herein.

The methods described herein can also be practiced to produce noncoding RNA, such as antisense RNA, RNAi or other functional RNA (e.g., a ribozyme) for systemic delivery.

In some embodiments, a method of treating and/or preventing congenital heart failure or PAD in a subject in need thereof comprises administering a treatment or prevention effective amount of a virus vector to a mammalian subject, wherein the virus vector comprises a heterologous nucleic acid encoding, for example, a sarcoplasmic endoreticulum $Ca^{2+}$-ATPase (SERCA2a), an angiogenic factor, phosphatase inhibitor I (I-1) and fragments thereof (e.g., I1C), RNAi against phospholamban; a phospholamban inhibitory or dominant-negative molecule such as phospholamban S16E, a zinc finger protein that regulates the phospholamban gene, beta-2-adrenergic receptor, beta-2-adrenergic receptor kinase (BARK), PI3 kinase, calsarcan, a β-adrenergic receptor kinase inhibitor (PARKct), inhibitor 1 of protein phosphatase 1 and fragments thereof (e.g., I1 C), S100A1, parvalbumin, adenylyl cyclase type 6, a molecule that effects G-protein coupled receptor kinase type 2 knockdown such as a truncated constitutively active bARKct, Pim-1, PGC-I α, SOD-1, SOD-2, EC-SOD, kallikrein, HIF, thymosin-p4, mir-1, mir-133, mir-206, mir-208 and/or mir-26a.

Injectables can be prepared in conventional forms, either as liquid solutions or suspensions, solid forms suitable for solution or suspension in liquid prior to injection, or as emulsions. Alternatively, one may administer the virus vector and/or viral-like particle in a local rather than systemic manner, for example, in a depot or sustained-release formulation. Further, the virus vector and/or viral-like particle can be delivered adhered to a surgically implantable matrix (e.g., as described in U.S. Patent Publication No. US-2004-0013645-A1).

The virus vectors and/or virus-like particles disclosed herein can be administered to the lungs of a subject by any suitable means, optionally by administering an aerosol suspension of respirable particles comprised of the virus vectors and/or virus-like particles, which the subject inhales. The respirable particles can be liquid or solid. Aerosols of liquid particles comprising the virus vectors and/or virus-like particles may be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the virus vectors and/or viral-like particles may likewise be produced with any solid particulate medicament aerosol generator, by techniques known in the pharmaceutical art.

The virus vectors and virus-like particles can be administered to tissues of the CNS (e.g., brain, eye) and may advantageously result in broader distribution of the virus vector or virus-like particles than would be observed in the absence of the compositions and methods described herein.

In some embodiments, the virus vectors described herein may be administered to treat diseases of the CNS, including genetic disorders, neurodegenerative disorders, psychiatric disorders and tumors. Illustrative diseases of the CNS include, but are not limited to Adrenomyeloneuropathy (AMN), Alzheimer's disease, Angelman Syndrome, Frontotemporal Dementia, Parkinson's disease, Huntington's disease, Fragile X syndrome, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease (GM2 Gangliosidosis), Lesch-Nyhan disease, MC4R Obesity, Metachromatic Leukodystrophy (MLD), MPS I (Hurler/Scheie), MPS IIIA (Sanfilippo A), Niemann Pick C1, Rett Syndrome, Spinal Muscular Atrophy (SMA), AADC Deficiency, Monogenic Amyotropic Lateral Sclerosis (ALS), Alpha mannosidosis, Aspartylglucosaminuria, Dravet Syndrome, Giant Axonal Neuropathy, Globoid Cell Leukodystrophy (Krabbe), Glut 1 Deficiency, GM1 Gangliosidosis, Infantile Neuronal Ceroid Lipfuscinosis (INCL, Batten), Juvenile Neuronal Ceroid Lipfuscinosis (JNCL, Batten), Late Infantile Neuronal Ceroid Lipfuscinosis (LINCL, Batten), MPS II (Hunter), MPS IIIB (Sanfilippo B), MPS IIIC (Sanfilippo C), MPS IVA (Morquio Syndrome), MPS VI (Maroteaux-Lamy), Peroxisome Biogenesis Disorders (Zellweger Syndrome Spectrum), Sandhoff Disease (GM2 Gangliosidosis), epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The viral vectors described herein can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a viral vector.

Retinitis pigmentosa, by comparison, is characterized by retinal degeneration. In some embodiments, retinitis pigmentosa can be treated by intraocular (e.g., vitreal administration) of a viral vector encoding one or more neurotrophic factors.

Age-related macular degeneration involves both angiogenesis and retinal degeneration. This disorder can be treated by administering the inventive viral vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive viral vectors. Such agents include N-methyl-D-aspartate (NMDA) antagonists, cytokines, and neurotrophic factors, delivered intraocularly, optionally intravitreally.

In some embodiments, the compositions and methods described herein may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, epilepsy, which is marked by multiple seizures over time, may also be treated.

In some embodiments, a method of treating a subject in need thereof comprises administering to the subject an AAV vector comprising a protein capsid comprising capsid protein subunit, wherein the capsid protein subunit comprises the amino acid sequence of any one of SEQ ID NO: 165-187. In some embodiments, the AAV vector comprises a protein capsid comprising a capsid protein subunit comprising the amino acid sequence of SEQ ID NO: 175, or a sequence at least 95% identical thereto. In some embodiments, the AAV vector comprises a protein capsid comprising a capsid protein subunit comprising the amino acid sequence of SEQ ID NO: 175, or a sequence at least 95% identical thereto. In some embodiments, the subject has Dravet syndrome. In some embodiments, the subject has Rett syndrome. In some embodiments, the subject has Angelman syndrome. In some embodiments, the subject has Niemann-Pick disease. In some embodiments, the subject has Fragile X syndrome. In some embodiments, the subject has Alzheimer's disease. In some embodiments, the subject has Gaucher's disease. In some embodiments, the subject has Huntington's disease. In some embodiments, the subject has Parkinson's disease. In some embodiments, the subject has Friedrich's ataxia. In some embodiments, the AAV vector is administered to the subject by intracerebroventricular (ICV) injection. In some embodiments, the AAV vector is administered to the subject by intrathecal (IT) injection. In some embodiments, the AAV vector is administered to the subject by intravenous (IV) injection.

In some embodiments, a method of treating a subject in need thereof comprises administering to the subject an AAV vector comprising a protein capsid comprising a capsid protein subunit, wherein the capsid protein subunit comprises the amino acid sequence of SEQ ID NO: 175 or 180, wherein the subject has Dravet syndrome, Rett syndrome, Angelman syndrome, Niemann-Pick disease, or Fragile X syndrome, and wherein the AAV vector is administered to the subject by ICV or IT injection.

In some embodiments, a method of treating a subject in need thereof comprises administering to the subject an AAV vector comprising a protein capsid comprising a capsid protein subunit, wherein the capsid protein subunit comprises the amino acid sequence of SEQ ID NO: 175 or 180, wherein the subject has Gaucher's disease, Huntington's disease, Parkinson's disease, or Friedrich's ataxia, and wherein the AAV vector is administered to the subject by ICV or IT injection.

In some embodiments, somatostatin (or an active fragment thereof) is administered to the brain using a viral vector to treat a pituitary tumor. According to this embodiment, the viral vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In some embodiments, the virus vector can comprise a secretory signal as described in U.S. Pat. No. 7,071,172.

In some embodiments, the virus vector and/or viral-like particle is administered to the CNS (e.g., to the brain or to the eye). The virus vector and/or viral-like particle may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes, cortex, basal ganglia, hippocampus and portaamygdala), limbic system, neocortex, corpus striatum, cerebrum, and inferior colliculus. The virus vector and/or viral-like particle may also be administered to different regions of the eye such as the retina, cornea and/or optic nerve.

The virus vector and/or viral-like particle may be delivered into the cerebrospinal fluid (e.g., by lumbar puncture) for more disperse administration of the vector. The virus vector and/or viral-like particle may further be administered intravascularly to the CNS in situations in which the blood-brain barrier has been perturbed (e.g., brain tumor or cerebral infarct).

The virus vector and/or viral-like particle can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons. In some embodiments, the virus vector and/or viral-like particle is administered in a liquid formulation by direct injection (e.g., stereotactic injection) to the desired region or compartment in the CNS. In some embodiments, the virus vector and/or viral-like particle may be provided by topical application to the desired region or by intra-nasal administration of an aerosol formulation. Administration to the eye, may be by topical application of liquid droplets. As a further alternative, the virus vector and/or viral-like particle may be administered as a solid, slow-release formulation (see, e.g., U.S. Pat. No. 7,201,898).

In some embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

EXAMPLES

The following examples, which are included herein for illustration purposes only, are not intended to be limiting. As used herein, the terms STRD.101 and STRD.102 are used to describe capsid protein subunit sequences, and AAV-STRD.101 and AAV-STRD.102 are used to describe AAV vectors comprising recombinant or modified capsid protein subunit sequences. However, the terms STRD.101 and STRD.102 may be used in some contexts to describe AAV vectors comprising a protein capsid comprising the named capsid protein subunits, as will be apparent to the skilled artisan.

Figure 3:
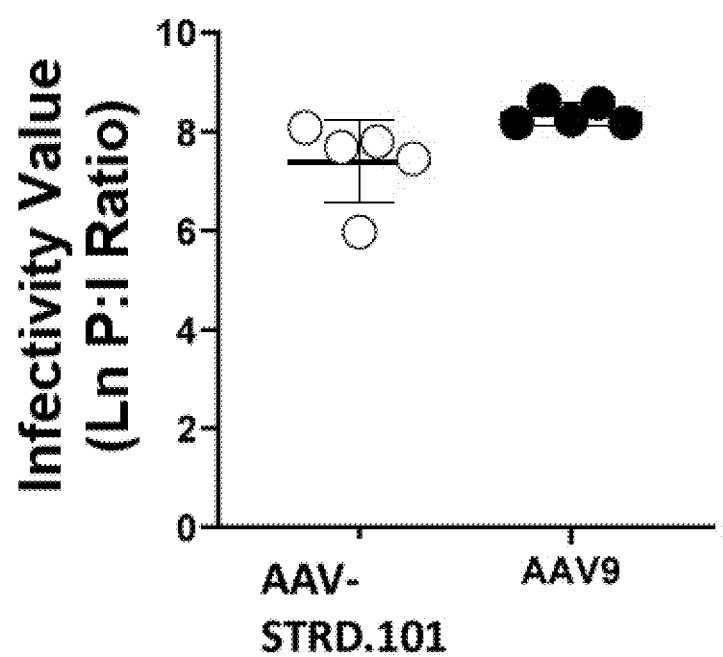
FIG. 3. Infectivity values of AAV-STRD.101 and wildtype AAV9 determined using a standard TCID50 assay. Data are graphed as the natural log of the number of particles required to generate an infectious unit (P:I Ratio). Error bars represent standard deviation.

Example 1. Combinatorial Engineering and Selection of Antibody-Evading AAV Vectors Antibody evading AAV mutants are prepared according to the following method. The first step involves identification of conformational 3D antigenic epitopes on the AAV capsid protein capsid surface, for example using cryo-electron microscopy. Selected residues within antigenic motifs are then subjected to mutagenesis using degenerate primers with each codon substituted by nucleotides NNK and gene fragments combined together by Gibson assembly and/or multistep PCR. Capsid protein subunit-encoding genes containing a degenerate library of mutated antigenic motifs are cloned into a wild type AAV genome to replace the original Cap encoding DNA sequence, yielding a plasmid library. Plasmid libraries are then transfected into 293 producer cell lines with an adenoviral helper plasmid to generate AAV capsid protein subunit libraries, which can then be subjected to selection. Successful generation of AAV libraries is confirmed via DNA sequencing.

In order to select for new AAV strains that can escape neutralizing antibodies (NAbs) and/or target the central nervous system (CNS), AAV libraries are subjected to multiple rounds of infection in non-human primates. At each stage, tissues of interest are isolated from animal subjects. Cell lysates harvested from the tissues of interest are sequenced to identify AAV isolates escaping antibody neutralization. After multiple rounds of infection in non-human primates, the isolated sequences from each mutagenized region are combined in all permutations and combinations.

As a specific example, a common antigenic motif on an AAV capsid protein subunit (VP1) was subjected to mutagenesis as described above. The degenerate libraries (FIG. 1A) were then subjected to a first round of infection in a non-human primate (intravenous injection). Tissues were harvested at day 7 post-infection and sequenced to identify single AAV isolates.

Various recombinant AAV isolates were identified in tissue samples, including the spinal cord, dorsal root ganglion, frontal lobe, temporal lobe, occipital lobe, putamen, globus pallidus, thalamus, amygdala, hippocampus, substantia nigra, pons, cerebellum, medulla. Results from this first round of evolution are shown in FIG. 1B.

The recombinant AAVs isolated during the first round of evolution (FIG. 1B) were then reintroduced into a second non-human primate. Tissues were harvested at day 7 post-infection and sequenced to identify single AAV isolates. The results from this second round of evolution are shown in FIG. 1C.

Recombinant AAVs with the highest frequency were sequenced. Substitutions present in these AAVs are shown in Tables 7.1 and 7.2. These data demonstrate that recombinant AAV virions having capsid protein subunits comprising the substitutions listed in Tables 7.1 and 7.2 evade neutralizing antibodies in vivo in non-human primates and have a tropism for the desired target tissues.

Example 2: Manufacturability of Recombinant AAV Vectors

To determine whether various recombinant AAVs identified in Example 1 may be manufactured in large-scale systems, the AAVs were produced according to standard methods, and yield was compared to that of wildtype AAV vectors.

AAVs were produced in HEK293 cells according to a standard triple transfection protocol. Briefly, the cells were transfected with (i) a plasmid comprising either the wildtype AAV9 capsid protein subunit sequence, the STRD.101 capsid protein subunit variant sequence (SEQ ID NO: 180), or the STRD.102 capsid protein subunit variant sequence (SEQ ID NO: 175), (ii) a plasmid comprising a 5'ITR, a transgene, and a 3' ITR sequence, and (ii) a plasmid comprising helper genes necessary for AAV production. Two different transgenes were used with each capsid protein subunit, in self-complementary constructs. The cells were subsequently lysed and the virions were purified using an affinity column, CsCl density ultracentrifugation, and dialysis. Subsequently, yield of each AAV was measured using a PCR-based quantification approach.

As shown in FIG. 2, recombinant AAV vectors comprising the STRD.101 and STRD.102 capsid protein subunits had a yield that was similar to the yield of wildtype AAV9. This data confirms that recombinant AAVs comprising the recombinant capsid protein subunits are suitable for commercial manufacturing.

Example 3: In Vitro Transduction Using Recombinant AAV Viral Vectors

To confirm whether the recombinant AAV vectors of Example 1 are generally infective and able to transduce cells in culture, various AAV vectors were prepared according to a standard protocol.

The infectivity of the recombinant AAVs was tested using a standard TCID50 assay. Briefly, HeLaRC32 cells were infected with recombinant AAV particles in the presence of Adenovirus (Ad5) at doses spanning 5 orders of magnitude. After 72 hours, DNA was extracted and vector genome replication was quantified by qPCR.

The particle to infectivity ratio was calculated to determine infectivity. As shown in FIG. 3, the infectivity ratio of an AAV-STRD.101 vector was lower compared to that of wildtype AAV9. Because a lower infectivity ratio translates to a higher potency, AAV-STRD.101 is more infectious than wildtype AAV9.

Separately, infectivity was also determined in various cell lines. Recombinant AAVs packaging a luciferase transgene were generated and contacted with the cells in culture at a dose of 10,000 vector genomes (vg) per cell. 48-hours post infection, cells were lysed. The lysate was contacted with a bioluminescent substrate, and relative fluorescence units (RFUs) were measured. As shown in FIG. 4A-4D, AAV-STRD.101 vectors infected U87 cells (human glioblastoma cell line, FIG. 4A), N2A cells (mouse neural crest-derived cell line, FIG. 4B), SY5Y cells (human neuroblastoma cell line, FIG. 4C), and U2OS cells (human osteosarcoma cell line, FIG. 4D) at levels comparable to wildtype AAV9.

Accordingly, this data demonstrates that the recombinant AAV vectors of Example 1 can effectively transduce cells in culture.

Figure 5:
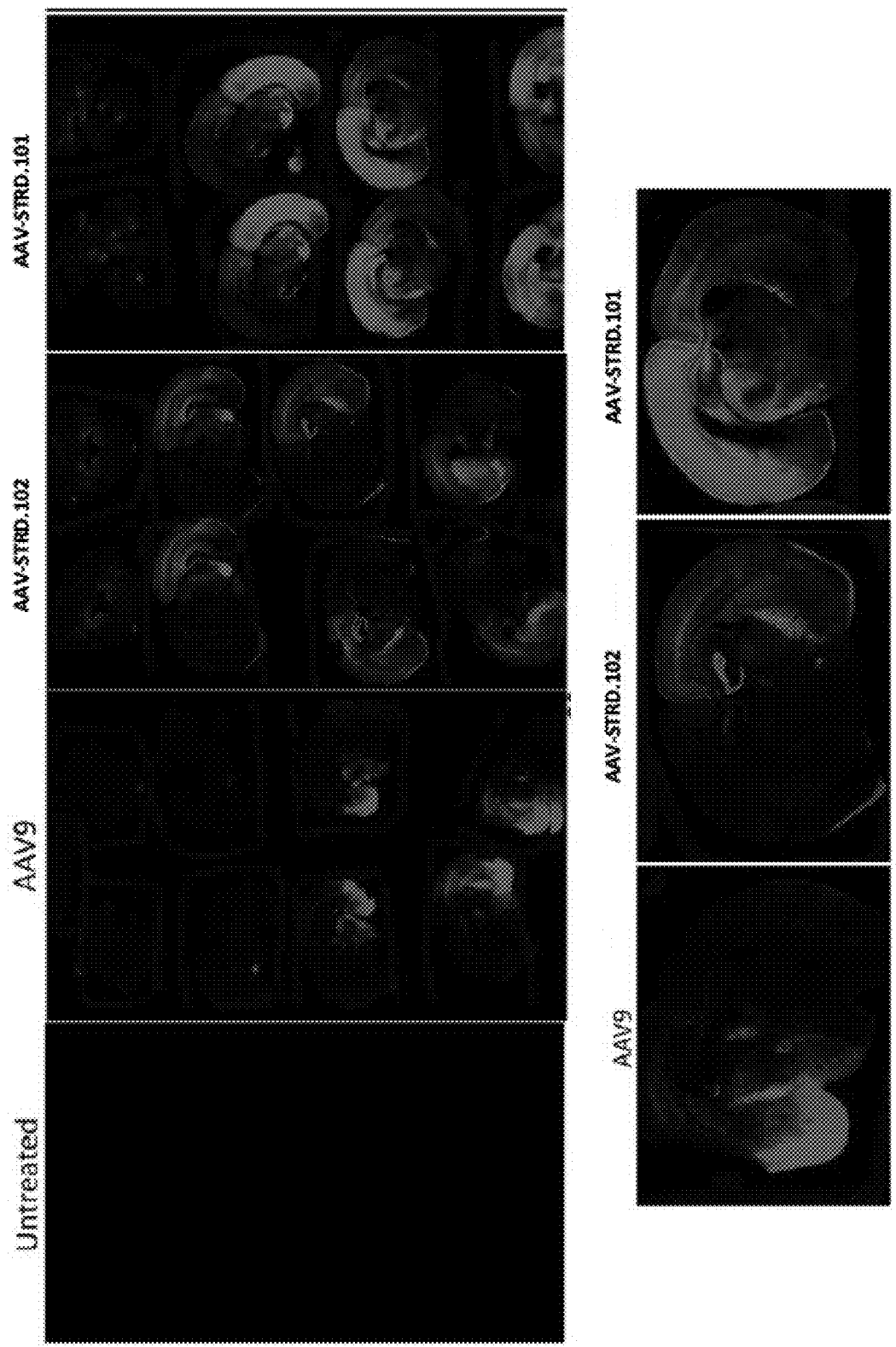
FIG. 5. Representative fluorescent microscopy images showing tdTomato expression in coronal vibratome sections 24 hours post-fixation with 4% PFA. Each section is 25 µm thick. Top panel shows images obtained using a 4× objective lens with native tdTomato fluorescence. The bottom panel shows images obtained using a 10× objective lens with native tdTomato fluorescence.
Figure 6:
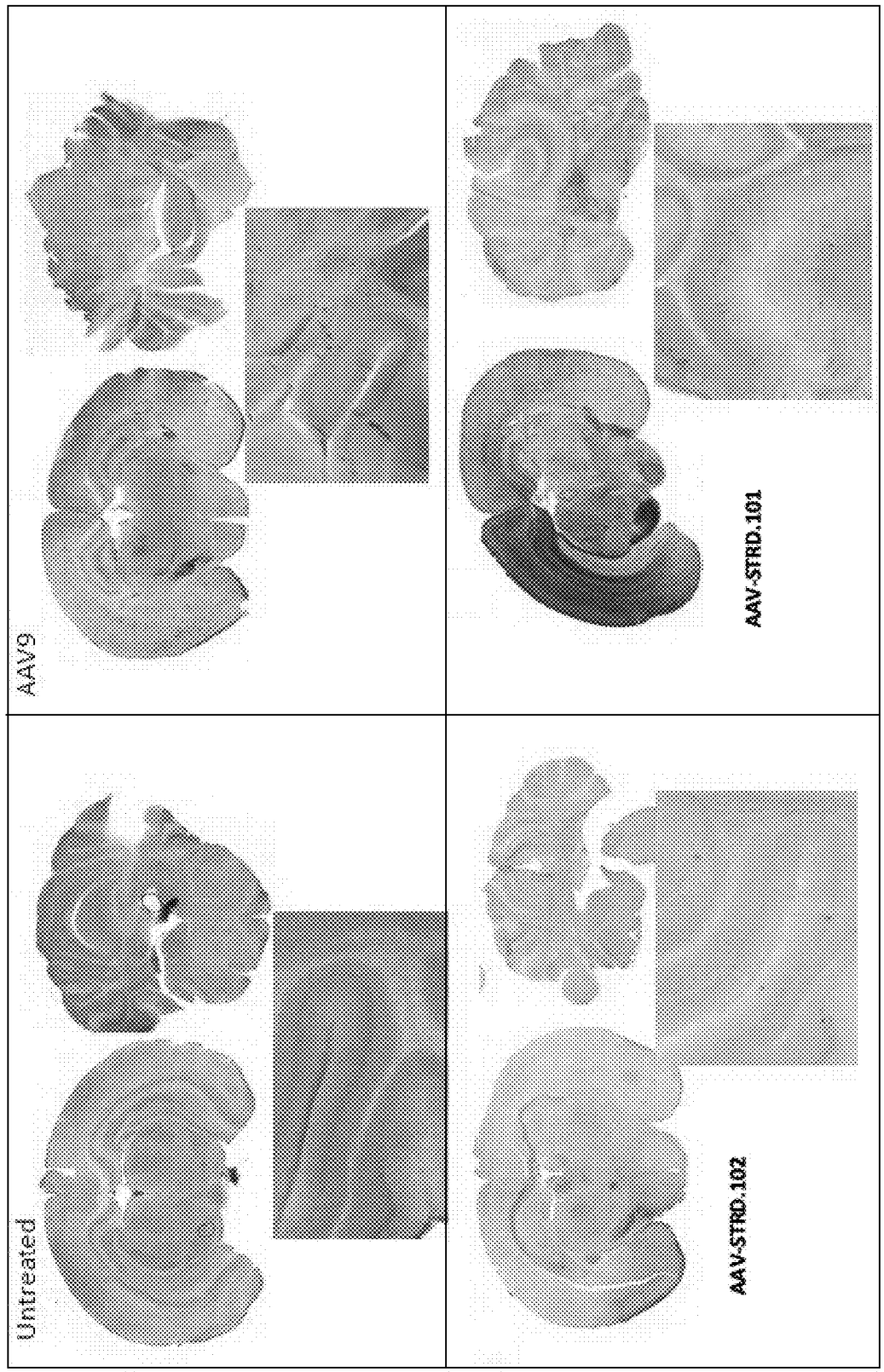
FIG. 6. Representative immunohistochemistry images showing tdTomato expression in coronal vibratome sections 24 hours post-fixation with 4% PFA. Each section is 25 µm thick.

Example 4: In Vivo Characterization of Recombinant AAVs Targeting the Central Nervous System Recombinant capsid protein subunits STRD.101 and STRD.102 were selected for in vivo characterization. Recombinant AAVs comprising these capsid protein subunits and packaging a native tdTomato fluorescent transgene were generated. The recombinant AAVs were administered to neonatal mice by intracerebroventricular injection at day 0. At three weeks post-injection, brain tissues were harvested and fixed to evaluate the expression by visual assessment of the tdTomato fluorescence. FIG. 5 provides representative images showing tdTomato expression in coronal vibratome sections after 24 hours post-fixation with 4% PFA. These same sections were also visualized using immunohistochemistry (FIG. 6). As shown in the images of FIG. 5 and FIG. 6, AAV9, AAV-STRD.102 and AAV-STRD.101 vectors each had different distribution in the brain tissues, with the highest transgene expression localized near the site of injection. Taken together, this data shows that the recombinant AAVs tested successfully deliver a transgene to target cells in vivo after intracerbroventricular injection.

The AAV-STRD.101 and AAV-STRD.102 vectors packaging tdTomato were also administered to four adult mice by intravenous injection at a dose of $5.5 \times 10^{13}$ vg/kg. Three weeks post-injection, liver and heart were harvested and fixed to evaluate the expression profile by visual assessment of tdTomato fluorescence.

Figure 7:
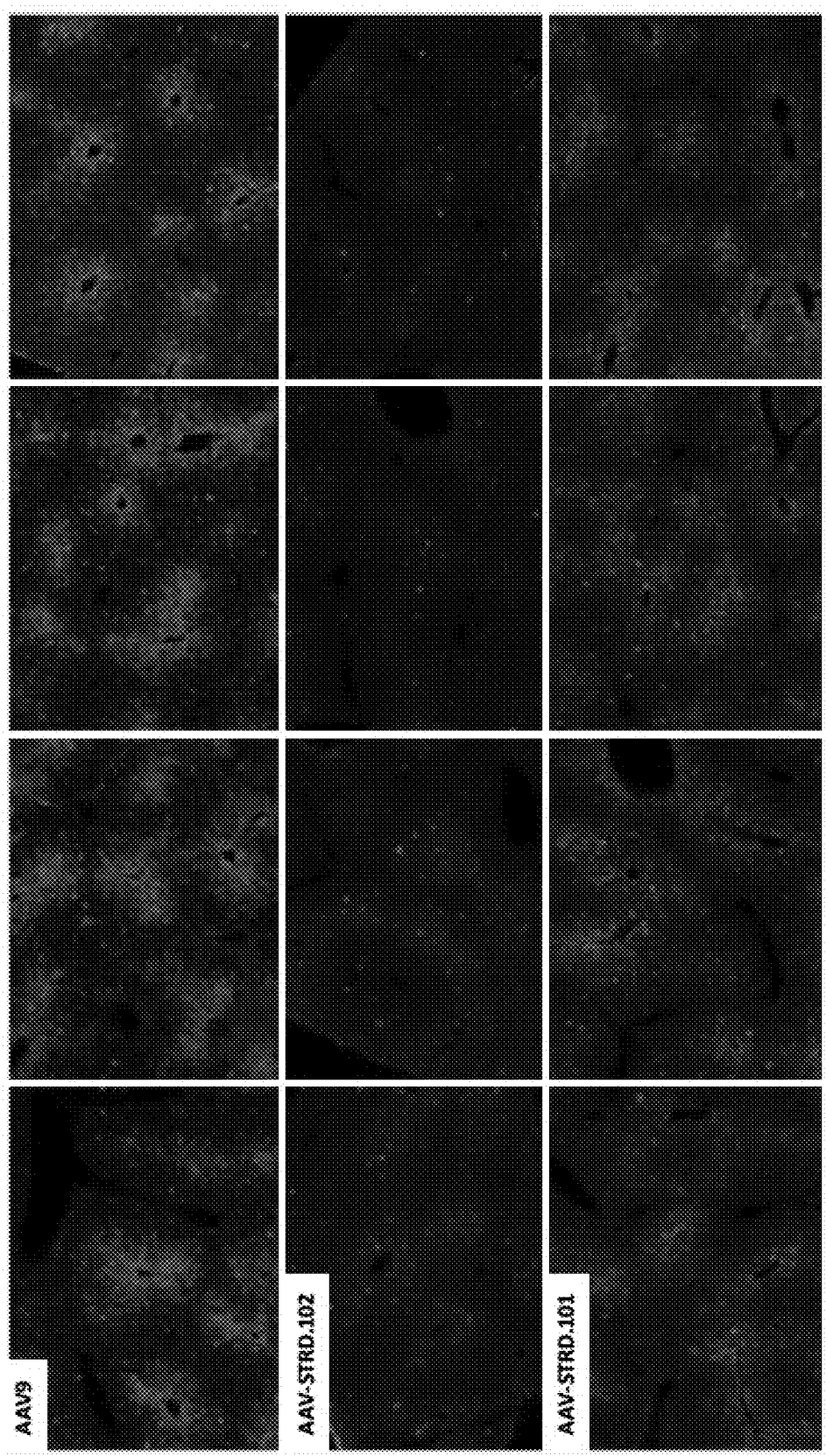
FIG. 7. Representative fluorescent microscopy images showing TdTomato expression in vibratrome liver sections 24 hours post-fixation with 4% PFA. Each section is 25 µm in thick. Panels show native tdTomato fluorescence with DAPI counterstain.

Representative images from one mouse showing TdTomato expression in vibratrome liver sections after 24 hours post-fixation with 4% PFA are provided in FIG. 7. Notably, the AAV-STRD.102 and AAV-STRD.101 vectors were detargeted to the liver compared to wildtype AAV9. This desirable property was unexpected, as no counter screen in the liver was performed during evolution.

Figure 8:
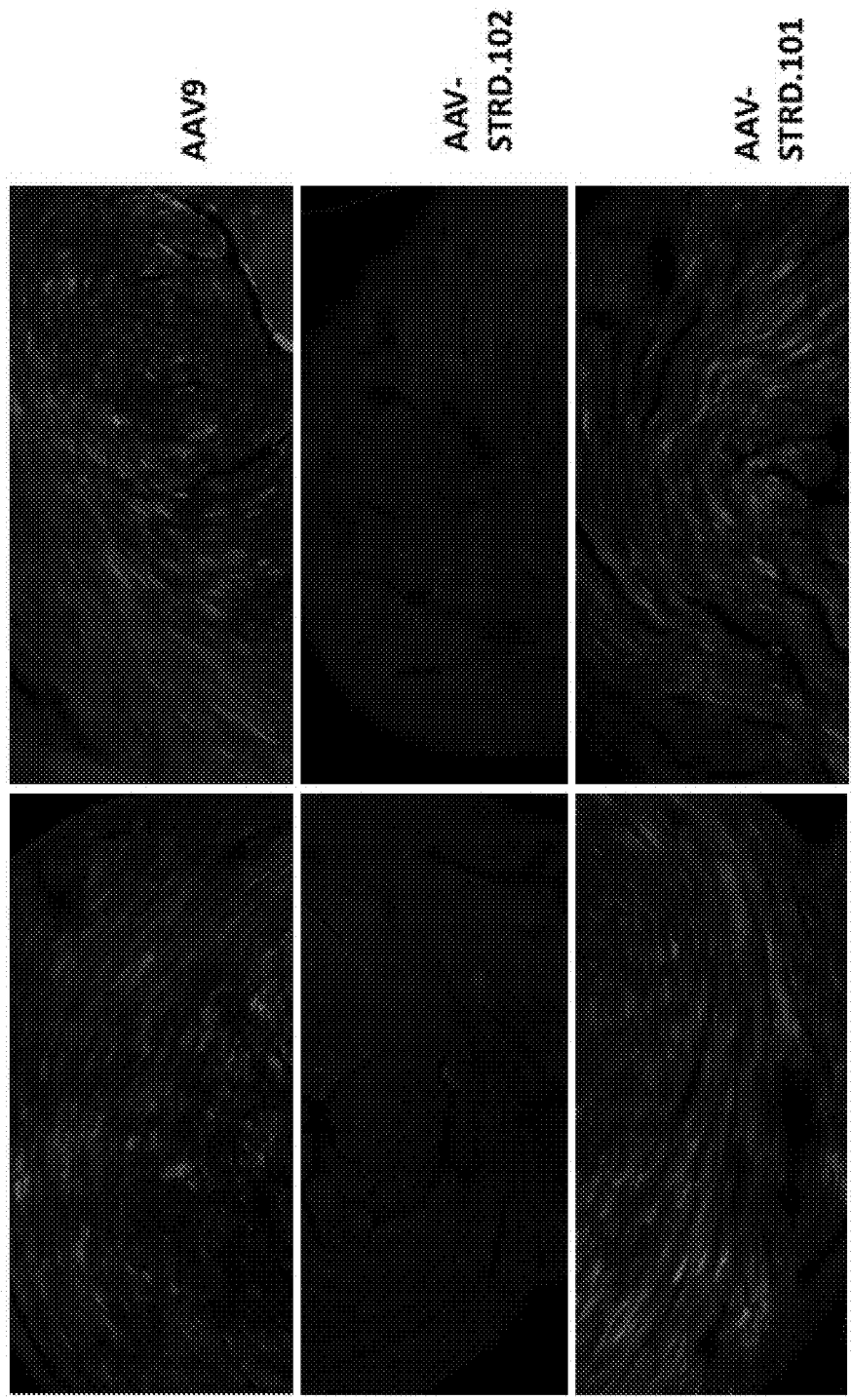
FIG. 8. Representative fluorescent microscopy images showing TdTomato expression in vibratrome heart sections 24 hours post-fixation with 4% PFA. Each section is 50 µm in thick. Panels show native tdTomato fluorescence with DAPI counterstain.

Representative images from one mouse showing TdTomato expression in vibratrome heart sections after 24 hours post-fixation with 4% PFA are provided in FIG. 8. Notably, the vectors tested had different tropism for the heart. Specifically, the AAV-STRD.102 vector was less infective in heart compared to AAV-STRD.101. Because no heart screen was performed during evolution, this differential transduction was wholly unexpected.

Taken together, this data indicates that the AAV-STRD.102 and AAV-STRD.101 vectors can be successfully used to target CNS tissues in vivo, avoid clearance by the liver, and are powerful tools for gene therapy. Given their different tropisms (i.e., AAV-STRD.101 was more infective in the heart than AAV-STRD.102), these vectors will be powerful tools for targeting gene therapy treatments to specifically desired tissues.

Example 5: Biodistribution of Recombinant AAVs in Non-Human Primates

Figure 9:
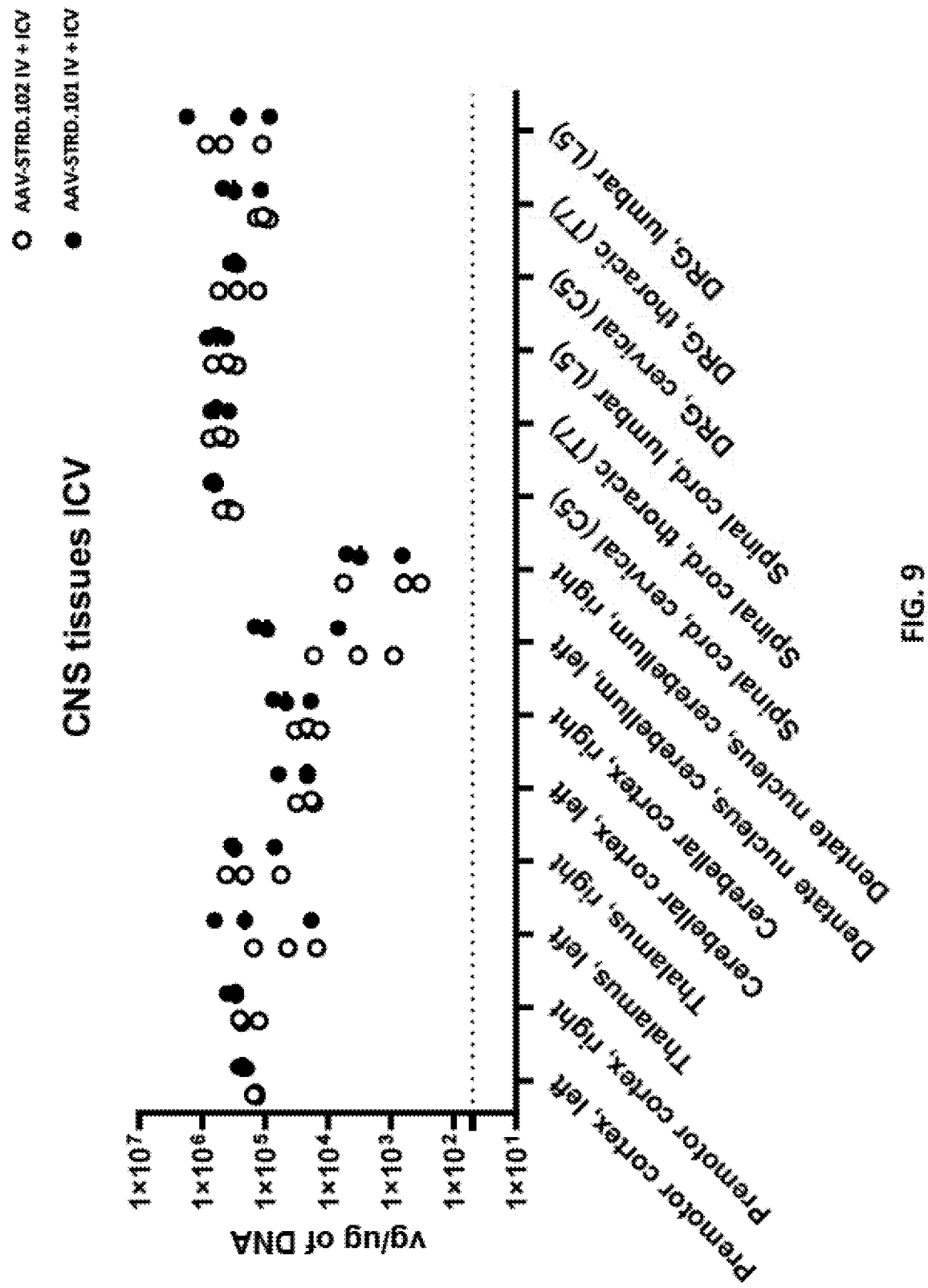
FIG. 9. Biodistribution of recombinant AAVs in non-human primates. Horizontal line shows limit of detection.

Recombinant AAVs were administered to non-human primates, in order to determine biodistribution. Recombinant AAVs were administered by intravenous (IV) and intracerebrovascular (ICV) injection (FIG. 9). AAV-STRD.101 was administered at a dose of $2.9 \times 10^{13}$ vector genomes per kilogram (vg/kg) by IV injection, and $2.1 \times 10^{13}$ vg by ICV injection (black dots). AAV-STRD.102 was administered at a dose of $2.8 \times 10^{13}$ vg/kg by IV injection, and $3.0 \times 10^{13}$ vg by ICV injection (white dots). After 30 days, the animals were sacrificed, and viral load in various CNS tissues was measured by qPCR.

As shown in FIG. 9, both AAV-STRD.102 and AAV-STRD.101 infected various CNS tissues. Additionally, because the AAVs showed high levels of transduction, this data suggest that these AAVs likely avoid neutralizing antibodies in vivo.

Example 6: Cell Therapy Method for Treating a Subject in Need Thereof

Cells are transduced using an AAV vector ex vivo. For some purposes, the cells may be autologous (i.e., derived from the subject to be treated) or allogenic (i.e., derived from a different subject/donor). After transduction of the cells using an AAV, and after expression of a transgene has been verified, the cells are administered to the subject using standard clinical methods.

Cells may be administered to the subject once, or administration may be repeated multiple times. The number of cells administered varies depending on, for example, the disease or condition to be treated, the severity of the subject's disease/condition, and the subject's height and weight.

Example 7: Gene Therapy Method for Treating a Subject in Need Thereof

An AAV vector described herein (e.g., an AAV vector comprising a capsid protein subunit having the sequence of SEQ ID NO: 175 or 180) is administered to a subject in need thereof, wherein the subject has a disease or disorder of the CNS. The AAV vector is administered to the subject once, or administration may be repeated multiple times. The administration is by one or more routes, such as intravenous (IV), intracerebroventricular (ICV), or intrathecal (IT) injection. The dose of AAV vector varies depending on, for example, the disease or condition to be treated, the severity of the subject's disease/condition, and the subject's height and weight. For example, the dose of AAV administered to the subject may be $2.8 \times 10^{13}$ vg/kg or $2.9 \times 10^{13}$ vg/kg when the AAV vector is administered by IV injection. When the AAV vector is administered by ICV injection, the dose may be $2.1 \times 10^{13}$ vg or $3.0 \times 10^{13}$ vg. In some protocols, the AAV vector may be administered to the subject by both IV and ICV injection.

Example 8: Preparation of a Recombinant AAV Vector in Mammalian Cells

Three plasmids are provided. The first plasmid comprises a transfer cassette comprising a transgene (SEQ ID NO: 3002) encoding NPC1 flanked by two ITRs (SEQ ID NO: 3003 and 3004). The first plasmid comprises the sequence of any one of SEQ ID NO: 3014-3019. The second plasmid comprises sequences encoding the Rep and Cap genes. The third plasmid comprises various "helper" sequences required for AAV production (E4, E2a, and VA).

The three plasmids are transfected into viral production cells (e.g., HEK293) using an appropriate transfection reagent (e.g., Lipofectamine™). After incubation at 37° C. for a predetermined period of time, AAV particles are collected from the media or the cells are lysed to release the AAV particles. The AAV particles are then purified and titered using either quantitative PCR (qPCR) or droplet digital PCR (ddPCR) according to standard methods. The AAV particles may be stored at −80° C. for later use.

Example 9: Preparation of a Recombinant AAV Vector in Insect Cells

A first recombinant baculoviral vector is provided. The first recombinant baculoviral vector comprises a transfer cassette sequence comprising a transgene (SEQ ID NO: 3002) encoding NPC1 flanked by two ITRs (SEQ ID NO: 3003 and 3004). The transfer cassette comprises the sequence of any one of SEQ ID NO: 3014-3019.

Insect cells (e.g., Sf9) are co-infected in suspension culture with the first recombinant baculoviral vector and a least one additional recombinant baculoviral vector comprising sequences encoding the AAV Rep and Cap proteins (e.g., the STRD.101 or STRD.012 capsid protein subunit). After incubation at 28° C. for a predetermined period of time, AAV particles are collected from the media or the cells are lysed to release the AAV particles. The AAV particles are then purified and titered using either quantitative PCR (qPCR) or droplet digital PCR (ddPCR) according to standard methods. The AAV particles may be stored at −80° C. for later use.

Example 10: In Vitro Potency Assay

To determine whether the AAV transfer cassettes described herein are able to rescue the NPC1 lysosomal phenotype in cultured cells, a recombinant AAV2 vector packaging a hNPC1 transfer cassette (SEQ ID NO: 3014) was prepared in HEK293 cells using a triple-transfection protocol (See, e.g., Example 1). The AAV2-hNPC1 vector was then used to transduce wildtype U2OS cells (osteosarcoma), and U2OS cells which do not express NPC1 (NPC$^{-/-}$) in vitro at a multiplicity of infection (MOI) of either $5\times10^3$ (5K) or $10\times10^3$ (10K). Cells were then incubated at 37° C. in a 5% $CO_2$ atmosphere.

NPC1 cells exhibit a characteristic accumulation of cholesterol in lysosomes, which can be monitored by observing the size and number of lysosomes in a cell. In this assay, lysosomal phenotype was monitored by measuring accumulation of a fluorescent organelle dye, LysoTracker® (ThermoFisher Scientific®), in the cells. 72 hours after transduction with the AAV2-hNPC1 vector, 50 mM of LysoTracker® was added to the cells. After 2 hours, the cells were fixed and LysoTracker® fluorescence was measured.

Figures 10A, 10B:
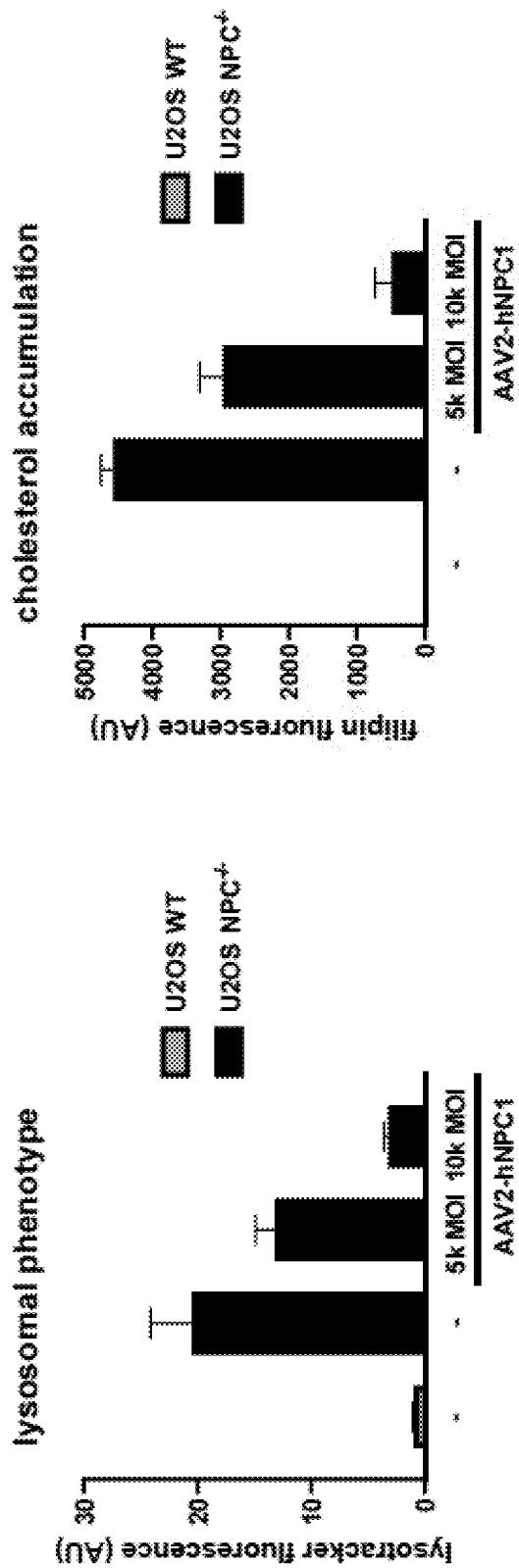
FIG. 10A is a graph that shows lysosomal phenotype, as determined by measuring LysoTracker® accumulation, in wildtype U2OS cells, NPC1-definicent (NPC1$^{-/-}$) U2OS cells, and NPC1$^{-/-}$ cells transduced with AAV2-hNPC at a Multiplicity of Infection (MOI) of either $5\times10^3$ or $10\times10^3$. Statistical significance determined using one-way ANOVA. Error bars represent standard error of the mean (SEM).
FIG. 10B is a graph that shows cholesterol accumulation, as determined using filipin staining, in wildtype U2OS cells, NPC1-definicent (NPC1$^{-/-}$) U2OS cells, and NPC1$^{-/-}$ cells transduced with AAV2-hNPC at a Multiplicity of Infection (MOI) of either $5\times10^3$ or $10\times10^3$. Statistical significance determined using one-way ANOVA. Error bars represent SEM.

Results are shown in FIG. 10A. As expected, wildtype U2OS cells did not show significant accumulation of LysoTracker® fluorescence in lysosomes, whereas the NPC1$^{-/-}$ cells did. Cells transduced with AAV2-hNPC1 at a MOI of either 5K or 10K had significantly reduced accumulation of LysoTracker® fluorescence in lysosomes.

In a separate assay, cells transduced with hNPC1 were fixed and stained using filipin, a histochemical stain for cholesterol. The filipin stain, derived from *Streptomyces filipinensis*, was purchased from Polysciences, and was used at a final concentration of 50 µg/mL. The cells were visualized using a Pico Automated Cell Imaging System (ImageXpress®), and filipin stain was quantified. Results are shown in FIG. 10B. As expected, wildtype U2OS cells did not show significant cholesterol accumulation, whereas the NPC1$^{-/-}$ cells did. Cells transduced with AAV2-hNPC1 at a MOI of either 5K or 10K had significantly reduced cholesterol accumulation.

Taken together, these data show that transduction of cells using AAV2-hNPC successfully rescued lysosomal phenotype in NPC1-deficient U2OS cells.

Example 11: In Vivo Potency Assay

Figure 11:
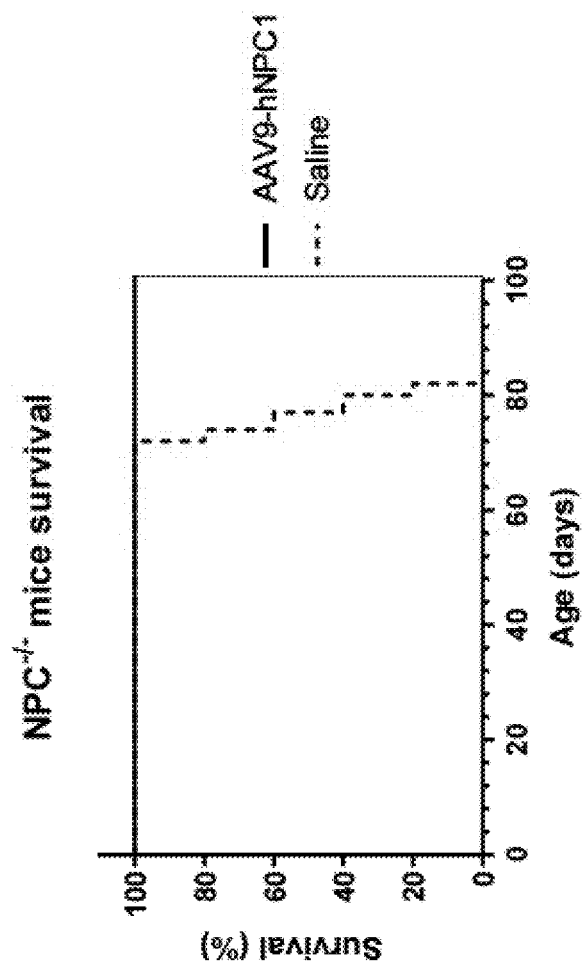
FIG. 11 is a Kaplan-Meier survival curve, showing survival of NPC1$^{-/-}$ mice after retro-orbital injection with saline or with AAV9-hNPC1. All AAV9-hNPC1-injected animals survived through the duration of the experiment, and were sacrificed around 100 days of age for histological analysis.

To determine whether the AAV transfer cassettes described herein are able to rescue the NPC1 phenotype in vivo, a recombinant AAV9 vector packaging a hNPC1 transfer cassette (SEQ ID NO: 3014) was prepared in HEK293 cells using a triple-transfection protocol (See, e.g., Example 1). Mice deficient for NPC1 (i.e., NPC1$^{-/-}$ mice) were injected intravenously at a dose of $3.0\times10^{14}$ vector genomes per kilogram (vg/kg), by retro-orbital injection, with either saline or with the AAV9-hNPC1 vector around the age of 24-28 days. Results are shown in FIG. 11. All saline-treated mice died by the age of about 80 days. However, all AAV9-hNPC1-injected animals survived through the duration of experiment. The AAV9-hNPC1-injected mice were sacrificed around 100 days of age for analysis.

Figure 13:
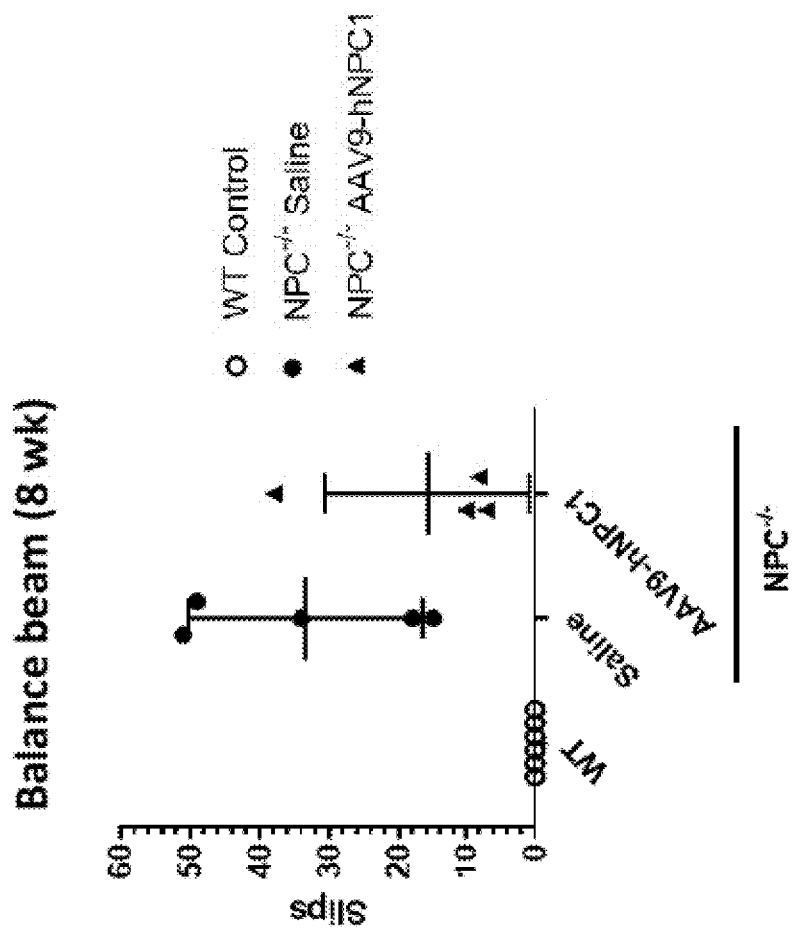
FIG. 13 shows number of slips in a balance beam walking test at about 8 weeks (56 days) of age in wildtype mice, saline-treated NPC1$^{-/-}$ mice, or NPC1$^{-/-}$ mice treated with AAV9-hNPC1. Error bars represent standard deviation.

Mice were also challenged in a balance beam walking test, wherein number of slips were measured as mice walked across a balance beam. The test was performed at about 8 weeks (56 days) of age. As shown in FIG. 13, wildtype mice did not slip off the balance beam. Although there was no statistically significant difference in the number of slips between NPC1$^{-/-}$ mice treated with AAV9-hNPC1 and saline-treated NPC1$^{-/-}$ mice, the average number of slips observed in the AAV9-hNPC1 group was less.

Figure 12:
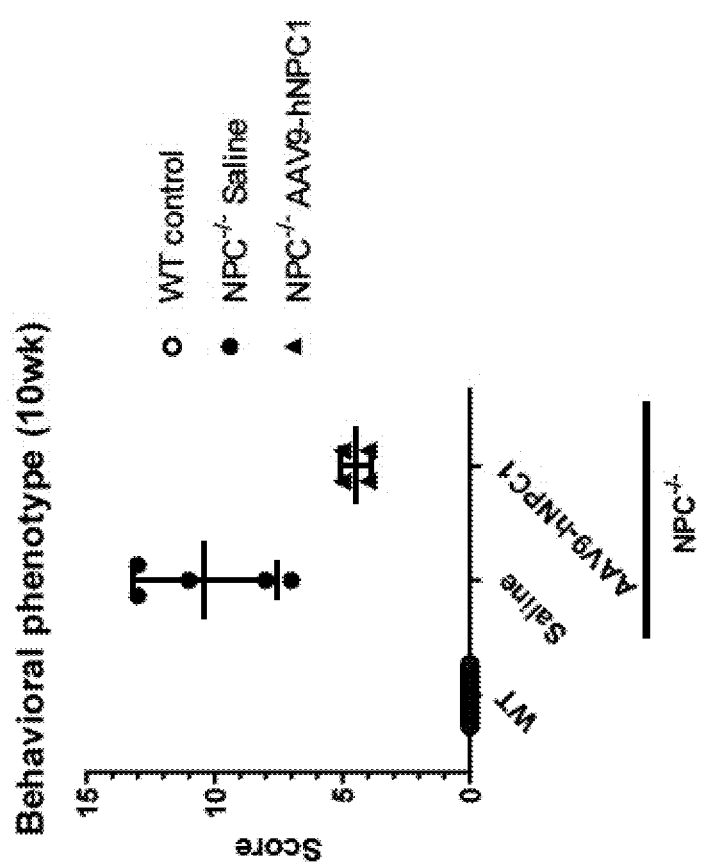
FIG. 12 shows behavioral phenotype score at about 10 weeks (70 days) of age in wildtype mice, saline-treated NPC1$^{-/-}$ mice, or NPC1$^{-/-}$ mice injected with AAV9-hNPC1. Statistical significance was determined using an unpaired T-test, and error bars represent SEM.

Behavioral phenotype score of the mice was also assessed at about 10 weeks (70 days) of age. The behavioral phenotype score is a composite score measuring various disease symptoms, including grooming, gait, kyphosis, ledge test, hindlimb clasp, and tremor. (See Alam et al, Sci Transl Med, 2016; Guyenet et al, J Vis Exp, 2010). As shown in FIG. 12, NPC1$^{-/-}$ mice treated with AAV9-hNPC1 had a significantly reduced score as compared to saline-treated NPC1$^{-/-}$ mice.

Taken together, these data demonstrate that AAV9-hNPC1 can at least partially rescue the disease phenotype of NPC1 deficient mice.

Example 12: Testing a STRD.101 Vector Packaging a Cassette Encoding NPC1 in Vitro and In Vivo An AAV-STRD.101 vector comprising a nucleic acid comprising a transfer cassette encoding human NPC1 (e.g., the transfer cassette of SEQ ID NO: 14) is prepared according to the method of Example 8 or 9. This vector is referred to herein as AAV-STRD.101-hNPC1

To determine whether the AAV-STRD.101 vector is able to rescue the NPC1 lysosomal phenotype in cultured cells, the AAV-STRD.101-hNPC1 vector is then used to transduce wildtype U2OS cells (osteosarcoma), and U2OS cells which do not express NPC1 (NPC$^{-/-}$) in vitro at a multiplicity of infection (MOI) of either 5×10$^3$ (5K) or 10×10$^3$ (10K). Cells are then incubated at 37° C. in a 5% CO$_2$ atmosphere.

NPC1 cells exhibit a characteristic accumulation of cholesterol in lysosomes, which can be monitored by observing the size and number of lysosomes in a cell. Accordingly, lysosomal phenotype is monitored by measuring accumulation of a fluorescent organelle dye, LysoTracker® (ThermoFisher Scientific®), in the cells. 72 hours after transduction with the AAV2-hNPC1 vector, 50 mM of LysoTracker® is added to the cells. After 2 hours, the cells are fixed and LysoTracker® fluorescence is measured.

In a separate assay, cells transduced with the AAV-STRD.101-hNPC1 vector are fixed and stained using filipin, a histochemical stain for cholesterol. The filipin stain, derived from *Streptomyces filipinensis*, is used at a final concentration of 50 μg/mL. The cells are visualized using a Pico Automated Cell Imaging System (ImageXpress®), and filipin stain iss quantified.

The AAV-STRD.101-hNPC1 vector is also tested to determine whether it can rescue the NPC1 phenotype in vivo. Mice deficient for NPC1 (i.e., NPC1$^{-/-}$ mice) are injected intravenously at a dose of 3.0×10$^{14}$ vg/kg, by retro-orbital injection, with either saline or with the AAV9-hNPC1 vector around the age of 24-28 days. Survival is monitored until at least 100 days of age.

Mice are also challenged in a balance beam walking test, wherein number of slips are measured as mice walked across a balance beam. The test is performed at about 8 weeks (56 days) of age.

Behavioral phenotype score of the mice is also assessed at about 10 weeks (70 days) of age. The behavioral phenotype score is a composite score measuring various disease symptoms, including grooming, gait, kyphosis, ledge test, hindlimb clasp, and tremor. (See Alam et al, Sci Transl Med, 2016; Guyenet et al, J Vis Exp, 2010).

The foregoing is illustrative of the present invention, and is not to be construed as limiting thereof. The invention is defined by the following claims, with equivalents of the claims to be included therein.

NUMBERED EMBODIMENTS

Notwithstanding the appended claims, the disclosure sets forth the following numbered embodiments:

1. An adeno-associated virus (AAV) vector comprising: (i) a protein capsid comprising a capsid protein subunit comprising the sequence of SEQ ID NO: 180 or 175; and (ii) a nucleic acid encapsidated by the protein capsid; wherein the nucleic acid comprises a transfer cassette; wherein the transfer cassette comprises from 5' to 3': a 5' inverted terminal repeat (ITR); a promoter; a transgene sequence which encodes the NPC1 protein; a polyadenylation signal; and a 3' ITR.

2. The AAV vector of embodiment 1, wherein at least one of the 5' ITR and the 3' ITR is about 110 to about 160 nucleotides in length.

3. The AAV vector of embodiment 1 or 2, wherein the 5' ITR is the same length as the 3' ITR.

4. The AAV vector of embodiment 1 or 2, wherein the 5' ITR and the 3' ITR have different lengths.

5. The AAV vector of any one of embodiments 1-4, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

6. The AAV vector of embodiment 1, wherein the 5' ITR comprises the sequence of SEQ ID NO: 3003.

7. The AAV vector of embodiment 1, wherein the 3' ITR comprises the sequence of SEQ ID NO: 3004.

8. The AAV vector of any one of embodiments 1-7, wherein the promoter is a constitutive promoter.

9. The AAV vector of any one of embodiments 1-7, wherein the promoter is an inducible promoter.

10. The AAV vector of any one of embodiments 1-9, wherein the promoter is a tissue-specific promoter.

11. The AAV vector of any one of embodiments 1-7, wherein the promoter is selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the dihydrofolate reductase (DHFR) promoter, and the phosphoglycerol kinase (PGK) promoter.

12. The AAV vector of embodiment 11, wherein the promoter is selected from the group consisting of the CBA promoter, the GUSB240 promoter, the GUSB379 promoter, and the HSVTK promoter.

13. The AAV vector of any one of embodiments 1-7, wherein the promoter comprises a sequence at least 95% or 100% identical to any one of SEQ ID NO: 3005, SEQ ID NO: 3006, SEQ ID NO: 3007, or SEQ ID NO: 3008.

14. The AAV vector of any one of embodiments 1-13, wherein the NPC1 protein is the human NPC1 protein.

15. The AAV vector of any one of embodiments 1-13, wherein the NPC1 protein has a sequence that is at least 90% identical to the sequence of the human NPC1 protein.

16. The AAV vector of embodiment 15, wherein the NPC1 protein has a sequence that is at least 95% identical to the sequence of the human NPC1 protein.

17. The AAV vector of embodiment 16, wherein the NPC1 protein has a sequence that is at least 98% identical to the sequence of the human NPC1 protein.

18. The AAV vector of any one of embodiments 1-13, wherein the NPC1 protein comprises the sequence of SEQ ID NO: 3001.

19. The AAV vector of any one of embodiments 1-13, wherein the transgene comprises the sequence of SEQ ID NO: 3002.

20. The AAV vector of any one of embodiments 1-18, wherein the polyadenylation signal is selected from simian virus 40 (SV40), rBG, α-globin, β-globin, human collagen, human growth hormone (hGH), polyoma virus, human growth hormone (hGH) and bovine growth hormone (bGH).

21. The AAV vector of embodiment 20, wherein the polyadenylation signal is the SV40 polyadenylation signal.

22. The AAV vector of embodiment 20, wherein the polyadenylation signal is the rBG polyadenylation signal.

23. The AAV vector of any one of embodiments 1-19, wherein the polyadenylation signal comprises the sequence at least 95% or 100% identical to SEQ ID NO: 3012 or to SEQ ID NO: 3013.

24. The AAV vector of any one of embodiments 1-23, wherein the cassette further comprises an enhancer.

25. The AAV vector of embodiment 24, wherein the enhancer is the CMV enhancer.

26. The AAV vector of embodiment 24, wherein the enhancer comprises the sequence of SEQ ID NO: 3009, or a sequence at least 95% identical thereto.

27. The AAV vector of any one of embodiments 1-26, wherein the cassette further comprises an intronic sequence.

28. The AAV vector of embodiment 27, wherein the intronic sequence is a chimeric sequence.

29. The AAV vector of embodiment 27, wherein the intronic sequence is a hybrid sequence.

30. The AAV vector of embodiment 27, wherein the intronic sequence comprises a sequence isolated or derived from SV40.

31. The AAV vector of embodiment 27, wherein the intronic sequence comprises the sequence of any one of SEQ ID NO: 3010-3011.

32. The AAV vector of embodiment 1, wherein the AAV transfer cassette comprises the sequence of any one of SEQ ID NO: 3014-3019.

33. An adeno-associated virus (AAV) vector comprising: (i) a protein capsid comprising a capsid protein subunit comprising the sequence of SEQ ID NO: 180 or 175, or a sequence comprising about 1 to about 25 amino acid mutations relative to SEQ ID NO: 180 or 175; and (ii) a transfer cassette encapsidated by the protein capsid; wherein the transfer cassette comprises from 5' to 3': a 5' inverted terminal repeat (ITR); a promoter; a transgene sequence which encodes the NPC1 protein; a polyadenylation signal; and a 3' ITR.

34. A composition comprising the AAV vector of any one of embodiments 1-33.

35. The composition of embodiment 34, wherein the composition comprises a pharmaceutically acceptable carrier or excipient.

36. A method for treating a subject in need thereof comprising administering to the subject a therapeutically effective amount of the AAV vector of any one of embodiments 1-33, or the composition of any one of embodiments 34-35.

37. The method of embodiment 36, wherein the subject has Neimann-Pick Disease Type C.

38. The method of embodiment 36 or 37, wherein the subject is a human subject.

39. An adeno-associated virus (AAV) vector comprising: (i) a protein capsid comprising a capsid protein subunit comprising the sequence of SEQ ID NO: 180 or 175; and (ii) a transfer cassette encapsidated by the protein capsid; wherein the transfer cassette comprises from 5' to 3': a 5' inverted terminal repeat (ITR); a promoter; a transgene sequence comprising the sequence of SEQ ID NO: 3002; a polyadenylation signal; and a 3' ITR.

40. An adeno-associated virus (AAV) vector comprising: (i) a protein capsid comprising a capsid protein comprising the sequence of SEQ ID NO: 180 or 175; and (ii) a nucleic acid encapsidated by the protein capsid; wherein the nucleic acid comprises a transfer cassette; wherein the transfer cassette comprises from 5' to 3': a 5' inverted terminal repeat (ITR); a promoter; a transgene sequence which encodes the NPC1 protein, wherein the NPC1 protein comprises the sequence of SEQ ID NO: 3001; a polyadenylation signal; and a 3' ITR.

41. The AAV vector of any one of embodiments 1-33, 39 and 40, wherein the AAV vector selectively delivers the transfer cassette to a cell or tissue of the central nervous system.

42. The AAV vector of embodiment 41, wherein the tissue of the central nervous system is the premotor cortex, the thalamus, the cerebellar cortex, the dentate nucleus, the spinal cord, or the dorsal root ganglion.

43. The AAV vector of any one of embodiments 1-33, 39 and 40, wherein the AAV vector delivers the transfer cassette to the brain, but does not deliver the AAV vector to the heart.

44. The AAV vector of any one of embodiments 1-33, 39 and 40, wherein the AAV vector delivers the transfer cassette to the brain and to the heart.

45. The AAV vector of embodiment 44, wherein delivery of the transfer cassette is greater to the brain than to the heart.

46. The AAV vector of embodiment 44, wherein delivery of the transfer cassette is approximately equal in the brain in the heart.

47. A cell comprising the AAV vector of any one of embodiments 1-33 and 39-46.

48. An in vitro method of introducing a transfer cassette into a cell, comprising contacting the cell with the AAV vector of any one of embodiments 1-33 and 39-46.

49. An AAV vector of any one of embodiments 1-33 and 39-46 for use as a medicament.

50. An AAV vector of any one of embodiments 1-33 and 39-46 for use in a method of treating or preventing Neimann-Pick Disease Type C in a subject in need thereof.

51. The AAV vector of any one of embodiments 1-33 and 39-46, wherein the capsid protein subunit comprises the sequence of SEQ ID NO: 180.

52. The AAV vector of any one of embodiments 1-33 and 39-46, wherein the capsid protein subunit comprises the sequence of SEQ ID NO: 175.

53. An Adeno-Associated Virus (AAV) transfer cassette comprising, from 5' to 3': a 5' inverted terminal repeat (ITR); a promoter; a transgene; a polyadenylation signal; and a 3' ITR; wherein the transgene encodes the NPC1 protein.

54. The AAV transfer cassette of embodiment 53, wherein at least one of the 5' ITR and the 3' ITR is about 110 to about 160 nucleotides in length.

55. The AAV transfer cassette of embodiment 53 or 54, wherein the 5' ITR is the same length as the 3' ITR.

56. The AAV transfer cassette of embodiment 53 or 54, wherein the 5' ITR and the 3' ITR have different lengths.

57. The AAV transfer cassette of any one of embodiments 53-56, wherein at least one of the 5' ITR and the 3' ITR is isolated or derived from the genome of AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV.

58. The AAV transfer cassette of embodiment 53 wherein the 5' ITR comprises the sequence of SEQ ID NO: 3003.

59. The AAV transfer cassette of embodiment 53, wherein the 3' ITR comprises the sequence of SEQ ID NO: 3004.

60. The AAV transfer cassette of any one of embodiments 53-59, wherein the promoter is a constitutive promoter.

61. The AAV transfer cassette of any one of embodiments 53-59, wherein the promoter is an inducible promoter.

62. The AAV transfer cassette of any one of embodiments 53-59, wherein the promoter is a tissue-specific promoter.

63. The AAV transfer cassette of any one of embodiments 53-59, wherein the promoter is selected from the group consisting of the CBA promoter, the GUSB240 promoter, the GUSB379 promoter, the HSVTK promoter, the CMV promoter, the SV40 early promoter, the SV40 late promoter, the metallothionein promoter, the murine mammary tumor virus (MMTV) promoter, the Rous sarcoma virus (RSV) promoter, the polyhedrin promoter, the chicken β-actin (CBA) promoter, the EF-1 alpha promoter, the dihydrofolate reductase (DHFR) promoter, and the phosphoglycerol kinase (PGK) promoter.

64. The AAV transfer cassette of embodiment 63, wherein the promoter is selected from the group consisting of the CBA promoter, the GUSB240 promoter, the GUSB379 promoter, and the HSVTK promoter.

65. The AAV transfer cassette of any one of embodiments 53-59, wherein the promoter comprises a sequence at least 95% or 100% identical to any one of SEQ ID NO: 3005, SEQ ID NO: 3006, SEQ ID NO: 3007, or SEQ ID NO: 3008.

66. The AAV transfer cassette of any one of embodiments 53-65, wherein the NPC1 protein is the human NPC1 protein.

67. The AAV transfer cassette of any one of embodiments 53-65, wherein the NPC1 protein has a sequence that is at least 90% identical to the sequence of the human NPC1 protein.

68. The AAV transfer cassette of embodiment 67, wherein the NPC1 protein has a sequence that is at least 95% identical to the sequence of the human NPC1 protein.

69. The AAV transfer cassette of embodiment 68, wherein the NPC1 protein has a sequence that is at least 98% identical to the sequence of the human NPC1 protein.

70. The AAV transfer cassette of any one of embodiments 53-65, wherein the NPC1 protein comprises the sequence of SEQ ID NO: 3001.

71. The AAV transfer cassette of any one of embodiments 53-65, wherein the transgene comprises the sequence of SEQ ID NO: 3002.

72. The AAV transfer cassette of any one of embodiments 53-71, wherein the polyadenylation signal is selected from simian virus 40 (SV40), rBG, α-globin, β-globin, human collagen, human growth hormone (hGH), polyoma virus, human growth hormone (hGH) and bovine growth hormone (bGH).

73. The AAV transfer cassette of embodiment 72, wherein the polyadenylation signal is the SV40 polyadenylation signal.

74. The AAV transfer cassette of embodiment 72, wherein the polyadenylation signal is the rBG polyadenylation signal.

75. The AAV transfer cassette of any one of embodiments 53-71, wherein the polyadenylation signal comprises the sequence at least 95% or 100% identical to SEQ ID NO: 3012 or to SEQ ID NO: 3013.

76. The AAV transfer cassette of any one of embodiments 53-75, wherein the cassette further comprises an enhancer.

77. The AAV transfer cassette of embodiment 76, wherein the enhancer is the CMV enhancer.

78. The AAV transfer cassette of embodiment 76, wherein the enhancer comprises the sequence of SEQ ID NO: 3009, or a sequence at least 95% identical thereto.

79. The AAV transfer cassette of any one of embodiments 53-78, wherein the cassette further comprises an intronic sequence.

80. The AAV transfer cassette of embodiment 79, wherein the intronic sequence is a chimeric sequence.

81. The AAV transfer cassette of embodiment 79, wherein the intronic sequence is a hybrid sequence.

82. The AAV transfer cassette of embodiment 79, wherein the intronic sequence comprises sequences isolated or derived from SV40.

83. The AAV transfer cassette of embodiment 79, wherein the intronic sequence comprises the sequence of any one of SEQ ID NO: 3010-3011.

84. The AAV transfer cassette of embodiment 53, wherein the AAV transfer cassette comprises the sequence of any one of SEQ ID NO: 3014-3019.

85. A plasmid comprising the AAV transfer cassette of any one of embodiments 53-84.

86. A cell comprising the AAV transfer cassette of any one of embodiments 53-84 or the plasmid of embodiment 85.

87. A method of producing a recombinant AAV vector, the method comprising contacting an AAV producer cell with the AAV transfer cassette of any one of embodiments 53-84 or the plasmid of embodiment 85.

88. A recombinant AAV vector produced by the method of embodiment 87.

89. The recombinant AAV vector of embodiment 88, wherein the vector is of a serotype selected from AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV and Bovine AAV.

90. A composition comprising the AAV transfer cassette of any one of embodiments 53-84, the plasmid of embodiment 85, the cell of embodiment 86, or the recombinant AAV vector of embodiment 88 or 89.

91. A method for treating a subject in need thereof comprising administering to the subject an effective amount of the AAV transfer cassette of any one of embodiments 53-84, the plasmid of embodiment 85, the cell of embodiment 86, or the recombinant AAV vector of embodiment 88 or 89.

92. The method of embodiment 91, wherein the subject suffers from the disease NPC1.

93. The method of embodiment 91 or 92, wherein the subject is a human subject.

94. An adeno-associated virus (AAV) vector comprising: (i) a protein capsid comprising a capsid protein subunit comprising the sequence of SEQ ID NO: 180; and (ii) a nucleic acid encapsidated by the protein capsid; wherein the nucleic acid comprises a transfer cassette; wherein the transfer cassette comprises, from 5' to 3': a 5' inverted terminal repeat (ITR); a promoter; a transgene that encodes the NPC1 protein; a polyadenylation signal; and a 3' ITR.

95. An adeno-associated virus (AAV) vector comprising: (i) a protein capsid comprising a capsid protein subunit comprising the sequence of SEQ ID NO: 180, or a sequence comprising about 1 to about 25 amino acid mutations relative to SEQ ID NO: 180; and (ii) a nucleic acid encapsidated by the protein capsid; wherein the nucleic acid comprises a transfer cassette; wherein the transfer cassette comprises from 5' to 3': a 5' inverted terminal repeat (ITR); a promoter; a transgene which encodes the NPC1 protein; a polyadenylation signal; and a 3' ITR.

96. The AAV vector of embodiment 94 of 95, wherein the transfer cassette comprises an intronic sequence.

97. The AAV vector of any one of embodiments 94-96, wherein the intronic sequence comprises the sequence of SEQ ID NO: 10.

98. The AAV vector of any one of embodiments 94-97, wherein the 5' ITR comprises the sequence of SEQ ID NO: 3003.

99. The AAV vector of any one of embodiments 94-98, wherein the 3' ITR comprises the sequence of SEQ ID NO: 3004.

100. The AAV vector of any one of embodiments 94-99, wherein the promoter is the CBA promoter.

101. The AAV vector of any one of embodiments 94-99, wherein the promoter comprises the sequence of SEQ ID NO: 3005.

102. The AAV vector of any one of embodiments 94-101, wherein the NPC1 protein is the human NPC1 protein.

103. The AAV vector of any one of embodiments 94-101, wherein the NPC1 protein comprises the sequence of SEQ ID NO: 3001.

104. The AAV vector of any one of embodiments 94-101, wherein the transgene comprises the sequence of SEQ ID NO: 3002.

105. The AAV vector of any one of embodiments 94-104, wherein the polyadenylation signal is the SV40 polyadenylation signal.

106. The AAV vector of any one of embodiments 94-104, wherein the polyadenylation signal comprises the sequence of SEQ ID NO: 3012.

107. The AAV vector of any one of embodiments 94-106, wherein the cassette comprises an enhancer.

108. The AAV vector of embodiment 94, wherein the AAV transfer cassette comprises the sequence of SEQ ID NO: 3014

109. The AAV vector of embodiment 94, wherein the AAV transfer cassette comprises the sequence of any one of SEQ ID NO: 3015-3019.

110. A composition comprising the AAV vector of any one of embodiments 94-109.

111. A cell comprising the AAV vector of any one of embodiments 94-109.

112. A method for treating a subject in need thereof comprising administering to the subject an effective amount of the AAV vector of any one of embodiments 94-109, the composition of embodiment 110, or the cell of embodiment 111.

113. The method of embodiment 112, wherein the subject has Neimann-Pick Disease Type C.

114. The method of embodiment 112 or 113, wherein the subject is a human subject.

What is claimed is:

1. An adeno-associated virus (AAV) vector comprising:
   (i) a protein capsid comprising a capsid protein subunit comprising the sequence of SEQ ID NO: 180; and
   (ii) a nucleic acid encapsidated by the protein capsid;
   wherein the nucleic acid comprises a transfer cassette;
   wherein the transfer cassette comprises, from 5' to 3':
   a 5' inverted terminal repeat (ITR);
   a promoter;
   a transgene that encodes a Niemann-Pick intracellular cholesterol transporter 1 (NPC1) protein;
   a polyadenylation signal; and
   a 3' ITR.

2. The AAV vector of claim 1, wherein the transfer cassette further comprises an intronic sequence.

3. The AAV vector of claim 2, wherein the intronic sequence comprises the sequence of SEQ ID NO: 3010 or 3011.

4. The AAV vector of claim 1, wherein the 5' ITR comprises the sequence of SEQ ID NO: 3003.

5. The AAV vector of claim 1, wherein the 3' ITR comprises the sequence of SEQ ID NO: 3004.

6. The AAV vector of claim 1, wherein the promoter is a chicken β-actin (CBA) promoter.

7. The AAV vector of claim 6, wherein the CBA promoter comprises the sequence of SEQ ID NO: 3005.

8. The AAV vector of claim 1, wherein the NPC1 protein is a human NPC1 protein.

9. The AAV vector of claim 8, wherein the human NPC1 protein comprises the sequence of SEQ ID NO: 3001.

10. The AAV vector of claim 1, wherein the transgene comprises the sequence of SEQ ID NO: 3002.

11. The AAV vector of claim 1, wherein the polyadenylation signal is a SV40 polyadenylation signal.

12. The AAV vector of claim 11, wherein the SV40 polyadenylation signal comprises the sequence of SEQ ID NO: 3012.

13. The AAV vector of claim 1, wherein the transfer cassette further comprises an enhancer.

14. The AAV vector of claim 1, wherein the transfer cassette comprises the sequence of SEQ ID NO: 3014.

15. The AAV vector of claim 1, wherein the transfer cassette comprises the sequence of any one of SEQ ID NO: 3015-3019.

16. A composition comprising the AAV vector of claim 1.

17. A cell comprising the AAV vector of claim 1.

18. A method for treating a subject in need thereof comprising administering to the subject an effective amount of the AAV vector of claim 1.

19. The method of claim 18, wherein the subject has Neimann-Pick Disease Type C.

20. The method of claim 18, wherein the subject is a human subject.

* * * * *

SEQUENCE LISTING

<160> NUMBER OF SEQ ID NOS: 3020

<210> SEQ ID NO 1
<211> LENGTH: 736
<212> TYPE: PRT
<213> ORGANISM: Dependovirus adeno-associated virus 1

<400> SEQUENCE: 1

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240
```

```
Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Glu Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg
                565                 570                 575

Phe Gly Thr Val Ala Val Asn Phe Gln Ser Ser Ser Thr Asp Pro Ala
            580                 585                 590

Thr Gly Asp Val His Ala Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys Asn Pro Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
```

```
                    660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Val Gln Tyr Thr Ser Asn
            690                 695                 700
Tyr Ala Lys Ser Ala Asn Val Asp Phe Thr Val Asp Asn Asn Gly Leu
705                 710                 715                 720
Tyr Thr Glu Pro Arg Pro Ile Gly Thr Arg Tyr Leu Thr Arg Pro Leu
                725                 730                 735

<210> SEQ ID NO 2
<211> LENGTH: 735
<212> TYPE: PRT
<213> ORGANISM: Dependovirus adeno-associated virus 2

<400> SEQUENCE: 2

Met Ala Ala Asp Gly Tyr Leu Pro Asp Trp Leu Glu Asp Thr Leu Ser
1               5                   10                  15
Glu Gly Ile Arg Gln Trp Trp Lys Leu Lys Pro Gly Pro Pro Pro
            20                  25                  30
Lys Pro Ala Glu Arg His Lys Asp Asp Ser Arg Gly Leu Val Leu Pro
        35                  40                  45
Gly Tyr Lys Tyr Leu Gly Pro Phe Asn Gly Leu Asp Lys Gly Glu Pro
    50                  55                  60
Val Asn Glu Ala Asp Ala Ala Leu Glu His Asp Lys Ala Tyr Asp
65                  70                  75                  80
Arg Gln Leu Asp Ser Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Pro Val Lys Thr Ala Pro Gly Lys Lys Arg
    130                 135                 140
Pro Val Glu His Ser Pro Val Glu Pro Asp Ser Ser Ser Gly Thr Gly
145                 150                 155                 160
Lys Ala Gly Gln Gln Pro Ala Arg Lys Arg Leu Asn Phe Gly Gln Thr
                165                 170                 175
Gly Asp Ala Asp Ser Val Pro Asp Pro Gln Pro Leu Gly Gln Pro Pro
            180                 185                 190
Ala Ala Pro Ser Gly Leu Gly Thr Asn Thr Met Ala Thr Gly Ser Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Thr Trp Met Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
```

```
Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
            325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
        370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
            515                 520                 525

Asp Glu Glu Lys Phe Phe Pro Gln Ser Gly Val Leu Ile Phe Gly Lys
            530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
            595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
            675                 680                 685

Glu Asn Ser Lys Arg Trp Asn Pro Glu Ile Gln Tyr Thr Ser Asn Tyr
            690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
```

```
                725                 730                 735

<210> SEQ ID NO 3
<211> LENGTH: 736
<212> TYPE: PRT
<213> ORGANISM: Dependovirus adeno-associated virus 3

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365
```

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 734
<212> TYPE: PRT
<213> ORGANISM: Dependovirus adeno-associated virus 4

<400> SEQUENCE: 4

Met Thr Asp Gly Tyr Leu Pro Asp Trp Leu Glu Asp Asn Leu Ser Glu
1               5                   10                  15

Gly Val Arg Glu Trp Trp Ala Leu Gln Pro Gly Ala Pro Lys Pro Lys
            20                  25                  30

Ala Asn Gln Gln His Gln Asp Asn Ala Arg Gly Leu Val Leu Pro Gly
            35                  40                  45

Tyr Lys Tyr Leu Gly Pro Gly Asn Gly Leu Asp Lys Gly Glu Pro Val
 50                  55                  60

Asn Ala Ala Asp Ala Ala Ala Leu Glu His Asp Lys Ala Tyr Asp Gln
 65                  70                  75                  80

Gln Leu Lys Ala Gly Asp Asn Pro Tyr Leu Lys Tyr Asn His Ala Asp
                85                  90                  95

Ala Glu Phe Gln Gln Arg Leu Gln Gly Asp Thr Ser Phe Gly Gly Asn
            100                 105                 110

Leu Gly Arg Ala Val Phe Gln Ala Lys Lys Arg Val Leu Glu Pro Leu
            115                 120                 125

Gly Leu Val Glu Gln Ala Gly Glu Thr Ala Pro Gly Lys Lys Arg Pro
130                 135                 140

Leu Ile Glu Ser Pro Gln Gln Pro Asp Ser Ser Thr Gly Ile Gly Lys
145                 150                 155                 160

Lys Gly Lys Gln Pro Ala Lys Lys Lys Leu Val Phe Glu Asp Glu Thr
                165                 170                 175

Gly Ala Gly Asp Gly Pro Pro Glu Gly Ser Thr Ser Gly Ala Met Ser
            180                 185                 190

Asp Asp Ser Glu Met Arg Ala Ala Gly Gly Ala Ala Val Glu Gly
            195                 200                 205

Gly Gln Gly Ala Asp Gly Val Gly Asn Ala Ser Gly Asp Trp His Cys
            210                 215                 220

Asp Ser Thr Trp Ser Glu Gly His Val Thr Thr Thr Ser Thr Arg Thr
225                 230                 235                 240

Trp Val Leu Pro Thr Tyr Asn Asn His Leu Tyr Lys Arg Leu Gly Glu
                245                 250                 255

Ser Leu Gln Ser Asn Thr Tyr Asn Gly Phe Ser Thr Pro Trp Gly Tyr
            260                 265                 270

Phe Asp Phe Asn Arg Phe His Cys His Phe Ser Pro Arg Asp Trp Gln
            275                 280                 285

Arg Leu Ile Asn Asn Asn Trp Gly Met Arg Pro Lys Ala Met Arg Val
            290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
            355                 360                 365

Cys Gly Leu Val Thr Gly Asn Thr Ser Gln Gln Gln Thr Asp Arg Asn
            370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

```
Asp Gln Tyr Leu Trp Gly Leu Gln Ser Thr Thr Thr Gly Thr Thr Leu
            435                 440                 445

Asn Ala Gly Thr Ala Thr Thr Asn Phe Thr Lys Leu Arg Pro Thr Asn
450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
                500                 505                 510

Arg Trp Ser Ala Leu Thr Pro Gly Pro Pro Met Ala Thr Ala Gly Pro
            515                 520                 525

Ala Asp Ser Lys Phe Ser Asn Ser Gln Leu Ile Phe Ala Gly Pro Lys
530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
            595                 600                 605

Asp Ile Tyr Tyr Gln Gly Pro Ile Trp Ala Lys Ile Pro His Thr Asp
            610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
                660                 665                 670

Ser Thr Gly Gln Val Ser Val Gln Ile Asp Trp Glu Ile Gln Lys Glu
            675                 680                 685

Arg Ser Lys Arg Trp Asn Pro Glu Val Gln Phe Thr Ser Asn Tyr Gly
690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730

<210> SEQ ID NO 5
<211> LENGTH: 724
<212> TYPE: PRT
<213> ORGANISM: Dependovirus adeno-associated virus 5

<400> SEQUENCE: 5

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
                20                  25                  30

Pro Asn Gln Gln His Gln Asp Gln Ala Arg Gly Leu Val Leu Pro Gly
            35                  40                  45

Tyr Asn Tyr Leu Gly Pro Gly Asn Gly Leu Asp Arg Gly Glu Pro Val
        50                  55                  60

Asn Arg Ala Asp Glu Val Ala Arg Glu His Asp Ile Ser Tyr Asn Glu
65                  70                  75                  80
```

```
Gln Leu Glu Ala Gly Asp Asn Pro Tyr Leu Lys Tyr Asn His Ala Asp
                 85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
    275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
            325                 330                 335

Asp Asp Tyr Gln Leu Pro Tyr Val Val Gly Asn Gly Thr Glu Gly Cys
        340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
            405                 410                 415

Phe Ala Pro Ser Gln Asn Leu Phe Lys Leu Ala Asn Pro Leu Val Asp
        420                 425                 430

Gln Tyr Leu Tyr Arg Phe Val Ser Thr Asn Asn Thr Gly Gly Val Gln
    435                 440                 445

Phe Asn Lys Asn Leu Ala Gly Arg Tyr Ala Asn Thr Tyr Lys Asn Trp
450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
            485                 490                 495
```

Leu Glu Gly Ala Ser Tyr Gln Val Pro Pro Gln Pro Asn Gly Met Thr
                500                 505                 510

Asn Asn Leu Gln Gly Ser Asn Thr Tyr Ala Leu Glu Asn Thr Met Ile
            515                 520                 525

Phe Asn Ser Gln Pro Ala Asn Pro Gly Thr Thr Ala Thr Tyr Leu Glu
        530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
610                 615                 620

Gly Gly Phe Gly Leu Lys His Pro Pro Met Met Leu Ile Lys Asn
625                 630                 635                 640

Thr Pro Val Pro Gly Asn Ile Thr Ser Phe Ser Asp Val Pro Val Ser
            645                 650                 655

Ser Phe Ile Thr Gln Tyr Ser Thr Gly Gln Val Thr Val Glu Met Glu
        660                 665                 670

Trp Glu Leu Lys Lys Glu Asn Ser Lys Arg Trp Asn Pro Glu Ile Gln
675                 680                 685

Tyr Thr Asn Asn Tyr Asn Asp Pro Gln Phe Val Asp Phe Ala Pro Asp
                690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 6
<211> LENGTH: 736
<212> TYPE: PRT
<213> ORGANISM: Dependovirus adeno-associated virus 6

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495

Asn Asn Ser Asn Phe Thr Trp Thr Gly Ala Ser Lys Tyr Asn Leu Asn
            500                 505                 510

Gly Arg Glu Ser Ile Ile Asn Pro Gly Thr Ala Met Ala Ser His Lys
        515                 520                 525

Asp Asp Lys Asp Lys Phe Phe Pro Met Ser Gly Val Met Ile Phe Gly
    530                 535                 540

Lys Glu Ser Ala Gly Ala Ser Asn Thr Ala Leu Asp Asn Val Met Ile
545                 550                 555                 560

Thr Asp Glu Glu Glu Ile Lys Ala Thr Asn Pro Val Ala Thr Glu Arg

-continued

```
                565                 570                 575
Phe Gly Thr Val Ala Val Asn Leu Gln Ser Ser Thr Asp Pro Ala
            580                 585                 590

Thr Gly Asp Val His Val Met Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Phe Gly Leu
625                 630                 635                 640

Lys His Pro Pro Gln Ile Leu Ile Lys Asn Thr Pro Val Pro Ala
                645                 650                 655

Asn Pro Pro Ala Glu Phe Ser Ala Thr Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Val Gln Tyr Thr Ser Asn
    690                 695                 700

Tyr Ala Lys Ser Ala Asn Val Asp Phe Thr Val Asp Asn Asn Gly Leu
705                 710                 715                 720

Tyr Thr Glu Pro Arg Pro Ile Gly Thr Arg Tyr Leu Thr Arg Pro Leu
                725                 730                 735

<210> SEQ ID NO 7
<211> LENGTH: 737
<212> TYPE: PRT
<213> ORGANISM: Dependovirus adeno-associated virus 7

<400> SEQUENCE: 7

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205
```

```
Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                    245                 250                 255

Leu Tyr Lys Gln Ile Ser Ser Glu Thr Ala Gly Ser Thr Asn Asp Asn
                260                 265                 270

Thr Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                    325                 330                 335

Asn Leu Thr Ser Thr Ile Gln Val Phe Ser Asp Ser Glu Tyr Gln Leu
                340                 345                 350

Pro Tyr Val Leu Gly Ser Ala His Gln Gly Cys Leu Pro Pro Phe Pro
            355                 360                 365

Ala Asp Val Phe Met Ile Pro Gln Tyr Gly Tyr Leu Thr Leu Asn Asn
370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460

Phe Tyr Gln Gly Gly Pro Ser Thr Met Ala Glu Gln Ala Lys Asn Trp
465                 470                 475                 480

Leu Pro Gly Pro Cys Phe Arg Gln Gln Arg Val Ser Lys Thr Leu Asp
                485                 490                 495

Gln Asn Asn Asn Ser Asn Phe Ala Trp Thr Gly Ala Thr Lys Tyr His
                500                 505                 510

Leu Asn Gly Arg Asn Ser Leu Val Asn Pro Gly Val Ala Met Ala Thr
            515                 520                 525

His Lys Asp Asp Glu Asp Arg Phe Phe Pro Ser Ser Gly Val Leu Ile
        530                 535                 540

Phe Gly Lys Thr Gly Ala Thr Asn Lys Thr Thr Leu Glu Asn Val Leu
545                 550                 555                 560

Met Thr Asn Glu Glu Glu Ile Arg Pro Thr Asn Pro Val Ala Thr Glu
                565                 570                 575

Glu Tyr Gly Ile Val Ser Ser Asn Leu Gln Ala Ala Asn Thr Ala Ala
            580                 585                 590

Gln Thr Gln Val Val Asn Asn Gln Gly Ala Leu Pro Gly Met Val Trp
        595                 600                 605

Gln Asn Arg Asp Val Tyr Leu Gln Gly Pro Ile Trp Ala Lys Ile Pro
    610                 615                 620

His Thr Asp Gly Asn Phe His Pro Ser Pro Leu Met Gly Gly Phe Gly
```

-continued

```
            625                 630                 635                 640

Leu Lys His Pro Pro Gln Ile Leu Ile Lys Asn Thr Pro Val Pro
                645                 650                 655

Ala Asn Pro Pro Glu Val Phe Thr Pro Ala Lys Phe Ala Ser Phe Ile
            660                 665                 670

Thr Gln Tyr Ser Thr Gly Gln Val Ser Val Glu Ile Glu Trp Glu Leu
                675                 680                 685

Gln Lys Glu Asn Ser Lys Arg Trp Asn Pro Glu Ile Gln Tyr Thr Ser
        690                 695                 700

Asn Phe Glu Lys Gln Thr Gly Val Asp Phe Ala Val Asp Ser Gln Gly
705                 710                 715                 720

Val Tyr Ser Glu Pro Arg Pro Ile Gly Thr Arg Tyr Leu Thr Arg Asn
                725                 730                 735

Leu
```

<210> SEQ ID NO 8
<211> LENGTH: 738
<212> TYPE: PRT
<213> ORGANISM: Dependovirus adeno-associated virus 8

<400> SEQUENCE: 8

```
Met Ala Ala Asp Gly Tyr Leu Pro Asp Trp Leu Glu Asp Asn Leu Ser
1                   5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
```

-continued

```
              260                 265                 270
Asn Thr Tyr Phe Gly Tyr Ser Thr Pro Trp Gly Tyr Phe Asp Phe Asn
                275                 280                 285
Arg Phe His Cys His Phe Ser Pro Arg Asp Trp Gln Arg Leu Ile Asn
                290                 295                 300
Asn Asn Trp Gly Phe Arg Pro Lys Arg Leu Ser Phe Lys Leu Phe Asn
305                 310                 315                 320
Ile Gln Val Lys Glu Val Thr Gln Asn Glu Gly Thr Lys Thr Ile Ala
                    325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
                355                 360                 365
Pro Ala Asp Val Phe Met Ile Pro Gln Tyr Gly Tyr Leu Thr Leu Asn
                370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Gln Phe Thr Tyr
                    405                 410                 415
Thr Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
                435                 440                 445
Ser Arg Thr Gln Thr Thr Gly Gly Thr Ala Asn Thr Gln Thr Leu Gly
                450                 455                 460
Phe Ser Gln Gly Gly Pro Asn Thr Met Ala Asn Gln Ala Lys Asn Trp
465                 470                 475                 480
Leu Pro Gly Pro Cys Tyr Arg Gln Gln Arg Val Ser Thr Thr Thr Gly
                    485                 490                 495
Gln Asn Asn Asn Ser Asn Phe Ala Trp Thr Ala Gly Thr Lys Tyr His
                500                 505                 510
Leu Asn Gly Arg Asn Ser Leu Ala Asn Pro Gly Ile Ala Met Ala Thr
                515                 520                 525
His Lys Asp Asp Glu Glu Arg Phe Phe Pro Ser Asn Gly Ile Leu Ile
                530                 535                 540
Phe Gly Lys Gln Asn Ala Ala Arg Asp Asn Ala Asp Tyr Ser Asp Val
545                 550                 555                 560
Met Leu Thr Ser Glu Glu Glu Ile Lys Thr Thr Asn Pro Val Ala Thr
                    565                 570                 575
Glu Glu Tyr Gly Ile Val Ala Asp Asn Leu Gln Gln Gln Asn Thr Ala
                580                 585                 590
Pro Gln Ile Gly Thr Val Asn Ser Gln Gly Ala Leu Pro Gly Met Val
                595                 600                 605
Trp Gln Asn Arg Asp Val Tyr Leu Gln Gly Pro Ile Trp Ala Lys Ile
                610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                    645                 650                 655
Pro Ala Asp Pro Pro Thr Thr Phe Asn Gln Ser Lys Leu Asn Ser Phe
                660                 665                 670
Ile Thr Gln Tyr Ser Thr Gly Gln Val Ser Val Glu Ile Glu Trp Glu
                675                 680                 685
```

-continued

```
Leu Gln Lys Glu Asn Ser Lys Arg Trp Asn Pro Glu Ile Gln Tyr Thr
            690                 695                 700
Ser Asn Tyr Tyr Lys Ser Thr Ser Val Asp Phe Ala Val Asn Thr Glu
705                 710                 715                 720
Gly Val Tyr Ser Glu Pro Arg Pro Ile Gly Thr Arg Tyr Leu Thr Arg
                725                 730                 735
Asn Leu

<210> SEQ ID NO 9
<211> LENGTH: 736
<212> TYPE: PRT
<213> ORGANISM: Dependovirus adeno-associated virus 9

<400> SEQUENCE: 9

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
```

```
Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 10
<211> LENGTH: 738
<212> TYPE: PRT
<213> ORGANISM: Dependovirus adeno-associated virus rh.10

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
            405                 410                 415

Gln Phe Glu Asp Val Pro Phe His Ser Ser Tyr Ala His Ser Gln Ser
        420                 425                 430

Leu Asp Arg Leu Met Asn Pro Leu Ile Asp Gln Tyr Leu Tyr Tyr Leu
    435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 11
<211> LENGTH: 733
<212> TYPE: PRT
<213> ORGANISM: Dependovirus adeno-associated virus 11

<400> SEQUENCE: 11

Met Ala Ala Asp Gly Tyr Leu Pro Asp Trp Leu Glu Asp Asn Leu Ser
1               5                   10                  15

```
Glu Gly Ile Arg Glu Trp Trp Asp Leu Lys Pro Gly Ala Pro Lys Pro
             20                  25                  30

Lys Ala Asn Gln Gln Lys Gln Asp Gly Arg Gly Leu Val Leu Pro
         35                  40                  45

Gly Tyr Lys Tyr Leu Gly Pro Phe Asn Gly Leu Asp Lys Gly Glu Pro
 50                  55                  60

Val Asn Ala Ala Asp Ala Ala Leu Glu His Asp Lys Ala Tyr Asp
 65              70                  75                  80

Gln Gln Leu Lys Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
             100                 105                 110

Asn Leu Gly Arg Ala Val Phe Gln Ala Lys Lys Arg Val Leu Glu Pro
             115                 120                 125

Leu Gly Leu Val Glu Glu Gly Ala Lys Thr Ala Pro Gly Lys Lys Arg
130                 135                 140

Pro Leu Glu Ser Pro Gln Glu Pro Asp Ser Ser Ser Gly Ile Gly Lys
145                 150                 155                 160

Lys Gly Lys Gln Pro Ala Arg Lys Arg Leu Asn Phe Glu Glu Asp Thr
                 165                 170                 175

Gly Ala Gly Asp Gly Pro Pro Glu Gly Ser Asp Thr Ser Ala Met Ser
             180                 185                 190

Ser Asp Ile Glu Met Arg Ala Ala Pro Gly Gly Asn Ala Val Asp Ala
             195                 200                 205

Gly Gln Gly Ser Asp Gly Val Gly Asn Ala Ser Gly Asp Trp His Cys
             210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                 245                 250                 255

Thr Ser Ser Ser Asn Thr Tyr Asn Gly Phe Ser Thr Pro Trp Gly Tyr
             260                 265                 270

Phe Asp Phe Asn Arg Phe His Cys His Phe Ser Pro Arg Asp Trp Gln
             275                 280                 285

Arg Leu Ile Asn Asn Asn Trp Gly Leu Arg Pro Lys Ala Met Arg Val
             290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                 325                 330                 335

Ser Ser Tyr Glu Leu Pro Tyr Val Met Asp Ala Gly Gln Glu Gly Ser
             340                 345                 350

Leu Pro Pro Phe Pro Asn Asp Val Phe Met Val Pro Gln Tyr Gly Tyr
             355                 360                 365

Cys Gly Ile Val Thr Gly Glu Asn Gln Asn Gln Thr Asp Arg Asn Ala
             370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                 405                 410                 415

Tyr Ala His Ser Gln Ser Leu Asp Arg Leu Met Asn Pro Leu Leu Asp
                 420                 425                 430
```

```
Gln Tyr Leu Trp His Leu Gln Ser Thr Thr Ser Gly Glu Thr Leu Asn
                435                 440                 445

Gln Gly Asn Ala Ala Thr Thr Phe Gly Lys Ile Arg Ser Gly Asp Phe
450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
                500                 505                 510

Trp Ser Asn Ile Ala Pro Gly Pro Met Ala Thr Ala Gly Pro Ser
                515                 520                 525

Asp Gly Asp Phe Ser Asn Ala Gln Leu Ile Phe Pro Gly Pro Ser Val
530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
                580                 585                 590

Val Thr Ala Met Gly Val Leu Pro Gly Met Val Trp Gln Asn Arg Asp
                595                 600                 605

Ile Tyr Tyr Gln Gly Pro Ile Trp Ala Lys Ile Pro His Ala Asp Gly
                610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
                660                 665                 670

Thr Gly Gln Val Ala Val Gln Ile Glu Trp Glu Ile Glu Lys Glu Arg
                675                 680                 685

Ser Lys Arg Trp Asn Pro Glu Val Gln Phe Thr Ser Asn Tyr Gly Asn
690                 695                 700

Gln Ser Ser Met Leu Trp Ala Pro Asp Thr Thr Gly Lys Tyr Thr Glu
705                 710                 715                 720

Pro Arg Val Ile Gly Ser Arg Tyr Leu Thr Asn His Leu
                725                 730

<210> SEQ ID NO 12
<211> LENGTH: 8
<212> TYPE: PRT
<213> ORGANISM: Artificial Sequence
<220> FEATURE:
<223> OTHER INFORMATION: Amino acid substitution

<400> SEQUENCE: 12

Ser Cys Gln Pro Thr Val Met Asn
1               5

<210> SEQ ID NO 13
<211> LENGTH: 8
<212> TYPE: PRT
<213> ORGANISM: Artificial Sequence
<220> FEATURE:
<223> OTHER INFORMATION: Amino acid substitution

<400> SEQUENCE: 13
```

```
Phe Gly Val Pro Asn Gln Pro Leu
1               5

<210> SEQ ID NO 14
<211> LENGTH: 8
<212> TYPE: PRT
<213> ORGANISM: Artificial Sequence
<220> FEATURE:
<223> OTHER INFORMATION: Amino acid substitution

<400> SEQUENCE: 14

Gln Arg Gly Gln Ala Ala Pro Phe
1               5

<210> SEQ ID NO 15
<211> LENGTH: 8
<212> TYPE: PRT
<213> ORGANISM: Artificial Sequence
<220> FEATURE:
<223> OTHER INFORMATION: Amino acid substitution

<400> SEQUENCE: 15

Gly Asp Tyr Ala Pro Ile Arg Glu
1               5

<210> SEQ ID NO 16
<211> LENGTH: 8
<212> TYPE: PRT
<213> ORGANISM: Artificial Sequence
<220> FEATURE:
<223> OTHER INFORMATION: Amino acid substitution

<400> SEQUENCE: 16

Lys Thr Arg Arg Ile Val Gln His
1               5

<210> SEQ ID NO 17
<211> LENGTH: 8
<212> TYPE: PRT
<213> ORGANISM: Artificial Sequence
<220> FEATURE:
<223> OTHER INFORMATION: Amino acid substitution

<400> SEQUENCE: 17

Phe Gly Phe Pro Asn Gln Pro Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Amino acid substitution

<400> SEQUENCE: 18

Arg Gln Asp Gln Pro Ile Asn Ala
1               5

<210> SEQ ID NO 19
<211> LENGTH: 8
<212> TYPE: PRT
<213> ORGANISM: Artificial Sequence
<220> FEATURE:
<223> OTHER INFORMATION: Amino acid substitution

<400> SEQUENCE: 19
```

Ser Lys Val Glu Ser Trp Thr Glu
1               5

<210> SEQ ID NO 20
<211> LENGTH: 8
<212> TYPE: PRT
<213> ORGANISM: Artificial Sequence
<220> FEATURE:
<223> OTHER INFORMATION: Amino acid substitution

<400> SEQUENCE: 20

Ser Thr Val Asp Ser Ile Ala Ile
1               5

<210> SEQ ID NO 21

<400> SEQUENCE: 21

000

<210> SEQ ID NO 22
<211> LENGTH: 5
<212> TYPE: PRT
<213> ORGANISM: Artificial Sequence
<220> FEATURE:
<223> OTHER INFORMATION: peptide motif

<400> SEQUENCE: 22

Phe Val Phe Leu Pro
1               5

<210> SEQ ID NO 23
<211> LENGTH: 4
<212> TYPE: PRT
<213> ORGANISM: Artificial Sequence
<220> FEATURE:
<223> OTHER INFORMATION: peptide motif
<220> FEATURE:
<221> NAME/KEY: MISC_FEATURE
<222> LOCATION: (1)..(1)
<223> OTHER INFORMATION: Xaa is a basic residue
<220> FEATURE:
<221> NAME/KEY: MISC_FEATURE
<222> LOCATION: (2)..(3)
<223> OTHER INFORMATION: Xaa is a neutral and/or hydrophobic residue
<220> FEATURE:
<221> NAME/KEY: MISC_FEATURE
<222> LOCATION: (4)..(4)
<223> OTHER INFORMATION: Xaa is a basic residue

<400> SEQUENCE: 23

Xaa Xaa Xaa Xaa
1

<210> SEQ ID NO 24
<211> LENGTH: 4
<212> TYPE: PRT
<213> ORGANISM: Artificial Sequence
<220> FEATURE:
<223> OTHER INFORMATION: peptide motif

<400> SEQUENCE: 24

Arg Gly Asn Arg
1

<210> SEQ ID NO 25
<211> LENGTH: 7
<212> TYPE: PRT
<213> ORGANISM: Artificial Sequence

```
<220> FEATURE:
<223> OTHER INFORMATION: targeting sequence
<220> FEATURE:
<221> NAME/KEY: MISC_FEATURE
<222> LOCATION: (7)..(7)
<223> OTHER INFORMATION: Xaa is Gly or Ser

<400> SEQUENCE: 25

Asn Ser Val Arg Asp Leu Xaa
1               5

<210> SEQ ID NO 26
<211> LENGTH: 7
<212> TYPE: PRT
<213> ORGANISM: Artificial Sequence
<220> FEATURE:
<223> OTHER INFORMATION: targeting sequence

<400> SEQUENCE: 26

Pro Arg Ser Val Thr Val Pro
1               5

<210> SEQ ID NO 27
<211> LENGTH: 7
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is Ser or Ala

<400> SEQUENCE: 27

Asn Ser Val Ser Ser Xaa Xaa
1               5

<210> SEQ ID NO 28
<211> LENGTH: 6
<212> TYPE: PRT
<213> ORGANISM: Artificial Sequence
<220> FEATURE:
<223> OTHER INFORMATION: targeting sequence

<400> SEQUENCE: 28

Asn Gly Arg Ala His Ala
1               5

<210> SEQ ID NO 29
<211> LENGTH: 7
<212> TYPE: PRT
<213> ORGANISM: Artificial Sequence
<220> FEATURE:
<223> OTHER INFORMATION: targeting sequence

<400> SEQUENCE: 29

Gln Pro Glu His Ser Ser Thr
1               5

<210> SEQ ID NO 30
<211> LENGTH: 7
<212> TYPE: PRT
<213> ORGANISM: Artificial Sequence
<220> FEATURE:
<223> OTHER INFORMATION: targeting sequence
```

```
<400> SEQUENCE: 30

Val Asn Thr Ala Asn Ser Thr
1               5

<210> SEQ ID NO 31
<211> LENGTH: 6
<212> TYPE: PRT
<213> ORGANISM: Artificial Sequence
<220> FEATURE:
<223> OTHER INFORMATION: targeting sequence

<400> SEQUENCE: 31

His Gly Pro Met Gln Ser
1               5

<210> SEQ ID NO 32
<211> LENGTH: 7
<212> TYPE: PRT
<213> ORGANISM: Artificial Sequence
<220> FEATURE:
<223> OTHER INFORMATION: targeting sequence

<400> SEQUENCE: 32

Pro His Lys Pro Pro Leu Ala
1               5

<210> SEQ ID NO 33
<211> LENGTH: 7
<212> TYPE: PRT
<213> ORGANISM: Artificial Sequence
<220> FEATURE:
<223> OTHER INFORMATION: targeting sequence

<400> SEQUENCE: 33

Ile Lys Asn Asn Glu Met Trp
1               5

<210> SEQ ID NO 34
<211> LENGTH: 7
<212> TYPE: PRT
<213> ORGANISM: Artificial Sequence
<220> FEATURE:
<223> OTHER INFORMATION: targeting sequence

<400> SEQUENCE: 34

Arg Asn Leu Asp Thr Pro Met
1               5

<210> SEQ ID NO 35
<211> LENGTH: 7
<212> TYPE: PRT
<213> ORGANISM: Artificial Sequence
<220> FEATURE:
<223> OTHER INFORMATION: targeting sequence

<400> SEQUENCE: 35

Val Asp Ser His Arg Gln Ser
1               5

<210> SEQ ID NO 36
<211> LENGTH: 7
<212> TYPE: PRT
<213> ORGANISM: Artificial Sequence
<220> FEATURE:
<223> OTHER INFORMATION: targeting sequence
```

```
<400> SEQUENCE: 36

Tyr Asp Ser Lys Thr Lys Thr
1               5

<210> SEQ ID NO 37
<211> LENGTH: 7
<212> TYPE: PRT
<213> ORGANISM: Artificial Sequence
<220> FEATURE:
<223> OTHER INFORMATION: targeting sequence

<400> SEQUENCE: 37

Ser Gln Leu Pro His Gln Lys
1               5

<210> SEQ ID NO 38
<211> LENGTH: 7
<212> TYPE: PRT
<213> ORGANISM: Artificial Sequence
<220> FEATURE:
<223> OTHER INFORMATION: targeting sequence

<400> SEQUENCE: 38

Ser Thr Met Gln Gln Asn Thr
1               5

<210> SEQ ID NO 39
<211> LENGTH: 7
<212> TYPE: PRT
<213> ORGANISM: Artificial Sequence
<220> FEATURE:
<223> OTHER INFORMATION: targeting sequence

<400> SEQUENCE: 39

Thr Glu Arg Tyr Met Thr Gln
1               5

<210> SEQ ID NO 40
<211> LENGTH: 7
<212> TYPE: PRT
<213> ORGANISM: Artificial Sequence
<220> FEATURE:
<223> OTHER INFORMATION: targeting sequence

<400> SEQUENCE: 40

Gln Pro Glu His Ser Ser Thr
1               5

<210> SEQ ID NO 41
<211> LENGTH: 7
<212> TYPE: PRT
<213> ORGANISM: Artificial Sequence
<220> FEATURE:
<223> OTHER INFORMATION: targeting sequence

<400> SEQUENCE: 41

Asp Ala Ser Leu Ser Thr Ser
1               5

<210> SEQ ID NO 42
<211> LENGTH: 6
<212> TYPE: PRT
<213> ORGANISM: Artificial Sequence
<220> FEATURE:
<223> OTHER INFORMATION: targeting sequence

<400> SEQUENCE: 42
```

```
Asp Leu Pro Asn Lys Thr
1               5

<210> SEQ ID NO 43
<211> LENGTH: 7
<212> TYPE: PRT
<213> ORGANISM: Artificial Sequence
<220> FEATURE:
<223> OTHER INFORMATION: targeting sequence

<400> SEQUENCE: 43

Asp Leu Thr Ala Ala Arg Leu
1               5

<210> SEQ ID NO 44
<211> LENGTH: 7
<212> TYPE: PRT
<213> ORGANISM: Artificial Sequence
<220> FEATURE:
<223> OTHER INFORMATION: targeting sequence

<400> SEQUENCE: 44

Glu Pro His Gln Phe Asn Tyr
1               5

<210> SEQ ID NO 45
<211> LENGTH: 7
<212> TYPE: PRT
<213> ORGANISM: Artificial Sequence
<220> FEATURE:
<223> OTHER INFORMATION: targeting sequence

<400> SEQUENCE: 45

Glu Pro Gln Ser Asn His Thr
1               5

<210> SEQ ID NO 46
<211> LENGTH: 7
<212> TYPE: PRT
<213> ORGANISM: Artificial Sequence
<220> FEATURE:
<223> OTHER INFORMATION: targeting sequence

<400> SEQUENCE: 46

Met Ser Ser Trp Pro Ser Gln
1               5

<210> SEQ ID NO 47
<211> LENGTH: 7
<212> TYPE: PRT
<213> ORGANISM: Artificial Sequence
<220> FEATURE:
<223> OTHER INFORMATION: targeting sequence

<400> SEQUENCE: 47

Asn Pro Lys His Asn Ala Thr
1               5

<210> SEQ ID NO 48
<211> LENGTH: 7
<212> TYPE: PRT
<213> ORGANISM: Artificial Sequence
<220> FEATURE:
<223> OTHER INFORMATION: targeting sequence

<400> SEQUENCE: 48
```

-continued

Pro Asp Gly Met Arg Thr Thr
1               5

<210> SEQ ID NO 49
<211> LENGTH: 7
<212> TYPE: PRT
<213> ORGANISM: Artificial Sequence
<220> FEATURE:
<223> OTHER INFORMATION: targeting sequence

<400> SEQUENCE: 49

Pro Asn Asn Asn Lys Thr Thr
1               5

<210> SEQ ID NO 50
<211> LENGTH: 7
<212> TYPE: PRT
<213> ORGANISM: Artificial Sequence
<220> FEATURE:
<223> OTHER INFORMATION: targeting sequence

<400> SEQUENCE: 50

Gln Ser Thr Thr His Asp Ser
1               5

<210> SEQ ID NO 51
<211> LENGTH: 7
<212> TYPE: PRT
<213> ORGANISM: Artificial Sequence
<220> FEATURE:
<223> OTHER INFORMATION: targeting sequence

<400> SEQUENCE: 51

Thr Gly Ser Lys Gln Lys Gln
1               5

<210> SEQ ID NO 52
<211> LENGTH: 7
<212> TYPE: PRT
<213> ORGANISM: Artificial Sequence
<220> FEATURE:
<223> OTHER INFORMATION: targeting sequence

<400> SEQUENCE: 52

Ser Leu Lys His Gln Ala Leu
1               5

<210> SEQ ID NO 53
<211> LENGTH: 7
<212> TYPE: PRT
<213> ORGANISM: Artificial Sequence
<220> FEATURE:
<223> OTHER INFORMATION: targeting sequence

<400> SEQUENCE: 53

Ser Pro Ile Asp Gly Glu Gln
1               5

<210> SEQ ID NO 54
<211> LENGTH: 8
<212> TYPE: PRT
<213> ORGANISM: Artificial Sequence
<220> FEATURE:
<223> OTHER INFORMATION: targeting sequence

<400> SEQUENCE: 54

Trp Ile Phe Pro Trp Ile Gln Leu

```
1               5

<210> SEQ ID NO 55
<211> LENGTH: 9
<212> TYPE: PRT
<213> ORGANISM: Artificial Sequence
<220> FEATURE:
<223> OTHER INFORMATION: targeting sequence

<400> SEQUENCE: 55

Cys Asp Cys Arg Gly Asp Cys Phe Cys
1               5

<210> SEQ ID NO 56
<211> LENGTH: 5
<212> TYPE: PRT
<213> ORGANISM: Artificial Sequence
<220> FEATURE:
<223> OTHER INFORMATION: targeting sequence

<400> SEQUENCE: 56

Cys Asn Gly Arg Cys
1               5

<210> SEQ ID NO 57
<211> LENGTH: 7
<212> TYPE: PRT
<213> ORGANISM: Artificial Sequence
<220> FEATURE:
<223> OTHER INFORMATION: targeting sequence

<400> SEQUENCE: 57

Cys Pro Arg Glu Cys Glu Ser
1               5

<210> SEQ ID NO 58
<211> LENGTH: 10
<212> TYPE: PRT
<213> ORGANISM: Artificial Sequence
<220> FEATURE:
<223> OTHER INFORMATION: targeting sequence

<400> SEQUENCE: 58

Cys Thr Thr His Trp Gly Phe Thr Leu Cys
1               5                   10

<210> SEQ ID NO 59
<211> LENGTH: 9
<212> TYPE: PRT
<213> ORGANISM: Artificial Sequence
<220> FEATURE:
<223> OTHER INFORMATION: targeting sequence

<400> SEQUENCE: 59

Cys Gly Arg Arg Ala Gly Gly Ser Cys
1               5

<210> SEQ ID NO 60
<211> LENGTH: 9
<212> TYPE: PRT
<213> ORGANISM: Artificial Sequence
<220> FEATURE:
<223> OTHER INFORMATION: targeting sequence

<400> SEQUENCE: 60

Cys Lys Gly Gly Arg Ala Lys Asp Cys
1               5
```

```
<210> SEQ ID NO 61
<211> LENGTH: 9
<212> TYPE: PRT
<213> ORGANISM: Artificial Sequence
<220> FEATURE:
<223> OTHER INFORMATION: targeting sequence

<400> SEQUENCE: 61

Cys Val Pro Glu Leu Gly His Glu Cys
1               5

<210> SEQ ID NO 62
<211> LENGTH: 9
<212> TYPE: PRT
<213> ORGANISM: Artificial Sequence
<220> FEATURE:
<223> OTHER INFORMATION: targeting sequence

<400> SEQUENCE: 62

Cys Arg Arg Glu Thr Ala Trp Ala Lys
1               5

<210> SEQ ID NO 63
<211> LENGTH: 14
<212> TYPE: PRT
<213> ORGANISM: Artificial Sequence
<220> FEATURE:
<223> OTHER INFORMATION: targeting sequence

<400> SEQUENCE: 63

Val Ser Trp Phe Ser His Arg Tyr Ser Pro Phe Ala Val Ser
1               5                   10

<210> SEQ ID NO 64
<211> LENGTH: 13
<212> TYPE: PRT
<213> ORGANISM: Artificial Sequence
<220> FEATURE:
<223> OTHER INFORMATION: targeting sequence

<400> SEQUENCE: 64

Gly Tyr Arg Asp Gly Tyr Ala Gly Pro Ile Leu Tyr Asn
1               5                   10

<210> SEQ ID NO 65
<211> LENGTH: 7
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (1)..(3)
<223> OTHER INFORMATION: Xaa is any amino acid
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MISC_FEATURE
<222> LOCATION: (5)..(7)
<223> OTHER INFORMATION: Xaa is any amino acid

<400> SEQUENCE: 65

Xaa Xaa Xaa Tyr Xaa Xaa Xaa
1               5
```

-continued

```
<210> SEQ ID NO 66
<211> LENGTH: 4
<212> TYPE: PRT
<213> ORGANISM: Artificial Sequence
<220> FEATURE:
<223> OTHER INFORMATION: targeting sequence
<220> FEATURE:
<221> NAME/KEY: MOD_RES
<222> LOCATION: (1)..(1)
<223> OTHER INFORMATION: PHOSPHORYLATION
<220> FEATURE:
<221> NAME/KEY: MISC_FEATURE
<222> LOCATION: (2)..(2)
<223> OTHER INFORMATION: Xaa is Glu or Met

<400> SEQUENCE: 66

Tyr Xaa Asn Trp
1

<210> SEQ ID NO 67
<211> LENGTH: 7
<212> TYPE: PRT
<213> ORGANISM: Artificial Sequence
<220> FEATURE:
<223> OTHER INFORMATION: targeting sequence

<400> SEQUENCE: 67

Arg Pro Leu Pro Pro Leu Pro
1               5

<210> SEQ ID NO 68
<211> LENGTH: 7
<212> TYPE: PRT
<213> ORGANISM: Artificial Sequence
<220> FEATURE:
<223> OTHER INFORMATION: targeting sequence

<400> SEQUENCE: 68

Ala Pro Pro Leu Pro Pro Arg
1               5

<210> SEQ ID NO 69
<211> LENGTH: 12
<212> TYPE: PRT
<213> ORGANISM: Artificial Sequence
<220> FEATURE:
<223> OTHER INFORMATION: targeting sequence

<400> SEQUENCE: 69

Asp Val Phe Tyr Pro Tyr Pro Tyr Ala Ser Gly Ser
1               5                   10

<210> SEQ ID NO 70
<211> LENGTH: 6
<212> TYPE: PRT
<213> ORGANISM: Artificial Sequence
<220> FEATURE:
<223> OTHER INFORMATION: targeting sequence

<400> SEQUENCE: 70

Met Tyr Trp Tyr Pro Tyr
1               5

<210> SEQ ID NO 71
<211> LENGTH: 12
<212> TYPE: PRT
<213> ORGANISM: Artificial Sequence
<220> FEATURE:
<223> OTHER INFORMATION: targeting sequence
```

```
<400> SEQUENCE: 71

Asp Ile Thr Trp Asp Gln Leu Trp Asp Leu Met Lys
1               5                   10

<210> SEQ ID NO 72
<211> LENGTH: 8
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (5)..(5)
<223> OTHER INFORMATION: Xaa is Gly or Leu

<400> SEQUENCE: 72

Cys Trp Asp Asp Xaa Trp Leu Cys
1               5

<210> SEQ ID NO 73
<211> LENGTH: 14
<212> TYPE: PRT
<213> ORGANISM: Artificial Sequence
<220> FEATURE:
<223> OTHER INFORMATION: targeting sequence

<400> SEQUENCE: 73

Glu Trp Cys Glu Tyr Leu Gly Gly Tyr Leu Arg Cys Tyr Ala
1               5                   10

<210> SEQ ID NO 74
<211> LENGTH: 14
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (2)..(2)
<223> OTHER INFORMATION: Xaa is any amino acid
<220> FEATURE:
<221> NAME/KEY: MISC_FEATURE
<222> LOCATION: (4)..(5)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid

<400> SEQUENCE: 74

Tyr Xaa Cys Xaa Xaa Gly Pro Xaa Thr Trp Xaa Cys Xaa Pro
1               5                   10

<210> SEQ ID NO 75
<211> LENGTH: 14
<212> TYPE: PRT
<213> ORGANISM: Artificial Sequence
<220> FEATURE:
<223> OTHER INFORMATION: targeting sequence

<400> SEQUENCE: 75
```

```
Ile Glu Gly Pro Thr Leu Arg Gln Trp Leu Ala Ala Arg Ala
1               5                   10
```

<210> SEQ ID NO 76
<211> LENGTH: 5
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (3)..(4)
<223> OTHER INFORMATION: Xaa is any amino acid
<220> FEATURE:
<221> NAME/KEY: MISC_FEATURE
<222> LOCATION: (5)..(5)
<223> OTHER INFORMATION: Xaa is Tyr, Trp, Phe or His

<400> SEQUENCE: 76

```
Leu Trp Xaa Xaa Xaa
1               5
```

<210> SEQ ID NO 77
<211> LENGTH: 7
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(4)
<223> OTHER INFORMATION: Xaa is any amino acid

<400> SEQUENCE: 77

```
Xaa Phe Xaa Xaa Tyr Leu Trp
1               5
```

<210> SEQ ID NO 78
<211> LENGTH: 6
<212> TYPE: PRT
<213> ORGANISM: Artificial Sequence
<220> FEATURE:
<223> OTHER INFORMATION: targeting sequence

<400> SEQUENCE: 78

```
Arg Trp Gly Leu Cys Asp
1               5
```

<210> SEQ ID NO 79
<211> LENGTH: 13
<212> TYPE: PRT
<213> ORGANISM: Artificial Sequence
<220> FEATURE:
<223> OTHER INFORMATION: targeting sequence

<400> SEQUENCE: 79

```
Met Ser Arg Pro Ala Cys Pro Pro Asn Asp Lys Tyr Glu
1               5                   10
```

<210> SEQ ID NO 80
<211> LENGTH: 8
<212> TYPE: PRT
<213> ORGANISM: Artificial Sequence
<220> FEATURE:
<223> OTHER INFORMATION: targeting sequence

```
<400> SEQUENCE: 80

Cys Leu Arg Ser Gly Arg Gly Cys
1               5

<210> SEQ ID NO 81
<211> LENGTH: 9
<212> TYPE: PRT
<213> ORGANISM: Artificial Sequence
<220> FEATURE:
<223> OTHER INFORMATION: targeting sequence

<400> SEQUENCE: 81

Cys His Trp Met Phe Ser Pro Trp Cys
1               5

<210> SEQ ID NO 82
<211> LENGTH: 4
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (2)..(3)
<223> OTHER INFORMATION: Xaa is any amino acid

<400> SEQUENCE: 82

Trp Xaa Xaa Phe
1

<210> SEQ ID NO 83
<211> LENGTH: 8
<212> TYPE: PRT
<213> ORGANISM: Artificial Sequence
<220> FEATURE:
<223> OTHER INFORMATION: targeting sequence

<400> SEQUENCE: 83

Cys Ser Ser Arg Leu Asp Ala Cys
1               5

<210> SEQ ID NO 84
<211> LENGTH: 7
<212> TYPE: PRT
<213> ORGANISM: Artificial Sequence
<220> FEATURE:
<223> OTHER INFORMATION: targeting sequence

<400> SEQUENCE: 84

Cys Leu Pro Val Ala Ser Cys
1               5

<210> SEQ ID NO 85
<211> LENGTH: 13
<212> TYPE: PRT
<213> ORGANISM: Artificial Sequence
<220> FEATURE:
<223> OTHER INFORMATION: targeting sequence

<400> SEQUENCE: 85

Cys Gly Phe Glu Cys Val Arg Gln Cys Pro Glu Arg Cys
1               5                   10

<210> SEQ ID NO 86
<211> LENGTH: 13
<212> TYPE: PRT
<213> ORGANISM: Artificial Sequence
```

```
<220> FEATURE:
<223> OTHER INFORMATION: targeting sequence

<400> SEQUENCE: 86

Cys Val Ala Leu Cys Arg Glu Ala Cys Gly Glu Gly Cys
1               5                   10

<210> SEQ ID NO 87
<211> LENGTH: 9
<212> TYPE: PRT
<213> ORGANISM: Artificial Sequence
<220> FEATURE:
<223> OTHER INFORMATION: targeting sequence

<400> SEQUENCE: 87

Ser Trp Cys Glu Pro Gly Trp Cys Arg
1               5

<210> SEQ ID NO 88
<211> LENGTH: 6
<212> TYPE: PRT
<213> ORGANISM: Artificial Sequence
<220> FEATURE:
<223> OTHER INFORMATION: targeting sequence

<400> SEQUENCE: 88

Tyr Ser Gly Trp Gly Trp
1               5

<210> SEQ ID NO 89
<211> LENGTH: 7
<212> TYPE: PRT
<213> ORGANISM: Artificial Sequence
<220> FEATURE:
<223> OTHER INFORMATION: targeting sequence

<400> SEQUENCE: 89

Gly Leu Ser Gly Gly Arg Ser
1               5

<210> SEQ ID NO 90
<211> LENGTH: 7
<212> TYPE: PRT
<213> ORGANISM: Artificial Sequence
<220> FEATURE:
<223> OTHER INFORMATION: targeting sequence

<400> SEQUENCE: 90

Leu Met Leu Pro Arg Ala Asp
1               5

<210> SEQ ID NO 91
<211> LENGTH: 9
<212> TYPE: PRT
<213> ORGANISM: Artificial Sequence
<220> FEATURE:
<223> OTHER INFORMATION: targeting sequence

<400> SEQUENCE: 91

Cys Ser Cys Phe Arg Asp Val Cys Cys
1               5

<210> SEQ ID NO 92
<211> LENGTH: 9
<212> TYPE: PRT
<213> ORGANISM: Artificial Sequence
<220> FEATURE:
```

```
<223> OTHER INFORMATION: targeting sequence

<400> SEQUENCE: 92

Cys Arg Asp Val Val Ser Val Ile Cys
1               5

<210> SEQ ID NO 93
<211> LENGTH: 5
<212> TYPE: PRT
<213> ORGANISM: Artificial Sequence
<220> FEATURE:
<223> OTHER INFORMATION: targeting sequence

<400> SEQUENCE: 93

Cys Asn Gly Arg Cys
1               5

<210> SEQ ID NO 94
<211> LENGTH: 6
<212> TYPE: PRT
<213> ORGANISM: Artificial Sequence
<220> FEATURE:
<223> OTHER INFORMATION: targeting sequence

<400> SEQUENCE: 94

Met Ala Arg Ser Gly Leu
1               5

<210> SEQ ID NO 95
<211> LENGTH: 6
<212> TYPE: PRT
<213> ORGANISM: Artificial Sequence
<220> FEATURE:
<223> OTHER INFORMATION: targeting sequence

<400> SEQUENCE: 95

Met Ala Arg Ala Lys Glu
1               5

<210> SEQ ID NO 96
<211> LENGTH: 6
<212> TYPE: PRT
<213> ORGANISM: Artificial Sequence
<220> FEATURE:
<223> OTHER INFORMATION: targeting sequence

<400> SEQUENCE: 96

Met Ser Arg Thr Met Ser
1               5

<210> SEQ ID NO 97
<211> LENGTH: 6
<212> TYPE: PRT
<213> ORGANISM: Artificial Sequence
<220> FEATURE:
<223> OTHER INFORMATION: targeting sequence

<400> SEQUENCE: 97

Lys Cys Cys Tyr Ser Leu
1               5

<210> SEQ ID NO 98
<211> LENGTH: 14
<212> TYPE: PRT
<213> ORGANISM: Artificial Sequence
<220> FEATURE:
<223> OTHER INFORMATION: targeting sequence
```

```
<400> SEQUENCE: 98

Met Tyr Trp Gly Asp Ser His Trp Leu Gln Tyr Trp Tyr Glu
1               5                   10

<210> SEQ ID NO 99
<211> LENGTH: 7
<212> TYPE: PRT
<213> ORGANISM: Artificial Sequence
<220> FEATURE:
<223> OTHER INFORMATION: targeting sequence

<400> SEQUENCE: 99

Met Gln Leu Pro Leu Ala Thr
1               5

<210> SEQ ID NO 100
<211> LENGTH: 4
<212> TYPE: PRT
<213> ORGANISM: Artificial Sequence
<220> FEATURE:
<223> OTHER INFORMATION: targeting sequence

<400> SEQUENCE: 100

Glu Trp Leu Ser
1

<210> SEQ ID NO 101
<211> LENGTH: 4
<212> TYPE: PRT
<213> ORGANISM: Artificial Sequence
<220> FEATURE:
<223> OTHER INFORMATION: targeting sequence

<400> SEQUENCE: 101

Ser Asn Glu Trp
1

<210> SEQ ID NO 102
<211> LENGTH: 4
<212> TYPE: PRT
<213> ORGANISM: Artificial Sequence
<220> FEATURE:
<223> OTHER INFORMATION: targeting sequence

<400> SEQUENCE: 102

Thr Asn Tyr Leu
1

<210> SEQ ID NO 103
<211> LENGTH: 8
<212> TYPE: PRT
<213> ORGANISM: Artificial Sequence
<220> FEATURE:
<223> OTHER INFORMATION: targeting sequence

<400> SEQUENCE: 103

Trp Ile Phe Pro Trp Ile Gln Leu
1               5

<210> SEQ ID NO 104
<211> LENGTH: 12
<212> TYPE: PRT
<213> ORGANISM: Artificial Sequence
<220> FEATURE:
<223> OTHER INFORMATION: targeting sequence
```

```
<400> SEQUENCE: 104

Trp Asp Leu Ala Trp Met Phe Arg Leu Pro Val Gly
1               5                   10

<210> SEQ ID NO 105
<211> LENGTH: 13
<212> TYPE: PRT
<213> ORGANISM: Artificial Sequence
<220> FEATURE:
<223> OTHER INFORMATION: targeting sequence

<400> SEQUENCE: 105

Cys Thr Val Ala Leu Pro Gly Gly Tyr Val Arg Val Cys
1               5                   10

<210> SEQ ID NO 106
<211> LENGTH: 9
<212> TYPE: PRT
<213> ORGANISM: Artificial Sequence
<220> FEATURE:
<223> OTHER INFORMATION: targeting sequence

<400> SEQUENCE: 106

Cys Val Pro Glu Leu Gly His Glu Cys
1               5

<210> SEQ ID NO 107
<211> LENGTH: 9
<212> TYPE: PRT
<213> ORGANISM: Artificial Sequence
<220> FEATURE:
<223> OTHER INFORMATION: targeting sequence

<400> SEQUENCE: 107

Cys Gly Arg Arg Ala Gly Gly Ser Cys
1               5

<210> SEQ ID NO 108
<211> LENGTH: 13
<212> TYPE: PRT
<213> ORGANISM: Artificial Sequence
<220> FEATURE:
<223> OTHER INFORMATION: targeting sequence

<400> SEQUENCE: 108

Cys Val Ala Tyr Cys Ile Glu His His Cys Trp Thr Cys
1               5                   10

<210> SEQ ID NO 109
<211> LENGTH: 12
<212> TYPE: PRT
<213> ORGANISM: Artificial Sequence
<220> FEATURE:
<223> OTHER INFORMATION: targeting sequence

<400> SEQUENCE: 109

Cys Val Phe Ala His Asn Tyr Asp Tyr Leu Val Cys
1               5                   10

<210> SEQ ID NO 110
<211> LENGTH: 10
<212> TYPE: PRT
<213> ORGANISM: Artificial Sequence
<220> FEATURE:
<223> OTHER INFORMATION: targeting sequence

<400> SEQUENCE: 110
```

```
Cys Val Phe Thr Ser Asn Tyr Ala Phe Cys
1               5                   10

<210> SEQ ID NO 111
<211> LENGTH: 7
<212> TYPE: PRT
<213> ORGANISM: Artificial Sequence
<220> FEATURE:
<223> OTHER INFORMATION: targeting sequence

<400> SEQUENCE: 111

Val His Ser Pro Asn Lys Lys
1               5

<210> SEQ ID NO 112
<211> LENGTH: 9
<212> TYPE: PRT
<213> ORGANISM: Artificial Sequence
<220> FEATURE:
<223> OTHER INFORMATION: targeting sequence

<400> SEQUENCE: 112

Cys Asp Cys Arg Gly Asp Cys Phe Cys
1               5

<210> SEQ ID NO 113
<211> LENGTH: 7
<212> TYPE: PRT
<213> ORGANISM: Artificial Sequence
<220> FEATURE:
<223> OTHER INFORMATION: targeting sequence

<400> SEQUENCE: 113

Cys Arg Gly Asp Gly Trp Cys
1               5

<210> SEQ ID NO 114
<211> LENGTH: 6
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 114

Xaa Arg Gly Cys Asp Xaa
1               5

<210> SEQ ID NO 115
<211> LENGTH: 4
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is Ser or Thr
```

```
<400> SEQUENCE: 115

Pro Xaa Xaa Xaa
1

<210> SEQ ID NO 116
<211> LENGTH: 10
<212> TYPE: PRT
<213> ORGANISM: Artificial Sequence
<220> FEATURE:
<223> OTHER INFORMATION: targeting sequence

<400> SEQUENCE: 116

Cys Thr Thr His Trp Gly Phe Thr Leu Cys
1               5                   10

<210> SEQ ID NO 117
<211> LENGTH: 11
<212> TYPE: PRT
<213> ORGANISM: Artificial Sequence
<220> FEATURE:
<223> OTHER INFORMATION: targeting sequence

<400> SEQUENCE: 117

Ser Gly Lys Gly Pro Arg Gln Ile Thr Ala Leu
1               5                   10

<210> SEQ ID NO 118
<211> LENGTH: 6
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (2)..(2)
<223> OTHER INFORMATION: Xaa is Ala or Gln
<220> FEATURE:
<221> NAME/KEY: MISC_FEATURE
<222> LOCATION: (3)..(3)
<223> OTHER INFORMATION: Xaa is Asn or Ala
<220> FEATURE:
<221> NAME/KEY: MISC_FEATURE
<222> LOCATION: (4)..(4)
<223> OTHER INFORMATION: Xaa is Leu or Tyr
<220> FEATURE:
<221> NAME/KEY: MISC_FEATURE
<222> LOCATION: (5)..(5)
<223> OTHER INFORMATION: Xaa is Thr, Val, Met or Arg
<220> FEATURE:
<221> NAME/KEY: MISC_FEATURE
<222> LOCATION: (6)..(6)
<223> OTHER INFORMATION: Xaa is Arg or Lys

<400> SEQUENCE: 118

Ala Xaa Xaa Xaa Xaa Xaa
1               5

<210> SEQ ID NO 119
<211> LENGTH: 6
<212> TYPE: PRT
<213> ORGANISM: Artificial Sequence
<220> FEATURE:
<223> OTHER INFORMATION: targeting sequence

<400> SEQUENCE: 119

Val Tyr Met Ser Pro Phe
1               5
```

-continued

```
<210> SEQ ID NO 120
<211> LENGTH: 7
<212> TYPE: PRT
<213> ORGANISM: Artificial Sequence
<220> FEATURE:
<223> OTHER INFORMATION: targeting sequence

<400> SEQUENCE: 120

Met Gln Leu Pro Leu Ala Thr
1               5

<210> SEQ ID NO 121
<211> LENGTH: 7
<212> TYPE: PRT
<213> ORGANISM: Artificial Sequence
<220> FEATURE:
<223> OTHER INFORMATION: targeting sequence

<400> SEQUENCE: 121

Ala Thr Trp Leu Pro Pro Arg
1               5

<210> SEQ ID NO 122
<211> LENGTH: 12
<212> TYPE: PRT
<213> ORGANISM: Artificial Sequence
<220> FEATURE:
<223> OTHER INFORMATION: targeting sequence

<400> SEQUENCE: 122

His Thr Met Tyr Tyr His His Tyr Gln His His Leu
1               5                   10

<210> SEQ ID NO 123
<211> LENGTH: 19
<212> TYPE: PRT
<213> ORGANISM: Artificial Sequence
<220> FEATURE:
<223> OTHER INFORMATION: targeting sequence

<400> SEQUENCE: 123

Ser Glu Val Gly Cys Arg Ala Gly Pro Leu Gln Trp Leu Cys Glu Lys
1               5                   10                  15

Tyr Phe Gly

<210> SEQ ID NO 124
<211> LENGTH: 18
<212> TYPE: PRT
<213> ORGANISM: Artificial Sequence
<220> FEATURE:
<223> OTHER INFORMATION: targeting sequence

<400> SEQUENCE: 124

Cys Gly Leu Leu Pro Val Gly Arg Pro Asp Arg Asn Val Trp Arg Trp
1               5                   10                  15

Leu Cys

<210> SEQ ID NO 125
<211> LENGTH: 15
<212> TYPE: PRT
<213> ORGANISM: Artificial Sequence
<220> FEATURE:
<223> OTHER INFORMATION: targeting sequence

<400> SEQUENCE: 125

Cys Lys Gly Gln Cys Asp Arg Phe Lys Gly Leu Pro Trp Glu Cys
```

-continued

```
1               5                   10                  15

<210> SEQ ID NO 126
<211> LENGTH: 5
<212> TYPE: PRT
<213> ORGANISM: Artificial Sequence
<220> FEATURE:
<223> OTHER INFORMATION: targeting sequence

<400> SEQUENCE: 126

Ser Gly Arg Ser Ala
1               5

<210> SEQ ID NO 127
<211> LENGTH: 4
<212> TYPE: PRT
<213> ORGANISM: Artificial Sequence
<220> FEATURE:
<223> OTHER INFORMATION: targeting sequence

<400> SEQUENCE: 127

Trp Gly Phe Pro
1

<210> SEQ ID NO 128
<211> LENGTH: 6
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (3)..(4)
<223> OTHER INFORMATION: Xaa is any amino acid

<400> SEQUENCE: 128

Leu Trp Xaa Xaa Ala Arg
1               5

<210> SEQ ID NO 129
<211> LENGTH: 7
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (1)..(1)
<223> OTHER INFORMATION: Xaa is any amino acid
<220> FEATURE:
<221> NAME/KEY: MISC_FEATURE
<222> LOCATION: (3)..(4)
<223> OTHER INFORMATION: Xaa is any amino acid

<400> SEQUENCE: 129

Xaa Phe Xaa Xaa Tyr Leu Trp
1               5

<210> SEQ ID NO 130
<211> LENGTH: 17
<212> TYPE: PRT
<213> ORGANISM: Artificial Sequence
<220> FEATURE:
<223> OTHER INFORMATION: targeting sequence

<400> SEQUENCE: 130

Ala Glu Pro Met Pro His Ser Leu Asn Phe Ser Gln Tyr Leu Trp Tyr
1               5                   10                  15
```

Thr

<210> SEQ ID NO 131
<211> LENGTH: 6
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (4)..(4)
<223> OTHER INFORMATION: Xaa is Trp or Phe

<400> SEQUENCE: 131

Trp Ala Tyr Xaa Ser Pro
1               5

<210> SEQ ID NO 132
<211> LENGTH: 7
<212> TYPE: PRT
<213> ORGANISM: Artificial Sequence
<220> FEATURE:
<223> OTHER INFORMATION: targeting sequence

<400> SEQUENCE: 132

Ile Glu Leu Leu Gln Ala Arg
1               5

<210> SEQ ID NO 133
<211> LENGTH: 12
<212> TYPE: PRT
<213> ORGANISM: Artificial Sequence
<220> FEATURE:
<223> OTHER INFORMATION: targeting sequence

<400> SEQUENCE: 133

Asp Ile Thr Trp Asp Gln Leu Trp Asp Leu Met Lys
1               5                   10

<210> SEQ ID NO 134
<211> LENGTH: 16
<212> TYPE: PRT
<213> ORGANISM: Artificial Sequence
<220> FEATURE:
<223> OTHER INFORMATION: targeting sequence

<400> SEQUENCE: 134

Ala Tyr Thr Lys Cys Ser Arg Gln Trp Arg Thr Cys Met Thr Thr His
1               5                   10                  15

<210> SEQ ID NO 135
<211> LENGTH: 15
<212> TYPE: PRT
<213> ORGANISM: Artificial Sequence
<220> FEATURE:
<223> OTHER INFORMATION: targeting sequence

<400> SEQUENCE: 135

Pro Gln Asn Ser Lys Ile Pro Gly Pro Thr Phe Leu Asp Pro His
1               5                   10                  15

<210> SEQ ID NO 136
<211> LENGTH: 15
<212> TYPE: PRT
<213> ORGANISM: Artificial Sequence
<220> FEATURE:
<223> OTHER INFORMATION: targeting sequence

<400> SEQUENCE: 136

Ser Met Glu Pro Ala Leu Pro Asp Trp Trp Trp Lys Met Phe Lys
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: targeting sequence

<400> SEQUENCE: 137

Ala Asn Thr Pro Cys Gly Pro Tyr Thr His Asp Cys Pro Val Lys Arg
1               5                   10                  15

<210> SEQ ID NO 138
<211> LENGTH: 12
<212> TYPE: PRT
<213> ORGANISM: Artificial Sequence
<220> FEATURE:
<223> OTHER INFORMATION: targeting sequence

<400> SEQUENCE: 138

Thr Ala Cys His Gln His Val Arg Met Val Arg Pro
1               5                   10

<210> SEQ ID NO 139
<211> LENGTH: 12
<212> TYPE: PRT
<213> ORGANISM: Artificial Sequence
<220> FEATURE:
<223> OTHER INFORMATION: targeting sequence

<400> SEQUENCE: 139

Val Pro Trp Met Glu Pro Ala Tyr Gln Arg Phe Leu
1               5                   10

<210> SEQ ID NO 140
<211> LENGTH: 8
<212> TYPE: PRT
<213> ORGANISM: Artificial Sequence
<220> FEATURE:
<223> OTHER INFORMATION: targeting sequence

<400> SEQUENCE: 140

Asp Pro Arg Ala Thr Pro Gly Ser
1               5

<210> SEQ ID NO 141
<211> LENGTH: 12
<212> TYPE: PRT
<213> ORGANISM: Artificial Sequence
<220> FEATURE:
<223> OTHER INFORMATION: targeting sequence

<400> SEQUENCE: 141

Phe Arg Pro Asn Arg Ala Gln Asp Tyr Asn Thr Asn
1               5                   10

<210> SEQ ID NO 142
<211> LENGTH: 9
<212> TYPE: PRT
<213> ORGANISM: Artificial Sequence
<220> FEATURE:
<223> OTHER INFORMATION: targeting sequence

<400> SEQUENCE: 142

```
Cys Thr Lys Asn Ser Tyr Leu Met Cys
1               5
```

<210> SEQ ID NO 143
<211> LENGTH: 11
<212> TYPE: PRT
<213> ORGANISM: Artificial Sequence
<220> FEATURE:
<223> OTHER INFORMATION: targeting sequence
<220> FEATURE:
<221> NAME/KEY: MISC_FEATURE
<222> LOCATION: (2)..(2)
<223> OTHER INFORMATION: Xaa is Arg or Gln
<220> FEATURE:
<221> NAME/KEY: MISC_FEATURE
<222> LOCATION: (3)..(3)
<223> OTHER INFORMATION: Xaa is Leu or Arg
<220> FEATURE:
<221> NAME/KEY: MISC_FEATURE
<222> LOCATION: (5)..(5)
<223> OTHER INFORMATION: Xaa is Gly or Asn
<220> FEATURE:
<221> NAME/KEY: MISC_FEATURE
<222> LOCATION: (6)..(7)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is Ala or Val

<400> SEQUENCE: 143

```
Cys Xaa Xaa Thr Xaa Xaa Xaa Gly Xaa Gly Cys
1               5                   10
```

<210> SEQ ID NO 144
<211> LENGTH: 9
<212> TYPE: PRT
<213> ORGANISM: Artificial Sequence
<220> FEATURE:
<223> OTHER INFORMATION: targeting sequence

<400> SEQUENCE: 144

```
Cys Pro Ile Glu Asp Arg Pro Met Cys
1               5
```

<210> SEQ ID NO 145
<211> LENGTH: 12
<212> TYPE: PRT
<213> ORGANISM: Artificial Sequence
<220> FEATURE:
<223> OTHER INFORMATION: targeting sequence

<400> SEQUENCE: 145

```
His Glu Trp Ser Tyr Leu Ala Pro Tyr Pro Trp Phe
1               5                   10
```

<210> SEQ ID NO 146
<211> LENGTH: 9
<212> TYPE: PRT
<213> ORGANISM: Artificial Sequence
<220> FEATURE:
<223> OTHER INFORMATION: targeting sequence

<400> SEQUENCE: 146

```
Met Cys Pro Lys His Pro Leu Gly Cys
1               5
```

<210> SEQ ID NO 147
<211> LENGTH: 15

```
<212> TYPE: PRT
<213> ORGANISM: Artificial Sequence
<220> FEATURE:
<223> OTHER INFORMATION: targeting sequence

<400> SEQUENCE: 147

Arg Met Trp Pro Ser Ser Thr Val Asn Leu Ser Ala Gly Arg Arg
1               5                   10                  15

<210> SEQ ID NO 148
<211> LENGTH: 20
<212> TYPE: PRT
<213> ORGANISM: Artificial Sequence
<220> FEATURE:
<223> OTHER INFORMATION: targeting sequence

<400> SEQUENCE: 148

Ser Ala Lys Thr Ala Val Ser Gln Arg Val Trp Leu Pro Ser His Arg
1               5                   10                  15

Gly Gly Glu Pro
            20

<210> SEQ ID NO 149
<211> LENGTH: 20
<212> TYPE: PRT
<213> ORGANISM: Artificial Sequence
<220> FEATURE:
<223> OTHER INFORMATION: targeting sequence

<400> SEQUENCE: 149

Lys Ser Arg Glu His Val Asn Asn Ser Ala Cys Pro Ser Lys Arg Ile
1               5                   10                  15

Thr Ala Ala Leu
            20

<210> SEQ ID NO 150
<211> LENGTH: 4
<212> TYPE: PRT
<213> ORGANISM: Artificial Sequence
<220> FEATURE:
<223> OTHER INFORMATION: targeting sequence

<400> SEQUENCE: 150

Glu Gly Phe Arg
1

<210> SEQ ID NO 151
<211> LENGTH: 6
<212> TYPE: PRT
<213> ORGANISM: Artificial Sequence
<220> FEATURE:
<223> OTHER INFORMATION: targeting sequence

<400> SEQUENCE: 151

Ala Gly Leu Gly Val Arg
1               5

<210> SEQ ID NO 152
<211> LENGTH: 15
<212> TYPE: PRT
<213> ORGANISM: Artificial Sequence
<220> FEATURE:
<223> OTHER INFORMATION: targeting sequence

<400> SEQUENCE: 152

Gly Thr Arg Gln Gly His Thr Met Arg Leu Gly Val Ser Asp Gly
```

```
<210> SEQ ID NO 153
<211> LENGTH: 15
<212> TYPE: PRT
<213> ORGANISM: Artificial Sequence
<220> FEATURE:
<223> OTHER INFORMATION: targeting sequence

<400> SEQUENCE: 153

Ile Ala Gly Leu Ala Thr Pro Gly Trp Ser His Trp Leu Ala Leu
1               5                   10                  15

<210> SEQ ID NO 154
<211> LENGTH: 7
<212> TYPE: PRT
<213> ORGANISM: Artificial Sequence
<220> FEATURE:
<223> OTHER INFORMATION: targeting sequence

<400> SEQUENCE: 154

Ser Met Ser Ile Ala Arg Leu
1               5

<210> SEQ ID NO 155
<211> LENGTH: 7
<212> TYPE: PRT
<213> ORGANISM: Artificial Sequence
<220> FEATURE:
<223> OTHER INFORMATION: targeting sequence

<400> SEQUENCE: 155

His Thr Phe Glu Pro Gly Val
1               5

<210> SEQ ID NO 156
<211> LENGTH: 14
<212> TYPE: PRT
<213> ORGANISM: Artificial Sequence
<220> FEATURE:
<223> OTHER INFORMATION: targeting sequence

<400> SEQUENCE: 156

Asn Thr Ser Leu Lys Arg Ile Ser Asn Lys Arg Arg Arg Lys
1               5                   10

<210> SEQ ID NO 157
<211> LENGTH: 15
<212> TYPE: PRT
<213> ORGANISM: Artificial Sequence
<220> FEATURE:
<223> OTHER INFORMATION: targeting sequence

<400> SEQUENCE: 157

Leu Arg Ile Lys Arg Lys Arg Arg Lys Arg Lys Lys Thr Arg Lys
1               5                   10                  15

<210> SEQ ID NO 158
<211> LENGTH: 8
<212> TYPE: PRT
<213> ORGANISM: Artificial Sequence
<220> FEATURE:
<223> OTHER INFORMATION: Amino acid substitution
<220> FEATURE:
<221> NAME/KEY: MISC_FEATURE
<222> LOCATION: (1)..(8)
<223> OTHER INFORMATION: Xaa is any amino acid
```

```
<400> SEQUENCE: 158

Xaa Xaa Xaa Xaa Xaa Xaa Xaa Xaa
1               5

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000

<210> SEQ ID NO 163

<400> SEQUENCE: 163

000

<210> SEQ ID NO 164

<400> SEQUENCE: 164

000

<210> SEQ ID NO 165
<211> LENGTH: 736
<212> TYPE: PRT
<213> ORGANISM: Artificial Sequence
<220> FEATURE:
<223> OTHER INFORMATION: AAV capsid variant

<400> SEQUENCE: 165

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
```

```
            115                 120                 125
Leu Gly Leu Val Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
                180                 185                 190
Ala Ala Pro Ser Gly Val Gly Ser Leu Thr Met Ala Ser Gly Gly Gly
                195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
                275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
        435                 440                 445
Lys Thr Ser Cys Gln Pro Thr Val Met Asn Gln Thr Leu Lys Phe Ser
        450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
```

Lys Gln Gly Thr Gly Arg Asp Asn Val Asp Ala Asp Lys Val Met Ile
545                 550                 555                 560

Thr Asn Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 166
<211> LENGTH: 736
<212> TYPE: PRT
<213> ORGANISM: Artificial Sequence
<220> FEATURE:
<223> OTHER INFORMATION: AAV capsid variant

<400> SEQUENCE: 166

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
            165                 170                 175

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
            210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Phe Gly Val Pro Asn Gln Pro Leu Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590
```

```
Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 167
<211> LENGTH: 736
<212> TYPE: PRT
<213> ORGANISM: Artificial Sequence
<220> FEATURE:
<223> OTHER INFORMATION: AAV capsid variant

<400> SEQUENCE: 167

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Glu Gly Ala Asp Gly Val Gly Ser Ser
    210                 215                 220
```

```
Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
        260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Gln Arg Gly Gln Ala Ala Pro Phe Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
```

```
            645                 650                 655
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
            690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735
```

<210> SEQ ID NO 168
<211> LENGTH: 736
<212> TYPE: PRT
<213> ORGANISM: Artificial Sequence
<220> FEATURE:
<223> OTHER INFORMATION: AAV capsid variant

<400> SEQUENCE: 168

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
```

```
                275                 280                 285
Phe His Cys His Phe Ser Pro Arg Asp Trp Gln Arg Leu Ile Asn Asn
290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
                340                 345                 350
Pro Tyr Val Leu Gly Ser Ala His Glu Gly Cys Leu Pro Pro Phe Pro
                355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Gly Asp Tyr Ala Pro Ile Arg Glu Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ala Gln Ala Gln Ala Gln
                580                 585                 590
Thr Gly Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 169
<211> LENGTH: 736
<212> TYPE: PRT
<213> ORGANISM: Artificial Sequence
<220> FEATURE:
<223> OTHER INFORMATION: AAV capsid variant

<400> SEQUENCE: 169

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Lys Thr Arg Arg Ile Val Gln His Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 170
<211> LENGTH: 736

```
<212> TYPE: PRT
<213> ORGANISM: Artificial Sequence
<220> FEATURE:
<223> OTHER INFORMATION: AAV capsid variant

<400> SEQUENCE: 170
```

| | | | | | | | | | | | | | | |
|---|---|---|---|---|---|---|---|---|---|---|---|---|---|---|
| Met | Ala | Ala | Asp | Gly | Tyr | Leu | Pro | Asp | Trp | Leu | Glu | Asp | Asn | Leu | Ser |
| 1 | | | | 5 | | | | | 10 | | | | | 15 | |
| Glu | Gly | Ile | Arg | Glu | Trp | Trp | Ala | Leu | Lys | Pro | Gly | Ala | Pro | Gln | Pro |
| | | | 20 | | | | | 25 | | | | | 30 | | |
| Lys | Ala | Asn | Gln | Gln | His | Gln | Asp | Asn | Ala | Arg | Gly | Leu | Val | Leu | Pro |
| | | | 35 | | | | | 40 | | | | | 45 | | |
| Gly | Tyr | Lys | Tyr | Leu | Gly | Pro | Gly | Asn | Gly | Leu | Asp | Lys | Gly | Glu | Pro |
| | 50 | | | | | 55 | | | | | 60 | | | | |
| Val | Asn | Ala | Ala | Asp | Ala | Ala | Ala | Leu | Glu | His | Asp | Lys | Ala | Tyr | Asp |
| 65 | | | | | 70 | | | | | 75 | | | | | 80 |
| Gln | Gln | Leu | Lys | Ala | Gly | Asp | Asn | Pro | Tyr | Leu | Lys | Tyr | Asn | His | Ala |
| | | | | 85 | | | | | 90 | | | | | 95 | |
| Asp | Ala | Glu | Phe | Gln | Glu | Arg | Leu | Lys | Glu | Asp | Thr | Ser | Phe | Gly | Gly |
| | | | | 100 | | | | | 105 | | | | | 110 | |
| Asn | Leu | Gly | Arg | Ala | Val | Phe | Gln | Ala | Lys | Lys | Arg | Leu | Leu | Glu | Pro |
| | | | | 115 | | | | | 120 | | | | | 125 | |
| Leu | Gly | Leu | Val | Glu | Glu | Ala | Ala | Lys | Thr | Ala | Pro | Gly | Lys | Lys | Arg |
| | 130 | | | | | 135 | | | | | 140 | | | | |
| Pro | Val | Glu | Gln | Ser | Pro | Gln | Glu | Pro | Asp | Ser | Ser | Ala | Gly | Ile | Gly |
| 145 | | | | | 150 | | | | | 155 | | | | | 160 |
| Lys | Ser | Gly | Ala | Gln | Pro | Ala | Lys | Lys | Arg | Leu | Asn | Phe | Gly | Gln | Thr |
| | | | | 165 | | | | | 170 | | | | | 175 | |
| Gly | Asp | Thr | Glu | Ser | Val | Pro | Asp | Pro | Gln | Pro | Ile | Gly | Glu | Pro | Pro |
| | | | | 180 | | | | | 185 | | | | | 190 | |
| Ala | Ala | Pro | Ser | Gly | Val | Gly | Ser | Leu | Thr | Met | Ala | Ser | Gly | Gly | Gly |
| | | | | 195 | | | | | 200 | | | | | 205 | |
| Ala | Pro | Val | Ala | Asp | Asn | Asn | Glu | Gly | Ala | Asp | Gly | Val | Gly | Ser | Ser |
| | 210 | | | | | 215 | | | | | 220 | | | | |
| Ser | Gly | Asn | Trp | His | Cys | Asp | Ser | Gln | Trp | Leu | Gly | Asp | Arg | Val | Ile |
| 225 | | | | | 230 | | | | | 235 | | | | | 240 |
| Thr | Thr | Ser | Thr | Arg | Thr | Trp | Ala | Leu | Pro | Thr | Tyr | Asn | Asn | His | Leu |
| | | | | 245 | | | | | 250 | | | | | 255 | |
| Tyr | Lys | Gln | Ile | Ser | Asn | Ser | Thr | Ser | Gly | Gly | Ser | Ser | Asn | Asp | Asn |
| | | | | 260 | | | | | 265 | | | | | 270 | |
| Ala | Tyr | Phe | Gly | Tyr | Ser | Thr | Pro | Trp | Gly | Tyr | Phe | Asp | Phe | Asn | Arg |
| | | | | 275 | | | | | 280 | | | | | 285 | |
| Phe | His | Cys | His | Phe | Ser | Pro | Arg | Asp | Trp | Gln | Arg | Leu | Ile | Asn | Asn |
| | | | | 290 | | | | | 295 | | | | | 300 | |
| Asn | Trp | Gly | Phe | Arg | Pro | Lys | Arg | Leu | Asn | Phe | Lys | Leu | Phe | Asn | Ile |
| 305 | | | | | 310 | | | | | 315 | | | | | 320 |
| Gln | Val | Lys | Glu | Val | Thr | Asp | Asn | Asn | Gly | Val | Lys | Thr | Ile | Ala | Asn |
| | | | | 325 | | | | | 330 | | | | | 335 | |
| Asn | Leu | Thr | Ser | Thr | Val | Gln | Val | Phe | Thr | Asp | Ser | Asp | Tyr | Gln | Leu |
| | | | | 340 | | | | | 345 | | | | | 350 | |
| Pro | Tyr | Val | Leu | Gly | Ser | Ala | His | Glu | Gly | Cys | Leu | Pro | Pro | Phe | Pro |
| | | | | 355 | | | | | 360 | | | | | 365 | |
| Ala | Asp | Val | Phe | Met | Ile | Pro | Gln | Tyr | Gly | Tyr | Leu | Thr | Leu | Asn | Asp |
| | 370 | | | | | 375 | | | | | 380 | | | | |

```
Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
        420                 425                 430

Asp Arg Leu Met Asn Pro Leu Ile Asp Gln Tyr Leu Tyr Tyr Leu Ser
    435                 440                 445

Lys Thr Phe Gly Phe Pro Asn Gln Pro Leu Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
        500                 505                 510

Gly Arg Asn Ser Leu Met Asn Pro Gly Pro Ala Met Ala Ser His Lys
    515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
        580                 585                 590

Thr Gly Trp Val Gln Asn Gln Gly Ile Leu Pro Gly Met Val Trp Gln
    595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
        660                 665                 670

Gln Tyr Ser Thr Gly Gln Val Ser Val Glu Ile Glu Trp Glu Leu Gln
    675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 171
<211> LENGTH: 736
<212> TYPE: PRT
<213> ORGANISM: Artificial Sequence
<220> FEATURE:
<223> OTHER INFORMATION: AAV capsid variant

<400> SEQUENCE: 171

Met Ala Ala Asp Gly Tyr Leu Pro Asp Trp Leu Glu Asp Asn Leu Ser
1               5                   10                  15
```

-continued

```
Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
```

435                 440                 445
Lys Thr Arg Gln Asp Gln Pro Ile Asn Ala Gln Thr Leu Lys Phe Ser
                450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                    485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
                530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                    565                 570                 575

Tyr Gly Gln Val Ala Thr Asn His Gln Ser Ala Gln Ala Gln Ala Gln
                580                 585                 590

Thr Gly Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                    645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
                690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                    725                 730                 735

<210> SEQ ID NO 172
<211> LENGTH: 736
<212> TYPE: PRT
<213> ORGANISM: Artificial Sequence
<220> FEATURE:
<223> OTHER INFORMATION: AAV capsid variant

<400> SEQUENCE: 172

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp

```
                65                  70                  75                  80
Gln Gln Leu Lys Ala Gly Asp Asn Pro Tyr Leu Lys Tyr Asn His Ala
                        85                  90                  95

Asp Ala Glu Phe Gln Glu Arg Leu Lys Glu Asp Thr Ser Phe Gly Gly
                        100                 105                 110

Asn Leu Gly Arg Ala Val Phe Gln Ala Lys Lys Arg Leu Leu Glu Pro
                115                 120                 125

Leu Gly Leu Val Glu Glu Ala Lys Thr Ala Pro Gly Lys Lys Arg
            130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                        165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
                195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
                275                 280                 285

Phe His Cys His Phe Ser Pro Arg Asp Trp Gln Arg Leu Ile Asn Asn
                290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
                340                 345                 350

Pro Tyr Val Leu Gly Ser Ala His Glu Gly Cys Leu Pro Pro Phe Pro
                355                 360                 365

Ala Asp Val Phe Met Ile Pro Gln Tyr Gly Tyr Leu Thr Leu Asn Asp
                370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
                435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Lys Val Glu Ser Trp
            580                 585                 590

Thr Glu Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 173
<211> LENGTH: 736
<212> TYPE: PRT
<213> ORGANISM: Artificial Sequence
<220> FEATURE:
<223> OTHER INFORMATION: AAV capsid variant

<400> SEQUENCE: 173

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

```
Leu Gly Leu Val Glu Ala Ala Lys Thr Ala Pro Gly Lys Lys Arg
    130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Ile Asn Gly Ser Gly Gln Asn Gln Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
```

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ser Thr Val Asp Ser Ile
            580                 585                 590

Ala Ile Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 174
<211> LENGTH: 736
<212> TYPE: PRT
<213> ORGANISM: Artificial Sequence
<220> FEATURE:
<223> OTHER INFORMATION: AAV capsid variant

<400> SEQUENCE: 174

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

```
Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ser Cys Gln Pro Thr Val Met Asn Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Lys Val Glu Ser Trp
            580                 585                 590

Thr Glu Trp Val Gln Asn Gln Gly Ile Leu Pro Gly Met Val Trp Gln
```

```
                595                 600                 605
Asp Arg Asp Val Tyr Leu Gln Gly Pro Ile Trp Ala Lys Ile Pro His
610                 615                 620

Thr Asp Gly Asn Phe His Pro Ser Pro Leu Met Gly Phe Gly Met
625                 630                 635                 640

Lys His Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 175
<211> LENGTH: 736
<212> TYPE: PRT
<213> ORGANISM: Artificial Sequence
<220> FEATURE:
<223> OTHER INFORMATION: AAV capsid variant

<400> SEQUENCE: 175

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
                20                  25                  30

Lys Ala Asn Gln Gln His Gln Asp Asn Ala Arg Gly Leu Val Leu Pro
            35                  40                  45

Gly Tyr Lys Tyr Leu Gly Pro Gly Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
                100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
```

```
            225                 230                 235                 240

Thr Thr Ser Thr Arg Thr Trp Ala Leu Pro Thr Tyr Asn Asn His Leu
                        245                 250                 255

Tyr Lys Gln Ile Ser Asn Ser Thr Ser Gly Ser Ser Asn Asp Asn
                        260                 265                 270

Ala Tyr Phe Gly Tyr Ser Thr Pro Trp Gly Tyr Phe Asp Phe Asn Arg
                        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
        305                 310                 315                 320

Gln Val Lys Glu Val Thr Asp Asn Asn Gly Val Lys Thr Ile Ala Asn
                        325                 330                 335

Asn Leu Thr Ser Thr Val Gln Val Phe Thr Asp Ser Asp Tyr Gln Leu
                        340                 345                 350

Pro Tyr Val Leu Gly Ser Ala His Glu Gly Cys Leu Pro Pro Phe Pro
                        355                 360                 365

Ala Asp Val Phe Met Ile Pro Gln Tyr Gly Tyr Leu Thr Leu Asn Asp
                        370                 375                 380

Gly Ser Gln Ala Val Gly Arg Ser Ser Phe Tyr Cys Leu Glu Tyr Phe
        385                 390                 395                 400

Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                        420                 425                 430

Asp Arg Leu Met Asn Pro Leu Ile Asp Gln Tyr Leu Tyr Tyr Leu Ser
                        435                 440                 445

Lys Thr Phe Gly Val Pro Asn Gln Pro Leu Gln Thr Leu Lys Phe Ser
                        450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                        500                 505                 510

Gly Arg Asn Ser Leu Met Asn Pro Gly Pro Ala Met Ala Ser His Lys
                        515                 520                 525

Glu Gly Glu Asp Arg Phe Phe Pro Leu Ser Gly Ser Leu Ile Phe Gly
                        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ser Lys Val Glu Ser Trp
                        580                 585                 590

Thr Glu Trp Val Gln Asn Gln Gly Ile Leu Pro Gly Met Val Trp Gln
                        595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 176
<211> LENGTH: 736
<212> TYPE: PRT
<213> ORGANISM: Artificial Sequence
<220> FEATURE:
<223> OTHER INFORMATION: AAV capsid variant

<400> SEQUENCE: 176

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
    370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Gln Arg Gly Gln Ala Ala Pro Phe Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ser Lys Val Glu Ser Trp
            580                 585                 590
Thr Glu Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
```

```
Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735
```

<210> SEQ ID NO 177
<211> LENGTH: 736
<212> TYPE: PRT
<213> ORGANISM: Artificial Sequence
<220> FEATURE:
<223> OTHER INFORMATION: AAV capsid variant

<400> SEQUENCE: 177

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335
```

```
Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Gly Asp Tyr Ala Pro Ile Arg Glu Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Lys Val Glu Ser Trp
            580                 585                 590

Thr Glu Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 178
<211> LENGTH: 736
<212> TYPE: PRT
```

<213> ORGANISM: Artificial Sequence
<220> FEATURE:
<223> OTHER INFORMATION: AAV capsid variant

<400> SEQUENCE: 178

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe

```
                385                 390                 395                 400
        Pro Ser Gln Met Leu Arg Thr Gly Asn Asn Phe Gln Phe Ser Tyr Glu
                        405                 410                 415

Phe Glu Asn Val Pro Phe His Ser Ser Tyr Ala His Ser Gln Ser Leu
                    420                 425                 430

Asp Arg Leu Met Asn Pro Leu Ile Asp Gln Tyr Leu Tyr Tyr Leu Ser
                435                 440                 445

Lys Thr Lys Thr Arg Arg Ile Val Gln His Gln Thr Leu Lys Phe Ser
        450                 455                 460

Val Ala Gly Pro Ser Asn Met Ala Val Gln Gly Arg Asn Tyr Ile Pro
        465                 470                 475                 480

Gly Pro Ser Tyr Arg Gln Gln Arg Val Ser Thr Thr Val Thr Gln Asn
                        485                 490                 495

Asn Asn Ser Glu Phe Ala Trp Pro Gly Ala Ser Ser Trp Ala Leu Asn
                    500                 505                 510

Gly Arg Asn Ser Leu Met Asn Pro Gly Pro Ala Met Ala Ser His Lys
                515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
        545                 550                 555                 560

Thr Asn Glu Glu Glu Ile Lys Thr Thr Asn Pro Val Ala Thr Glu Ser
                        565                 570                 575

Tyr Gly Gln Val Ala Thr Asn His Gln Ser Ser Lys Val Glu Ser Trp
                    580                 585                 590

Thr Glu Trp Val Gln Asn Gln Gly Ile Leu Pro Gly Met Val Trp Gln
                595                 600                 605

Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
        625                 630                 635                 640

Lys His Pro Pro Pro Gln Ile Leu Ile Lys Asn Thr Pro Val Pro Ala
                        645                 650                 655

Asp Pro Pro Thr Ala Phe Asn Lys Asp Lys Leu Asn Ser Phe Ile Thr
                    660                 665                 670

Gln Tyr Ser Thr Gly Gln Val Ser Val Glu Ile Glu Trp Glu Leu Gln
                675                 680                 685

Lys Glu Asn Ser Lys Arg Trp Asn Pro Glu Ile Gln Tyr Thr Ser Asn
        690                 695                 700

Tyr Tyr Lys Ser Asn Asn Val Glu Phe Ala Val Asn Thr Glu Gly Val
        705                 710                 715                 720

Tyr Ser Glu Pro Arg Pro Ile Gly Thr Arg Tyr Leu Thr Arg Asn Leu
                        725                 730                 735

<210> SEQ ID NO 179
<211> LENGTH: 736
<212> TYPE: PRT
<213> ORGANISM: Artificial Sequence
<220> FEATURE:
<223> OTHER INFORMATION: AAV capsid variant

<400> SEQUENCE: 179

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
```

-continued

```
                20                  25                  30
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
        50                  55                  60
Val Asn Ala Ala Asp Ala Ala Leu Glu His Asp Lys Ala Tyr Asp
 65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
Leu Gly Leu Val Glu Glu Ala Ala Lys Thr Ala Pro Gly Lys Lys Arg
        130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
        195                 200                 205
Ala Pro Val Ala Asp Asn Asn Glu Gly Ala Asp Gly Val Gly Ser Ser
        210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
            260                 265                 270
Ala Tyr Phe Gly Tyr Ser Thr Pro Trp Gly Tyr Phe Asp Phe Asn Arg
        275                 280                 285
Phe His Cys His Phe Ser Pro Arg Asp Trp Gln Arg Leu Ile Asn Asn
        290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
        355                 360                 365
Ala Asp Val Phe Met Ile Pro Gln Tyr Gly Tyr Leu Thr Leu Asn Asp
        370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
```

Lys Thr Phe Gly Phe Pro Asn Gln Pro Leu Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Lys Val Glu Ser Trp
            580                 585                 590

Thr Glu Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 180
<211> LENGTH: 736
<212> TYPE: PRT
<213> ORGANISM: Artificial Sequence
<220> FEATURE:
<223> OTHER INFORMATION: AAV capsid variant

<400> SEQUENCE: 180

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

-continued

```
Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
            115                 120                 125

Leu Gly Leu Val Glu Glu Ala Ala Lys Thr Ala Pro Gly Lys Lys Arg
        130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
        210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
        370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Arg Gln Asp Gln Pro Ile Asn Ala Gln Thr Leu Lys Phe Ser
        450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495
```

```
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
        530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ser Lys Val Glu Ser Trp
            580                 585                 590
Thr Glu Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
        610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 181
<211> LENGTH: 736
<212> TYPE: PRT
<213> ORGANISM: Artificial Sequence
<220> FEATURE:
<223> OTHER INFORMATION: AAV capsid variant

<400> SEQUENCE: 181

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
Lys Ala Asn Gln Gln His Gln Asp Asn Ala Arg Gly Leu Val Leu Pro
        35                  40                  45
Gly Tyr Lys Tyr Leu Gly Pro Gly Asn Gly Leu Asp Lys Gly Glu Pro
    50                  55                  60
Val Asn Ala Ala Asp Ala Ala Leu Glu His Asp Lys Ala Tyr Asp
65                  70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
            100                 105                 110
Asn Leu Gly Arg Ala Val Phe Gln Ala Lys Lys Arg Leu Leu Glu Pro
        115                 120                 125
```

```
Leu Gly Leu Val Glu Glu Ala Ala Lys Thr Ala Pro Gly Lys Lys Arg
130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
                180                 185                 190

Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
                260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
                420                 425                 430

Asp Arg Leu Met Asn Pro Leu Ile Asp Gln Tyr Leu Tyr Tyr Leu Ser
            435                 440                 445

Lys Thr Ser Cys Gln Pro Thr Val Met Asn Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
```

```
                545                 550                 555                 560
            Thr Asn Glu Glu Ile Lys Thr Thr Asn Pro Val Ala Thr Glu Ser
                            565                 570                 575

Tyr Gly Gln Val Ala Thr Asn His Gln Ser Ser Thr Val Asp Ser Ile
                            580                 585                 590

Ala Ile Trp Val Gln Asn Gln Gly Ile Leu Pro Gly Met Val Trp Gln
                            595                 600                 605

Asp Arg Asp Val Tyr Leu Gln Gly Pro Ile Trp Ala Lys Ile Pro His
                        610                 615                 620

Thr Asp Gly Asn Phe His Pro Ser Pro Leu Met Gly Gly Phe Gly Met
            625                 630                 635                 640

Lys His Pro Pro Pro Gln Ile Leu Ile Lys Asn Thr Pro Val Pro Ala
                            645                 650                 655

Asp Pro Pro Thr Ala Phe Asn Lys Asp Lys Leu Asn Ser Phe Ile Thr
                            660                 665                 670

Gln Tyr Ser Thr Gly Gln Val Ser Val Glu Ile Glu Trp Glu Leu Gln
                            675                 680                 685

Lys Glu Asn Ser Lys Arg Trp Asn Pro Glu Ile Gln Tyr Thr Ser Asn
                        690                 695                 700

Tyr Tyr Lys Ser Asn Asn Val Glu Phe Ala Val Asn Thr Glu Gly Val
            705                 710                 715                 720

Tyr Ser Glu Pro Arg Pro Ile Gly Thr Arg Tyr Leu Thr Arg Asn Leu
                            725                 730                 735

<210> SEQ ID NO 182
<211> LENGTH: 736
<212> TYPE: PRT
<213> ORGANISM: Artificial Sequence
<220> FEATURE:
<223> OTHER INFORMATION: AAV capsid variant

<400> SEQUENCE: 182

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
```

-continued

```
                180                 185                 190
Ala Ala Pro Ser Gly Val Gly Ser Leu Thr Met Ala Ser Gly Gly Gly
            195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Phe Gly Val Pro Asn Gln Pro Leu Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Thr Val Asp Ser Ile
            580                 585                 590

Ala Ile Trp Val Gln Asn Gln Gly Ile Leu Pro Gly Met Val Trp Gln
        595                 600                 605
```

```
Asp Arg Asp Val Tyr Leu Gln Gly Pro Ile Trp Ala Lys Ile Pro His
        610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 183
<211> LENGTH: 736
<212> TYPE: PRT
<213> ORGANISM: Artificial Sequence
<220> FEATURE:
<223> OTHER INFORMATION: AAV capsid variant

<400> SEQUENCE: 183

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240
```

```
Thr Thr Ser Thr Arg Thr Trp Ala Leu Pro Thr Tyr Asn Asn His Leu
            245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
            275                 280                 285

Phe His Cys His Phe Ser Pro Arg Asp Trp Gln Arg Leu Ile Asn Asn
            290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
            355                 360                 365

Ala Asp Val Phe Met Ile Pro Gln Tyr Gly Tyr Leu Thr Leu Asn Asp
            370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Gln Arg Gly Gln Ala Ala Pro Phe Gln Thr Leu Lys Phe Ser
            450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ser Thr Val Asp Ser Ile
            580                 585                 590

Ala Ile Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
            645                 650                 655
```

```
Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 184
<211> LENGTH: 736
<212> TYPE: PRT
<213> ORGANISM: Artificial Sequence
<220> FEATURE:
<223> OTHER INFORMATION: AAV capsid variant

<400> SEQUENCE: 184

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285
```

```
Phe His Cys His Phe Ser Pro Arg Asp Trp Gln Arg Leu Ile Asn Asn
    290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
Lys Thr Gly Asp Tyr Ala Pro Ile Arg Glu Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
            515                 520                 525
Glu Gly Glu Asp Arg Phe Phe Pro Leu Ser Gly Ser Leu Ile Phe Gly
530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ser Thr Val Asp Ser Ile
            580                 585                 590
Ala Ile Trp Val Gln Asn Gln Gly Ile Leu Pro Gly Met Val Trp Gln
            595                 600                 605
Asp Arg Asp Val Tyr Leu Gln Gly Pro Ile Trp Ala Lys Ile Pro His
610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
            675                 680                 685
Lys Glu Asn Ser Lys Arg Trp Asn Pro Glu Ile Gln Tyr Thr Ser Asn
690                 695                 700
Tyr Tyr Lys Ser Asn Asn Val Glu Phe Ala Val Asn Thr Glu Gly Val
```

```
                705                 710                 715                 720
Tyr Ser Glu Pro Arg Pro Ile Gly Thr Arg Tyr Leu Thr Arg Asn Leu
                    725                 730                 735

<210> SEQ ID NO 185
<211> LENGTH: 736
<212> TYPE: PRT
<213> ORGANISM: Artificial Sequence
<220> FEATURE:
<223> OTHER INFORMATION: AAV capsid variant

<400> SEQUENCE: 185

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
```

```
                340                 345                 350
Pro Tyr Val Leu Gly Ser Ala His Glu Gly Cys Leu Pro Phe Pro
                355                 360                 365
Ala Asp Val Phe Met Ile Pro Gln Tyr Gly Tyr Leu Thr Leu Asn Asp
370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
                420                 425                 430
Asp Arg Leu Met Asn Pro Leu Ile Asp Gln Tyr Leu Tyr Tyr Leu Ser
                435                 440                 445
Lys Thr Lys Thr Arg Arg Ile Val Gln His Gln Thr Leu Lys Phe Ser
450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
                500                 505                 510
Gly Arg Asn Ser Leu Met Asn Pro Gly Pro Ala Met Ala Ser His Lys
                515                 520                 525
Glu Gly Glu Asp Arg Phe Phe Pro Leu Ser Gly Ser Leu Ile Phe Gly
                530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ser Thr Val Asp Ser Ile
                580                 585                 590
Ala Ile Trp Val Gln Asn Gln Gly Ile Leu Pro Gly Met Val Trp Gln
                595                 600                 605
Asp Arg Asp Val Tyr Leu Gln Gly Pro Ile Trp Ala Lys Ile Pro His
                610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
                660                 665                 670
Gln Tyr Ser Thr Gly Gln Val Ser Val Glu Ile Glu Trp Glu Leu Gln
                675                 680                 685
Lys Glu Asn Ser Lys Arg Trp Asn Pro Glu Ile Gln Tyr Thr Ser Asn
                690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 186
<211> LENGTH: 736
<212> TYPE: PRT
<213> ORGANISM: Artificial Sequence
```

```
<220> FEATURE:
<223> OTHER INFORMATION: AAV capsid variant

<400> SEQUENCE: 186

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400
```

```
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
        435                 440                 445
Lys Thr Phe Gly Phe Pro Asn Gln Pro Leu Gln Thr Leu Lys Phe Ser
    450                 455                 460
Val Ala Gly Pro Ser Asn Met Ala Val Gln Gly Arg Asn Tyr Ile Pro
465                 470                 475                 480
Gly Pro Ser Tyr Arg Gln Gln Arg Val Ser Thr Thr Val Thr Gln Asn
                485                 490                 495
Asn Asn Ser Glu Phe Ala Trp Pro Gly Ala Ser Ser Trp Ala Leu Asn
            500                 505                 510
Gly Arg Asn Ser Leu Met Asn Pro Gly Pro Ala Met Ala Ser His Lys
        515                 520                 525
Glu Gly Glu Asp Arg Phe Phe Pro Leu Ser Gly Ser Leu Ile Phe Gly
    530                 535                 540
Lys Gln Gly Thr Gly Arg Asp Asn Val Asp Ala Asp Lys Val Met Ile
545                 550                 555                 560
Thr Asn Glu Glu Glu Ile Lys Thr Thr Asn Pro Val Ala Thr Glu Ser
                565                 570                 575
Tyr Gly Gln Val Ala Thr Asn His Gln Ser Ser Thr Val Asp Ser Ile
            580                 585                 590
Ala Ile Trp Val Gln Asn Gln Gly Ile Leu Pro Gly Met Val Trp Gln
        595                 600                 605
Asp Arg Asp Val Tyr Leu Gln Gly Pro Ile Trp Ala Lys Ile Pro His
    610                 615                 620
Thr Asp Gly Asn Phe His Pro Ser Pro Leu Met Gly Gly Phe Gly Met
625                 630                 635                 640
Lys His Pro Pro Pro Gln Ile Leu Ile Lys Asn Thr Pro Val Pro Ala
                645                 650                 655
Asp Pro Pro Thr Ala Phe Asn Lys Asp Lys Leu Asn Ser Phe Ile Thr
            660                 665                 670
Gln Tyr Ser Thr Gly Gln Val Ser Val Glu Ile Glu Trp Glu Leu Gln
        675                 680                 685
Lys Glu Asn Ser Lys Arg Trp Asn Pro Glu Ile Gln Tyr Thr Ser Asn
    690                 695                 700
Tyr Tyr Lys Ser Asn Asn Val Glu Phe Ala Val Asn Thr Glu Gly Val
705                 710                 715                 720
Tyr Ser Glu Pro Arg Pro Ile Gly Thr Arg Tyr Leu Thr Arg Asn Leu
                725                 730                 735

<210> SEQ ID NO 187
<211> LENGTH: 736
<212> TYPE: PRT
<213> ORGANISM: Artificial Sequence
<220> FEATURE:
<223> OTHER INFORMATION: AAV capsid variant

<400> SEQUENCE: 187

Met Ala Ala Asp Gly Tyr Leu Pro Asp Trp Leu Glu Asp Asn Leu Ser
1               5                   10                  15
Glu Gly Ile Arg Glu Trp Trp Ala Leu Lys Pro Gly Ala Pro Gln Pro
            20                  25                  30
```

-continued

```
Lys Ala Asn Gln Gln His Gln Asp Asn Ala Arg Gly Leu Val Leu Pro
            35                  40                  45
Gly Tyr Lys Tyr Leu Gly Pro Gly Asn Gly Leu Asp Lys Gly Glu Pro
 50                  55                  60
Val Asn Ala Ala Asp Ala Ala Leu Glu His Asp Lys Ala Tyr Asp
 65              70                  75                  80
Gln Gln Leu Lys Ala Gly Asp Asn Pro Tyr Leu Lys Tyr Asn His Ala
                85                  90                  95
Asp Ala Glu Phe Gln Glu Arg Leu Lys Glu Asp Thr Ser Phe Gly Gly
                100                 105                 110
Asn Leu Gly Arg Ala Val Phe Gln Ala Lys Lys Arg Leu Leu Glu Pro
            115                 120                 125
Leu Gly Leu Val Glu Glu Ala Ala Lys Thr Ala Pro Gly Lys Lys Arg
            130                 135                 140
Pro Val Glu Gln Ser Pro Gln Glu Pro Asp Ser Ser Ala Gly Ile Gly
145                 150                 155                 160
Lys Ser Gly Ala Gln Pro Ala Lys Lys Arg Leu Asn Phe Gly Gln Thr
                165                 170                 175
Gly Asp Thr Glu Ser Val Pro Asp Pro Gln Pro Ile Gly Glu Pro Pro
            180                 185                 190
Ala Ala Pro Ser Gly Val Gly Ser Leu Thr Met Ala Ser Gly Gly Gly
            195                 200                 205
Ala Pro Val Ala Asp Asn Asn Glu Gly Ala Asp Gly Val Gly Ser Ser
            210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Asn Ser Thr Ser Gly Gly Ser Ser Asn Asp Asn
                260                 265                 270
Ala Tyr Phe Gly Tyr Ser Thr Pro Trp Gly Tyr Phe Asp Phe Asn Arg
            275                 280                 285
Phe His Cys His Phe Ser Pro Arg Asp Trp Gln Arg Leu Ile Asn Asn
            290                 295                 300
Asn Trp Gly Phe Arg Pro Lys Arg Leu Asn Phe Lys Leu Phe Asn Ile
305                 310                 315                 320
Gln Val Lys Glu Val Thr Asp Asn Asn Gly Val Lys Thr Ile Ala Asn
                325                 330                 335
Asn Leu Thr Ser Thr Val Gln Val Phe Thr Asp Ser Asp Tyr Gln Leu
            340                 345                 350
Pro Tyr Val Leu Gly Ser Ala His Glu Gly Cys Leu Pro Pro Phe Pro
            355                 360                 365
Ala Asp Val Phe Met Ile Pro Gln Tyr Gly Tyr Leu Thr Leu Asn Asp
            370                 375                 380
Gly Ser Gln Ala Val Gly Arg Ser Ser Phe Tyr Cys Leu Glu Tyr Phe
385                 390                 395                 400
Pro Ser Gln Met Leu Arg Thr Gly Asn Asn Phe Gln Phe Ser Tyr Glu
                405                 410                 415
Phe Glu Asn Val Pro Phe His Ser Ser Tyr Ala His Ser Gln Ser Leu
            420                 425                 430
Asp Arg Leu Met Asn Pro Leu Ile Asp Gln Tyr Leu Tyr Tyr Leu Ser
            435                 440                 445
```

Lys Thr Arg Gln Asp Gln Pro Ile Asn Ala Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Val Thr Gln Asn
            485                 490                 495

Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ser Thr Val Asp Ser Ile
            580                 585                 590

Ala Ile Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
610                 615                 620

Thr Asp Gly Asn Phe His Pro Ser Pro Leu Met Gly Gly Phe Gly Met
625                 630                 635                 640

Lys His Pro Pro Gln Ile Leu Ile Lys Asn Thr Pro Val Pro Ala
            645                 650                 655

Asp Pro Pro Thr Ala Phe Asn Lys Asp Lys Leu Asn Ser Phe Ile Thr
                660                 665                 670

Gln Tyr Ser Thr Gly Gln Val Ser Val Glu Ile Glu Trp Glu Leu Gln
            675                 680                 685

Lys Glu Asn Ser Lys Arg Trp Asn Pro Glu Ile Gln Tyr Thr Ser Asn
690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
            725                 730                 735

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000

<210> SEQ ID NO 204

<400> SEQUENCE: 204

000

<210> SEQ ID NO 205

<400> SEQUENCE: 205

000

<210> SEQ ID NO 206

<400> SEQUENCE: 206

000

<210> SEQ ID NO 207

<400> SEQUENCE: 207

000

<210> SEQ ID NO 208

<400> SEQUENCE: 208

000

<210> SEQ ID NO 209

<400> SEQUENCE: 209

000

<210> SEQ ID NO 210

<400> SEQUENCE: 210

000

<210> SEQ ID NO 211

<400> SEQUENCE: 211

000

<210> SEQ ID NO 212

<400> SEQUENCE: 212

000

<210> SEQ ID NO 213

<400> SEQUENCE: 213

000

-continued

<210> SEQ ID NO 214
<400> SEQUENCE: 214
000

<210> SEQ ID NO 215
<400> SEQUENCE: 215
000

<210> SEQ ID NO 216
<400> SEQUENCE: 216
000

<210> SEQ ID NO 217
<400> SEQUENCE: 217
000

<210> SEQ ID NO 218
<400> SEQUENCE: 218
000

<210> SEQ ID NO 219
<400> SEQUENCE: 219
000

<210> SEQ ID NO 220
<400> SEQUENCE: 220
000

<210> SEQ ID NO 221
<400> SEQUENCE: 221
000

<210> SEQ ID NO 222
<400> SEQUENCE: 222
000

<210> SEQ ID NO 223
<400> SEQUENCE: 223
000

<210> SEQ ID NO 224
<400> SEQUENCE: 224
000

<210> SEQ ID NO 225

```
<400> SEQUENCE: 225

000

<210> SEQ ID NO 226

<400> SEQUENCE: 226

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236
```

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

```
<210> SEQ ID NO 248
<400> SEQUENCE: 248
000

<210> SEQ ID NO 249
<400> SEQUENCE: 249
000

<210> SEQ ID NO 250
<400> SEQUENCE: 250
000

<210> SEQ ID NO 251
<400> SEQUENCE: 251
000

<210> SEQ ID NO 252
<400> SEQUENCE: 252
000

<210> SEQ ID NO 253
<400> SEQUENCE: 253
000

<210> SEQ ID NO 254
<400> SEQUENCE: 254
000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
```

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

```
<210> SEQ ID NO 293
<400> SEQUENCE: 293
000

<210> SEQ ID NO 294
<400> SEQUENCE: 294
000

<210> SEQ ID NO 295
<400> SEQUENCE: 295
000

<210> SEQ ID NO 296
<400> SEQUENCE: 296
000

<210> SEQ ID NO 297
<400> SEQUENCE: 297
000

<210> SEQ ID NO 298
<400> SEQUENCE: 298
000

<210> SEQ ID NO 299
<400> SEQUENCE: 299
000

<210> SEQ ID NO 300
<400> SEQUENCE: 300
000

<210> SEQ ID NO 301
<400> SEQUENCE: 301
000

<210> SEQ ID NO 302
<400> SEQUENCE: 302
000

<210> SEQ ID NO 303
<400> SEQUENCE: 303
000

<210> SEQ ID NO 304
```

```
<400> SEQUENCE: 304
000

<210> SEQ ID NO 305
<400> SEQUENCE: 305
000

<210> SEQ ID NO 306
<400> SEQUENCE: 306
000

<210> SEQ ID NO 307
<400> SEQUENCE: 307
000

<210> SEQ ID NO 308
<400> SEQUENCE: 308
000

<210> SEQ ID NO 309
<400> SEQUENCE: 309
000

<210> SEQ ID NO 310
<400> SEQUENCE: 310
000

<210> SEQ ID NO 311
<400> SEQUENCE: 311
000

<210> SEQ ID NO 312
<400> SEQUENCE: 312
000

<210> SEQ ID NO 313
<400> SEQUENCE: 313
000

<210> SEQ ID NO 314
<400> SEQUENCE: 314
000

<210> SEQ ID NO 315
<400> SEQUENCE: 315
```

000

<210> SEQ ID NO 316

<400> SEQUENCE: 316

000

<210> SEQ ID NO 317

<400> SEQUENCE: 317

000

<210> SEQ ID NO 318

<400> SEQUENCE: 318

000

<210> SEQ ID NO 319

<400> SEQUENCE: 319

000

<210> SEQ ID NO 320

<400> SEQUENCE: 320

000

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

```
<400> SEQUENCE: 338
000

<210> SEQ ID NO 339
<400> SEQUENCE: 339
000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
```

000

<210> SEQ ID NO 350

<400> SEQUENCE: 350

000

<210> SEQ ID NO 351

<400> SEQUENCE: 351

000

<210> SEQ ID NO 352

<400> SEQUENCE: 352

000

<210> SEQ ID NO 353

<400> SEQUENCE: 353

000

<210> SEQ ID NO 354

<400> SEQUENCE: 354

000

<210> SEQ ID NO 355

<400> SEQUENCE: 355

000

<210> SEQ ID NO 356

<400> SEQUENCE: 356

000

<210> SEQ ID NO 357

<400> SEQUENCE: 357

000

<210> SEQ ID NO 358

<400> SEQUENCE: 358

000

<210> SEQ ID NO 359

<400> SEQUENCE: 359

000

<210> SEQ ID NO 360

<400> SEQUENCE: 360

000

<210> SEQ ID NO 361

<400> SEQUENCE: 361

000

<210> SEQ ID NO 362

<400> SEQUENCE: 362

000

<210> SEQ ID NO 363

<400> SEQUENCE: 363

000

<210> SEQ ID NO 364

<400> SEQUENCE: 364

000

<210> SEQ ID NO 365

<400> SEQUENCE: 365

000

<210> SEQ ID NO 366

<400> SEQUENCE: 366

000

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

-continued

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401

<400> SEQUENCE: 401

000

<210> SEQ ID NO 402

<400> SEQUENCE: 402

000

<210> SEQ ID NO 403

<400> SEQUENCE: 403

000

<210> SEQ ID NO 404

<400> SEQUENCE: 404

000

<210> SEQ ID NO 405

<400> SEQUENCE: 405

000

<210> SEQ ID NO 406

<400> SEQUENCE: 406

000

<210> SEQ ID NO 407

<400> SEQUENCE: 407

000

<210> SEQ ID NO 408

<400> SEQUENCE: 408

000

<210> SEQ ID NO 409

<400> SEQUENCE: 409

000

<210> SEQ ID NO 410

<400> SEQUENCE: 410

000

<210> SEQ ID NO 411

<400> SEQUENCE: 411

000

<210> SEQ ID NO 412

<400> SEQUENCE: 412

000

<210> SEQ ID NO 413

<400> SEQUENCE: 413

000

<210> SEQ ID NO 414

<400> SEQUENCE: 414

000

<210> SEQ ID NO 415

<400> SEQUENCE: 415

000

<210> SEQ ID NO 416

<400> SEQUENCE: 416

000

<210> SEQ ID NO 417

-continued

<400> SEQUENCE: 417

000

<210> SEQ ID NO 418

<400> SEQUENCE: 418

000

<210> SEQ ID NO 419

<400> SEQUENCE: 419

000

<210> SEQ ID NO 420

<400> SEQUENCE: 420

000

<210> SEQ ID NO 421

<400> SEQUENCE: 421

000

<210> SEQ ID NO 422

<400> SEQUENCE: 422

000

<210> SEQ ID NO 423

<400> SEQUENCE: 423

000

<210> SEQ ID NO 424

<400> SEQUENCE: 424

000

<210> SEQ ID NO 425

<400> SEQUENCE: 425

000

<210> SEQ ID NO 426

<400> SEQUENCE: 426

000

<210> SEQ ID NO 427

<400> SEQUENCE: 427

000

<210> SEQ ID NO 428

<400> SEQUENCE: 428

000

<210> SEQ ID NO 429

<400> SEQUENCE: 429

000

<210> SEQ ID NO 430

<400> SEQUENCE: 430

000

<210> SEQ ID NO 431

<400> SEQUENCE: 431

000

<210> SEQ ID NO 432

<400> SEQUENCE: 432

000

<210> SEQ ID NO 433

<400> SEQUENCE: 433

000

<210> SEQ ID NO 434

<400> SEQUENCE: 434

000

<210> SEQ ID NO 435

<400> SEQUENCE: 435

000

<210> SEQ ID NO 436

<400> SEQUENCE: 436

000

<210> SEQ ID NO 437

<400> SEQUENCE: 437

000

<210> SEQ ID NO 438

<400> SEQUENCE: 438

000

<210> SEQ ID NO 439

<400> SEQUENCE: 439

000

<210> SEQ ID NO 440

<400> SEQUENCE: 440

000

<210> SEQ ID NO 441

<400> SEQUENCE: 441

000

<210> SEQ ID NO 442

<400> SEQUENCE: 442

000

<210> SEQ ID NO 443

<400> SEQUENCE: 443

000

<210> SEQ ID NO 444

<400> SEQUENCE: 444

000

<210> SEQ ID NO 445

<400> SEQUENCE: 445

000

<210> SEQ ID NO 446

<400> SEQUENCE: 446

000

<210> SEQ ID NO 447

<400> SEQUENCE: 447

000

<210> SEQ ID NO 448

<400> SEQUENCE: 448

000

<210> SEQ ID NO 449

<400> SEQUENCE: 449

000

<210> SEQ ID NO 450

<400> SEQUENCE: 450

000

<210> SEQ ID NO 451

<400> SEQUENCE: 451

000

<210> SEQ ID NO 452

<400> SEQUENCE: 452

000

<210> SEQ ID NO 453

<400> SEQUENCE: 453

000

<210> SEQ ID NO 454

<400> SEQUENCE: 454

000

<210> SEQ ID NO 455

<400> SEQUENCE: 455

000

<210> SEQ ID NO 456

<400> SEQUENCE: 456

000

<210> SEQ ID NO 457

<400> SEQUENCE: 457

000

<210> SEQ ID NO 458

<400> SEQUENCE: 458

000

<210> SEQ ID NO 459

<400> SEQUENCE: 459

000

<210> SEQ ID NO 460

<400> SEQUENCE: 460

000

<210> SEQ ID NO 461

<400> SEQUENCE: 461

000

<210> SEQ ID NO 462

<400> SEQUENCE: 462

000

<210> SEQ ID NO 463

<400> SEQUENCE: 463

000

<210> SEQ ID NO 464

<400> SEQUENCE: 464

000

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

-continued

000

<210> SEQ ID NO 474

<400> SEQUENCE: 474

000

<210> SEQ ID NO 475

<400> SEQUENCE: 475

000

<210> SEQ ID NO 476

<400> SEQUENCE: 476

000

<210> SEQ ID NO 477

<400> SEQUENCE: 477

000

<210> SEQ ID NO 478

<400> SEQUENCE: 478

000

<210> SEQ ID NO 479

<400> SEQUENCE: 479

000

<210> SEQ ID NO 480

<400> SEQUENCE: 480

000

<210> SEQ ID NO 481

<400> SEQUENCE: 481

000

<210> SEQ ID NO 482

<400> SEQUENCE: 482

000

<210> SEQ ID NO 483

<400> SEQUENCE: 483

000

<210> SEQ ID NO 484

<400> SEQUENCE: 484

000

```
<210> SEQ ID NO 485
<400> SEQUENCE: 485
000

<210> SEQ ID NO 486
<400> SEQUENCE: 486
000

<210> SEQ ID NO 487
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
```

```
<400> SEQUENCE: 496

000

<210> SEQ ID NO 497

<400> SEQUENCE: 497

000

<210> SEQ ID NO 498

<400> SEQUENCE: 498

000

<210> SEQ ID NO 499

<400> SEQUENCE: 499

000

<210> SEQ ID NO 500

<400> SEQUENCE: 500

000

<210> SEQ ID NO 501

<400> SEQUENCE: 501

000

<210> SEQ ID NO 502

<400> SEQUENCE: 502

000

<210> SEQ ID NO 503

<400> SEQUENCE: 503

000

<210> SEQ ID NO 504

<400> SEQUENCE: 504

000

<210> SEQ ID NO 505

<400> SEQUENCE: 505

000

<210> SEQ ID NO 506

<400> SEQUENCE: 506

000

<210> SEQ ID NO 507

<400> SEQUENCE: 507
```

000

<210> SEQ ID NO 508

<400> SEQUENCE: 508

000

<210> SEQ ID NO 509

<400> SEQUENCE: 509

000

<210> SEQ ID NO 510

<400> SEQUENCE: 510

000

<210> SEQ ID NO 511

<400> SEQUENCE: 511

000

<210> SEQ ID NO 512

<400> SEQUENCE: 512

000

<210> SEQ ID NO 513

<400> SEQUENCE: 513

000

<210> SEQ ID NO 514

<400> SEQUENCE: 514

000

<210> SEQ ID NO 515

<400> SEQUENCE: 515

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

<210> SEQ ID NO 527

<400> SEQUENCE: 527

000

<210> SEQ ID NO 528

<400> SEQUENCE: 528

000

<210> SEQ ID NO 529

<400> SEQUENCE: 529

000

<210> SEQ ID NO 530

<400> SEQUENCE: 530

000

<210> SEQ ID NO 531

<400> SEQUENCE: 531

000

<210> SEQ ID NO 532

<400> SEQUENCE: 532

000

<210> SEQ ID NO 533

<400> SEQUENCE: 533

000

<210> SEQ ID NO 534

<400> SEQUENCE: 534

000

<210> SEQ ID NO 535

<400> SEQUENCE: 535

000

<210> SEQ ID NO 536

<400> SEQUENCE: 536

000

<210> SEQ ID NO 537

<400> SEQUENCE: 537

000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550

<400> SEQUENCE: 550

000

<210> SEQ ID NO 551

<400> SEQUENCE: 551

000

<210> SEQ ID NO 552

<400> SEQUENCE: 552

000

<210> SEQ ID NO 553

<400> SEQUENCE: 553

000

<210> SEQ ID NO 554

<400> SEQUENCE: 554

000

<210> SEQ ID NO 555

<400> SEQUENCE: 555

000

<210> SEQ ID NO 556

<400> SEQUENCE: 556

000

<210> SEQ ID NO 557

<400> SEQUENCE: 557

000

<210> SEQ ID NO 558

<400> SEQUENCE: 558

000

<210> SEQ ID NO 559

<400> SEQUENCE: 559

000

<210> SEQ ID NO 560

<400> SEQUENCE: 560

000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584

<400> SEQUENCE: 584

000

<210> SEQ ID NO 585

<400> SEQUENCE: 585

000

<210> SEQ ID NO 586

<400> SEQUENCE: 586

000

<210> SEQ ID NO 587

<400> SEQUENCE: 587

000

<210> SEQ ID NO 588

<400> SEQUENCE: 588

000

<210> SEQ ID NO 589

<400> SEQUENCE: 589

000

<210> SEQ ID NO 590

<400> SEQUENCE: 590

000

<210> SEQ ID NO 591

<400> SEQUENCE: 591

000

<210> SEQ ID NO 592

<400> SEQUENCE: 592

000

<210> SEQ ID NO 593

<400> SEQUENCE: 593

000

<210> SEQ ID NO 594

<400> SEQUENCE: 594

000

<210> SEQ ID NO 595

<400> SEQUENCE: 595

000

<210> SEQ ID NO 596

<400> SEQUENCE: 596

000

<210> SEQ ID NO 597

<400> SEQUENCE: 597

000

<210> SEQ ID NO 598

<400> SEQUENCE: 598

000

<210> SEQ ID NO 599

<400> SEQUENCE: 599

000

<210> SEQ ID NO 600

<400> SEQUENCE: 600

000

<210> SEQ ID NO 601

<400> SEQUENCE: 601

000

<210> SEQ ID NO 602

<400> SEQUENCE: 602

000

<210> SEQ ID NO 603

<400> SEQUENCE: 603

000

<210> SEQ ID NO 604

<400> SEQUENCE: 604

000

<210> SEQ ID NO 605

<400> SEQUENCE: 605

000

<210> SEQ ID NO 606

<400> SEQUENCE: 606

000

<210> SEQ ID NO 607

<400> SEQUENCE: 607

000

<210> SEQ ID NO 608

<400> SEQUENCE: 608

000

```
<210> SEQ ID NO 609
<400> SEQUENCE: 609
000

<210> SEQ ID NO 610
<400> SEQUENCE: 610
000

<210> SEQ ID NO 611
<400> SEQUENCE: 611
000

<210> SEQ ID NO 612
<400> SEQUENCE: 612
000

<210> SEQ ID NO 613
<400> SEQUENCE: 613
000

<210> SEQ ID NO 614
<400> SEQUENCE: 614
000

<210> SEQ ID NO 615
<400> SEQUENCE: 615
000

<210> SEQ ID NO 616
<400> SEQUENCE: 616
000

<210> SEQ ID NO 617
<400> SEQUENCE: 617
000

<210> SEQ ID NO 618
<400> SEQUENCE: 618
000

<210> SEQ ID NO 619
<400> SEQUENCE: 619
000

<210> SEQ ID NO 620
```

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

<400> SEQUENCE: 638

000

<210> SEQ ID NO 639

<400> SEQUENCE: 639

000

<210> SEQ ID NO 640

<400> SEQUENCE: 640

000

<210> SEQ ID NO 641

<400> SEQUENCE: 641

000

<210> SEQ ID NO 642

<400> SEQUENCE: 642

000

<210> SEQ ID NO 643

<400> SEQUENCE: 643

000

<210> SEQ ID NO 644

<400> SEQUENCE: 644

000

<210> SEQ ID NO 645

<400> SEQUENCE: 645

000

<210> SEQ ID NO 646

<400> SEQUENCE: 646

000

<210> SEQ ID NO 647

<400> SEQUENCE: 647

000

<210> SEQ ID NO 648

<400> SEQUENCE: 648

000

<210> SEQ ID NO 649

<400> SEQUENCE: 649

000

<210> SEQ ID NO 650

<400> SEQUENCE: 650

000

<210> SEQ ID NO 651

<400> SEQUENCE: 651

000

<210> SEQ ID NO 652

<400> SEQUENCE: 652

000

<210> SEQ ID NO 653

<400> SEQUENCE: 653

000

<210> SEQ ID NO 654

<400> SEQUENCE: 654

000

<210> SEQ ID NO 655

<400> SEQUENCE: 655

000

<210> SEQ ID NO 656

<400> SEQUENCE: 656

000

<210> SEQ ID NO 657

<400> SEQUENCE: 657

000

<210> SEQ ID NO 658

<400> SEQUENCE: 658

000

<210> SEQ ID NO 659

<400> SEQUENCE: 659

000

<210> SEQ ID NO 660

<400> SEQUENCE: 660

000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678

<400> SEQUENCE: 678

000

<210> SEQ ID NO 679

<400> SEQUENCE: 679

000

<210> SEQ ID NO 680

<400> SEQUENCE: 680

000

<210> SEQ ID NO 681

<400> SEQUENCE: 681

000

<210> SEQ ID NO 682

<400> SEQUENCE: 682

000

<210> SEQ ID NO 683

<400> SEQUENCE: 683

000

<210> SEQ ID NO 684

<400> SEQUENCE: 684

000

<210> SEQ ID NO 685

<400> SEQUENCE: 685

000

<210> SEQ ID NO 686

<400> SEQUENCE: 686

000

<210> SEQ ID NO 687

<400> SEQUENCE: 687

000

```
<210> SEQ ID NO 688
<400> SEQUENCE: 688
000

<210> SEQ ID NO 689
<400> SEQUENCE: 689
000

<210> SEQ ID NO 690
<400> SEQUENCE: 690
000

<210> SEQ ID NO 691
<400> SEQUENCE: 691
000

<210> SEQ ID NO 692
<400> SEQUENCE: 692
000

<210> SEQ ID NO 693
<400> SEQUENCE: 693
000

<210> SEQ ID NO 694
<400> SEQUENCE: 694
000

<210> SEQ ID NO 695
<400> SEQUENCE: 695
000

<210> SEQ ID NO 696
<400> SEQUENCE: 696
000

<210> SEQ ID NO 697
<400> SEQUENCE: 697
000

<210> SEQ ID NO 698
<400> SEQUENCE: 698
000

<210> SEQ ID NO 699
```

<400> SEQUENCE: 699

000

<210> SEQ ID NO 700
<400> SEQUENCE: 700

000

<210> SEQ ID NO 701
<400> SEQUENCE: 701

000

<210> SEQ ID NO 702
<400> SEQUENCE: 702

000

<210> SEQ ID NO 703
<400> SEQUENCE: 703

000

<210> SEQ ID NO 704
<400> SEQUENCE: 704

000

<210> SEQ ID NO 705
<400> SEQUENCE: 705

000

<210> SEQ ID NO 706
<400> SEQUENCE: 706

000

<210> SEQ ID NO 707
<400> SEQUENCE: 707

000

<210> SEQ ID NO 708
<400> SEQUENCE: 708

000

<210> SEQ ID NO 709
<400> SEQUENCE: 709

000

<210> SEQ ID NO 710
<400> SEQUENCE: 710

000

<210> SEQ ID NO 711
<400> SEQUENCE: 711
000

<210> SEQ ID NO 712
<400> SEQUENCE: 712
000

<210> SEQ ID NO 713
<400> SEQUENCE: 713
000

<210> SEQ ID NO 714
<400> SEQUENCE: 714
000

<210> SEQ ID NO 715
<400> SEQUENCE: 715
000

<210> SEQ ID NO 716
<400> SEQUENCE: 716
000

<210> SEQ ID NO 717
<400> SEQUENCE: 717
000

<210> SEQ ID NO 718
<400> SEQUENCE: 718
000

<210> SEQ ID NO 719
<400> SEQUENCE: 719
000

<210> SEQ ID NO 720
<400> SEQUENCE: 720
000

<210> SEQ ID NO 721
<400> SEQUENCE: 721
000

```
<210> SEQ ID NO 722
<400> SEQUENCE: 722
000

<210> SEQ ID NO 723
<400> SEQUENCE: 723
000

<210> SEQ ID NO 724
<400> SEQUENCE: 724
000

<210> SEQ ID NO 725
<400> SEQUENCE: 725
000

<210> SEQ ID NO 726
<400> SEQUENCE: 726
000

<210> SEQ ID NO 727
<400> SEQUENCE: 727
000

<210> SEQ ID NO 728
<400> SEQUENCE: 728
000

<210> SEQ ID NO 729
<400> SEQUENCE: 729
000

<210> SEQ ID NO 730
<400> SEQUENCE: 730
000

<210> SEQ ID NO 731
<400> SEQUENCE: 731
000

<210> SEQ ID NO 732
<400> SEQUENCE: 732
000

<210> SEQ ID NO 733
```

<400> SEQUENCE: 733

000

<210> SEQ ID NO 734

<400> SEQUENCE: 734

000

<210> SEQ ID NO 735

<400> SEQUENCE: 735

000

<210> SEQ ID NO 736

<400> SEQUENCE: 736

000

<210> SEQ ID NO 737

<400> SEQUENCE: 737

000

<210> SEQ ID NO 738

<400> SEQUENCE: 738

000

<210> SEQ ID NO 739

<400> SEQUENCE: 739

000

<210> SEQ ID NO 740

<400> SEQUENCE: 740

000

<210> SEQ ID NO 741

<400> SEQUENCE: 741

000

<210> SEQ ID NO 742

<400> SEQUENCE: 742

000

<210> SEQ ID NO 743

<400> SEQUENCE: 743

000

<210> SEQ ID NO 744

<400> SEQUENCE: 744

000

<210> SEQ ID NO 745
<400> SEQUENCE: 745
000

<210> SEQ ID NO 746
<400> SEQUENCE: 746
000

<210> SEQ ID NO 747
<400> SEQUENCE: 747
000

<210> SEQ ID NO 748
<400> SEQUENCE: 748
000

<210> SEQ ID NO 749
<400> SEQUENCE: 749
000

<210> SEQ ID NO 750
<400> SEQUENCE: 750
000

<210> SEQ ID NO 751
<400> SEQUENCE: 751
000

<210> SEQ ID NO 752
<400> SEQUENCE: 752
000

<210> SEQ ID NO 753
<400> SEQUENCE: 753
000

<210> SEQ ID NO 754
<400> SEQUENCE: 754
000

<210> SEQ ID NO 755
<400> SEQUENCE: 755
000

<210> SEQ ID NO 756

<400> SEQUENCE: 756

000

<210> SEQ ID NO 757

<400> SEQUENCE: 757

000

<210> SEQ ID NO 758

<400> SEQUENCE: 758

000

<210> SEQ ID NO 759

<400> SEQUENCE: 759

000

<210> SEQ ID NO 760

<400> SEQUENCE: 760

000

<210> SEQ ID NO 761

<400> SEQUENCE: 761

000

<210> SEQ ID NO 762

<400> SEQUENCE: 762

000

<210> SEQ ID NO 763

<400> SEQUENCE: 763

000

<210> SEQ ID NO 764

<400> SEQUENCE: 764

000

<210> SEQ ID NO 765

<400> SEQUENCE: 765

000

<210> SEQ ID NO 766

<400> SEQUENCE: 766

000

<210> SEQ ID NO 767

<400> SEQUENCE: 767

000

<210> SEQ ID NO 768

<400> SEQUENCE: 768

000

<210> SEQ ID NO 769

<400> SEQUENCE: 769

000

<210> SEQ ID NO 770

<400> SEQUENCE: 770

000

<210> SEQ ID NO 771

<400> SEQUENCE: 771

000

<210> SEQ ID NO 772

<400> SEQUENCE: 772

000

<210> SEQ ID NO 773

<400> SEQUENCE: 773

000

<210> SEQ ID NO 774

<400> SEQUENCE: 774

000

<210> SEQ ID NO 775

<400> SEQUENCE: 775

000

<210> SEQ ID NO 776

<400> SEQUENCE: 776

000

<210> SEQ ID NO 777

<400> SEQUENCE: 777

000

<210> SEQ ID NO 778

```
<400> SEQUENCE: 778

000

<210> SEQ ID NO 779

<400> SEQUENCE: 779

000

<210> SEQ ID NO 780

<400> SEQUENCE: 780

000

<210> SEQ ID NO 781

<400> SEQUENCE: 781

000

<210> SEQ ID NO 782

<400> SEQUENCE: 782

000

<210> SEQ ID NO 783

<400> SEQUENCE: 783

000

<210> SEQ ID NO 784

<400> SEQUENCE: 784

000

<210> SEQ ID NO 785

<400> SEQUENCE: 785

000

<210> SEQ ID NO 786

<400> SEQUENCE: 786

000

<210> SEQ ID NO 787

<400> SEQUENCE: 787

000

<210> SEQ ID NO 788

<400> SEQUENCE: 788

000

<210> SEQ ID NO 789

<400> SEQUENCE: 789
```

000

<210> SEQ ID NO 790
<400> SEQUENCE: 790
000

<210> SEQ ID NO 791
<400> SEQUENCE: 791
000

<210> SEQ ID NO 792
<400> SEQUENCE: 792
000

<210> SEQ ID NO 793
<400> SEQUENCE: 793
000

<210> SEQ ID NO 794
<400> SEQUENCE: 794
000

<210> SEQ ID NO 795
<400> SEQUENCE: 795
000

<210> SEQ ID NO 796
<400> SEQUENCE: 796
000

<210> SEQ ID NO 797
<400> SEQUENCE: 797
000

<210> SEQ ID NO 798
<400> SEQUENCE: 798
000

<210> SEQ ID NO 799
<400> SEQUENCE: 799
000

<210> SEQ ID NO 800
<400> SEQUENCE: 800
000

<210> SEQ ID NO 801

<400> SEQUENCE: 801

000

<210> SEQ ID NO 802

<400> SEQUENCE: 802

000

<210> SEQ ID NO 803

<400> SEQUENCE: 803

000

<210> SEQ ID NO 804

<400> SEQUENCE: 804

000

<210> SEQ ID NO 805

<400> SEQUENCE: 805

000

<210> SEQ ID NO 806

<400> SEQUENCE: 806

000

<210> SEQ ID NO 807

<400> SEQUENCE: 807

000

<210> SEQ ID NO 808

<400> SEQUENCE: 808

000

<210> SEQ ID NO 809

<400> SEQUENCE: 809

000

<210> SEQ ID NO 810

<400> SEQUENCE: 810

000

<210> SEQ ID NO 811

<400> SEQUENCE: 811

000

<210> SEQ ID NO 812

<400> SEQUENCE: 812

000

<210> SEQ ID NO 813

<400> SEQUENCE: 813

000

<210> SEQ ID NO 814

<400> SEQUENCE: 814

000

<210> SEQ ID NO 815

<400> SEQUENCE: 815

000

<210> SEQ ID NO 816

<400> SEQUENCE: 816

000

<210> SEQ ID NO 817

<400> SEQUENCE: 817

000

<210> SEQ ID NO 818

<400> SEQUENCE: 818

000

<210> SEQ ID NO 819

<400> SEQUENCE: 819

000

<210> SEQ ID NO 820

<400> SEQUENCE: 820

000

<210> SEQ ID NO 821

<400> SEQUENCE: 821

000

<210> SEQ ID NO 822

<400> SEQUENCE: 822

000

<210> SEQ ID NO 823

<400> SEQUENCE: 823

000

<210> SEQ ID NO 824

<400> SEQUENCE: 824

000

<210> SEQ ID NO 825

<400> SEQUENCE: 825

000

<210> SEQ ID NO 826

<400> SEQUENCE: 826

000

<210> SEQ ID NO 827

<400> SEQUENCE: 827

000

<210> SEQ ID NO 828

<400> SEQUENCE: 828

000

<210> SEQ ID NO 829

<400> SEQUENCE: 829

000

<210> SEQ ID NO 830

<400> SEQUENCE: 830

000

<210> SEQ ID NO 831

<400> SEQUENCE: 831

000

<210> SEQ ID NO 832

<400> SEQUENCE: 832

000

<210> SEQ ID NO 833

<400> SEQUENCE: 833

000

<210> SEQ ID NO 834

<400> SEQUENCE: 834

000

```
<210> SEQ ID NO 835
<400> SEQUENCE: 835
000

<210> SEQ ID NO 836
<400> SEQUENCE: 836
000

<210> SEQ ID NO 837
<400> SEQUENCE: 837
000

<210> SEQ ID NO 838
<400> SEQUENCE: 838
000

<210> SEQ ID NO 839
<400> SEQUENCE: 839
000

<210> SEQ ID NO 840
<400> SEQUENCE: 840
000

<210> SEQ ID NO 841
<400> SEQUENCE: 841
000

<210> SEQ ID NO 842
<400> SEQUENCE: 842
000

<210> SEQ ID NO 843
<400> SEQUENCE: 843
000

<210> SEQ ID NO 844
<400> SEQUENCE: 844
000

<210> SEQ ID NO 845
<400> SEQUENCE: 845
000
```

-continued

<210> SEQ ID NO 846

<400> SEQUENCE: 846

000

<210> SEQ ID NO 847

<400> SEQUENCE: 847

000

<210> SEQ ID NO 848

<400> SEQUENCE: 848

000

<210> SEQ ID NO 849

<400> SEQUENCE: 849

000

<210> SEQ ID NO 850

<400> SEQUENCE: 850

000

<210> SEQ ID NO 851

<400> SEQUENCE: 851

000

<210> SEQ ID NO 852

<400> SEQUENCE: 852

000

<210> SEQ ID NO 853

<400> SEQUENCE: 853

000

<210> SEQ ID NO 854

<400> SEQUENCE: 854

000

<210> SEQ ID NO 855

<400> SEQUENCE: 855

000

<210> SEQ ID NO 856

<400> SEQUENCE: 856

000

<210> SEQ ID NO 857

<400> SEQUENCE: 857

000

<210> SEQ ID NO 858

<400> SEQUENCE: 858

000

<210> SEQ ID NO 859

<400> SEQUENCE: 859

000

<210> SEQ ID NO 860

<400> SEQUENCE: 860

000

<210> SEQ ID NO 861

<400> SEQUENCE: 861

000

<210> SEQ ID NO 862

<400> SEQUENCE: 862

000

<210> SEQ ID NO 863

<400> SEQUENCE: 863

000

<210> SEQ ID NO 864

<400> SEQUENCE: 864

000

<210> SEQ ID NO 865

<400> SEQUENCE: 865

000

<210> SEQ ID NO 866

<400> SEQUENCE: 866

000

<210> SEQ ID NO 867

<400> SEQUENCE: 867

000

<210> SEQ ID NO 868

<400> SEQUENCE: 868

000

<210> SEQ ID NO 869

<400> SEQUENCE: 869

000

<210> SEQ ID NO 870

<400> SEQUENCE: 870

000

<210> SEQ ID NO 871

<400> SEQUENCE: 871

000

<210> SEQ ID NO 872

<400> SEQUENCE: 872

000

<210> SEQ ID NO 873

<400> SEQUENCE: 873

000

<210> SEQ ID NO 874

<400> SEQUENCE: 874

000

<210> SEQ ID NO 875

<400> SEQUENCE: 875

000

<210> SEQ ID NO 876

<400> SEQUENCE: 876

000

<210> SEQ ID NO 877

<400> SEQUENCE: 877

000

<210> SEQ ID NO 878

<400> SEQUENCE: 878

000

<210> SEQ ID NO 879

<400> SEQUENCE: 879

000

<210> SEQ ID NO 880

<400> SEQUENCE: 880

000

<210> SEQ ID NO 881

<400> SEQUENCE: 881

000

<210> SEQ ID NO 882

<400> SEQUENCE: 882

000

<210> SEQ ID NO 883

<400> SEQUENCE: 883

000

<210> SEQ ID NO 884

<400> SEQUENCE: 884

000

<210> SEQ ID NO 885

<400> SEQUENCE: 885

000

<210> SEQ ID NO 886

<400> SEQUENCE: 886

000

<210> SEQ ID NO 887

<400> SEQUENCE: 887

000

<210> SEQ ID NO 888

<400> SEQUENCE: 888

000

<210> SEQ ID NO 889

<400> SEQUENCE: 889

000

<210> SEQ ID NO 890

<400> SEQUENCE: 890

000

<210> SEQ ID NO 891

```
<400> SEQUENCE: 891

000

<210> SEQ ID NO 892

<400> SEQUENCE: 892

000

<210> SEQ ID NO 893

<400> SEQUENCE: 893

000

<210> SEQ ID NO 894

<400> SEQUENCE: 894

000

<210> SEQ ID NO 895

<400> SEQUENCE: 895

000

<210> SEQ ID NO 896

<400> SEQUENCE: 896

000

<210> SEQ ID NO 897

<400> SEQUENCE: 897

000

<210> SEQ ID NO 898

<400> SEQUENCE: 898

000

<210> SEQ ID NO 899

<400> SEQUENCE: 899

000

<210> SEQ ID NO 900

<400> SEQUENCE: 900

000

<210> SEQ ID NO 901

<400> SEQUENCE: 901

000

<210> SEQ ID NO 902

<400> SEQUENCE: 902
```

000

<210> SEQ ID NO 903

<400> SEQUENCE: 903

000

<210> SEQ ID NO 904

<400> SEQUENCE: 904

000

<210> SEQ ID NO 905

<400> SEQUENCE: 905

000

<210> SEQ ID NO 906

<400> SEQUENCE: 906

000

<210> SEQ ID NO 907

<400> SEQUENCE: 907

000

<210> SEQ ID NO 908

<400> SEQUENCE: 908

000

<210> SEQ ID NO 909

<400> SEQUENCE: 909

000

<210> SEQ ID NO 910

<400> SEQUENCE: 910

000

<210> SEQ ID NO 911

<400> SEQUENCE: 911

000

<210> SEQ ID NO 912

<400> SEQUENCE: 912

000

<210> SEQ ID NO 913

<400> SEQUENCE: 913

000

-continued

<210> SEQ ID NO 914

<400> SEQUENCE: 914

000

<210> SEQ ID NO 915

<400> SEQUENCE: 915

000

<210> SEQ ID NO 916

<400> SEQUENCE: 916

000

<210> SEQ ID NO 917

<400> SEQUENCE: 917

000

<210> SEQ ID NO 918

<400> SEQUENCE: 918

000

<210> SEQ ID NO 919

<400> SEQUENCE: 919

000

<210> SEQ ID NO 920

<400> SEQUENCE: 920

000

<210> SEQ ID NO 921

<400> SEQUENCE: 921

000

<210> SEQ ID NO 922

<400> SEQUENCE: 922

000

<210> SEQ ID NO 923

<400> SEQUENCE: 923

000

<210> SEQ ID NO 924

<400> SEQUENCE: 924

000

```
<210> SEQ ID NO 925
<400> SEQUENCE: 925
000

<210> SEQ ID NO 926
<400> SEQUENCE: 926
000

<210> SEQ ID NO 927
<400> SEQUENCE: 927
000

<210> SEQ ID NO 928
<400> SEQUENCE: 928
000

<210> SEQ ID NO 929
<400> SEQUENCE: 929
000

<210> SEQ ID NO 930
<400> SEQUENCE: 930
000

<210> SEQ ID NO 931
<400> SEQUENCE: 931
000

<210> SEQ ID NO 932
<400> SEQUENCE: 932
000

<210> SEQ ID NO 933
<400> SEQUENCE: 933
000

<210> SEQ ID NO 934
<400> SEQUENCE: 934
000

<210> SEQ ID NO 935
<400> SEQUENCE: 935
000

<210> SEQ ID NO 936
```

<400> SEQUENCE: 936

000

<210> SEQ ID NO 937

<400> SEQUENCE: 937

000

<210> SEQ ID NO 938

<400> SEQUENCE: 938

000

<210> SEQ ID NO 939

<400> SEQUENCE: 939

000

<210> SEQ ID NO 940

<400> SEQUENCE: 940

000

<210> SEQ ID NO 941

<400> SEQUENCE: 941

000

<210> SEQ ID NO 942

<400> SEQUENCE: 942

000

<210> SEQ ID NO 943

<400> SEQUENCE: 943

000

<210> SEQ ID NO 944

<400> SEQUENCE: 944

000

<210> SEQ ID NO 945

<400> SEQUENCE: 945

000

<210> SEQ ID NO 946

<400> SEQUENCE: 946

000

<210> SEQ ID NO 947

<400> SEQUENCE: 947

<210> SEQ ID NO 948

<400> SEQUENCE: 948

000

<210> SEQ ID NO 949

<400> SEQUENCE: 949

000

<210> SEQ ID NO 950

<400> SEQUENCE: 950

000

<210> SEQ ID NO 951

<400> SEQUENCE: 951

000

<210> SEQ ID NO 952

<400> SEQUENCE: 952

000

<210> SEQ ID NO 953

<400> SEQUENCE: 953

000

<210> SEQ ID NO 954

<400> SEQUENCE: 954

000

<210> SEQ ID NO 955

<400> SEQUENCE: 955

000

<210> SEQ ID NO 956

<400> SEQUENCE: 956

000

<210> SEQ ID NO 957

<400> SEQUENCE: 957

000

<210> SEQ ID NO 958

<400> SEQUENCE: 958

000

<210> SEQ ID NO 959
<400> SEQUENCE: 959
000

<210> SEQ ID NO 960
<400> SEQUENCE: 960
000

<210> SEQ ID NO 961
<400> SEQUENCE: 961
000

<210> SEQ ID NO 962
<400> SEQUENCE: 962
000

<210> SEQ ID NO 963
<400> SEQUENCE: 963
000

<210> SEQ ID NO 964
<400> SEQUENCE: 964
000

<210> SEQ ID NO 965
<400> SEQUENCE: 965
000

<210> SEQ ID NO 966
<400> SEQUENCE: 966
000

<210> SEQ ID NO 967
<400> SEQUENCE: 967
000

<210> SEQ ID NO 968
<400> SEQUENCE: 968
000

<210> SEQ ID NO 969
<400> SEQUENCE: 969
000

<210> SEQ ID NO 970

<400> SEQUENCE: 970

000

<210> SEQ ID NO 971

<400> SEQUENCE: 971

000

<210> SEQ ID NO 972

<400> SEQUENCE: 972

000

<210> SEQ ID NO 973

<400> SEQUENCE: 973

000

<210> SEQ ID NO 974

<400> SEQUENCE: 974

000

<210> SEQ ID NO 975

<400> SEQUENCE: 975

000

<210> SEQ ID NO 976

<400> SEQUENCE: 976

000

<210> SEQ ID NO 977

<400> SEQUENCE: 977

000

<210> SEQ ID NO 978

<400> SEQUENCE: 978

000

<210> SEQ ID NO 979

<400> SEQUENCE: 979

000

<210> SEQ ID NO 980

<400> SEQUENCE: 980

000

<210> SEQ ID NO 981

<400> SEQUENCE: 981

000

<210> SEQ ID NO 982

<400> SEQUENCE: 982

000

<210> SEQ ID NO 983

<400> SEQUENCE: 983

000

<210> SEQ ID NO 984

<400> SEQUENCE: 984

000

<210> SEQ ID NO 985

<400> SEQUENCE: 985

000

<210> SEQ ID NO 986

<400> SEQUENCE: 986

000

<210> SEQ ID NO 987

<400> SEQUENCE: 987

000

<210> SEQ ID NO 988

<400> SEQUENCE: 988

000

<210> SEQ ID NO 989

<400> SEQUENCE: 989

000

<210> SEQ ID NO 990

<400> SEQUENCE: 990

000

<210> SEQ ID NO 991

<400> SEQUENCE: 991

000

<210> SEQ ID NO 992

<400> SEQUENCE: 992

000

<210> SEQ ID NO 993

<400> SEQUENCE: 993

000

<210> SEQ ID NO 994

<400> SEQUENCE: 994

000

<210> SEQ ID NO 995

<400> SEQUENCE: 995

000

<210> SEQ ID NO 996

<400> SEQUENCE: 996

000

<210> SEQ ID NO 997

<400> SEQUENCE: 997

000

<210> SEQ ID NO 998

<400> SEQUENCE: 998

000

<210> SEQ ID NO 999

<400> SEQUENCE: 999

000

<210> SEQ ID NO 1000

<400> SEQUENCE: 1000

000

<210> SEQ ID NO 1001

<400> SEQUENCE: 1001

000

<210> SEQ ID NO 1002

<400> SEQUENCE: 1002

000

<210> SEQ ID NO 1003

<400> SEQUENCE: 1003

000

<210> SEQ ID NO 1004

<400> SEQUENCE: 1004

000

<210> SEQ ID NO 1005

<400> SEQUENCE: 1005

000

<210> SEQ ID NO 1006

<400> SEQUENCE: 1006

000

<210> SEQ ID NO 1007

<400> SEQUENCE: 1007

000

<210> SEQ ID NO 1008

<400> SEQUENCE: 1008

000

<210> SEQ ID NO 1009

<400> SEQUENCE: 1009

000

<210> SEQ ID NO 1010

<400> SEQUENCE: 1010

000

<210> SEQ ID NO 1011

<400> SEQUENCE: 1011

000

<210> SEQ ID NO 1012

<400> SEQUENCE: 1012

000

<210> SEQ ID NO 1013

<400> SEQUENCE: 1013

000

<210> SEQ ID NO 1014

<400> SEQUENCE: 1014

000

<210> SEQ ID NO 1015

<400> SEQUENCE: 1015

000

<210> SEQ ID NO 1016

<400> SEQUENCE: 1016

000

<210> SEQ ID NO 1017

<400> SEQUENCE: 1017

000

<210> SEQ ID NO 1018

<400> SEQUENCE: 1018

000

<210> SEQ ID NO 1019

<400> SEQUENCE: 1019

000

<210> SEQ ID NO 1020

<400> SEQUENCE: 1020

000

<210> SEQ ID NO 1021

<400> SEQUENCE: 1021

000

<210> SEQ ID NO 1022

<400> SEQUENCE: 1022

000

<210> SEQ ID NO 1023

<400> SEQUENCE: 1023

000

<210> SEQ ID NO 1024

<400> SEQUENCE: 1024

000

<210> SEQ ID NO 1025

<400> SEQUENCE: 1025

000

<210> SEQ ID NO 1026

<400> SEQUENCE: 1026

000

<210> SEQ ID NO 1027

<400> SEQUENCE: 1027

000

<210> SEQ ID NO 1028

<400> SEQUENCE: 1028

000

<210> SEQ ID NO 1029

<400> SEQUENCE: 1029

000

<210> SEQ ID NO 1030

<400> SEQUENCE: 1030

000

<210> SEQ ID NO 1031

<400> SEQUENCE: 1031

000

<210> SEQ ID NO 1032

<400> SEQUENCE: 1032

000

<210> SEQ ID NO 1033

<400> SEQUENCE: 1033

000

<210> SEQ ID NO 1034

<400> SEQUENCE: 1034

000

<210> SEQ ID NO 1035

<400> SEQUENCE: 1035

000

<210> SEQ ID NO 1036

<400> SEQUENCE: 1036

000

<210> SEQ ID NO 1037

<400> SEQUENCE: 1037

000

<210> SEQ ID NO 1038

<400> SEQUENCE: 1038

000

<210> SEQ ID NO 1039

<400> SEQUENCE: 1039

000

<210> SEQ ID NO 1040

<400> SEQUENCE: 1040

000

<210> SEQ ID NO 1041

<400> SEQUENCE: 1041

000

<210> SEQ ID NO 1042

<400> SEQUENCE: 1042

000

<210> SEQ ID NO 1043

<400> SEQUENCE: 1043

000

<210> SEQ ID NO 1044

<400> SEQUENCE: 1044

000

<210> SEQ ID NO 1045

<400> SEQUENCE: 1045

000

<210> SEQ ID NO 1046

<400> SEQUENCE: 1046

000

<210> SEQ ID NO 1047

<400> SEQUENCE: 1047

000

<210> SEQ ID NO 1048

<400> SEQUENCE: 1048

000

<210> SEQ ID NO 1049

<400> SEQUENCE: 1049

000

<210> SEQ ID NO 1050

<400> SEQUENCE: 1050

000

<210> SEQ ID NO 1051

<400> SEQUENCE: 1051

000

<210> SEQ ID NO 1052

<400> SEQUENCE: 1052

000

<210> SEQ ID NO 1053

<400> SEQUENCE: 1053

000

<210> SEQ ID NO 1054

<400> SEQUENCE: 1054

000

<210> SEQ ID NO 1055

<400> SEQUENCE: 1055

000

<210> SEQ ID NO 1056

<400> SEQUENCE: 1056

000

<210> SEQ ID NO 1057

<400> SEQUENCE: 1057

000

<210> SEQ ID NO 1058

<400> SEQUENCE: 1058

000

<210> SEQ ID NO 1059

<400> SEQUENCE: 1059

000

<210> SEQ ID NO 1060

<400> SEQUENCE: 1060

000

<210> SEQ ID NO 1061

<400> SEQUENCE: 1061

000

<210> SEQ ID NO 1062

<400> SEQUENCE: 1062

000

<210> SEQ ID NO 1063

<400> SEQUENCE: 1063

000

<210> SEQ ID NO 1064

<400> SEQUENCE: 1064

000

<210> SEQ ID NO 1065

<400> SEQUENCE: 1065

000

<210> SEQ ID NO 1066

<400> SEQUENCE: 1066

000

<210> SEQ ID NO 1067

<400> SEQUENCE: 1067

000

<210> SEQ ID NO 1068

<400> SEQUENCE: 1068

000

<210> SEQ ID NO 1069

<400> SEQUENCE: 1069

000

<210> SEQ ID NO 1070

<400> SEQUENCE: 1070

000

<210> SEQ ID NO 1071

<400> SEQUENCE: 1071

000

<210> SEQ ID NO 1072

<400> SEQUENCE: 1072

000

<210> SEQ ID NO 1073

<400> SEQUENCE: 1073

000

<210> SEQ ID NO 1074

<400> SEQUENCE: 1074

000

<210> SEQ ID NO 1075

<400> SEQUENCE: 1075

000

<210> SEQ ID NO 1076

<400> SEQUENCE: 1076

000

<210> SEQ ID NO 1077

<400> SEQUENCE: 1077

000

<210> SEQ ID NO 1078

<400> SEQUENCE: 1078

000

<210> SEQ ID NO 1079

<400> SEQUENCE: 1079

000

<210> SEQ ID NO 1080

<400> SEQUENCE: 1080

000

<210> SEQ ID NO 1081

<400> SEQUENCE: 1081

000

<210> SEQ ID NO 1082

<400> SEQUENCE: 1082

000

-continued

<210> SEQ ID NO 1083

<400> SEQUENCE: 1083

000

<210> SEQ ID NO 1084

<400> SEQUENCE: 1084

000

<210> SEQ ID NO 1085

<400> SEQUENCE: 1085

000

<210> SEQ ID NO 1086

<400> SEQUENCE: 1086

000

<210> SEQ ID NO 1087

<400> SEQUENCE: 1087

000

<210> SEQ ID NO 1088

<400> SEQUENCE: 1088

000

<210> SEQ ID NO 1089

<400> SEQUENCE: 1089

000

<210> SEQ ID NO 1090

<400> SEQUENCE: 1090

000

<210> SEQ ID NO 1091

<400> SEQUENCE: 1091

000

<210> SEQ ID NO 1092

<400> SEQUENCE: 1092

000

<210> SEQ ID NO 1093

<400> SEQUENCE: 1093

000

<210> SEQ ID NO 1094

<400> SEQUENCE: 1094

000

<210> SEQ ID NO 1095

<400> SEQUENCE: 1095

000

<210> SEQ ID NO 1096

<400> SEQUENCE: 1096

000

<210> SEQ ID NO 1097

<400> SEQUENCE: 1097

000

<210> SEQ ID NO 1098

<400> SEQUENCE: 1098

000

<210> SEQ ID NO 1099

<400> SEQUENCE: 1099

000

<210> SEQ ID NO 1100

<400> SEQUENCE: 1100

000

<210> SEQ ID NO 1101

<400> SEQUENCE: 1101

000

<210> SEQ ID NO 1102

<400> SEQUENCE: 1102

000

<210> SEQ ID NO 1103

<400> SEQUENCE: 1103

000

<210> SEQ ID NO 1104

<400> SEQUENCE: 1104

000

<210> SEQ ID NO 1105

<400> SEQUENCE: 1105

000

<210> SEQ ID NO 1106

<400> SEQUENCE: 1106

000

<210> SEQ ID NO 1107

<400> SEQUENCE: 1107

000

<210> SEQ ID NO 1108

<400> SEQUENCE: 1108

000

<210> SEQ ID NO 1109

<400> SEQUENCE: 1109

000

<210> SEQ ID NO 1110

<400> SEQUENCE: 1110

000

<210> SEQ ID NO 1111

<400> SEQUENCE: 1111

000

<210> SEQ ID NO 1112

<400> SEQUENCE: 1112

000

<210> SEQ ID NO 1113

<400> SEQUENCE: 1113

000

<210> SEQ ID NO 1114

<400> SEQUENCE: 1114

000

<210> SEQ ID NO 1115

<400> SEQUENCE: 1115

000

<210> SEQ ID NO 1116

<400> SEQUENCE: 1116

000

<210> SEQ ID NO 1117

<400> SEQUENCE: 1117

000

<210> SEQ ID NO 1118

<400> SEQUENCE: 1118

000

<210> SEQ ID NO 1119

<400> SEQUENCE: 1119

000

<210> SEQ ID NO 1120

<400> SEQUENCE: 1120

000

<210> SEQ ID NO 1121

<400> SEQUENCE: 1121

000

<210> SEQ ID NO 1122

<400> SEQUENCE: 1122

000

<210> SEQ ID NO 1123

<400> SEQUENCE: 1123

000

<210> SEQ ID NO 1124

<400> SEQUENCE: 1124

000

<210> SEQ ID NO 1125

<400> SEQUENCE: 1125

000

<210> SEQ ID NO 1126

<400> SEQUENCE: 1126

000

<210> SEQ ID NO 1127

<400> SEQUENCE: 1127

000

<210> SEQ ID NO 1128

```
<400> SEQUENCE: 1128
000

<210> SEQ ID NO 1129
<400> SEQUENCE: 1129
000

<210> SEQ ID NO 1130
<400> SEQUENCE: 1130
000

<210> SEQ ID NO 1131
<400> SEQUENCE: 1131
000

<210> SEQ ID NO 1132
<400> SEQUENCE: 1132
000

<210> SEQ ID NO 1133
<400> SEQUENCE: 1133
000

<210> SEQ ID NO 1134
<400> SEQUENCE: 1134
000

<210> SEQ ID NO 1135
<400> SEQUENCE: 1135
000

<210> SEQ ID NO 1136
<400> SEQUENCE: 1136
000

<210> SEQ ID NO 1137
<400> SEQUENCE: 1137
000

<210> SEQ ID NO 1138
<400> SEQUENCE: 1138
000

<210> SEQ ID NO 1139
<400> SEQUENCE: 1139
```

000

<210> SEQ ID NO 1140

<400> SEQUENCE: 1140

000

<210> SEQ ID NO 1141

<400> SEQUENCE: 1141

000

<210> SEQ ID NO 1142

<400> SEQUENCE: 1142

000

<210> SEQ ID NO 1143

<400> SEQUENCE: 1143

000

<210> SEQ ID NO 1144

<400> SEQUENCE: 1144

000

<210> SEQ ID NO 1145

<400> SEQUENCE: 1145

000

<210> SEQ ID NO 1146

<400> SEQUENCE: 1146

000

<210> SEQ ID NO 1147

<400> SEQUENCE: 1147

000

<210> SEQ ID NO 1148

<400> SEQUENCE: 1148

000

<210> SEQ ID NO 1149

<400> SEQUENCE: 1149

000

<210> SEQ ID NO 1150

<400> SEQUENCE: 1150

000

<210> SEQ ID NO 1151

<400> SEQUENCE: 1151

000

<210> SEQ ID NO 1152

<400> SEQUENCE: 1152

000

<210> SEQ ID NO 1153

<400> SEQUENCE: 1153

000

<210> SEQ ID NO 1154

<400> SEQUENCE: 1154

000

<210> SEQ ID NO 1155

<400> SEQUENCE: 1155

000

<210> SEQ ID NO 1156

<400> SEQUENCE: 1156

000

<210> SEQ ID NO 1157

<400> SEQUENCE: 1157

000

<210> SEQ ID NO 1158

<400> SEQUENCE: 1158

000

<210> SEQ ID NO 1159

<400> SEQUENCE: 1159

000

<210> SEQ ID NO 1160

<400> SEQUENCE: 1160

000

<210> SEQ ID NO 1161

<400> SEQUENCE: 1161

000

<210> SEQ ID NO 1162

<400> SEQUENCE: 1162

000

<210> SEQ ID NO 1163

<400> SEQUENCE: 1163

000

<210> SEQ ID NO 1164

<400> SEQUENCE: 1164

000

<210> SEQ ID NO 1165

<400> SEQUENCE: 1165

000

<210> SEQ ID NO 1166

<400> SEQUENCE: 1166

000

<210> SEQ ID NO 1167

<400> SEQUENCE: 1167

000

<210> SEQ ID NO 1168

<400> SEQUENCE: 1168

000

<210> SEQ ID NO 1169

<400> SEQUENCE: 1169

000

<210> SEQ ID NO 1170

<400> SEQUENCE: 1170

000

<210> SEQ ID NO 1171

<400> SEQUENCE: 1171

000

<210> SEQ ID NO 1172

<400> SEQUENCE: 1172

000

<210> SEQ ID NO 1173

<400> SEQUENCE: 1173

000

<210> SEQ ID NO 1174

<400> SEQUENCE: 1174

000

<210> SEQ ID NO 1175

<400> SEQUENCE: 1175

000

<210> SEQ ID NO 1176

<400> SEQUENCE: 1176

000

<210> SEQ ID NO 1177

<400> SEQUENCE: 1177

000

<210> SEQ ID NO 1178

<400> SEQUENCE: 1178

000

<210> SEQ ID NO 1179

<400> SEQUENCE: 1179

000

<210> SEQ ID NO 1180

<400> SEQUENCE: 1180

000

<210> SEQ ID NO 1181

<400> SEQUENCE: 1181

000

<210> SEQ ID NO 1182

<400> SEQUENCE: 1182

000

<210> SEQ ID NO 1183

<400> SEQUENCE: 1183

000

<210> SEQ ID NO 1184

<400> SEQUENCE: 1184

000

<210> SEQ ID NO 1185
<400> SEQUENCE: 1185
000

<210> SEQ ID NO 1186
<400> SEQUENCE: 1186
000

<210> SEQ ID NO 1187
<400> SEQUENCE: 1187
000

<210> SEQ ID NO 1188
<400> SEQUENCE: 1188
000

<210> SEQ ID NO 1189
<400> SEQUENCE: 1189
000

<210> SEQ ID NO 1190
<400> SEQUENCE: 1190
000

<210> SEQ ID NO 1191
<400> SEQUENCE: 1191
000

<210> SEQ ID NO 1192
<400> SEQUENCE: 1192
000

<210> SEQ ID NO 1193
<400> SEQUENCE: 1193
000

<210> SEQ ID NO 1194
<400> SEQUENCE: 1194
000

<210> SEQ ID NO 1195
<400> SEQUENCE: 1195
000

```
<210> SEQ ID NO 1196
<400> SEQUENCE: 1196
000

<210> SEQ ID NO 1197
<400> SEQUENCE: 1197
000

<210> SEQ ID NO 1198
<400> SEQUENCE: 1198
000

<210> SEQ ID NO 1199
<400> SEQUENCE: 1199
000

<210> SEQ ID NO 1200
<400> SEQUENCE: 1200
000

<210> SEQ ID NO 1201
<400> SEQUENCE: 1201
000

<210> SEQ ID NO 1202
<400> SEQUENCE: 1202
000

<210> SEQ ID NO 1203
<400> SEQUENCE: 1203
000

<210> SEQ ID NO 1204
<400> SEQUENCE: 1204
000

<210> SEQ ID NO 1205
<400> SEQUENCE: 1205
000

<210> SEQ ID NO 1206
<400> SEQUENCE: 1206
000

<210> SEQ ID NO 1207
```

```
<400> SEQUENCE: 1207

000

<210> SEQ ID NO 1208

<400> SEQUENCE: 1208

000

<210> SEQ ID NO 1209

<400> SEQUENCE: 1209

000

<210> SEQ ID NO 1210

<400> SEQUENCE: 1210

000

<210> SEQ ID NO 1211

<400> SEQUENCE: 1211

000

<210> SEQ ID NO 1212

<400> SEQUENCE: 1212

000

<210> SEQ ID NO 1213

<400> SEQUENCE: 1213

000

<210> SEQ ID NO 1214

<400> SEQUENCE: 1214

000

<210> SEQ ID NO 1215

<400> SEQUENCE: 1215

000

<210> SEQ ID NO 1216

<400> SEQUENCE: 1216

000

<210> SEQ ID NO 1217

<400> SEQUENCE: 1217

000

<210> SEQ ID NO 1218

<400> SEQUENCE: 1218
```

000

<210> SEQ ID NO 1219

<400> SEQUENCE: 1219

000

<210> SEQ ID NO 1220

<400> SEQUENCE: 1220

000

<210> SEQ ID NO 1221

<400> SEQUENCE: 1221

000

<210> SEQ ID NO 1222

<400> SEQUENCE: 1222

000

<210> SEQ ID NO 1223

<400> SEQUENCE: 1223

000

<210> SEQ ID NO 1224

<400> SEQUENCE: 1224

000

<210> SEQ ID NO 1225

<400> SEQUENCE: 1225

000

<210> SEQ ID NO 1226

<400> SEQUENCE: 1226

000

<210> SEQ ID NO 1227

<400> SEQUENCE: 1227

000

<210> SEQ ID NO 1228

<400> SEQUENCE: 1228

000

<210> SEQ ID NO 1229

<400> SEQUENCE: 1229

000

<210> SEQ ID NO 1230

<400> SEQUENCE: 1230

000

<210> SEQ ID NO 1231

<400> SEQUENCE: 1231

000

<210> SEQ ID NO 1232

<400> SEQUENCE: 1232

000

<210> SEQ ID NO 1233

<400> SEQUENCE: 1233

000

<210> SEQ ID NO 1234

<400> SEQUENCE: 1234

000

<210> SEQ ID NO 1235

<400> SEQUENCE: 1235

000

<210> SEQ ID NO 1236

<400> SEQUENCE: 1236

000

<210> SEQ ID NO 1237

<400> SEQUENCE: 1237

000

<210> SEQ ID NO 1238

<400> SEQUENCE: 1238

000

<210> SEQ ID NO 1239

<400> SEQUENCE: 1239

000

<210> SEQ ID NO 1240

<400> SEQUENCE: 1240

000

<210> SEQ ID NO 1241

<400> SEQUENCE: 1241

000

<210> SEQ ID NO 1242

<400> SEQUENCE: 1242

000

<210> SEQ ID NO 1243

<400> SEQUENCE: 1243

000

<210> SEQ ID NO 1244

<400> SEQUENCE: 1244

000

<210> SEQ ID NO 1245

<400> SEQUENCE: 1245

000

<210> SEQ ID NO 1246

<400> SEQUENCE: 1246

000

<210> SEQ ID NO 1247

<400> SEQUENCE: 1247

000

<210> SEQ ID NO 1248

<400> SEQUENCE: 1248

000

<210> SEQ ID NO 1249

<400> SEQUENCE: 1249

000

<210> SEQ ID NO 1250

<400> SEQUENCE: 1250

000

<210> SEQ ID NO 1251

<400> SEQUENCE: 1251

000

<210> SEQ ID NO 1252

<400> SEQUENCE: 1252

000

<210> SEQ ID NO 1253

<400> SEQUENCE: 1253

000

<210> SEQ ID NO 1254

<400> SEQUENCE: 1254

000

<210> SEQ ID NO 1255

<400> SEQUENCE: 1255

000

<210> SEQ ID NO 1256

<400> SEQUENCE: 1256

000

<210> SEQ ID NO 1257

<400> SEQUENCE: 1257

000

<210> SEQ ID NO 1258

<400> SEQUENCE: 1258

000

<210> SEQ ID NO 1259

<400> SEQUENCE: 1259

000

<210> SEQ ID NO 1260

<400> SEQUENCE: 1260

000

<210> SEQ ID NO 1261

<400> SEQUENCE: 1261

000

<210> SEQ ID NO 1262

<400> SEQUENCE: 1262

000

<210> SEQ ID NO 1263

<400> SEQUENCE: 1263

000

<210> SEQ ID NO 1264
<400> SEQUENCE: 1264
000

<210> SEQ ID NO 1265
<400> SEQUENCE: 1265
000

<210> SEQ ID NO 1266
<400> SEQUENCE: 1266
000

<210> SEQ ID NO 1267
<400> SEQUENCE: 1267
000

<210> SEQ ID NO 1268
<400> SEQUENCE: 1268
000

<210> SEQ ID NO 1269
<400> SEQUENCE: 1269
000

<210> SEQ ID NO 1270
<400> SEQUENCE: 1270
000

<210> SEQ ID NO 1271
<400> SEQUENCE: 1271
000

<210> SEQ ID NO 1272
<400> SEQUENCE: 1272
000

<210> SEQ ID NO 1273
<400> SEQUENCE: 1273
000

<210> SEQ ID NO 1274
<400> SEQUENCE: 1274
000

<210> SEQ ID NO 1275
<400> SEQUENCE: 1275
000

<210> SEQ ID NO 1276
<400> SEQUENCE: 1276
000

<210> SEQ ID NO 1277
<400> SEQUENCE: 1277
000

<210> SEQ ID NO 1278
<400> SEQUENCE: 1278
000

<210> SEQ ID NO 1279
<400> SEQUENCE: 1279
000

<210> SEQ ID NO 1280
<400> SEQUENCE: 1280
000

<210> SEQ ID NO 1281
<400> SEQUENCE: 1281
000

<210> SEQ ID NO 1282
<400> SEQUENCE: 1282
000

<210> SEQ ID NO 1283
<400> SEQUENCE: 1283
000

<210> SEQ ID NO 1284
<400> SEQUENCE: 1284
000

<210> SEQ ID NO 1285
<400> SEQUENCE: 1285
000

<210> SEQ ID NO 1286

<400> SEQUENCE: 1286

000

<210> SEQ ID NO 1287

<400> SEQUENCE: 1287

000

<210> SEQ ID NO 1288

<400> SEQUENCE: 1288

000

<210> SEQ ID NO 1289

<400> SEQUENCE: 1289

000

<210> SEQ ID NO 1290

<400> SEQUENCE: 1290

000

<210> SEQ ID NO 1291

<400> SEQUENCE: 1291

000

<210> SEQ ID NO 1292

<400> SEQUENCE: 1292

000

<210> SEQ ID NO 1293

<400> SEQUENCE: 1293

000

<210> SEQ ID NO 1294

<400> SEQUENCE: 1294

000

<210> SEQ ID NO 1295

<400> SEQUENCE: 1295

000

<210> SEQ ID NO 1296

<400> SEQUENCE: 1296

000

<210> SEQ ID NO 1297

<400> SEQUENCE: 1297

000

<210> SEQ ID NO 1298

<400> SEQUENCE: 1298

000

<210> SEQ ID NO 1299

<400> SEQUENCE: 1299

000

<210> SEQ ID NO 1300

<400> SEQUENCE: 1300

000

<210> SEQ ID NO 1301

<400> SEQUENCE: 1301

000

<210> SEQ ID NO 1302

<400> SEQUENCE: 1302

000

<210> SEQ ID NO 1303

<400> SEQUENCE: 1303

000

<210> SEQ ID NO 1304

<400> SEQUENCE: 1304

000

<210> SEQ ID NO 1305

<400> SEQUENCE: 1305

000

<210> SEQ ID NO 1306

<400> SEQUENCE: 1306

000

<210> SEQ ID NO 1307

<400> SEQUENCE: 1307

000

<210> SEQ ID NO 1308

<400> SEQUENCE: 1308

000

<210> SEQ ID NO 1309

<400> SEQUENCE: 1309

000

<210> SEQ ID NO 1310

<400> SEQUENCE: 1310

000

<210> SEQ ID NO 1311

<400> SEQUENCE: 1311

000

<210> SEQ ID NO 1312

<400> SEQUENCE: 1312

000

<210> SEQ ID NO 1313

<400> SEQUENCE: 1313

000

<210> SEQ ID NO 1314

<400> SEQUENCE: 1314

000

<210> SEQ ID NO 1315

<400> SEQUENCE: 1315

000

<210> SEQ ID NO 1316

<400> SEQUENCE: 1316

000

<210> SEQ ID NO 1317

<400> SEQUENCE: 1317

000

<210> SEQ ID NO 1318

<400> SEQUENCE: 1318

000

<210> SEQ ID NO 1319

<400> SEQUENCE: 1319

000

<210> SEQ ID NO 1320

<400> SEQUENCE: 1320

000

<210> SEQ ID NO 1321

<400> SEQUENCE: 1321

000

<210> SEQ ID NO 1322

<400> SEQUENCE: 1322

000

<210> SEQ ID NO 1323

<400> SEQUENCE: 1323

000

<210> SEQ ID NO 1324

<400> SEQUENCE: 1324

000

<210> SEQ ID NO 1325

<400> SEQUENCE: 1325

000

<210> SEQ ID NO 1326

<400> SEQUENCE: 1326

000

<210> SEQ ID NO 1327

<400> SEQUENCE: 1327

000

<210> SEQ ID NO 1328

<400> SEQUENCE: 1328

000

<210> SEQ ID NO 1329

<400> SEQUENCE: 1329

000

<210> SEQ ID NO 1330

<400> SEQUENCE: 1330

000

<210> SEQ ID NO 1331

<400> SEQUENCE: 1331

000

<210> SEQ ID NO 1332

<400> SEQUENCE: 1332

000

<210> SEQ ID NO 1333

<400> SEQUENCE: 1333

000

<210> SEQ ID NO 1334

<400> SEQUENCE: 1334

000

<210> SEQ ID NO 1335

<400> SEQUENCE: 1335

000

<210> SEQ ID NO 1336

<400> SEQUENCE: 1336

000

<210> SEQ ID NO 1337

<400> SEQUENCE: 1337

000

<210> SEQ ID NO 1338

<400> SEQUENCE: 1338

000

<210> SEQ ID NO 1339

<400> SEQUENCE: 1339

000

<210> SEQ ID NO 1340

<400> SEQUENCE: 1340

000

<210> SEQ ID NO 1341

<400> SEQUENCE: 1341

000

<210> SEQ ID NO 1342

<400> SEQUENCE: 1342

000

<210> SEQ ID NO 1343

<400> SEQUENCE: 1343

000

<210> SEQ ID NO 1344

<400> SEQUENCE: 1344

000

<210> SEQ ID NO 1345

<400> SEQUENCE: 1345

000

<210> SEQ ID NO 1346

<400> SEQUENCE: 1346

000

<210> SEQ ID NO 1347

<400> SEQUENCE: 1347

000

<210> SEQ ID NO 1348

<400> SEQUENCE: 1348

000

<210> SEQ ID NO 1349

<400> SEQUENCE: 1349

000

<210> SEQ ID NO 1350

<400> SEQUENCE: 1350

000

<210> SEQ ID NO 1351

<400> SEQUENCE: 1351

000

<210> SEQ ID NO 1352

<400> SEQUENCE: 1352

000

<210> SEQ ID NO 1353

<400> SEQUENCE: 1353

000

<210> SEQ ID NO 1354

<400> SEQUENCE: 1354

000

<210> SEQ ID NO 1355

<400> SEQUENCE: 1355

000

<210> SEQ ID NO 1356

<400> SEQUENCE: 1356

000

<210> SEQ ID NO 1357

<400> SEQUENCE: 1357

000

<210> SEQ ID NO 1358

<400> SEQUENCE: 1358

000

<210> SEQ ID NO 1359

<400> SEQUENCE: 1359

000

<210> SEQ ID NO 1360

<400> SEQUENCE: 1360

000

<210> SEQ ID NO 1361

<400> SEQUENCE: 1361

000

<210> SEQ ID NO 1362

<400> SEQUENCE: 1362

000

<210> SEQ ID NO 1363

<400> SEQUENCE: 1363

000

<210> SEQ ID NO 1364

<400> SEQUENCE: 1364

000

<210> SEQ ID NO 1365

```
<400> SEQUENCE: 1365

000

<210> SEQ ID NO 1366

<400> SEQUENCE: 1366

000

<210> SEQ ID NO 1367

<400> SEQUENCE: 1367

000

<210> SEQ ID NO 1368

<400> SEQUENCE: 1368

000

<210> SEQ ID NO 1369

<400> SEQUENCE: 1369

000

<210> SEQ ID NO 1370

<400> SEQUENCE: 1370

000

<210> SEQ ID NO 1371

<400> SEQUENCE: 1371

000

<210> SEQ ID NO 1372

<400> SEQUENCE: 1372

000

<210> SEQ ID NO 1373

<400> SEQUENCE: 1373

000

<210> SEQ ID NO 1374
<211> LENGTH: 8
<212> TYPE: PRT
<213> ORGANISM: Artificial Sequence
<220> FEATURE:
<223> OTHER INFORMATION: AAV peptide sequence

<400> SEQUENCE: 1374

Leu Ser Lys Thr Gln Thr Leu Lys
1               5

<210> SEQ ID NO 1375
<211> LENGTH: 10
<212> TYPE: PRT
<213> ORGANISM: Artificial Sequence
```

<220> FEATURE:
<223> OTHER INFORMATION: AAV peptide sequence

<400> SEQUENCE: 1375

Leu Ser Lys Thr Asp Pro Gln Thr Leu Lys
1               5                   10

<210> SEQ ID NO 1376

<400> SEQUENCE: 1376

000

<210> SEQ ID NO 1377

<400> SEQUENCE: 1377

000

<210> SEQ ID NO 1378

<400> SEQUENCE: 1378

000

<210> SEQ ID NO 1379

<400> SEQUENCE: 1379

000

<210> SEQ ID NO 1380

<400> SEQUENCE: 1380

000

<210> SEQ ID NO 1381

<400> SEQUENCE: 1381

000

<210> SEQ ID NO 1382

<400> SEQUENCE: 1382

000

<210> SEQ ID NO 1383

<400> SEQUENCE: 1383

000

<210> SEQ ID NO 1384

<400> SEQUENCE: 1384

000

<210> SEQ ID NO 1385

<400> SEQUENCE: 1385

000

<210> SEQ ID NO 1386

<400> SEQUENCE: 1386

000

<210> SEQ ID NO 1387

<400> SEQUENCE: 1387

000

<210> SEQ ID NO 1388

<400> SEQUENCE: 1388

000

<210> SEQ ID NO 1389

<400> SEQUENCE: 1389

000

<210> SEQ ID NO 1390

<400> SEQUENCE: 1390

000

<210> SEQ ID NO 1391

<400> SEQUENCE: 1391

000

<210> SEQ ID NO 1392

<400> SEQUENCE: 1392

000

<210> SEQ ID NO 1393

<400> SEQUENCE: 1393

000

<210> SEQ ID NO 1394

<400> SEQUENCE: 1394

000

<210> SEQ ID NO 1395

<400> SEQUENCE: 1395

000

<210> SEQ ID NO 1396

<400> SEQUENCE: 1396

000

<210> SEQ ID NO 1397

<400> SEQUENCE: 1397

000

<210> SEQ ID NO 1398

<400> SEQUENCE: 1398

000

<210> SEQ ID NO 1399

<400> SEQUENCE: 1399

000

<210> SEQ ID NO 1400

<400> SEQUENCE: 1400

000

<210> SEQ ID NO 1401

<400> SEQUENCE: 1401

000

<210> SEQ ID NO 1402

<400> SEQUENCE: 1402

000

<210> SEQ ID NO 1403

<400> SEQUENCE: 1403

000

<210> SEQ ID NO 1404

<400> SEQUENCE: 1404

000

<210> SEQ ID NO 1405

<400> SEQUENCE: 1405

000

<210> SEQ ID NO 1406

<400> SEQUENCE: 1406

000

<210> SEQ ID NO 1407

<400> SEQUENCE: 1407

000

<210> SEQ ID NO 1408

<400> SEQUENCE: 1408

000

<210> SEQ ID NO 1409

<400> SEQUENCE: 1409

000

<210> SEQ ID NO 1410

<400> SEQUENCE: 1410

000

<210> SEQ ID NO 1411

<400> SEQUENCE: 1411

000

<210> SEQ ID NO 1412

<400> SEQUENCE: 1412

000

<210> SEQ ID NO 1413

<400> SEQUENCE: 1413

000

<210> SEQ ID NO 1414

<400> SEQUENCE: 1414

000

<210> SEQ ID NO 1415

<400> SEQUENCE: 1415

000

<210> SEQ ID NO 1416

<400> SEQUENCE: 1416

000

<210> SEQ ID NO 1417

<400> SEQUENCE: 1417

000

<210> SEQ ID NO 1418

<400> SEQUENCE: 1418

000

<210> SEQ ID NO 1419

<400> SEQUENCE: 1419

000

<210> SEQ ID NO 1420

<400> SEQUENCE: 1420

000

<210> SEQ ID NO 1421

<400> SEQUENCE: 1421

000

<210> SEQ ID NO 1422

<400> SEQUENCE: 1422

000

<210> SEQ ID NO 1423

<400> SEQUENCE: 1423

000

<210> SEQ ID NO 1424

<400> SEQUENCE: 1424

000

<210> SEQ ID NO 1425

<400> SEQUENCE: 1425

000

<210> SEQ ID NO 1426

<400> SEQUENCE: 1426

000

<210> SEQ ID NO 1427

<400> SEQUENCE: 1427

000

<210> SEQ ID NO 1428

<400> SEQUENCE: 1428

000

<210> SEQ ID NO 1429

<400> SEQUENCE: 1429

000

<210> SEQ ID NO 1430

<400> SEQUENCE: 1430

000

<210> SEQ ID NO 1431

<400> SEQUENCE: 1431

000

<210> SEQ ID NO 1432

<400> SEQUENCE: 1432

000

<210> SEQ ID NO 1433

<400> SEQUENCE: 1433

000

<210> SEQ ID NO 1434

<400> SEQUENCE: 1434

000

<210> SEQ ID NO 1435

<400> SEQUENCE: 1435

000

<210> SEQ ID NO 1436

<400> SEQUENCE: 1436

000

<210> SEQ ID NO 1437

<400> SEQUENCE: 1437

000

<210> SEQ ID NO 1438

<400> SEQUENCE: 1438

000

<210> SEQ ID NO 1439

<400> SEQUENCE: 1439

000

<210> SEQ ID NO 1440

<400> SEQUENCE: 1440

000

<210> SEQ ID NO 1441

<400> SEQUENCE: 1441

000

<210> SEQ ID NO 1442

<400> SEQUENCE: 1442

000

<210> SEQ ID NO 1443

<400> SEQUENCE: 1443

000

<210> SEQ ID NO 1444

<400> SEQUENCE: 1444

000

<210> SEQ ID NO 1445

<400> SEQUENCE: 1445

000

<210> SEQ ID NO 1446

<400> SEQUENCE: 1446

000

<210> SEQ ID NO 1447

<400> SEQUENCE: 1447

000

<210> SEQ ID NO 1448

<400> SEQUENCE: 1448

000

<210> SEQ ID NO 1449

<400> SEQUENCE: 1449

000

<210> SEQ ID NO 1450

<400> SEQUENCE: 1450

000

<210> SEQ ID NO 1451

<400> SEQUENCE: 1451

000

<210> SEQ ID NO 1452

<400> SEQUENCE: 1452

000

<210> SEQ ID NO 1453

<400> SEQUENCE: 1453

000

<210> SEQ ID NO 1454

<400> SEQUENCE: 1454

000

<210> SEQ ID NO 1455

<400> SEQUENCE: 1455

000

<210> SEQ ID NO 1456

<400> SEQUENCE: 1456

000

<210> SEQ ID NO 1457

<400> SEQUENCE: 1457

000

<210> SEQ ID NO 1458

<400> SEQUENCE: 1458

000

<210> SEQ ID NO 1459

<400> SEQUENCE: 1459

000

<210> SEQ ID NO 1460

<400> SEQUENCE: 1460

000

<210> SEQ ID NO 1461

<400> SEQUENCE: 1461

000

<210> SEQ ID NO 1462

<400> SEQUENCE: 1462

000

<210> SEQ ID NO 1463

<400> SEQUENCE: 1463

000

<210> SEQ ID NO 1464

<400> SEQUENCE: 1464

000

-continued

<210> SEQ ID NO 1465

<400> SEQUENCE: 1465

000

<210> SEQ ID NO 1466

<400> SEQUENCE: 1466

000

<210> SEQ ID NO 1467

<400> SEQUENCE: 1467

000

<210> SEQ ID NO 1468

<400> SEQUENCE: 1468

000

<210> SEQ ID NO 1469

<400> SEQUENCE: 1469

000

<210> SEQ ID NO 1470

<400> SEQUENCE: 1470

000

<210> SEQ ID NO 1471

<400> SEQUENCE: 1471

000

<210> SEQ ID NO 1472

<400> SEQUENCE: 1472

000

<210> SEQ ID NO 1473

<400> SEQUENCE: 1473

000

<210> SEQ ID NO 1474

<400> SEQUENCE: 1474

000

<210> SEQ ID NO 1475

<400> SEQUENCE: 1475

000

<210> SEQ ID NO 1476

<400> SEQUENCE: 1476

000

<210> SEQ ID NO 1477

<400> SEQUENCE: 1477

000

<210> SEQ ID NO 1478

<400> SEQUENCE: 1478

000

<210> SEQ ID NO 1479

<400> SEQUENCE: 1479

000

<210> SEQ ID NO 1480

<400> SEQUENCE: 1480

000

<210> SEQ ID NO 1481

<400> SEQUENCE: 1481

000

<210> SEQ ID NO 1482

<400> SEQUENCE: 1482

000

<210> SEQ ID NO 1483

<400> SEQUENCE: 1483

000

<210> SEQ ID NO 1484

<400> SEQUENCE: 1484

000

<210> SEQ ID NO 1485

<400> SEQUENCE: 1485

000

<210> SEQ ID NO 1486

<400> SEQUENCE: 1486

000

<210> SEQ ID NO 1487

<400> SEQUENCE: 1487

000

<210> SEQ ID NO 1488

<400> SEQUENCE: 1488

000

<210> SEQ ID NO 1489

<400> SEQUENCE: 1489

000

<210> SEQ ID NO 1490

<400> SEQUENCE: 1490

000

<210> SEQ ID NO 1491

<400> SEQUENCE: 1491

000

<210> SEQ ID NO 1492

<400> SEQUENCE: 1492

000

<210> SEQ ID NO 1493

<400> SEQUENCE: 1493

000

<210> SEQ ID NO 1494

<400> SEQUENCE: 1494

000

<210> SEQ ID NO 1495

<400> SEQUENCE: 1495

000

<210> SEQ ID NO 1496

<400> SEQUENCE: 1496

000

<210> SEQ ID NO 1497

<400> SEQUENCE: 1497

000

<210> SEQ ID NO 1498

<400> SEQUENCE: 1498

000

<210> SEQ ID NO 1499

<400> SEQUENCE: 1499

000

<210> SEQ ID NO 1500

<400> SEQUENCE: 1500

000

<210> SEQ ID NO 1501

<400> SEQUENCE: 1501

000

<210> SEQ ID NO 1502

<400> SEQUENCE: 1502

000

<210> SEQ ID NO 1503

<400> SEQUENCE: 1503

000

<210> SEQ ID NO 1504

<400> SEQUENCE: 1504

000

<210> SEQ ID NO 1505

<400> SEQUENCE: 1505

000

<210> SEQ ID NO 1506

<400> SEQUENCE: 1506

000

<210> SEQ ID NO 1507

<400> SEQUENCE: 1507

000

<210> SEQ ID NO 1508

<400> SEQUENCE: 1508

000

<210> SEQ ID NO 1509

<400> SEQUENCE: 1509

000

<210> SEQ ID NO 1510

<400> SEQUENCE: 1510

000

<210> SEQ ID NO 1511

<400> SEQUENCE: 1511

000

<210> SEQ ID NO 1512

<400> SEQUENCE: 1512

000

<210> SEQ ID NO 1513

<400> SEQUENCE: 1513

000

<210> SEQ ID NO 1514

<400> SEQUENCE: 1514

000

<210> SEQ ID NO 1515

<400> SEQUENCE: 1515

000

<210> SEQ ID NO 1516

<400> SEQUENCE: 1516

000

<210> SEQ ID NO 1517

<400> SEQUENCE: 1517

000

<210> SEQ ID NO 1518

<400> SEQUENCE: 1518

000

<210> SEQ ID NO 1519

<400> SEQUENCE: 1519

000

<210> SEQ ID NO 1520

<400> SEQUENCE: 1520

000

<210> SEQ ID NO 1521

<400> SEQUENCE: 1521

000

<210> SEQ ID NO 1522

<400> SEQUENCE: 1522

000

<210> SEQ ID NO 1523

<400> SEQUENCE: 1523

000

<210> SEQ ID NO 1524

<400> SEQUENCE: 1524

000

<210> SEQ ID NO 1525

<400> SEQUENCE: 1525

000

<210> SEQ ID NO 1526

<400> SEQUENCE: 1526

000

<210> SEQ ID NO 1527

<400> SEQUENCE: 1527

000

<210> SEQ ID NO 1528

<400> SEQUENCE: 1528

000

<210> SEQ ID NO 1529

<400> SEQUENCE: 1529

000

<210> SEQ ID NO 1530

<400> SEQUENCE: 1530

000

<210> SEQ ID NO 1531

<400> SEQUENCE: 1531

000

<210> SEQ ID NO 1532

<400> SEQUENCE: 1532

000

<210> SEQ ID NO 1533

<400> SEQUENCE: 1533

000

<210> SEQ ID NO 1534

<400> SEQUENCE: 1534

000

<210> SEQ ID NO 1535

<400> SEQUENCE: 1535

000

<210> SEQ ID NO 1536

<400> SEQUENCE: 1536

000

<210> SEQ ID NO 1537

<400> SEQUENCE: 1537

000

<210> SEQ ID NO 1538

<400> SEQUENCE: 1538

000

<210> SEQ ID NO 1539

<400> SEQUENCE: 1539

000

<210> SEQ ID NO 1540

<400> SEQUENCE: 1540

000

<210> SEQ ID NO 1541

<400> SEQUENCE: 1541

000

<210> SEQ ID NO 1542

<400> SEQUENCE: 1542

000

<210> SEQ ID NO 1543

<400> SEQUENCE: 1543

000

<210> SEQ ID NO 1544

<400> SEQUENCE: 1544

000

<210> SEQ ID NO 1545

<400> SEQUENCE: 1545

000

<210> SEQ ID NO 1546

<400> SEQUENCE: 1546

000

<210> SEQ ID NO 1547

<400> SEQUENCE: 1547

000

<210> SEQ ID NO 1548

<400> SEQUENCE: 1548

000

<210> SEQ ID NO 1549

<400> SEQUENCE: 1549

000

<210> SEQ ID NO 1550

<400> SEQUENCE: 1550

000

<210> SEQ ID NO 1551

<400> SEQUENCE: 1551

000

<210> SEQ ID NO 1552

<400> SEQUENCE: 1552

000

<210> SEQ ID NO 1553

<400> SEQUENCE: 1553

000

<210> SEQ ID NO 1554

<400> SEQUENCE: 1554

000

<210> SEQ ID NO 1555

<400> SEQUENCE: 1555

000

<210> SEQ ID NO 1556

<400> SEQUENCE: 1556

000

<210> SEQ ID NO 1557

<400> SEQUENCE: 1557

000

<210> SEQ ID NO 1558

<400> SEQUENCE: 1558

000

<210> SEQ ID NO 1559

<400> SEQUENCE: 1559

000

<210> SEQ ID NO 1560

<400> SEQUENCE: 1560

000

<210> SEQ ID NO 1561

<400> SEQUENCE: 1561

000

<210> SEQ ID NO 1562

<400> SEQUENCE: 1562

000

<210> SEQ ID NO 1563

<400> SEQUENCE: 1563

000

<210> SEQ ID NO 1564

<400> SEQUENCE: 1564

000

<210> SEQ ID NO 1565

<400> SEQUENCE: 1565

000

<210> SEQ ID NO 1566

<400> SEQUENCE: 1566

000

<210> SEQ ID NO 1567

<400> SEQUENCE: 1567

000

<210> SEQ ID NO 1568

<400> SEQUENCE: 1568

000

<210> SEQ ID NO 1569

<400> SEQUENCE: 1569

000

<210> SEQ ID NO 1570

<400> SEQUENCE: 1570

000

<210> SEQ ID NO 1571

<400> SEQUENCE: 1571

000

<210> SEQ ID NO 1572

<400> SEQUENCE: 1572

000

<210> SEQ ID NO 1573

<400> SEQUENCE: 1573

000

<210> SEQ ID NO 1574

<400> SEQUENCE: 1574

000

<210> SEQ ID NO 1575

<400> SEQUENCE: 1575

000

<210> SEQ ID NO 1576

<400> SEQUENCE: 1576

000

<210> SEQ ID NO 1577

<400> SEQUENCE: 1577

000

<210> SEQ ID NO 1578

<400> SEQUENCE: 1578

000

<210> SEQ ID NO 1579

<400> SEQUENCE: 1579

000

<210> SEQ ID NO 1580

<400> SEQUENCE: 1580

000

<210> SEQ ID NO 1581

<400> SEQUENCE: 1581

000

<210> SEQ ID NO 1582

<400> SEQUENCE: 1582

000

<210> SEQ ID NO 1583

<400> SEQUENCE: 1583

000

<210> SEQ ID NO 1584

<400> SEQUENCE: 1584

000

<210> SEQ ID NO 1585

<400> SEQUENCE: 1585

000

<210> SEQ ID NO 1586

<400> SEQUENCE: 1586

000

<210> SEQ ID NO 1587

<400> SEQUENCE: 1587

000

<210> SEQ ID NO 1588

<400> SEQUENCE: 1588

000

<210> SEQ ID NO 1589

<400> SEQUENCE: 1589

000

<210> SEQ ID NO 1590

<400> SEQUENCE: 1590

000

<210> SEQ ID NO 1591

<400> SEQUENCE: 1591

000

<210> SEQ ID NO 1592

<400> SEQUENCE: 1592

000

<210> SEQ ID NO 1593

<400> SEQUENCE: 1593

000

<210> SEQ ID NO 1594

<400> SEQUENCE: 1594

000

<210> SEQ ID NO 1595

<400> SEQUENCE: 1595

000

<210> SEQ ID NO 1596

<400> SEQUENCE: 1596

000

<210> SEQ ID NO 1597

<400> SEQUENCE: 1597

000

<210> SEQ ID NO 1598

<400> SEQUENCE: 1598

000

<210> SEQ ID NO 1599

<400> SEQUENCE: 1599

000

<210> SEQ ID NO 1600

<400> SEQUENCE: 1600

000

<210> SEQ ID NO 1601

<400> SEQUENCE: 1601

000

<210> SEQ ID NO 1602

<400> SEQUENCE: 1602

000

<210> SEQ ID NO 1603

<400> SEQUENCE: 1603

000

<210> SEQ ID NO 1604

<400> SEQUENCE: 1604

000

<210> SEQ ID NO 1605

<400> SEQUENCE: 1605

000

<210> SEQ ID NO 1606

<400> SEQUENCE: 1606

000

<210> SEQ ID NO 1607

<400> SEQUENCE: 1607

000

<210> SEQ ID NO 1608

<400> SEQUENCE: 1608

000

<210> SEQ ID NO 1609

<400> SEQUENCE: 1609

000

<210> SEQ ID NO 1610

<400> SEQUENCE: 1610

000

<210> SEQ ID NO 1611

<400> SEQUENCE: 1611

000

```
<210> SEQ ID NO 1612
<400> SEQUENCE: 1612
000

<210> SEQ ID NO 1613
<400> SEQUENCE: 1613
000

<210> SEQ ID NO 1614
<400> SEQUENCE: 1614
000

<210> SEQ ID NO 1615
<400> SEQUENCE: 1615
000

<210> SEQ ID NO 1616
<400> SEQUENCE: 1616
000

<210> SEQ ID NO 1617
<400> SEQUENCE: 1617
000

<210> SEQ ID NO 1618
<400> SEQUENCE: 1618
000

<210> SEQ ID NO 1619
<400> SEQUENCE: 1619
000

<210> SEQ ID NO 1620
<400> SEQUENCE: 1620
000

<210> SEQ ID NO 1621
<400> SEQUENCE: 1621
000

<210> SEQ ID NO 1622
<400> SEQUENCE: 1622
000
```

```
<210> SEQ ID NO 1623
<400> SEQUENCE: 1623
000

<210> SEQ ID NO 1624
<400> SEQUENCE: 1624
000

<210> SEQ ID NO 1625
<400> SEQUENCE: 1625
000

<210> SEQ ID NO 1626
<400> SEQUENCE: 1626
000

<210> SEQ ID NO 1627
<400> SEQUENCE: 1627
000

<210> SEQ ID NO 1628
<400> SEQUENCE: 1628
000

<210> SEQ ID NO 1629
<400> SEQUENCE: 1629
000

<210> SEQ ID NO 1630
<400> SEQUENCE: 1630
000

<210> SEQ ID NO 1631
<400> SEQUENCE: 1631
000

<210> SEQ ID NO 1632
<400> SEQUENCE: 1632
000

<210> SEQ ID NO 1633
<400> SEQUENCE: 1633
000

<210> SEQ ID NO 1634
```

<210> SEQ ID NO 1634

<400> SEQUENCE: 1634

000

<210> SEQ ID NO 1635

<400> SEQUENCE: 1635

000

<210> SEQ ID NO 1636

<400> SEQUENCE: 1636

000

<210> SEQ ID NO 1637

<400> SEQUENCE: 1637

000

<210> SEQ ID NO 1638

<400> SEQUENCE: 1638

000

<210> SEQ ID NO 1639

<400> SEQUENCE: 1639

000

<210> SEQ ID NO 1640

<400> SEQUENCE: 1640

000

<210> SEQ ID NO 1641

<400> SEQUENCE: 1641

000

<210> SEQ ID NO 1642

<400> SEQUENCE: 1642

000

<210> SEQ ID NO 1643

<400> SEQUENCE: 1643

000

<210> SEQ ID NO 1644

<400> SEQUENCE: 1644

000

<210> SEQ ID NO 1645

<400> SEQUENCE: 1645

000

<210> SEQ ID NO 1646

<400> SEQUENCE: 1646

000

<210> SEQ ID NO 1647

<400> SEQUENCE: 1647

000

<210> SEQ ID NO 1648

<400> SEQUENCE: 1648

000

<210> SEQ ID NO 1649

<400> SEQUENCE: 1649

000

<210> SEQ ID NO 1650

<400> SEQUENCE: 1650

000

<210> SEQ ID NO 1651

<400> SEQUENCE: 1651

000

<210> SEQ ID NO 1652

<400> SEQUENCE: 1652

000

<210> SEQ ID NO 1653

<400> SEQUENCE: 1653

000

<210> SEQ ID NO 1654

<400> SEQUENCE: 1654

000

<210> SEQ ID NO 1655

<400> SEQUENCE: 1655

000

<210> SEQ ID NO 1656

<400> SEQUENCE: 1656

000

<210> SEQ ID NO 1657

<400> SEQUENCE: 1657

000

<210> SEQ ID NO 1658

<400> SEQUENCE: 1658

000

<210> SEQ ID NO 1659

<400> SEQUENCE: 1659

000

<210> SEQ ID NO 1660

<400> SEQUENCE: 1660

000

<210> SEQ ID NO 1661

<400> SEQUENCE: 1661

000

<210> SEQ ID NO 1662

<400> SEQUENCE: 1662

000

<210> SEQ ID NO 1663

<400> SEQUENCE: 1663

000

<210> SEQ ID NO 1664

<400> SEQUENCE: 1664

000

<210> SEQ ID NO 1665

<400> SEQUENCE: 1665

000

<210> SEQ ID NO 1666

<400> SEQUENCE: 1666

000

<210> SEQ ID NO 1667

<400> SEQUENCE: 1667

000

<210> SEQ ID NO 1668

<400> SEQUENCE: 1668

000

<210> SEQ ID NO 1669

<400> SEQUENCE: 1669

000

<210> SEQ ID NO 1670

<400> SEQUENCE: 1670

000

<210> SEQ ID NO 1671

<400> SEQUENCE: 1671

000

<210> SEQ ID NO 1672

<400> SEQUENCE: 1672

000

<210> SEQ ID NO 1673

<400> SEQUENCE: 1673

000

<210> SEQ ID NO 1674

<400> SEQUENCE: 1674

000

<210> SEQ ID NO 1675

<400> SEQUENCE: 1675

000

<210> SEQ ID NO 1676

<400> SEQUENCE: 1676

000

<210> SEQ ID NO 1677

<400> SEQUENCE: 1677

000

<210> SEQ ID NO 1678

<400> SEQUENCE: 1678

000

<210> SEQ ID NO 1679

<400> SEQUENCE: 1679

000

<210> SEQ ID NO 1680

<400> SEQUENCE: 1680

000

<210> SEQ ID NO 1681

<400> SEQUENCE: 1681

000

<210> SEQ ID NO 1682

<400> SEQUENCE: 1682

000

<210> SEQ ID NO 1683

<400> SEQUENCE: 1683

000

<210> SEQ ID NO 1684

<400> SEQUENCE: 1684

000

<210> SEQ ID NO 1685

<400> SEQUENCE: 1685

000

<210> SEQ ID NO 1686

<400> SEQUENCE: 1686

000

<210> SEQ ID NO 1687

<400> SEQUENCE: 1687

000

<210> SEQ ID NO 1688

<400> SEQUENCE: 1688

000

<210> SEQ ID NO 1689

<400> SEQUENCE: 1689

000

<210> SEQ ID NO 1690

<400> SEQUENCE: 1690

000

<210> SEQ ID NO 1691

<400> SEQUENCE: 1691

000

<210> SEQ ID NO 1692

<400> SEQUENCE: 1692

000

<210> SEQ ID NO 1693

<400> SEQUENCE: 1693

000

<210> SEQ ID NO 1694

<400> SEQUENCE: 1694

000

<210> SEQ ID NO 1695

<400> SEQUENCE: 1695

000

<210> SEQ ID NO 1696

<400> SEQUENCE: 1696

000

<210> SEQ ID NO 1697

<400> SEQUENCE: 1697

000

<210> SEQ ID NO 1698

<400> SEQUENCE: 1698

000

<210> SEQ ID NO 1699

<400> SEQUENCE: 1699

000

<210> SEQ ID NO 1700

<400> SEQUENCE: 1700

000

<210> SEQ ID NO 1701

<400> SEQUENCE: 1701

000

<210> SEQ ID NO 1702

<400> SEQUENCE: 1702

000

<210> SEQ ID NO 1703

<400> SEQUENCE: 1703

000

<210> SEQ ID NO 1704

<400> SEQUENCE: 1704

000

<210> SEQ ID NO 1705

<400> SEQUENCE: 1705

000

<210> SEQ ID NO 1706

<400> SEQUENCE: 1706

000

<210> SEQ ID NO 1707

<400> SEQUENCE: 1707

000

<210> SEQ ID NO 1708

<400> SEQUENCE: 1708

000

<210> SEQ ID NO 1709

<400> SEQUENCE: 1709

000

<210> SEQ ID NO 1710

<400> SEQUENCE: 1710

000

<210> SEQ ID NO 1711

<400> SEQUENCE: 1711

000

<210> SEQ ID NO 1712

<400> SEQUENCE: 1712

000

<210> SEQ ID NO 1713

<400> SEQUENCE: 1713

000

<210> SEQ ID NO 1714

<400> SEQUENCE: 1714

000

<210> SEQ ID NO 1715

<400> SEQUENCE: 1715

000

<210> SEQ ID NO 1716

<400> SEQUENCE: 1716

000

<210> SEQ ID NO 1717

<400> SEQUENCE: 1717

000

<210> SEQ ID NO 1718

<400> SEQUENCE: 1718

000

<210> SEQ ID NO 1719

<400> SEQUENCE: 1719

000

<210> SEQ ID NO 1720

<400> SEQUENCE: 1720

000

<210> SEQ ID NO 1721

<400> SEQUENCE: 1721

000

<210> SEQ ID NO 1722

<400> SEQUENCE: 1722

000

<210> SEQ ID NO 1723

<400> SEQUENCE: 1723

000

<210> SEQ ID NO 1724

<400> SEQUENCE: 1724

000

<210> SEQ ID NO 1725

<400> SEQUENCE: 1725

000

<210> SEQ ID NO 1726

<400> SEQUENCE: 1726

000

<210> SEQ ID NO 1727

<400> SEQUENCE: 1727

000

<210> SEQ ID NO 1728

<400> SEQUENCE: 1728

000

<210> SEQ ID NO 1729

<400> SEQUENCE: 1729

000

<210> SEQ ID NO 1730

<400> SEQUENCE: 1730

000

<210> SEQ ID NO 1731

<400> SEQUENCE: 1731

000

<210> SEQ ID NO 1732

<400> SEQUENCE: 1732

000

<210> SEQ ID NO 1733

<400> SEQUENCE: 1733

000

<210> SEQ ID NO 1734

<400> SEQUENCE: 1734

000

<210> SEQ ID NO 1735

<400> SEQUENCE: 1735

000

<210> SEQ ID NO 1736

<400> SEQUENCE: 1736

000

<210> SEQ ID NO 1737

<400> SEQUENCE: 1737

000

<210> SEQ ID NO 1738

<400> SEQUENCE: 1738

000

<210> SEQ ID NO 1739

<400> SEQUENCE: 1739

000

<210> SEQ ID NO 1740

<400> SEQUENCE: 1740

000

<210> SEQ ID NO 1741

<400> SEQUENCE: 1741

000

<210> SEQ ID NO 1742

<400> SEQUENCE: 1742

000

<210> SEQ ID NO 1743

<400> SEQUENCE: 1743

000

<210> SEQ ID NO 1744

<400> SEQUENCE: 1744

000

<210> SEQ ID NO 1745

<400> SEQUENCE: 1745

000

<210> SEQ ID NO 1746

<400> SEQUENCE: 1746

000

<210> SEQ ID NO 1747

<400> SEQUENCE: 1747

000

<210> SEQ ID NO 1748

<400> SEQUENCE: 1748

000

<210> SEQ ID NO 1749

<400> SEQUENCE: 1749

000

<210> SEQ ID NO 1750

<400> SEQUENCE: 1750

000

<210> SEQ ID NO 1751

<400> SEQUENCE: 1751

000

<210> SEQ ID NO 1752

<400> SEQUENCE: 1752

000

<210> SEQ ID NO 1753

<400> SEQUENCE: 1753

000

<210> SEQ ID NO 1754

<400> SEQUENCE: 1754

000

<210> SEQ ID NO 1755

<400> SEQUENCE: 1755

000

<210> SEQ ID NO 1756

<400> SEQUENCE: 1756

000

<210> SEQ ID NO 1757

<400> SEQUENCE: 1757

000

<210> SEQ ID NO 1758

<400> SEQUENCE: 1758

000

<210> SEQ ID NO 1759

<400> SEQUENCE: 1759

000

<210> SEQ ID NO 1760

<400> SEQUENCE: 1760

000

<210> SEQ ID NO 1761

<400> SEQUENCE: 1761

000

<210> SEQ ID NO 1762

<400> SEQUENCE: 1762

000

<210> SEQ ID NO 1763

<400> SEQUENCE: 1763

000

<210> SEQ ID NO 1764

<400> SEQUENCE: 1764

000

<210> SEQ ID NO 1765

<400> SEQUENCE: 1765

000

<210> SEQ ID NO 1766

<400> SEQUENCE: 1766

000

<210> SEQ ID NO 1767

<400> SEQUENCE: 1767

000

<210> SEQ ID NO 1768

<400> SEQUENCE: 1768

000

<210> SEQ ID NO 1769

<400> SEQUENCE: 1769

000

<210> SEQ ID NO 1770

<400> SEQUENCE: 1770

000

<210> SEQ ID NO 1771

<400> SEQUENCE: 1771

000

<210> SEQ ID NO 1772

<400> SEQUENCE: 1772

000

<210> SEQ ID NO 1773

<400> SEQUENCE: 1773

000

<210> SEQ ID NO 1774

<400> SEQUENCE: 1774

000

<210> SEQ ID NO 1775

<400> SEQUENCE: 1775

000

<210> SEQ ID NO 1776

<400> SEQUENCE: 1776

000

<210> SEQ ID NO 1777

<400> SEQUENCE: 1777

000

<210> SEQ ID NO 1778

<400> SEQUENCE: 1778

000

<210> SEQ ID NO 1779

<400> SEQUENCE: 1779

000

<210> SEQ ID NO 1780

<400> SEQUENCE: 1780

000

<210> SEQ ID NO 1781

<400> SEQUENCE: 1781

000

<210> SEQ ID NO 1782

<400> SEQUENCE: 1782

000

<210> SEQ ID NO 1783

<400> SEQUENCE: 1783

000

<210> SEQ ID NO 1784

<400> SEQUENCE: 1784

000

<210> SEQ ID NO 1785

<400> SEQUENCE: 1785

000

<210> SEQ ID NO 1786

<400> SEQUENCE: 1786

000

<210> SEQ ID NO 1787

<400> SEQUENCE: 1787

000

<210> SEQ ID NO 1788

<400> SEQUENCE: 1788

000

<210> SEQ ID NO 1789

<400> SEQUENCE: 1789

000

<210> SEQ ID NO 1790

<400> SEQUENCE: 1790

000

<210> SEQ ID NO 1791

<400> SEQUENCE: 1791

000

<210> SEQ ID NO 1792

```
<400> SEQUENCE: 1792
000

<210> SEQ ID NO 1793
<400> SEQUENCE: 1793
000

<210> SEQ ID NO 1794
<400> SEQUENCE: 1794
000

<210> SEQ ID NO 1795
<400> SEQUENCE: 1795
000

<210> SEQ ID NO 1796
<400> SEQUENCE: 1796
000

<210> SEQ ID NO 1797
<400> SEQUENCE: 1797
000

<210> SEQ ID NO 1798
<400> SEQUENCE: 1798
000

<210> SEQ ID NO 1799
<400> SEQUENCE: 1799
000

<210> SEQ ID NO 1800
<400> SEQUENCE: 1800
000

<210> SEQ ID NO 1801
<400> SEQUENCE: 1801
000

<210> SEQ ID NO 1802
<400> SEQUENCE: 1802
000

<210> SEQ ID NO 1803
<400> SEQUENCE: 1803
```

000

<210> SEQ ID NO 1804

<400> SEQUENCE: 1804

000

<210> SEQ ID NO 1805

<400> SEQUENCE: 1805

000

<210> SEQ ID NO 1806

<400> SEQUENCE: 1806

000

<210> SEQ ID NO 1807

<400> SEQUENCE: 1807

000

<210> SEQ ID NO 1808

<400> SEQUENCE: 1808

000

<210> SEQ ID NO 1809

<400> SEQUENCE: 1809

000

<210> SEQ ID NO 1810

<400> SEQUENCE: 1810

000

<210> SEQ ID NO 1811

<400> SEQUENCE: 1811

000

<210> SEQ ID NO 1812

<400> SEQUENCE: 1812

000

<210> SEQ ID NO 1813

<400> SEQUENCE: 1813

000

<210> SEQ ID NO 1814

<400> SEQUENCE: 1814

000

<210> SEQ ID NO 1815

<400> SEQUENCE: 1815

000

<210> SEQ ID NO 1816

<400> SEQUENCE: 1816

000

<210> SEQ ID NO 1817

<400> SEQUENCE: 1817

000

<210> SEQ ID NO 1818

<400> SEQUENCE: 1818

000

<210> SEQ ID NO 1819

<400> SEQUENCE: 1819

000

<210> SEQ ID NO 1820

<400> SEQUENCE: 1820

000

<210> SEQ ID NO 1821

<400> SEQUENCE: 1821

000

<210> SEQ ID NO 1822

<400> SEQUENCE: 1822

000

<210> SEQ ID NO 1823

<400> SEQUENCE: 1823

000

<210> SEQ ID NO 1824

<400> SEQUENCE: 1824

000

<210> SEQ ID NO 1825

<400> SEQUENCE: 1825

000

<210> SEQ ID NO 1826

```
<400> SEQUENCE: 1826
000

<210> SEQ ID NO 1827
<400> SEQUENCE: 1827
000

<210> SEQ ID NO 1828
<400> SEQUENCE: 1828
000

<210> SEQ ID NO 1829
<400> SEQUENCE: 1829
000

<210> SEQ ID NO 1830
<400> SEQUENCE: 1830
000

<210> SEQ ID NO 1831
<400> SEQUENCE: 1831
000

<210> SEQ ID NO 1832
<400> SEQUENCE: 1832
000

<210> SEQ ID NO 1833
<400> SEQUENCE: 1833
000

<210> SEQ ID NO 1834
<400> SEQUENCE: 1834
000

<210> SEQ ID NO 1835
<400> SEQUENCE: 1835
000

<210> SEQ ID NO 1836
<400> SEQUENCE: 1836
000

<210> SEQ ID NO 1837
<400> SEQUENCE: 1837
```

000

<210> SEQ ID NO 1838
<400> SEQUENCE: 1838
000

<210> SEQ ID NO 1839
<400> SEQUENCE: 1839
000

<210> SEQ ID NO 1840
<400> SEQUENCE: 1840
000

<210> SEQ ID NO 1841
<400> SEQUENCE: 1841
000

<210> SEQ ID NO 1842
<400> SEQUENCE: 1842
000

<210> SEQ ID NO 1843
<400> SEQUENCE: 1843
000

<210> SEQ ID NO 1844
<400> SEQUENCE: 1844
000

<210> SEQ ID NO 1845
<400> SEQUENCE: 1845
000

<210> SEQ ID NO 1846
<400> SEQUENCE: 1846
000

<210> SEQ ID NO 1847
<400> SEQUENCE: 1847
000

<210> SEQ ID NO 1848
<400> SEQUENCE: 1848
000

<210> SEQ ID NO 1849

<400> SEQUENCE: 1849

000

<210> SEQ ID NO 1850

<400> SEQUENCE: 1850

000

<210> SEQ ID NO 1851

<400> SEQUENCE: 1851

000

<210> SEQ ID NO 1852

<400> SEQUENCE: 1852

000

<210> SEQ ID NO 1853

<400> SEQUENCE: 1853

000

<210> SEQ ID NO 1854

<400> SEQUENCE: 1854

000

<210> SEQ ID NO 1855

<400> SEQUENCE: 1855

000

<210> SEQ ID NO 1856

<400> SEQUENCE: 1856

000

<210> SEQ ID NO 1857

<400> SEQUENCE: 1857

000

<210> SEQ ID NO 1858

<400> SEQUENCE: 1858

000

<210> SEQ ID NO 1859

<400> SEQUENCE: 1859

000

<210> SEQ ID NO 1860

<400> SEQUENCE: 1860

000

<210> SEQ ID NO 1861

<400> SEQUENCE: 1861

000

<210> SEQ ID NO 1862

<400> SEQUENCE: 1862

000

<210> SEQ ID NO 1863

<400> SEQUENCE: 1863

000

<210> SEQ ID NO 1864

<400> SEQUENCE: 1864

000

<210> SEQ ID NO 1865

<400> SEQUENCE: 1865

000

<210> SEQ ID NO 1866

<400> SEQUENCE: 1866

000

<210> SEQ ID NO 1867

<400> SEQUENCE: 1867

000

<210> SEQ ID NO 1868

<400> SEQUENCE: 1868

000

<210> SEQ ID NO 1869

<400> SEQUENCE: 1869

000

<210> SEQ ID NO 1870

<400> SEQUENCE: 1870

000

<210> SEQ ID NO 1871

<400> SEQUENCE: 1871

000

<210> SEQ ID NO 1872

<400> SEQUENCE: 1872

000

<210> SEQ ID NO 1873

<400> SEQUENCE: 1873

000

<210> SEQ ID NO 1874

<400> SEQUENCE: 1874

000

<210> SEQ ID NO 1875

<400> SEQUENCE: 1875

000

<210> SEQ ID NO 1876

<400> SEQUENCE: 1876

000

<210> SEQ ID NO 1877

<400> SEQUENCE: 1877

000

<210> SEQ ID NO 1878

<400> SEQUENCE: 1878

000

<210> SEQ ID NO 1879

<400> SEQUENCE: 1879

000

<210> SEQ ID NO 1880

<400> SEQUENCE: 1880

000

<210> SEQ ID NO 1881

<400> SEQUENCE: 1881

000

<210> SEQ ID NO 1882

<400> SEQUENCE: 1882

000

<210> SEQ ID NO 1883

<400> SEQUENCE: 1883

000

<210> SEQ ID NO 1884

<400> SEQUENCE: 1884

000

<210> SEQ ID NO 1885

<400> SEQUENCE: 1885

000

<210> SEQ ID NO 1886

<400> SEQUENCE: 1886

000

<210> SEQ ID NO 1887

<400> SEQUENCE: 1887

000

<210> SEQ ID NO 1888

<400> SEQUENCE: 1888

000

<210> SEQ ID NO 1889

<400> SEQUENCE: 1889

000

<210> SEQ ID NO 1890

<400> SEQUENCE: 1890

000

<210> SEQ ID NO 1891

<400> SEQUENCE: 1891

000

<210> SEQ ID NO 1892

<400> SEQUENCE: 1892

000

<210> SEQ ID NO 1893

<400> SEQUENCE: 1893

000

<210> SEQ ID NO 1894

<400> SEQUENCE: 1894

000

<210> SEQ ID NO 1895

<400> SEQUENCE: 1895

000

<210> SEQ ID NO 1896

<400> SEQUENCE: 1896

000

<210> SEQ ID NO 1897

<400> SEQUENCE: 1897

000

<210> SEQ ID NO 1898

<400> SEQUENCE: 1898

000

<210> SEQ ID NO 1899

<400> SEQUENCE: 1899

000

<210> SEQ ID NO 1900

<400> SEQUENCE: 1900

000

<210> SEQ ID NO 1901

<400> SEQUENCE: 1901

000

<210> SEQ ID NO 1902

<400> SEQUENCE: 1902

000

<210> SEQ ID NO 1903

<400> SEQUENCE: 1903

000

<210> SEQ ID NO 1904

<400> SEQUENCE: 1904

000

<210> SEQ ID NO 1905

<400> SEQUENCE: 1905

000

<210> SEQ ID NO 1906

<400> SEQUENCE: 1906

000

<210> SEQ ID NO 1907

<400> SEQUENCE: 1907

000

<210> SEQ ID NO 1908

<400> SEQUENCE: 1908

000

<210> SEQ ID NO 1909

<400> SEQUENCE: 1909

000

<210> SEQ ID NO 1910

<400> SEQUENCE: 1910

000

<210> SEQ ID NO 1911

<400> SEQUENCE: 1911

000

<210> SEQ ID NO 1912

<400> SEQUENCE: 1912

000

<210> SEQ ID NO 1913

<400> SEQUENCE: 1913

000

<210> SEQ ID NO 1914

<400> SEQUENCE: 1914

000

<210> SEQ ID NO 1915

<400> SEQUENCE: 1915

000

<210> SEQ ID NO 1916

<400> SEQUENCE: 1916

000

<210> SEQ ID NO 1917

<400> SEQUENCE: 1917

000

<210> SEQ ID NO 1918

<400> SEQUENCE: 1918

000

<210> SEQ ID NO 1919

<400> SEQUENCE: 1919

000

<210> SEQ ID NO 1920

<400> SEQUENCE: 1920

000

<210> SEQ ID NO 1921

<400> SEQUENCE: 1921

000

<210> SEQ ID NO 1922

<400> SEQUENCE: 1922

000

<210> SEQ ID NO 1923

<400> SEQUENCE: 1923

000

<210> SEQ ID NO 1924

<400> SEQUENCE: 1924

000

<210> SEQ ID NO 1925

<400> SEQUENCE: 1925

000

<210> SEQ ID NO 1926

<400> SEQUENCE: 1926

000

<210> SEQ ID NO 1927

<400> SEQUENCE: 1927

000

```
<210> SEQ ID NO 1928
<400> SEQUENCE: 1928
000

<210> SEQ ID NO 1929
<400> SEQUENCE: 1929
000

<210> SEQ ID NO 1930
<400> SEQUENCE: 1930
000

<210> SEQ ID NO 1931
<400> SEQUENCE: 1931
000

<210> SEQ ID NO 1932
<400> SEQUENCE: 1932
000

<210> SEQ ID NO 1933
<400> SEQUENCE: 1933
000

<210> SEQ ID NO 1934
<400> SEQUENCE: 1934
000

<210> SEQ ID NO 1935
<400> SEQUENCE: 1935
000

<210> SEQ ID NO 1936
<400> SEQUENCE: 1936
000

<210> SEQ ID NO 1937
<400> SEQUENCE: 1937
000

<210> SEQ ID NO 1938
<400> SEQUENCE: 1938
000
```

-continued

<210> SEQ ID NO 1939
<400> SEQUENCE: 1939
000

<210> SEQ ID NO 1940
<400> SEQUENCE: 1940
000

<210> SEQ ID NO 1941
<400> SEQUENCE: 1941
000

<210> SEQ ID NO 1942
<400> SEQUENCE: 1942
000

<210> SEQ ID NO 1943
<400> SEQUENCE: 1943
000

<210> SEQ ID NO 1944
<400> SEQUENCE: 1944
000

<210> SEQ ID NO 1945
<400> SEQUENCE: 1945
000

<210> SEQ ID NO 1946
<400> SEQUENCE: 1946
000

<210> SEQ ID NO 1947
<400> SEQUENCE: 1947
000

<210> SEQ ID NO 1948
<400> SEQUENCE: 1948
000

<210> SEQ ID NO 1949
<400> SEQUENCE: 1949
000

<210> SEQ ID NO 1950

<400> SEQUENCE: 1950

000

<210> SEQ ID NO 1951

<400> SEQUENCE: 1951

000

<210> SEQ ID NO 1952

<400> SEQUENCE: 1952

000

<210> SEQ ID NO 1953

<400> SEQUENCE: 1953

000

<210> SEQ ID NO 1954

<400> SEQUENCE: 1954

000

<210> SEQ ID NO 1955

<400> SEQUENCE: 1955

000

<210> SEQ ID NO 1956

<400> SEQUENCE: 1956

000

<210> SEQ ID NO 1957

<400> SEQUENCE: 1957

000

<210> SEQ ID NO 1958

<400> SEQUENCE: 1958

000

<210> SEQ ID NO 1959

<400> SEQUENCE: 1959

000

<210> SEQ ID NO 1960

<400> SEQUENCE: 1960

000

<210> SEQ ID NO 1961

<400> SEQUENCE: 1961

000

<210> SEQ ID NO 1962
<400> SEQUENCE: 1962
000

<210> SEQ ID NO 1963
<400> SEQUENCE: 1963
000

<210> SEQ ID NO 1964
<400> SEQUENCE: 1964
000

<210> SEQ ID NO 1965
<400> SEQUENCE: 1965
000

<210> SEQ ID NO 1966
<400> SEQUENCE: 1966
000

<210> SEQ ID NO 1967
<400> SEQUENCE: 1967
000

<210> SEQ ID NO 1968
<400> SEQUENCE: 1968
000

<210> SEQ ID NO 1969
<400> SEQUENCE: 1969
000

<210> SEQ ID NO 1970
<400> SEQUENCE: 1970
000

<210> SEQ ID NO 1971
<400> SEQUENCE: 1971
000

<210> SEQ ID NO 1972
<400> SEQUENCE: 1972
000

<210> SEQ ID NO 1973
<400> SEQUENCE: 1973
000

<210> SEQ ID NO 1974
<400> SEQUENCE: 1974
000

<210> SEQ ID NO 1975
<400> SEQUENCE: 1975
000

<210> SEQ ID NO 1976
<400> SEQUENCE: 1976
000

<210> SEQ ID NO 1977
<400> SEQUENCE: 1977
000

<210> SEQ ID NO 1978
<400> SEQUENCE: 1978
000

<210> SEQ ID NO 1979
<400> SEQUENCE: 1979
000

<210> SEQ ID NO 1980
<400> SEQUENCE: 1980
000

<210> SEQ ID NO 1981
<400> SEQUENCE: 1981
000

<210> SEQ ID NO 1982
<400> SEQUENCE: 1982
000

<210> SEQ ID NO 1983
<400> SEQUENCE: 1983
000

<210> SEQ ID NO 1984

<400> SEQUENCE: 1984

000

<210> SEQ ID NO 1985

<400> SEQUENCE: 1985

000

<210> SEQ ID NO 1986

<400> SEQUENCE: 1986

000

<210> SEQ ID NO 1987

<400> SEQUENCE: 1987

000

<210> SEQ ID NO 1988

<400> SEQUENCE: 1988

000

<210> SEQ ID NO 1989

<400> SEQUENCE: 1989

000

<210> SEQ ID NO 1990

<400> SEQUENCE: 1990

000

<210> SEQ ID NO 1991

<400> SEQUENCE: 1991

000

<210> SEQ ID NO 1992

<400> SEQUENCE: 1992

000

<210> SEQ ID NO 1993

<400> SEQUENCE: 1993

000

<210> SEQ ID NO 1994

<400> SEQUENCE: 1994

000

<210> SEQ ID NO 1995

<400> SEQUENCE: 1995

000

<210> SEQ ID NO 1996

<400> SEQUENCE: 1996

000

<210> SEQ ID NO 1997

<400> SEQUENCE: 1997

000

<210> SEQ ID NO 1998

<400> SEQUENCE: 1998

000

<210> SEQ ID NO 1999

<400> SEQUENCE: 1999

000

<210> SEQ ID NO 2000

<400> SEQUENCE: 2000

000

<210> SEQ ID NO 2001

<400> SEQUENCE: 2001

000

<210> SEQ ID NO 2002

<400> SEQUENCE: 2002

000

<210> SEQ ID NO 2003

<400> SEQUENCE: 2003

000

<210> SEQ ID NO 2004

<400> SEQUENCE: 2004

000

<210> SEQ ID NO 2005

<400> SEQUENCE: 2005

000

<210> SEQ ID NO 2006

<400> SEQUENCE: 2006

000

<210> SEQ ID NO 2007

<400> SEQUENCE: 2007

000

<210> SEQ ID NO 2008

<400> SEQUENCE: 2008

000

<210> SEQ ID NO 2009

<400> SEQUENCE: 2009

000

<210> SEQ ID NO 2010

<400> SEQUENCE: 2010

000

<210> SEQ ID NO 2011

<400> SEQUENCE: 2011

000

<210> SEQ ID NO 2012

<400> SEQUENCE: 2012

000

<210> SEQ ID NO 2013

<400> SEQUENCE: 2013

000

<210> SEQ ID NO 2014

<400> SEQUENCE: 2014

000

<210> SEQ ID NO 2015

<400> SEQUENCE: 2015

000

<210> SEQ ID NO 2016

<400> SEQUENCE: 2016

000

<210> SEQ ID NO 2017

<400> SEQUENCE: 2017

000

-continued

<210> SEQ ID NO 2018

<400> SEQUENCE: 2018

000

<210> SEQ ID NO 2019

<400> SEQUENCE: 2019

000

<210> SEQ ID NO 2020

<400> SEQUENCE: 2020

000

<210> SEQ ID NO 2021

<400> SEQUENCE: 2021

000

<210> SEQ ID NO 2022

<400> SEQUENCE: 2022

000

<210> SEQ ID NO 2023

<400> SEQUENCE: 2023

000

<210> SEQ ID NO 2024

<400> SEQUENCE: 2024

000

<210> SEQ ID NO 2025

<400> SEQUENCE: 2025

000

<210> SEQ ID NO 2026

<400> SEQUENCE: 2026

000

<210> SEQ ID NO 2027

<400> SEQUENCE: 2027

000

<210> SEQ ID NO 2028

<400> SEQUENCE: 2028

000

<210> SEQ ID NO 2029

<400> SEQUENCE: 2029

000

<210> SEQ ID NO 2030

<400> SEQUENCE: 2030

000

<210> SEQ ID NO 2031

<400> SEQUENCE: 2031

000

<210> SEQ ID NO 2032

<400> SEQUENCE: 2032

000

<210> SEQ ID NO 2033

<400> SEQUENCE: 2033

000

<210> SEQ ID NO 2034

<400> SEQUENCE: 2034

000

<210> SEQ ID NO 2035

<400> SEQUENCE: 2035

000

<210> SEQ ID NO 2036

<400> SEQUENCE: 2036

000

<210> SEQ ID NO 2037

<400> SEQUENCE: 2037

000

<210> SEQ ID NO 2038

<400> SEQUENCE: 2038

000

<210> SEQ ID NO 2039

<400> SEQUENCE: 2039

000

<210> SEQ ID NO 2040

<400> SEQUENCE: 2040

000

<210> SEQ ID NO 2041

<400> SEQUENCE: 2041

000

<210> SEQ ID NO 2042

<400> SEQUENCE: 2042

000

<210> SEQ ID NO 2043

<400> SEQUENCE: 2043

000

<210> SEQ ID NO 2044

<400> SEQUENCE: 2044

000

<210> SEQ ID NO 2045

<400> SEQUENCE: 2045

000

<210> SEQ ID NO 2046

<400> SEQUENCE: 2046

000

<210> SEQ ID NO 2047

<400> SEQUENCE: 2047

000

<210> SEQ ID NO 2048

<400> SEQUENCE: 2048

000

<210> SEQ ID NO 2049

<400> SEQUENCE: 2049

000

<210> SEQ ID NO 2050

<400> SEQUENCE: 2050

000

<210> SEQ ID NO 2051

<400> SEQUENCE: 2051

000

```
<210> SEQ ID NO 2052
<400> SEQUENCE: 2052
000

<210> SEQ ID NO 2053
<400> SEQUENCE: 2053
000

<210> SEQ ID NO 2054
<400> SEQUENCE: 2054
000

<210> SEQ ID NO 2055
<400> SEQUENCE: 2055
000

<210> SEQ ID NO 2056
<400> SEQUENCE: 2056
000

<210> SEQ ID NO 2057
<400> SEQUENCE: 2057
000

<210> SEQ ID NO 2058
<400> SEQUENCE: 2058
000

<210> SEQ ID NO 2059
<400> SEQUENCE: 2059
000

<210> SEQ ID NO 2060
<400> SEQUENCE: 2060
000

<210> SEQ ID NO 2061
<400> SEQUENCE: 2061
000

<210> SEQ ID NO 2062
<400> SEQUENCE: 2062
000

<210> SEQ ID NO 2063
```

<400> SEQUENCE: 2063

000

<210> SEQ ID NO 2064

<400> SEQUENCE: 2064

000

<210> SEQ ID NO 2065

<400> SEQUENCE: 2065

000

<210> SEQ ID NO 2066

<400> SEQUENCE: 2066

000

<210> SEQ ID NO 2067

<400> SEQUENCE: 2067

000

<210> SEQ ID NO 2068

<400> SEQUENCE: 2068

000

<210> SEQ ID NO 2069

<400> SEQUENCE: 2069

000

<210> SEQ ID NO 2070

<400> SEQUENCE: 2070

000

<210> SEQ ID NO 2071

<400> SEQUENCE: 2071

000

<210> SEQ ID NO 2072

<400> SEQUENCE: 2072

000

<210> SEQ ID NO 2073

<400> SEQUENCE: 2073

000

<210> SEQ ID NO 2074

<400> SEQUENCE: 2074

000

<210> SEQ ID NO 2075

<400> SEQUENCE: 2075

000

<210> SEQ ID NO 2076

<400> SEQUENCE: 2076

000

<210> SEQ ID NO 2077

<400> SEQUENCE: 2077

000

<210> SEQ ID NO 2078

<400> SEQUENCE: 2078

000

<210> SEQ ID NO 2079

<400> SEQUENCE: 2079

000

<210> SEQ ID NO 2080

<400> SEQUENCE: 2080

000

<210> SEQ ID NO 2081

<400> SEQUENCE: 2081

000

<210> SEQ ID NO 2082

<400> SEQUENCE: 2082

000

<210> SEQ ID NO 2083

<400> SEQUENCE: 2083

000

<210> SEQ ID NO 2084

<400> SEQUENCE: 2084

000

<210> SEQ ID NO 2085

<400> SEQUENCE: 2085

000

<210> SEQ ID NO 2086

<400> SEQUENCE: 2086

000

<210> SEQ ID NO 2087

<400> SEQUENCE: 2087

000

<210> SEQ ID NO 2088

<400> SEQUENCE: 2088

000

<210> SEQ ID NO 2089

<400> SEQUENCE: 2089

000

<210> SEQ ID NO 2090

<400> SEQUENCE: 2090

000

<210> SEQ ID NO 2091

<400> SEQUENCE: 2091

000

<210> SEQ ID NO 2092

<400> SEQUENCE: 2092

000

<210> SEQ ID NO 2093

<400> SEQUENCE: 2093

000

<210> SEQ ID NO 2094

<400> SEQUENCE: 2094

000

<210> SEQ ID NO 2095

<400> SEQUENCE: 2095

000

<210> SEQ ID NO 2096

<400> SEQUENCE: 2096

000

<210> SEQ ID NO 2097

<400> SEQUENCE: 2097

000

<210> SEQ ID NO 2098

<400> SEQUENCE: 2098

000

<210> SEQ ID NO 2099

<400> SEQUENCE: 2099

000

<210> SEQ ID NO 2100

<400> SEQUENCE: 2100

000

<210> SEQ ID NO 2101

<400> SEQUENCE: 2101

000

<210> SEQ ID NO 2102

<400> SEQUENCE: 2102

000

<210> SEQ ID NO 2103

<400> SEQUENCE: 2103

000

<210> SEQ ID NO 2104

<400> SEQUENCE: 2104

000

<210> SEQ ID NO 2105

<400> SEQUENCE: 2105

000

<210> SEQ ID NO 2106

<400> SEQUENCE: 2106

000

<210> SEQ ID NO 2107

<400> SEQUENCE: 2107

000

<210> SEQ ID NO 2108

```
<400> SEQUENCE: 2108
000

<210> SEQ ID NO 2109
<400> SEQUENCE: 2109
000

<210> SEQ ID NO 2110
<400> SEQUENCE: 2110
000

<210> SEQ ID NO 2111
<400> SEQUENCE: 2111
000

<210> SEQ ID NO 2112
<400> SEQUENCE: 2112
000

<210> SEQ ID NO 2113
<400> SEQUENCE: 2113
000

<210> SEQ ID NO 2114
<400> SEQUENCE: 2114
000

<210> SEQ ID NO 2115
<400> SEQUENCE: 2115
000

<210> SEQ ID NO 2116
<400> SEQUENCE: 2116
000

<210> SEQ ID NO 2117
<400> SEQUENCE: 2117
000

<210> SEQ ID NO 2118
<400> SEQUENCE: 2118
000

<210> SEQ ID NO 2119
<400> SEQUENCE: 2119
```

000

<210> SEQ ID NO 2120

<400> SEQUENCE: 2120

000

<210> SEQ ID NO 2121

<400> SEQUENCE: 2121

000

<210> SEQ ID NO 2122

<400> SEQUENCE: 2122

000

<210> SEQ ID NO 2123

<400> SEQUENCE: 2123

000

<210> SEQ ID NO 2124

<400> SEQUENCE: 2124

000

<210> SEQ ID NO 2125

<400> SEQUENCE: 2125

000

<210> SEQ ID NO 2126

<400> SEQUENCE: 2126

000

<210> SEQ ID NO 2127

<400> SEQUENCE: 2127

000

<210> SEQ ID NO 2128

<400> SEQUENCE: 2128

000

<210> SEQ ID NO 2129

<400> SEQUENCE: 2129

000

<210> SEQ ID NO 2130

<400> SEQUENCE: 2130

000

<210> SEQ ID NO 2131

<400> SEQUENCE: 2131

000

<210> SEQ ID NO 2132

<400> SEQUENCE: 2132

000

<210> SEQ ID NO 2133

<400> SEQUENCE: 2133

000

<210> SEQ ID NO 2134

<400> SEQUENCE: 2134

000

<210> SEQ ID NO 2135

<400> SEQUENCE: 2135

000

<210> SEQ ID NO 2136

<400> SEQUENCE: 2136

000

<210> SEQ ID NO 2137

<400> SEQUENCE: 2137

000

<210> SEQ ID NO 2138

<400> SEQUENCE: 2138

000

<210> SEQ ID NO 2139

<400> SEQUENCE: 2139

000

<210> SEQ ID NO 2140

<400> SEQUENCE: 2140

000

<210> SEQ ID NO 2141

<400> SEQUENCE: 2141

000

<210> SEQ ID NO 2142

```
<400> SEQUENCE: 2142
000

<210> SEQ ID NO 2143
<400> SEQUENCE: 2143
000

<210> SEQ ID NO 2144
<400> SEQUENCE: 2144
000

<210> SEQ ID NO 2145
<400> SEQUENCE: 2145
000

<210> SEQ ID NO 2146
<400> SEQUENCE: 2146
000

<210> SEQ ID NO 2147
<400> SEQUENCE: 2147
000

<210> SEQ ID NO 2148
<400> SEQUENCE: 2148
000

<210> SEQ ID NO 2149
<400> SEQUENCE: 2149
000

<210> SEQ ID NO 2150
<400> SEQUENCE: 2150
000

<210> SEQ ID NO 2151
<400> SEQUENCE: 2151
000

<210> SEQ ID NO 2152
<400> SEQUENCE: 2152
000

<210> SEQ ID NO 2153
<400> SEQUENCE: 2153
```

000

<210> SEQ ID NO 2154

<400> SEQUENCE: 2154

000

<210> SEQ ID NO 2155

<400> SEQUENCE: 2155

000

<210> SEQ ID NO 2156

<400> SEQUENCE: 2156

000

<210> SEQ ID NO 2157

<400> SEQUENCE: 2157

000

<210> SEQ ID NO 2158

<400> SEQUENCE: 2158

000

<210> SEQ ID NO 2159

<400> SEQUENCE: 2159

000

<210> SEQ ID NO 2160

<400> SEQUENCE: 2160

000

<210> SEQ ID NO 2161

<400> SEQUENCE: 2161

000

<210> SEQ ID NO 2162

<400> SEQUENCE: 2162

000

<210> SEQ ID NO 2163

<400> SEQUENCE: 2163

000

<210> SEQ ID NO 2164

<400> SEQUENCE: 2164

000

<210> SEQ ID NO 2165

<400> SEQUENCE: 2165

000

<210> SEQ ID NO 2166

<400> SEQUENCE: 2166

000

<210> SEQ ID NO 2167

<400> SEQUENCE: 2167

000

<210> SEQ ID NO 2168

<400> SEQUENCE: 2168

000

<210> SEQ ID NO 2169

<400> SEQUENCE: 2169

000

<210> SEQ ID NO 2170

<400> SEQUENCE: 2170

000

<210> SEQ ID NO 2171

<400> SEQUENCE: 2171

000

<210> SEQ ID NO 2172

<400> SEQUENCE: 2172

000

<210> SEQ ID NO 2173

<400> SEQUENCE: 2173

000

<210> SEQ ID NO 2174

<400> SEQUENCE: 2174

000

<210> SEQ ID NO 2175

<400> SEQUENCE: 2175

000

<210> SEQ ID NO 2176

<400> SEQUENCE: 2176

000

<210> SEQ ID NO 2177

<400> SEQUENCE: 2177

000

<210> SEQ ID NO 2178

<400> SEQUENCE: 2178

000

<210> SEQ ID NO 2179

<400> SEQUENCE: 2179

000

<210> SEQ ID NO 2180

<400> SEQUENCE: 2180

000

<210> SEQ ID NO 2181

<400> SEQUENCE: 2181

000

<210> SEQ ID NO 2182

<400> SEQUENCE: 2182

000

<210> SEQ ID NO 2183

<400> SEQUENCE: 2183

000

<210> SEQ ID NO 2184

<400> SEQUENCE: 2184

000

<210> SEQ ID NO 2185

<400> SEQUENCE: 2185

000

<210> SEQ ID NO 2186

<400> SEQUENCE: 2186

000

<210> SEQ ID NO 2187

```
<400> SEQUENCE: 2187

000

<210> SEQ ID NO 2188

<400> SEQUENCE: 2188

000

<210> SEQ ID NO 2189

<400> SEQUENCE: 2189

000

<210> SEQ ID NO 2190

<400> SEQUENCE: 2190

000

<210> SEQ ID NO 2191

<400> SEQUENCE: 2191

000

<210> SEQ ID NO 2192

<400> SEQUENCE: 2192

000

<210> SEQ ID NO 2193

<400> SEQUENCE: 2193

000

<210> SEQ ID NO 2194

<400> SEQUENCE: 2194

000

<210> SEQ ID NO 2195

<400> SEQUENCE: 2195

000

<210> SEQ ID NO 2196

<400> SEQUENCE: 2196

000

<210> SEQ ID NO 2197

<400> SEQUENCE: 2197

000

<210> SEQ ID NO 2198

<400> SEQUENCE: 2198
```

000

<210> SEQ ID NO 2199

<400> SEQUENCE: 2199

000

<210> SEQ ID NO 2200

<400> SEQUENCE: 2200

000

<210> SEQ ID NO 2201

<400> SEQUENCE: 2201

000

<210> SEQ ID NO 2202

<400> SEQUENCE: 2202

000

<210> SEQ ID NO 2203

<400> SEQUENCE: 2203

000

<210> SEQ ID NO 2204

<400> SEQUENCE: 2204

000

<210> SEQ ID NO 2205

<400> SEQUENCE: 2205

000

<210> SEQ ID NO 2206

<400> SEQUENCE: 2206

000

<210> SEQ ID NO 2207

<400> SEQUENCE: 2207

000

<210> SEQ ID NO 2208

<400> SEQUENCE: 2208

000

<210> SEQ ID NO 2209

<400> SEQUENCE: 2209

000

```
<210> SEQ ID NO 2210
<400> SEQUENCE: 2210
000

<210> SEQ ID NO 2211
<400> SEQUENCE: 2211
000

<210> SEQ ID NO 2212
<400> SEQUENCE: 2212
000

<210> SEQ ID NO 2213
<400> SEQUENCE: 2213
000

<210> SEQ ID NO 2214
<400> SEQUENCE: 2214
000

<210> SEQ ID NO 2215
<400> SEQUENCE: 2215
000

<210> SEQ ID NO 2216
<400> SEQUENCE: 2216
000

<210> SEQ ID NO 2217
<400> SEQUENCE: 2217
000

<210> SEQ ID NO 2218
<400> SEQUENCE: 2218
000

<210> SEQ ID NO 2219
<400> SEQUENCE: 2219
000

<210> SEQ ID NO 2220
<400> SEQUENCE: 2220
000

<210> SEQ ID NO 2221
```

```
<400> SEQUENCE: 2221

000

<210> SEQ ID NO 2222

<400> SEQUENCE: 2222

000

<210> SEQ ID NO 2223

<400> SEQUENCE: 2223

000

<210> SEQ ID NO 2224

<400> SEQUENCE: 2224

000

<210> SEQ ID NO 2225

<400> SEQUENCE: 2225

000

<210> SEQ ID NO 2226

<400> SEQUENCE: 2226

000

<210> SEQ ID NO 2227

<400> SEQUENCE: 2227

000

<210> SEQ ID NO 2228

<400> SEQUENCE: 2228

000

<210> SEQ ID NO 2229

<400> SEQUENCE: 2229

000

<210> SEQ ID NO 2230

<400> SEQUENCE: 2230

000

<210> SEQ ID NO 2231

<400> SEQUENCE: 2231

000

<210> SEQ ID NO 2232

<400> SEQUENCE: 2232
```

000

<210> SEQ ID NO 2233

<400> SEQUENCE: 2233

000

<210> SEQ ID NO 2234

<400> SEQUENCE: 2234

000

<210> SEQ ID NO 2235

<400> SEQUENCE: 2235

000

<210> SEQ ID NO 2236

<400> SEQUENCE: 2236

000

<210> SEQ ID NO 2237

<400> SEQUENCE: 2237

000

<210> SEQ ID NO 2238

<400> SEQUENCE: 2238

000

<210> SEQ ID NO 2239

<400> SEQUENCE: 2239

000

<210> SEQ ID NO 2240

<400> SEQUENCE: 2240

000

<210> SEQ ID NO 2241

<400> SEQUENCE: 2241

000

<210> SEQ ID NO 2242

<400> SEQUENCE: 2242

000

<210> SEQ ID NO 2243

<400> SEQUENCE: 2243

000

```
<210> SEQ ID NO 2244
<400> SEQUENCE: 2244
000

<210> SEQ ID NO 2245
<400> SEQUENCE: 2245
000

<210> SEQ ID NO 2246
<400> SEQUENCE: 2246
000

<210> SEQ ID NO 2247
<400> SEQUENCE: 2247
000

<210> SEQ ID NO 2248
<400> SEQUENCE: 2248
000

<210> SEQ ID NO 2249
<400> SEQUENCE: 2249
000

<210> SEQ ID NO 2250
<400> SEQUENCE: 2250
000

<210> SEQ ID NO 2251
<400> SEQUENCE: 2251
000

<210> SEQ ID NO 2252
<400> SEQUENCE: 2252
000

<210> SEQ ID NO 2253
<400> SEQUENCE: 2253
000

<210> SEQ ID NO 2254
<400> SEQUENCE: 2254
000
```

-continued

<210> SEQ ID NO 2255

<400> SEQUENCE: 2255

000

<210> SEQ ID NO 2256

<400> SEQUENCE: 2256

000

<210> SEQ ID NO 2257

<400> SEQUENCE: 2257

000

<210> SEQ ID NO 2258

<400> SEQUENCE: 2258

000

<210> SEQ ID NO 2259

<400> SEQUENCE: 2259

000

<210> SEQ ID NO 2260

<400> SEQUENCE: 2260

000

<210> SEQ ID NO 2261

<400> SEQUENCE: 2261

000

<210> SEQ ID NO 2262

<400> SEQUENCE: 2262

000

<210> SEQ ID NO 2263

<400> SEQUENCE: 2263

000

<210> SEQ ID NO 2264

<400> SEQUENCE: 2264

000

<210> SEQ ID NO 2265

<400> SEQUENCE: 2265

000

<210> SEQ ID NO 2266

<400> SEQUENCE: 2266

000

<210> SEQ ID NO 2267

<400> SEQUENCE: 2267

000

<210> SEQ ID NO 2268

<400> SEQUENCE: 2268

000

<210> SEQ ID NO 2269

<400> SEQUENCE: 2269

000

<210> SEQ ID NO 2270

<400> SEQUENCE: 2270

000

<210> SEQ ID NO 2271

<400> SEQUENCE: 2271

000

<210> SEQ ID NO 2272

<400> SEQUENCE: 2272

000

<210> SEQ ID NO 2273

<400> SEQUENCE: 2273

000

<210> SEQ ID NO 2274

<400> SEQUENCE: 2274

000

<210> SEQ ID NO 2275

<400> SEQUENCE: 2275

000

<210> SEQ ID NO 2276

<400> SEQUENCE: 2276

000

<210> SEQ ID NO 2277

<400> SEQUENCE: 2277

-continued

000

<210> SEQ ID NO 2278

<400> SEQUENCE: 2278

000

<210> SEQ ID NO 2279

<400> SEQUENCE: 2279

000

<210> SEQ ID NO 2280

<400> SEQUENCE: 2280

000

<210> SEQ ID NO 2281

<400> SEQUENCE: 2281

000

<210> SEQ ID NO 2282

<400> SEQUENCE: 2282

000

<210> SEQ ID NO 2283

<400> SEQUENCE: 2283

000

<210> SEQ ID NO 2284

<400> SEQUENCE: 2284

000

<210> SEQ ID NO 2285

<400> SEQUENCE: 2285

000

<210> SEQ ID NO 2286

<400> SEQUENCE: 2286

000

<210> SEQ ID NO 2287

<400> SEQUENCE: 2287

000

<210> SEQ ID NO 2288

<400> SEQUENCE: 2288

000

<210> SEQ ID NO 2289
<400> SEQUENCE: 2289
000

<210> SEQ ID NO 2290
<400> SEQUENCE: 2290
000

<210> SEQ ID NO 2291
<400> SEQUENCE: 2291
000

<210> SEQ ID NO 2292
<400> SEQUENCE: 2292
000

<210> SEQ ID NO 2293
<400> SEQUENCE: 2293
000

<210> SEQ ID NO 2294
<400> SEQUENCE: 2294
000

<210> SEQ ID NO 2295
<400> SEQUENCE: 2295
000

<210> SEQ ID NO 2296
<400> SEQUENCE: 2296
000

<210> SEQ ID NO 2297
<400> SEQUENCE: 2297
000

<210> SEQ ID NO 2298
<400> SEQUENCE: 2298
000

<210> SEQ ID NO 2299
<400> SEQUENCE: 2299
000

<210> SEQ ID NO 2300

<400> SEQUENCE: 2300

000

<210> SEQ ID NO 2301

<400> SEQUENCE: 2301

000

<210> SEQ ID NO 2302

<400> SEQUENCE: 2302

000

<210> SEQ ID NO 2303

<400> SEQUENCE: 2303

000

<210> SEQ ID NO 2304

<400> SEQUENCE: 2304

000

<210> SEQ ID NO 2305

<400> SEQUENCE: 2305

000

<210> SEQ ID NO 2306

<400> SEQUENCE: 2306

000

<210> SEQ ID NO 2307

<400> SEQUENCE: 2307

000

<210> SEQ ID NO 2308

<400> SEQUENCE: 2308

000

<210> SEQ ID NO 2309

<400> SEQUENCE: 2309

000

<210> SEQ ID NO 2310

<400> SEQUENCE: 2310

000

<210> SEQ ID NO 2311

<400> SEQUENCE: 2311

000

<210> SEQ ID NO 2312

<400> SEQUENCE: 2312

000

<210> SEQ ID NO 2313

<400> SEQUENCE: 2313

000

<210> SEQ ID NO 2314

<400> SEQUENCE: 2314

000

<210> SEQ ID NO 2315

<400> SEQUENCE: 2315

000

<210> SEQ ID NO 2316

<400> SEQUENCE: 2316

000

<210> SEQ ID NO 2317

<400> SEQUENCE: 2317

000

<210> SEQ ID NO 2318

<400> SEQUENCE: 2318

000

<210> SEQ ID NO 2319

<400> SEQUENCE: 2319

000

<210> SEQ ID NO 2320

<400> SEQUENCE: 2320

000

<210> SEQ ID NO 2321

<400> SEQUENCE: 2321

000

<210> SEQ ID NO 2322

<400> SEQUENCE: 2322

000

<210> SEQ ID NO 2323

<400> SEQUENCE: 2323

000

<210> SEQ ID NO 2324

<400> SEQUENCE: 2324

000

<210> SEQ ID NO 2325

<400> SEQUENCE: 2325

000

<210> SEQ ID NO 2326

<400> SEQUENCE: 2326

000

<210> SEQ ID NO 2327

<400> SEQUENCE: 2327

000

<210> SEQ ID NO 2328

<400> SEQUENCE: 2328

000

<210> SEQ ID NO 2329

<400> SEQUENCE: 2329

000

<210> SEQ ID NO 2330

<400> SEQUENCE: 2330

000

<210> SEQ ID NO 2331

<400> SEQUENCE: 2331

000

<210> SEQ ID NO 2332

<400> SEQUENCE: 2332

000

<210> SEQ ID NO 2333

<400> SEQUENCE: 2333

000

<210> SEQ ID NO 2334

<400> SEQUENCE: 2334

000

<210> SEQ ID NO 2335

<400> SEQUENCE: 2335

000

<210> SEQ ID NO 2336

<400> SEQUENCE: 2336

000

<210> SEQ ID NO 2337

<400> SEQUENCE: 2337

000

<210> SEQ ID NO 2338

<400> SEQUENCE: 2338

000

<210> SEQ ID NO 2339

<400> SEQUENCE: 2339

000

<210> SEQ ID NO 2340

<400> SEQUENCE: 2340

000

<210> SEQ ID NO 2341

<400> SEQUENCE: 2341

000

<210> SEQ ID NO 2342

<400> SEQUENCE: 2342

000

<210> SEQ ID NO 2343

<400> SEQUENCE: 2343

000

<210> SEQ ID NO 2344

<400> SEQUENCE: 2344

000

<210> SEQ ID NO 2345

<400> SEQUENCE: 2345

000

<210> SEQ ID NO 2346

<400> SEQUENCE: 2346

000

<210> SEQ ID NO 2347

<400> SEQUENCE: 2347

000

<210> SEQ ID NO 2348

<400> SEQUENCE: 2348

000

<210> SEQ ID NO 2349

<400> SEQUENCE: 2349

000

<210> SEQ ID NO 2350

<400> SEQUENCE: 2350

000

<210> SEQ ID NO 2351

<400> SEQUENCE: 2351

000

<210> SEQ ID NO 2352

<400> SEQUENCE: 2352

000

<210> SEQ ID NO 2353

<400> SEQUENCE: 2353

000

<210> SEQ ID NO 2354

<400> SEQUENCE: 2354

000

<210> SEQ ID NO 2355

<400> SEQUENCE: 2355

000

<210> SEQ ID NO 2356

<400> SEQUENCE: 2356

000

<210> SEQ ID NO 2357

<400> SEQUENCE: 2357

000

<210> SEQ ID NO 2358

<400> SEQUENCE: 2358

000

<210> SEQ ID NO 2359

<400> SEQUENCE: 2359

000

<210> SEQ ID NO 2360

<400> SEQUENCE: 2360

000

<210> SEQ ID NO 2361

<400> SEQUENCE: 2361

000

<210> SEQ ID NO 2362

<400> SEQUENCE: 2362

000

<210> SEQ ID NO 2363

<400> SEQUENCE: 2363

000

<210> SEQ ID NO 2364

<400> SEQUENCE: 2364

000

<210> SEQ ID NO 2365

<400> SEQUENCE: 2365

000

<210> SEQ ID NO 2366

<400> SEQUENCE: 2366

000

<210> SEQ ID NO 2367

<400> SEQUENCE: 2367

000

<210> SEQ ID NO 2368

<400> SEQUENCE: 2368

000

<210> SEQ ID NO 2369

<400> SEQUENCE: 2369

000

<210> SEQ ID NO 2370

<400> SEQUENCE: 2370

000

<210> SEQ ID NO 2371

<400> SEQUENCE: 2371

000

<210> SEQ ID NO 2372

<400> SEQUENCE: 2372

000

<210> SEQ ID NO 2373

<400> SEQUENCE: 2373

000

<210> SEQ ID NO 2374

<400> SEQUENCE: 2374

000

<210> SEQ ID NO 2375

<400> SEQUENCE: 2375

000

<210> SEQ ID NO 2376

<400> SEQUENCE: 2376

000

<210> SEQ ID NO 2377

<400> SEQUENCE: 2377

000

<210> SEQ ID NO 2378

<400> SEQUENCE: 2378

000

<210> SEQ ID NO 2379

<400> SEQUENCE: 2379

000

<210> SEQ ID NO 2380

<400> SEQUENCE: 2380

000

<210> SEQ ID NO 2381

<400> SEQUENCE: 2381

000

<210> SEQ ID NO 2382

<400> SEQUENCE: 2382

000

<210> SEQ ID NO 2383

<400> SEQUENCE: 2383

000

<210> SEQ ID NO 2384

<400> SEQUENCE: 2384

000

<210> SEQ ID NO 2385

<400> SEQUENCE: 2385

000

<210> SEQ ID NO 2386

<400> SEQUENCE: 2386

000

<210> SEQ ID NO 2387

<400> SEQUENCE: 2387

000

<210> SEQ ID NO 2388

<400> SEQUENCE: 2388

000

<210> SEQ ID NO 2389

<400> SEQUENCE: 2389

000

<210> SEQ ID NO 2390

<400> SEQUENCE: 2390

000

<210> SEQ ID NO 2391

<400> SEQUENCE: 2391

000

<210> SEQ ID NO 2392

<400> SEQUENCE: 2392

000

<210> SEQ ID NO 2393

<400> SEQUENCE: 2393

000

<210> SEQ ID NO 2394

<400> SEQUENCE: 2394

000

<210> SEQ ID NO 2395

<400> SEQUENCE: 2395

000

<210> SEQ ID NO 2396

<400> SEQUENCE: 2396

000

<210> SEQ ID NO 2397

<400> SEQUENCE: 2397

000

<210> SEQ ID NO 2398

<400> SEQUENCE: 2398

000

<210> SEQ ID NO 2399

<400> SEQUENCE: 2399

000

<210> SEQ ID NO 2400

<400> SEQUENCE: 2400

000

<210> SEQ ID NO 2401

<400> SEQUENCE: 2401

000

<210> SEQ ID NO 2402

<400> SEQUENCE: 2402

000

<210> SEQ ID NO 2403

<400> SEQUENCE: 2403

000

<210> SEQ ID NO 2404

<400> SEQUENCE: 2404

000

<210> SEQ ID NO 2405

<400> SEQUENCE: 2405

000

<210> SEQ ID NO 2406

<400> SEQUENCE: 2406

000

<210> SEQ ID NO 2407

<400> SEQUENCE: 2407

000

<210> SEQ ID NO 2408

<400> SEQUENCE: 2408

000

<210> SEQ ID NO 2409

<400> SEQUENCE: 2409

000

<210> SEQ ID NO 2410

<400> SEQUENCE: 2410

000

<210> SEQ ID NO 2411

<400> SEQUENCE: 2411

000

<210> SEQ ID NO 2412

<400> SEQUENCE: 2412

000

```
<210> SEQ ID NO 2413
<400> SEQUENCE: 2413
000

<210> SEQ ID NO 2414
<400> SEQUENCE: 2414
000

<210> SEQ ID NO 2415
<400> SEQUENCE: 2415
000

<210> SEQ ID NO 2416
<400> SEQUENCE: 2416
000

<210> SEQ ID NO 2417
<400> SEQUENCE: 2417
000

<210> SEQ ID NO 2418
<400> SEQUENCE: 2418
000

<210> SEQ ID NO 2419
<400> SEQUENCE: 2419
000

<210> SEQ ID NO 2420
<400> SEQUENCE: 2420
000

<210> SEQ ID NO 2421
<400> SEQUENCE: 2421
000

<210> SEQ ID NO 2422
<400> SEQUENCE: 2422
000

<210> SEQ ID NO 2423
<400> SEQUENCE: 2423
000

<210> SEQ ID NO 2424
```

<400> SEQUENCE: 2424

000

<210> SEQ ID NO 2425

<400> SEQUENCE: 2425

000

<210> SEQ ID NO 2426

<400> SEQUENCE: 2426

000

<210> SEQ ID NO 2427

<400> SEQUENCE: 2427

000

<210> SEQ ID NO 2428

<400> SEQUENCE: 2428

000

<210> SEQ ID NO 2429

<400> SEQUENCE: 2429

000

<210> SEQ ID NO 2430

<400> SEQUENCE: 2430

000

<210> SEQ ID NO 2431

<400> SEQUENCE: 2431

000

<210> SEQ ID NO 2432

<400> SEQUENCE: 2432

000

<210> SEQ ID NO 2433

<400> SEQUENCE: 2433

000

<210> SEQ ID NO 2434

<400> SEQUENCE: 2434

000

<210> SEQ ID NO 2435

<400> SEQUENCE: 2435

000

<210> SEQ ID NO 2436

<400> SEQUENCE: 2436

000

<210> SEQ ID NO 2437

<400> SEQUENCE: 2437

000

<210> SEQ ID NO 2438

<400> SEQUENCE: 2438

000

<210> SEQ ID NO 2439

<400> SEQUENCE: 2439

000

<210> SEQ ID NO 2440

<400> SEQUENCE: 2440

000

<210> SEQ ID NO 2441

<400> SEQUENCE: 2441

000

<210> SEQ ID NO 2442

<400> SEQUENCE: 2442

000

<210> SEQ ID NO 2443

<400> SEQUENCE: 2443

000

<210> SEQ ID NO 2444

<400> SEQUENCE: 2444

000

<210> SEQ ID NO 2445

<400> SEQUENCE: 2445

000

<210> SEQ ID NO 2446

<400> SEQUENCE: 2446

000

-continued

<210> SEQ ID NO 2447
<400> SEQUENCE: 2447
000

<210> SEQ ID NO 2448
<400> SEQUENCE: 2448
000

<210> SEQ ID NO 2449
<400> SEQUENCE: 2449
000

<210> SEQ ID NO 2450
<400> SEQUENCE: 2450
000

<210> SEQ ID NO 2451
<400> SEQUENCE: 2451
000

<210> SEQ ID NO 2452
<400> SEQUENCE: 2452
000

<210> SEQ ID NO 2453
<400> SEQUENCE: 2453
000

<210> SEQ ID NO 2454
<400> SEQUENCE: 2454
000

<210> SEQ ID NO 2455
<400> SEQUENCE: 2455
000

<210> SEQ ID NO 2456
<400> SEQUENCE: 2456
000

<210> SEQ ID NO 2457
<400> SEQUENCE: 2457
000

<210> SEQ ID NO 2458

```
<400> SEQUENCE: 2458

000

<210> SEQ ID NO 2459

<400> SEQUENCE: 2459

000

<210> SEQ ID NO 2460

<400> SEQUENCE: 2460

000

<210> SEQ ID NO 2461

<400> SEQUENCE: 2461

000

<210> SEQ ID NO 2462

<400> SEQUENCE: 2462

000

<210> SEQ ID NO 2463

<400> SEQUENCE: 2463

000

<210> SEQ ID NO 2464

<400> SEQUENCE: 2464

000

<210> SEQ ID NO 2465

<400> SEQUENCE: 2465

000

<210> SEQ ID NO 2466

<400> SEQUENCE: 2466

000

<210> SEQ ID NO 2467

<400> SEQUENCE: 2467

000

<210> SEQ ID NO 2468

<400> SEQUENCE: 2468

000

<210> SEQ ID NO 2469

<400> SEQUENCE: 2469
```

000

<210> SEQ ID NO 2470

<400> SEQUENCE: 2470

000

<210> SEQ ID NO 2471

<400> SEQUENCE: 2471

000

<210> SEQ ID NO 2472

<400> SEQUENCE: 2472

000

<210> SEQ ID NO 2473

<400> SEQUENCE: 2473

000

<210> SEQ ID NO 2474

<400> SEQUENCE: 2474

000

<210> SEQ ID NO 2475

<400> SEQUENCE: 2475

000

<210> SEQ ID NO 2476

<400> SEQUENCE: 2476

000

<210> SEQ ID NO 2477

<400> SEQUENCE: 2477

000

<210> SEQ ID NO 2478

<400> SEQUENCE: 2478

000

<210> SEQ ID NO 2479

<400> SEQUENCE: 2479

000

<210> SEQ ID NO 2480

<400> SEQUENCE: 2480

000

<210> SEQ ID NO 2481

<400> SEQUENCE: 2481

000

<210> SEQ ID NO 2482

<400> SEQUENCE: 2482

000

<210> SEQ ID NO 2483

<400> SEQUENCE: 2483

000

<210> SEQ ID NO 2484

<400> SEQUENCE: 2484

000

<210> SEQ ID NO 2485

<400> SEQUENCE: 2485

000

<210> SEQ ID NO 2486

<400> SEQUENCE: 2486

000

<210> SEQ ID NO 2487

<400> SEQUENCE: 2487

000

<210> SEQ ID NO 2488

<400> SEQUENCE: 2488

000

<210> SEQ ID NO 2489

<400> SEQUENCE: 2489

000

<210> SEQ ID NO 2490

<400> SEQUENCE: 2490

000

<210> SEQ ID NO 2491

<400> SEQUENCE: 2491

000

<210> SEQ ID NO 2492

<400> SEQUENCE: 2492

000

<210> SEQ ID NO 2493

<400> SEQUENCE: 2493

000

<210> SEQ ID NO 2494

<400> SEQUENCE: 2494

000

<210> SEQ ID NO 2495

<400> SEQUENCE: 2495

000

<210> SEQ ID NO 2496

<400> SEQUENCE: 2496

000

<210> SEQ ID NO 2497

<400> SEQUENCE: 2497

000

<210> SEQ ID NO 2498

<400> SEQUENCE: 2498

000

<210> SEQ ID NO 2499

<400> SEQUENCE: 2499

000

<210> SEQ ID NO 2500

<400> SEQUENCE: 2500

000

<210> SEQ ID NO 2501

<400> SEQUENCE: 2501

000

<210> SEQ ID NO 2502

<400> SEQUENCE: 2502

000

<210> SEQ ID NO 2503

```
<400> SEQUENCE: 2503

000

<210> SEQ ID NO 2504

<400> SEQUENCE: 2504

000

<210> SEQ ID NO 2505

<400> SEQUENCE: 2505

000

<210> SEQ ID NO 2506

<400> SEQUENCE: 2506

000

<210> SEQ ID NO 2507

<400> SEQUENCE: 2507

000

<210> SEQ ID NO 2508

<400> SEQUENCE: 2508

000

<210> SEQ ID NO 2509

<400> SEQUENCE: 2509

000

<210> SEQ ID NO 2510

<400> SEQUENCE: 2510

000

<210> SEQ ID NO 2511

<400> SEQUENCE: 2511

000

<210> SEQ ID NO 2512

<400> SEQUENCE: 2512

000

<210> SEQ ID NO 2513

<400> SEQUENCE: 2513

000

<210> SEQ ID NO 2514

<400> SEQUENCE: 2514
```

000

<210> SEQ ID NO 2515
<400> SEQUENCE: 2515
000

<210> SEQ ID NO 2516
<400> SEQUENCE: 2516
000

<210> SEQ ID NO 2517
<400> SEQUENCE: 2517
000

<210> SEQ ID NO 2518
<400> SEQUENCE: 2518
000

<210> SEQ ID NO 2519
<400> SEQUENCE: 2519
000

<210> SEQ ID NO 2520
<400> SEQUENCE: 2520
000

<210> SEQ ID NO 2521
<400> SEQUENCE: 2521
000

<210> SEQ ID NO 2522
<400> SEQUENCE: 2522
000

<210> SEQ ID NO 2523
<400> SEQUENCE: 2523
000

<210> SEQ ID NO 2524
<400> SEQUENCE: 2524
000

<210> SEQ ID NO 2525
<400> SEQUENCE: 2525
000

```
<210> SEQ ID NO 2526
<400> SEQUENCE: 2526
000

<210> SEQ ID NO 2527
<400> SEQUENCE: 2527
000

<210> SEQ ID NO 2528
<400> SEQUENCE: 2528
000

<210> SEQ ID NO 2529
<400> SEQUENCE: 2529
000

<210> SEQ ID NO 2530
<400> SEQUENCE: 2530
000

<210> SEQ ID NO 2531
<400> SEQUENCE: 2531
000

<210> SEQ ID NO 2532
<400> SEQUENCE: 2532
000

<210> SEQ ID NO 2533
<400> SEQUENCE: 2533
000

<210> SEQ ID NO 2534
<400> SEQUENCE: 2534
000

<210> SEQ ID NO 2535
<400> SEQUENCE: 2535
000

<210> SEQ ID NO 2536
<400> SEQUENCE: 2536
000

<210> SEQ ID NO 2537
```

<400> SEQUENCE: 2537

000

<210> SEQ ID NO 2538

<400> SEQUENCE: 2538

000

<210> SEQ ID NO 2539

<400> SEQUENCE: 2539

000

<210> SEQ ID NO 2540

<400> SEQUENCE: 2540

000

<210> SEQ ID NO 2541

<400> SEQUENCE: 2541

000

<210> SEQ ID NO 2542

<400> SEQUENCE: 2542

000

<210> SEQ ID NO 2543

<400> SEQUENCE: 2543

000

<210> SEQ ID NO 2544

<400> SEQUENCE: 2544

000

<210> SEQ ID NO 2545

<400> SEQUENCE: 2545

000

<210> SEQ ID NO 2546

<400> SEQUENCE: 2546

000

<210> SEQ ID NO 2547

<400> SEQUENCE: 2547

000

<210> SEQ ID NO 2548

<400> SEQUENCE: 2548

000

<210> SEQ ID NO 2549

<400> SEQUENCE: 2549

000

<210> SEQ ID NO 2550

<400> SEQUENCE: 2550

000

<210> SEQ ID NO 2551

<400> SEQUENCE: 2551

000

<210> SEQ ID NO 2552

<400> SEQUENCE: 2552

000

<210> SEQ ID NO 2553

<400> SEQUENCE: 2553

000

<210> SEQ ID NO 2554

<400> SEQUENCE: 2554

000

<210> SEQ ID NO 2555

<400> SEQUENCE: 2555

000

<210> SEQ ID NO 2556

<400> SEQUENCE: 2556

000

<210> SEQ ID NO 2557

<400> SEQUENCE: 2557

000

<210> SEQ ID NO 2558

<400> SEQUENCE: 2558

000

<210> SEQ ID NO 2559

<400> SEQUENCE: 2559

000

<210> SEQ ID NO 2560

<400> SEQUENCE: 2560

000

<210> SEQ ID NO 2561

<400> SEQUENCE: 2561

000

<210> SEQ ID NO 2562

<400> SEQUENCE: 2562

000

<210> SEQ ID NO 2563

<400> SEQUENCE: 2563

000

<210> SEQ ID NO 2564

<400> SEQUENCE: 2564

000

<210> SEQ ID NO 2565

<400> SEQUENCE: 2565

000

<210> SEQ ID NO 2566

<400> SEQUENCE: 2566

000

<210> SEQ ID NO 2567

<400> SEQUENCE: 2567

000

<210> SEQ ID NO 2568

<400> SEQUENCE: 2568

000

<210> SEQ ID NO 2569

<400> SEQUENCE: 2569

000

<210> SEQ ID NO 2570

<400> SEQUENCE: 2570

000

<210> SEQ ID NO 2571

<400> SEQUENCE: 2571

000

<210> SEQ ID NO 2572

<400> SEQUENCE: 2572

000

<210> SEQ ID NO 2573

<400> SEQUENCE: 2573

000

<210> SEQ ID NO 2574

<400> SEQUENCE: 2574

000

<210> SEQ ID NO 2575

<400> SEQUENCE: 2575

000

<210> SEQ ID NO 2576

<400> SEQUENCE: 2576

000

<210> SEQ ID NO 2577

<400> SEQUENCE: 2577

000

<210> SEQ ID NO 2578

<400> SEQUENCE: 2578

000

<210> SEQ ID NO 2579

<400> SEQUENCE: 2579

000

<210> SEQ ID NO 2580

<400> SEQUENCE: 2580

000

<210> SEQ ID NO 2581

<400> SEQUENCE: 2581

000

<210> SEQ ID NO 2582

```
<400> SEQUENCE: 2582

000

<210> SEQ ID NO 2583

<400> SEQUENCE: 2583

000

<210> SEQ ID NO 2584

<400> SEQUENCE: 2584

000

<210> SEQ ID NO 2585

<400> SEQUENCE: 2585

000

<210> SEQ ID NO 2586

<400> SEQUENCE: 2586

000

<210> SEQ ID NO 2587

<400> SEQUENCE: 2587

000

<210> SEQ ID NO 2588

<400> SEQUENCE: 2588

000

<210> SEQ ID NO 2589

<400> SEQUENCE: 2589

000

<210> SEQ ID NO 2590

<400> SEQUENCE: 2590

000

<210> SEQ ID NO 2591
<211> LENGTH: 7
<212> TYPE: PRT
<213> ORGANISM: Dependovirus adeno-associated virus

<400> SEQUENCE: 2591

Ser Ala Ser Thr Gly Ala Ser
1               5

<210> SEQ ID NO 2592
<211> LENGTH: 10
<212> TYPE: PRT
<213> ORGANISM: Dependovirus adeno-associated virus

<400> SEQUENCE: 2592
```

```
Val Phe Met Ile Pro Gln Tyr Gly Tyr Leu
1               5                   10

<210> SEQ ID NO 2593
<211> LENGTH: 9
<212> TYPE: PRT
<213> ORGANISM: Dependovirus adeno-associated virus

<400> SEQUENCE: 2593

Asn Gln Ser Gly Ser Ala Gln Asn Lys
1               5

<210> SEQ ID NO 2594
<211> LENGTH: 2
<212> TYPE: PRT
<213> ORGANISM: Dependovirus adeno-associated virus

<400> SEQUENCE: 2594

Ser Val
1

<210> SEQ ID NO 2595
<211> LENGTH: 8
<212> TYPE: PRT
<213> ORGANISM: Dependovirus adeno-associated virus

<400> SEQUENCE: 2595

Lys Thr Asp Asn Asn Asn Ser Asn
1               5

<210> SEQ ID NO 2596
<211> LENGTH: 7
<212> TYPE: PRT
<213> ORGANISM: Dependovirus adeno-associated virus

<400> SEQUENCE: 2596

Lys Asp Asp Glu Asp Lys Phe
1               5

<210> SEQ ID NO 2597
<211> LENGTH: 6
<212> TYPE: PRT
<213> ORGANISM: Dependovirus adeno-associated virus

<400> SEQUENCE: 2597

Ser Ala Gly Ala Ser Asn
1               5

<210> SEQ ID NO 2598
<211> LENGTH: 10
<212> TYPE: PRT
<213> ORGANISM: Dependovirus adeno-associated virus

<400> SEQUENCE: 2598

Ser Thr Asp Pro Ala Thr Gly Asp Val His
1               5                   10

<210> SEQ ID NO 2599
<211> LENGTH: 2
<212> TYPE: PRT
<213> ORGANISM: Dependovirus adeno-associated virus

<400> SEQUENCE: 2599

Ala Asn
1
```

```
<210> SEQ ID NO 2600
<211> LENGTH: 7
<212> TYPE: PRT
<213> ORGANISM: Dependovirus adeno-associated virus

<400> SEQUENCE: 2600

Asp Asn Asn Gly Leu Tyr Thr
1               5

<210> SEQ ID NO 2601
<211> LENGTH: 6
<212> TYPE: PRT
<213> ORGANISM: Dependovirus adeno-associated virus

<400> SEQUENCE: 2601

Ser Gln Ser Gly Ala Ser
1               5

<210> SEQ ID NO 2602
<211> LENGTH: 10
<212> TYPE: PRT
<213> ORGANISM: Dependovirus adeno-associated virus

<400> SEQUENCE: 2602

Val Phe Met Val Pro Gln Tyr Gly Tyr Leu
1               5                   10

<210> SEQ ID NO 2603
<211> LENGTH: 9
<212> TYPE: PRT
<213> ORGANISM: Dependovirus adeno-associated virus

<400> SEQUENCE: 2603

Thr Pro Ser Gly Thr Thr Thr Gln Ser
1               5

<210> SEQ ID NO 2604
<211> LENGTH: 2
<212> TYPE: PRT
<213> ORGANISM: Dependovirus adeno-associated virus

<400> SEQUENCE: 2604

Arg Asp
1

<210> SEQ ID NO 2605
<211> LENGTH: 8
<212> TYPE: PRT
<213> ORGANISM: Dependovirus adeno-associated virus

<400> SEQUENCE: 2605

Ser Ala Asp Asn Asn Asn Ser Glu
1               5

<210> SEQ ID NO 2606
<211> LENGTH: 7
<212> TYPE: PRT
<213> ORGANISM: Dependovirus adeno-associated virus

<400> SEQUENCE: 2606

Lys Asp Asp Glu Glu Lys Phe
1               5
```

```
<210> SEQ ID NO 2607
<211> LENGTH: 6
<212> TYPE: PRT
<213> ORGANISM: Dependovirus adeno-associated virus

<400> SEQUENCE: 2607

Gly Ser Glu Lys Thr Asn
1               5

<210> SEQ ID NO 2608
<211> LENGTH: 10
<212> TYPE: PRT
<213> ORGANISM: Dependovirus adeno-associated virus

<400> SEQUENCE: 2608

Asn Arg Gln Ala Ala Thr Ala Asp Val Asn
1               5                   10

<210> SEQ ID NO 2609
<211> LENGTH: 2
<212> TYPE: PRT
<213> ORGANISM: Dependovirus adeno-associated virus

<400> SEQUENCE: 2609

Val Asn
1

<210> SEQ ID NO 2610
<211> LENGTH: 7
<212> TYPE: PRT
<213> ORGANISM: Dependovirus adeno-associated virus

<400> SEQUENCE: 2610

Asp Thr Asn Gly Val Tyr Ser
1               5

<210> SEQ ID NO 2611
<211> LENGTH: 6
<212> TYPE: PRT
<213> ORGANISM: Dependovirus adeno-associated virus

<400> SEQUENCE: 2611

Ser Gln Ser Gly Ala Ser
1               5

<210> SEQ ID NO 2612
<211> LENGTH: 10
<212> TYPE: PRT
<213> ORGANISM: Dependovirus adeno-associated virus

<400> SEQUENCE: 2612

Val Phe Met Val Pro Gln Tyr Gly Tyr Leu
1               5                   10

<210> SEQ ID NO 2613
<211> LENGTH: 9
<212> TYPE: PRT
<213> ORGANISM: Dependovirus adeno-associated virus

<400> SEQUENCE: 2613

Thr Thr Ser Gly Thr Thr Asn Gln Ser
1               5

<210> SEQ ID NO 2614
<211> LENGTH: 2
```

```
<212> TYPE: PRT
<213> ORGANISM: Dependovirus adeno-associated virus

<400> SEQUENCE: 2614

Ser Leu
1

<210> SEQ ID NO 2615
<211> LENGTH: 8
<212> TYPE: PRT
<213> ORGANISM: Dependovirus adeno-associated virus

<400> SEQUENCE: 2615

Ala Asn Asp Asn Asn Asn Ser Asn
1               5

<210> SEQ ID NO 2616
<211> LENGTH: 7
<212> TYPE: PRT
<213> ORGANISM: Dependovirus adeno-associated virus

<400> SEQUENCE: 2616

Lys Asp Asp Glu Glu Lys Phe
1               5

<210> SEQ ID NO 2617
<211> LENGTH: 6
<212> TYPE: PRT
<213> ORGANISM: Dependovirus adeno-associated virus

<400> SEQUENCE: 2617

Gly Thr Thr Ala Ser Asn
1               5

<210> SEQ ID NO 2618
<211> LENGTH: 10
<212> TYPE: PRT
<213> ORGANISM: Dependovirus adeno-associated virus

<400> SEQUENCE: 2618

Asn Thr Ala Pro Thr Thr Gly Thr Val Asn
1               5                   10

<210> SEQ ID NO 2619
<211> LENGTH: 2
<212> TYPE: PRT
<213> ORGANISM: Dependovirus adeno-associated virus

<400> SEQUENCE: 2619

Val Asn
1

<210> SEQ ID NO 2620
<211> LENGTH: 7
<212> TYPE: PRT
<213> ORGANISM: Dependovirus adeno-associated virus

<400> SEQUENCE: 2620

Asp Thr Asn Gly Val Tyr Ser
1               5

<210> SEQ ID NO 2621
<211> LENGTH: 8
<212> TYPE: PRT
<213> ORGANISM: Dependovirus adeno-associated virus
```

```
<400> SEQUENCE: 2621

Arg Leu Gly Glu Ser Leu Gln Ser
1               5

<210> SEQ ID NO 2622
<211> LENGTH: 10
<212> TYPE: PRT
<213> ORGANISM: Dependovirus adeno-associated virus

<400> SEQUENCE: 2622

Val Phe Met Val Pro Gln Tyr Gly Tyr Cys
1               5                   10

<210> SEQ ID NO 2623
<211> LENGTH: 9
<212> TYPE: PRT
<213> ORGANISM: Dependovirus adeno-associated virus

<400> SEQUENCE: 2623

Gly Thr Thr Leu Asn Ala Gly Thr Ala
1               5

<210> SEQ ID NO 2624
<211> LENGTH: 2
<212> TYPE: PRT
<213> ORGANISM: Dependovirus adeno-associated virus

<400> SEQUENCE: 2624

Ser Asn
1

<210> SEQ ID NO 2625
<211> LENGTH: 12
<212> TYPE: PRT
<213> ORGANISM: Dependovirus adeno-associated virus

<400> SEQUENCE: 2625

Ala Asn Gln Asn Tyr Lys Ile Pro Ala Thr Gly Ser
1               5                   10

<210> SEQ ID NO 2626
<211> LENGTH: 7
<212> TYPE: PRT
<213> ORGANISM: Dependovirus adeno-associated virus

<400> SEQUENCE: 2626

Gly Pro Ala Asp Ser Lys Phe
1               5

<210> SEQ ID NO 2627
<211> LENGTH: 6
<212> TYPE: PRT
<213> ORGANISM: Dependovirus adeno-associated virus

<400> SEQUENCE: 2627

Gln Asn Gly Asn Thr Ala
1               5

<210> SEQ ID NO 2628
<211> LENGTH: 10
<212> TYPE: PRT
<213> ORGANISM: Dependovirus adeno-associated virus

<400> SEQUENCE: 2628
```

```
Ser Asn Leu Pro Thr Val Asp Arg Leu Thr
1               5                   10

<210> SEQ ID NO 2629
<211> LENGTH: 2
<212> TYPE: PRT
<213> ORGANISM: Dependovirus adeno-associated virus

<400> SEQUENCE: 2629

Asn Ser
1

<210> SEQ ID NO 2630
<211> LENGTH: 7
<212> TYPE: PRT
<213> ORGANISM: Dependovirus adeno-associated virus

<400> SEQUENCE: 2630

Asp Ala Ala Gly Lys Tyr Thr
1               5

<210> SEQ ID NO 2631
<211> LENGTH: 10
<212> TYPE: PRT
<213> ORGANISM: Dependovirus adeno-associated virus

<400> SEQUENCE: 2631

Glu Ile Lys Ser Gly Ser Val Asp Gly Ser
1               5                   10

<210> SEQ ID NO 2632
<211> LENGTH: 10
<212> TYPE: PRT
<213> ORGANISM: Dependovirus adeno-associated virus

<400> SEQUENCE: 2632

Val Phe Thr Leu Pro Gln Tyr Gly Tyr Ala
1               5                   10

<210> SEQ ID NO 2633
<211> LENGTH: 9
<212> TYPE: PRT
<213> ORGANISM: Dependovirus adeno-associated virus

<400> SEQUENCE: 2633

Ser Thr Asn Asn Thr Gly Gly Val Gln
1               5

<210> SEQ ID NO 2634
<211> LENGTH: 2
<212> TYPE: PRT
<213> ORGANISM: Dependovirus adeno-associated virus

<400> SEQUENCE: 2634

Ala Asn
1

<210> SEQ ID NO 2635
<211> LENGTH: 7
<212> TYPE: PRT
<213> ORGANISM: Dependovirus adeno-associated virus

<400> SEQUENCE: 2635

Ser Gly Val Asn Arg Ala Ser
```

<210> SEQ ID NO 2636
<211> LENGTH: 7
<212> TYPE: PRT
<213> ORGANISM: Dependovirus adeno-associated virus

<400> SEQUENCE: 2636

Leu Gln Gly Ser Asn Thr Tyr
1               5

<210> SEQ ID NO 2637
<211> LENGTH: 8
<212> TYPE: PRT
<213> ORGANISM: Dependovirus adeno-associated virus

<400> SEQUENCE: 2637

Ala Asn Pro Gly Thr Thr Ala Thr
1               5

<210> SEQ ID NO 2638
<211> LENGTH: 10
<212> TYPE: PRT
<213> ORGANISM: Dependovirus adeno-associated virus

<400> SEQUENCE: 2638

Thr Thr Ala Pro Ala Thr Gly Thr Tyr Asn
1               5                   10

<210> SEQ ID NO 2639
<211> LENGTH: 2
<212> TYPE: PRT
<213> ORGANISM: Dependovirus adeno-associated virus

<400> SEQUENCE: 2639

Gln Phe
1

<210> SEQ ID NO 2640
<211> LENGTH: 7
<212> TYPE: PRT
<213> ORGANISM: Dependovirus adeno-associated virus

<400> SEQUENCE: 2640

Asp Ser Thr Gly Glu Tyr Arg
1               5

<210> SEQ ID NO 2641
<211> LENGTH: 7
<212> TYPE: PRT
<213> ORGANISM: Dependovirus adeno-associated virus

<400> SEQUENCE: 2641

Ser Ala Ser Thr Gly Ala Ser
1               5

<210> SEQ ID NO 2642
<211> LENGTH: 10
<212> TYPE: PRT
<213> ORGANISM: Dependovirus adeno-associated virus

<400> SEQUENCE: 2642

Val Phe Met Ile Pro Gln Tyr Gly Tyr Leu
1               5                   10

<210> SEQ ID NO 2643
<211> LENGTH: 9
<212> TYPE: PRT
<213> ORGANISM: Dependovirus adeno-associated virus

<400> SEQUENCE: 2643

Asn Gln Ser Gly Ser Ala Gln Asn Lys
1               5

<210> SEQ ID NO 2644
<211> LENGTH: 2
<212> TYPE: PRT
<213> ORGANISM: Dependovirus adeno-associated virus

<400> SEQUENCE: 2644

Ser Val
1

<210> SEQ ID NO 2645
<211> LENGTH: 8
<212> TYPE: PRT
<213> ORGANISM: Dependovirus adeno-associated virus

<400> SEQUENCE: 2645

Lys Thr Asp Asn Asn Asn Ser Asn
1               5

<210> SEQ ID NO 2646
<211> LENGTH: 7
<212> TYPE: PRT
<213> ORGANISM: Dependovirus adeno-associated virus

<400> SEQUENCE: 2646

Lys Asp Asp Lys Asp Lys Phe
1               5

<210> SEQ ID NO 2647
<211> LENGTH: 6
<212> TYPE: PRT
<213> ORGANISM: Dependovirus adeno-associated virus

<400> SEQUENCE: 2647

Ser Ala Gly Ala Ser Asn
1               5

<210> SEQ ID NO 2648
<211> LENGTH: 10
<212> TYPE: PRT
<213> ORGANISM: Dependovirus adeno-associated virus

<400> SEQUENCE: 2648

Ser Thr Asp Pro Ala Thr Gly Asp Val His
1               5                   10

<210> SEQ ID NO 2649
<211> LENGTH: 2
<212> TYPE: PRT
<213> ORGANISM: Dependovirus adeno-associated virus

<400> SEQUENCE: 2649

Ala Asn
1

<210> SEQ ID NO 2650

```
<211> LENGTH: 7
<212> TYPE: PRT
<213> ORGANISM: Dependovirus adeno-associated virus

<400> SEQUENCE: 2650

Asp Asn Asn Gly Leu Tyr Thr
1               5

<210> SEQ ID NO 2651
<211> LENGTH: 7
<212> TYPE: PRT
<213> ORGANISM: Dependovirus adeno-associated virus

<400> SEQUENCE: 2651

Ser Glu Thr Ala Gly Ser Thr
1               5

<210> SEQ ID NO 2652
<211> LENGTH: 10
<212> TYPE: PRT
<213> ORGANISM: Dependovirus adeno-associated virus

<400> SEQUENCE: 2652

Val Phe Met Ile Pro Gln Tyr Gly Tyr Leu
1               5                   10

<210> SEQ ID NO 2653
<211> LENGTH: 9
<212> TYPE: PRT
<213> ORGANISM: Dependovirus adeno-associated virus

<400> SEQUENCE: 2653

Asn Pro Gly Gly Thr Ala Gly Asn Arg
1               5

<210> SEQ ID NO 2654
<211> LENGTH: 2
<212> TYPE: PRT
<213> ORGANISM: Dependovirus adeno-associated virus

<400> SEQUENCE: 2654

Ala Asn
1

<210> SEQ ID NO 2655
<211> LENGTH: 8
<212> TYPE: PRT
<213> ORGANISM: Dependovirus adeno-associated virus

<400> SEQUENCE: 2655

Leu Asp Gln Asn Asn Asn Ser Asn
1               5

<210> SEQ ID NO 2656
<211> LENGTH: 7
<212> TYPE: PRT
<213> ORGANISM: Dependovirus adeno-associated virus

<400> SEQUENCE: 2656

Lys Asp Asp Glu Asp Arg Phe
1               5

<210> SEQ ID NO 2657
<211> LENGTH: 6
<212> TYPE: PRT
```

<213> ORGANISM: Dependovirus adeno-associated virus

<400> SEQUENCE: 2657

Gly Ala Thr Asn Lys Thr
1               5

<210> SEQ ID NO 2658
<211> LENGTH: 10
<212> TYPE: PRT
<213> ORGANISM: Dependovirus adeno-associated virus

<400> SEQUENCE: 2658

Asn Thr Ala Ala Gln Thr Gln Val Val Asn
1               5                   10

<210> SEQ ID NO 2659
<211> LENGTH: 2
<212> TYPE: PRT
<213> ORGANISM: Dependovirus adeno-associated virus

<400> SEQUENCE: 2659

Thr Gly
1

<210> SEQ ID NO 2660
<211> LENGTH: 7
<212> TYPE: PRT
<213> ORGANISM: Dependovirus adeno-associated virus

<400> SEQUENCE: 2660

Asp Ser Gln Gly Val Tyr Ser
1               5

<210> SEQ ID NO 2661
<211> LENGTH: 8
<212> TYPE: PRT
<213> ORGANISM: Dependovirus adeno-associated virus

<400> SEQUENCE: 2661

Asn Gly Thr Ser Gly Gly Ala Thr
1               5

<210> SEQ ID NO 2662
<211> LENGTH: 10
<212> TYPE: PRT
<213> ORGANISM: Dependovirus adeno-associated virus

<400> SEQUENCE: 2662

Val Phe Met Ile Pro Gln Tyr Gly Tyr Leu
1               5                   10

<210> SEQ ID NO 2663
<211> LENGTH: 9
<212> TYPE: PRT
<213> ORGANISM: Dependovirus adeno-associated virus

<400> SEQUENCE: 2663

Thr Thr Gly Gly Thr Ala Asn Thr Gln
1               5

<210> SEQ ID NO 2664
<211> LENGTH: 2
<212> TYPE: PRT
<213> ORGANISM: Dependovirus adeno-associated virus

<400> SEQUENCE: 2664

Ala Asn
1

<210> SEQ ID NO 2665
<211> LENGTH: 8
<212> TYPE: PRT
<213> ORGANISM: Dependovirus adeno-associated virus

<400> SEQUENCE: 2665

Thr Gly Gln Asn Asn Asn Ser Asn
1               5

<210> SEQ ID NO 2666
<211> LENGTH: 7
<212> TYPE: PRT
<213> ORGANISM: Dependovirus adeno-associated virus

<400> SEQUENCE: 2666

Lys Asp Asp Glu Glu Arg Phe
1               5

<210> SEQ ID NO 2667
<211> LENGTH: 6
<212> TYPE: PRT
<213> ORGANISM: Dependovirus adeno-associated virus

<400> SEQUENCE: 2667

Asn Ala Ala Arg Asp Asn
1               5

<210> SEQ ID NO 2668
<211> LENGTH: 11
<212> TYPE: PRT
<213> ORGANISM: Dependovirus adeno-associated virus

<400> SEQUENCE: 2668

Asn Thr Ala Pro Gln Ile Gly Thr Val Asn Ser
1               5                   10

<210> SEQ ID NO 2669
<211> LENGTH: 2
<212> TYPE: PRT
<213> ORGANISM: Dependovirus adeno-associated virus

<400> SEQUENCE: 2669

Thr Ser
1

<210> SEQ ID NO 2670
<211> LENGTH: 7
<212> TYPE: PRT
<213> ORGANISM: Dependovirus adeno-associated virus

<400> SEQUENCE: 2670

Asn Thr Glu Gly Val Tyr Ser
1               5

<210> SEQ ID NO 2671
<211> LENGTH: 8
<212> TYPE: PRT
<213> ORGANISM: Dependovirus adeno-associated virus

<400> SEQUENCE: 2671

Asn Ser Thr Ser Gly Gly Ser Ser
1               5

<210> SEQ ID NO 2672
<211> LENGTH: 10
<212> TYPE: PRT
<213> ORGANISM: Dependovirus adeno-associated virus

<400> SEQUENCE: 2672

Val Phe Met Ile Pro Gln Tyr Gly Tyr Leu
1               5                   10

<210> SEQ ID NO 2673
<211> LENGTH: 9
<212> TYPE: PRT
<213> ORGANISM: Dependovirus adeno-associated virus

<400> SEQUENCE: 2673

Ile Asn Gly Ser Gly Gln Asn Gln Gln
1               5

<210> SEQ ID NO 2674
<211> LENGTH: 2
<212> TYPE: PRT
<213> ORGANISM: Dependovirus adeno-associated virus

<400> SEQUENCE: 2674

Ala Val
1

<210> SEQ ID NO 2675
<211> LENGTH: 8
<212> TYPE: PRT
<213> ORGANISM: Dependovirus adeno-associated virus

<400> SEQUENCE: 2675

Val Thr Gln Asn Asn Asn Ser Glu
1               5

<210> SEQ ID NO 2676
<211> LENGTH: 7
<212> TYPE: PRT
<213> ORGANISM: Dependovirus adeno-associated virus

<400> SEQUENCE: 2676

Lys Glu Gly Glu Asp Arg Phe
1               5

<210> SEQ ID NO 2677
<211> LENGTH: 6
<212> TYPE: PRT
<213> ORGANISM: Dependovirus adeno-associated virus

<400> SEQUENCE: 2677

Gly Thr Gly Arg Asp Asn
1               5

<210> SEQ ID NO 2678
<211> LENGTH: 10
<212> TYPE: PRT
<213> ORGANISM: Dependovirus adeno-associated virus

<400> SEQUENCE: 2678

Gln Ala Gln Ala Gln Thr Gly Trp Val Gln
1               5                   10

<210> SEQ ID NO 2679
<211> LENGTH: 2
<212> TYPE: PRT
<213> ORGANISM: Dependovirus adeno-associated virus

<400> SEQUENCE: 2679

Asn Asn
1

<210> SEQ ID NO 2680
<211> LENGTH: 7
<212> TYPE: PRT
<213> ORGANISM: Dependovirus adeno-associated virus

<400> SEQUENCE: 2680

Asn Thr Glu Gly Val Tyr Ser
1               5

<210> SEQ ID NO 2681
<211> LENGTH: 8
<212> TYPE: PRT
<213> ORGANISM: Dependovirus adeno-associated virus

<400> SEQUENCE: 2681

Asn Gly Thr Ser Gly Gly Ser Thr
1               5

<210> SEQ ID NO 2682
<211> LENGTH: 10
<212> TYPE: PRT
<213> ORGANISM: Dependovirus adeno-associated virus

<400> SEQUENCE: 2682

Val Phe Met Val Pro Gln Tyr Gly Tyr Leu
1               5                   10

<210> SEQ ID NO 2683
<211> LENGTH: 9
<212> TYPE: PRT
<213> ORGANISM: Dependovirus adeno-associated virus

<400> SEQUENCE: 2683

Gln Thr Thr Gly Thr Gly Gly Thr Gln
1               5

<210> SEQ ID NO 2684
<211> LENGTH: 2
<212> TYPE: PRT
<213> ORGANISM: Dependovirus adeno-associated virus

<400> SEQUENCE: 2684

Ala Asn
1

<210> SEQ ID NO 2685
<211> LENGTH: 8
<212> TYPE: PRT
<213> ORGANISM: Dependovirus adeno-associated virus

<400> SEQUENCE: 2685

Thr Asn Gln Asn Asn Asn Ser Asn
1               5

<210> SEQ ID NO 2686
<211> LENGTH: 7
<212> TYPE: PRT
<213> ORGANISM: Dependovirus adeno-associated virus

<400> SEQUENCE: 2686

Lys Asp Asp Asp Arg Phe
1               5

<210> SEQ ID NO 2687
<211> LENGTH: 6
<212> TYPE: PRT
<213> ORGANISM: Dependovirus adeno-associated virus

<400> SEQUENCE: 2687

Gly Ala Gly Asn Asp Gly
1               5

<210> SEQ ID NO 2688
<211> LENGTH: 10
<212> TYPE: PRT
<213> ORGANISM: Dependovirus adeno-associated virus

<400> SEQUENCE: 2688

Asn Thr Gln Ala Gln Thr Gly Leu Val His
1               5                   10

<210> SEQ ID NO 2689
<211> LENGTH: 2
<212> TYPE: PRT
<213> ORGANISM: Dependovirus adeno-associated virus

<400> SEQUENCE: 2689

Thr Asn
1

<210> SEQ ID NO 2690
<211> LENGTH: 7
<212> TYPE: PRT
<213> ORGANISM: Dependovirus adeno-associated virus

<400> SEQUENCE: 2690

Asn Thr Glu Gly Val Tyr Ser
1               5

<210> SEQ ID NO 2691
<211> LENGTH: 8
<212> TYPE: PRT
<213> ORGANISM: Dependovirus adeno-associated virus

<400> SEQUENCE: 2691

Asn Gly Thr Ser Gly Gly Ser Thr
1               5

<210> SEQ ID NO 2692
<211> LENGTH: 10
<212> TYPE: PRT
<213> ORGANISM: Dependovirus adeno-associated virus

<400> SEQUENCE: 2692

Val Phe Met Ile Pro Gln Tyr Gly Tyr Leu
1               5                   10

<210> SEQ ID NO 2693
<211> LENGTH: 9

-continued

```
<212> TYPE: PRT
<213> ORGANISM: Dependovirus adeno-associated virus

<400> SEQUENCE: 2693

Ser Thr Gly Gly Thr Ala Gly Thr Gln
1               5

<210> SEQ ID NO 2694
<211> LENGTH: 2
<212> TYPE: PRT
<213> ORGANISM: Dependovirus adeno-associated virus

<400> SEQUENCE: 2694

Ser Ala
1

<210> SEQ ID NO 2695
<211> LENGTH: 8
<212> TYPE: PRT
<213> ORGANISM: Dependovirus adeno-associated virus

<400> SEQUENCE: 2695

Leu Ser Gln Asn Asn Asn Ser Asn
1               5

<210> SEQ ID NO 2696
<211> LENGTH: 7
<212> TYPE: PRT
<213> ORGANISM: Dependovirus adeno-associated virus

<400> SEQUENCE: 2696

Lys Asp Asp Glu Glu Arg Phe
1               5

<210> SEQ ID NO 2697
<211> LENGTH: 6
<212> TYPE: PRT
<213> ORGANISM: Dependovirus adeno-associated virus

<400> SEQUENCE: 2697

Gly Ala Gly Lys Asp Asn
1               5

<210> SEQ ID NO 2698
<211> LENGTH: 10
<212> TYPE: PRT
<213> ORGANISM: Dependovirus adeno-associated virus

<400> SEQUENCE: 2698

Asn Ala Ala Pro Ile Val Gly Ala Val Asn
1               5                   10

<210> SEQ ID NO 2699
<211> LENGTH: 2
<212> TYPE: PRT
<213> ORGANISM: Dependovirus adeno-associated virus

<400> SEQUENCE: 2699

Thr Asn
1

<210> SEQ ID NO 2700
<211> LENGTH: 7
<212> TYPE: PRT
<213> ORGANISM: Dependovirus adeno-associated virus
```

<400> SEQUENCE: 2700

Asn Thr Asp Gly Thr Tyr Ser
1               5

<210> SEQ ID NO 2701
<211> LENGTH: 8
<212> TYPE: PRT
<213> ORGANISM: Dependovirus adeno-associated virus

<400> SEQUENCE: 2701

Asn Gly Thr Ser Gly Gly Ser Thr
1               5

<210> SEQ ID NO 2702
<211> LENGTH: 10
<212> TYPE: PRT
<213> ORGANISM: Dependovirus adeno-associated virus

<400> SEQUENCE: 2702

Val Phe Met Ile Pro Gln Tyr Gly Tyr Leu
1               5                   10

<210> SEQ ID NO 2703
<211> LENGTH: 9
<212> TYPE: PRT
<213> ORGANISM: Dependovirus adeno-associated virus

<400> SEQUENCE: 2703

Ser Thr Gly Gly Thr Gln Gly Thr Gln
1               5

<210> SEQ ID NO 2704
<211> LENGTH: 2
<212> TYPE: PRT
<213> ORGANISM: Dependovirus adeno-associated virus

<400> SEQUENCE: 2704

Ser Ala
1

<210> SEQ ID NO 2705
<211> LENGTH: 8
<212> TYPE: PRT
<213> ORGANISM: Dependovirus adeno-associated virus

<400> SEQUENCE: 2705

Leu Ser Gln Asn Asn Asn Ser Asn
1               5

<210> SEQ ID NO 2706
<211> LENGTH: 7
<212> TYPE: PRT
<213> ORGANISM: Dependovirus adeno-associated virus

<400> SEQUENCE: 2706

Lys Asp Asp Glu Glu Arg Phe
1               5

<210> SEQ ID NO 2707
<211> LENGTH: 6
<212> TYPE: PRT
<213> ORGANISM: Dependovirus adeno-associated virus

<400> SEQUENCE: 2707

-continued

Gly Ala Gly Arg Asp Asn
1               5

<210> SEQ ID NO 2708
<211> LENGTH: 10
<212> TYPE: PRT
<213> ORGANISM: Dependovirus adeno-associated virus

<400> SEQUENCE: 2708

Asn Thr Gly Pro Ile Val Gly Asn Val Asn
1               5                   10

<210> SEQ ID NO 2709
<211> LENGTH: 2
<212> TYPE: PRT
<213> ORGANISM: Dependovirus adeno-associated virus

<400> SEQUENCE: 2709

Thr Asn
1

<210> SEQ ID NO 2710
<211> LENGTH: 7
<212> TYPE: PRT
<213> ORGANISM: Dependovirus adeno-associated virus

<400> SEQUENCE: 2710

Asn Thr Glu Gly Thr Tyr Ser
1               5

<210> SEQ ID NO 2711
<211> LENGTH: 8
<212> TYPE: PRT
<213> ORGANISM: Dependovirus adeno-associated virus

<400> SEQUENCE: 2711

Arg Leu Gly Thr Thr Ser Ser Ser
1               5

<210> SEQ ID NO 2712
<211> LENGTH: 10
<212> TYPE: PRT
<213> ORGANISM: Dependovirus adeno-associated virus

<400> SEQUENCE: 2712

Val Phe Met Val Pro Gln Tyr Gly Tyr Cys
1               5                   10

<210> SEQ ID NO 2713
<211> LENGTH: 9
<212> TYPE: PRT
<213> ORGANISM: Dependovirus adeno-associated virus

<400> SEQUENCE: 2713

Gly Glu Thr Leu Asn Gln Gly Asn Ala
1               5

<210> SEQ ID NO 2714
<211> LENGTH: 2
<212> TYPE: PRT
<213> ORGANISM: Dependovirus adeno-associated virus

<400> SEQUENCE: 2714

Ala Phe

```
<210> SEQ ID NO 2715
<211> LENGTH: 12
<212> TYPE: PRT
<213> ORGANISM: Dependovirus adeno-associated virus

<400> SEQUENCE: 2715

Ala Ser Gln Asn Tyr Lys Ile Pro Ala Ser Gly Gly
1               5                   10

<210> SEQ ID NO 2716
<211> LENGTH: 7
<212> TYPE: PRT
<213> ORGANISM: Dependovirus adeno-associated virus

<400> SEQUENCE: 2716

Gly Pro Ser Asp Gly Asp Phe
1               5

<210> SEQ ID NO 2717
<211> LENGTH: 6
<212> TYPE: PRT
<213> ORGANISM: Dependovirus adeno-associated virus

<400> SEQUENCE: 2717

Val Thr Gly Asn Thr Thr
1               5

<210> SEQ ID NO 2718
<211> LENGTH: 10
<212> TYPE: PRT
<213> ORGANISM: Dependovirus adeno-associated virus

<400> SEQUENCE: 2718

Thr Thr Ala Pro Ile Thr Gly Asn Val Thr
1               5                   10

<210> SEQ ID NO 2719
<211> LENGTH: 2
<212> TYPE: PRT
<213> ORGANISM: Dependovirus adeno-associated virus

<400> SEQUENCE: 2719

Ser Ser
1

<210> SEQ ID NO 2720
<211> LENGTH: 7
<212> TYPE: PRT
<213> ORGANISM: Dependovirus adeno-associated virus

<400> SEQUENCE: 2720

Asp Thr Thr Gly Lys Tyr Thr
1               5

<210> SEQ ID NO 2721
<211> LENGTH: 8
<212> TYPE: PRT
<213> ORGANISM: Dependovirus adeno-associated virus

<400> SEQUENCE: 2721

Arg Ile Gly Thr Thr Ala Asn Ser
1               5
```

<210> SEQ ID NO 2722
<211> LENGTH: 10
<212> TYPE: PRT
<213> ORGANISM: Dependovirus adeno-associated virus

<400> SEQUENCE: 2722

Val Phe Met Val Pro Gln Tyr Gly Tyr Cys
1               5                   10

<210> SEQ ID NO 2723
<211> LENGTH: 9
<212> TYPE: PRT
<213> ORGANISM: Dependovirus adeno-associated virus

<400> SEQUENCE: 2723

Gly Asn Ser Leu Asn Gln Gly Thr Ala
1               5

<210> SEQ ID NO 2724
<211> LENGTH: 2
<212> TYPE: PRT
<213> ORGANISM: Dependovirus adeno-associated virus

<400> SEQUENCE: 2724

Ala Tyr
1

<210> SEQ ID NO 2725
<211> LENGTH: 12
<212> TYPE: PRT
<213> ORGANISM: Dependovirus adeno-associated virus

<400> SEQUENCE: 2725

Ala Asn Gln Asn Tyr Lys Ile Pro Ala Ser Gly Gly
1               5                   10

<210> SEQ ID NO 2726
<211> LENGTH: 7
<212> TYPE: PRT
<213> ORGANISM: Dependovirus adeno-associated virus

<400> SEQUENCE: 2726

Gly Ala Gly Asp Ser Asp Phe
1               5

<210> SEQ ID NO 2727
<211> LENGTH: 6
<212> TYPE: PRT
<213> ORGANISM: Dependovirus adeno-associated virus

<400> SEQUENCE: 2727

Pro Ser Gly Asn Thr Thr
1               5

<210> SEQ ID NO 2728
<211> LENGTH: 10
<212> TYPE: PRT
<213> ORGANISM: Dependovirus adeno-associated virus

<400> SEQUENCE: 2728

Thr Thr Ala Pro His Ile Ala Asn Leu Asp
1               5                   10

<210> SEQ ID NO 2729

```
<211> LENGTH: 2
<212> TYPE: PRT
<213> ORGANISM: Dependovirus adeno-associated virus

<400> SEQUENCE: 2729

Asn Ser
1

<210> SEQ ID NO 2730
<211> LENGTH: 7
<212> TYPE: PRT
<213> ORGANISM: Dependovirus adeno-associated virus

<400> SEQUENCE: 2730

Asp Asn Ala Gly Asn Tyr His
1               5

<210> SEQ ID NO 2731
<211> LENGTH: 8
<212> TYPE: PRT
<213> ORGANISM: Dependovirus adeno-associated virus

<400> SEQUENCE: 2731

Arg Leu Gly Thr Thr Ser Asn Ser
1               5

<210> SEQ ID NO 2732
<211> LENGTH: 10
<212> TYPE: PRT
<213> ORGANISM: Dependovirus adeno-associated virus

<400> SEQUENCE: 2732

Val Phe Met Val Pro Gln Tyr Gly Tyr Cys
1               5                   10

<210> SEQ ID NO 2733
<211> LENGTH: 9
<212> TYPE: PRT
<213> ORGANISM: Dependovirus adeno-associated virus

<400> SEQUENCE: 2733

Gly Glu Thr Leu Asn Gln Gly Asn Ala
1               5

<210> SEQ ID NO 2734
<211> LENGTH: 2
<212> TYPE: PRT
<213> ORGANISM: Dependovirus adeno-associated virus

<400> SEQUENCE: 2734

Ala Phe
1

<210> SEQ ID NO 2735
<211> LENGTH: 12
<212> TYPE: PRT
<213> ORGANISM: Dependovirus adeno-associated virus

<400> SEQUENCE: 2735

Ala Ser Gln Asn Tyr Lys Ile Pro Ala Ser Gly Gly
1               5                   10

<210> SEQ ID NO 2736
<211> LENGTH: 7
<212> TYPE: PRT
```

<213> ORGANISM: Dependovirus adeno-associated virus

<400> SEQUENCE: 2736

Gly Pro Ser Asp Gly Asp Phe
1               5

<210> SEQ ID NO 2737
<211> LENGTH: 6
<212> TYPE: PRT
<213> ORGANISM: Dependovirus adeno-associated virus

<400> SEQUENCE: 2737

Val Thr Gly Asn Thr Thr
1               5

<210> SEQ ID NO 2738
<211> LENGTH: 10
<212> TYPE: PRT
<213> ORGANISM: Dependovirus adeno-associated virus

<400> SEQUENCE: 2738

Thr Thr Ala Pro Ile Thr Gly Asn Val Thr
1               5                   10

<210> SEQ ID NO 2739
<211> LENGTH: 2
<212> TYPE: PRT
<213> ORGANISM: Dependovirus adeno-associated virus

<400> SEQUENCE: 2739

Ser Ser
1

<210> SEQ ID NO 2740
<211> LENGTH: 7
<212> TYPE: PRT
<213> ORGANISM: Dependovirus adeno-associated virus

<400> SEQUENCE: 2740

Asp Thr Thr Gly Lys Tyr Thr
1               5

<210> SEQ ID NO 2741
<211> LENGTH: 8
<212> TYPE: PRT
<213> ORGANISM: Dependovirus adeno-associated virus

<400> SEQUENCE: 2741

Arg Leu Gly Ser Ser Asn Ala Ser
1               5

<210> SEQ ID NO 2742
<211> LENGTH: 10
<212> TYPE: PRT
<213> ORGANISM: Dependovirus adeno-associated virus

<400> SEQUENCE: 2742

Val Phe Met Val Pro Gln Tyr Gly Tyr Cys
1               5                   10

<210> SEQ ID NO 2743
<211> LENGTH: 9
<212> TYPE: PRT
<213> ORGANISM: Dependovirus adeno-associated virus

```
<400> SEQUENCE: 2743

Gly Gly Thr Leu Asn Gln Gly Asn Ser
1               5

<210> SEQ ID NO 2744
<211> LENGTH: 2
<212> TYPE: PRT
<213> ORGANISM: Dependovirus adeno-associated virus

<400> SEQUENCE: 2744

Ser Gly
1

<210> SEQ ID NO 2745
<211> LENGTH: 12
<212> TYPE: PRT
<213> ORGANISM: Dependovirus adeno-associated virus

<400> SEQUENCE: 2745

Ala Ser Gln Asn Tyr Lys Ile Pro Gln Gly Arg Asn
1               5                   10

<210> SEQ ID NO 2746
<211> LENGTH: 7
<212> TYPE: PRT
<213> ORGANISM: Dependovirus adeno-associated virus

<400> SEQUENCE: 2746

Ala Asn Asp Ala Thr Asp Phe
1               5

<210> SEQ ID NO 2747
<211> LENGTH: 6
<212> TYPE: PRT
<213> ORGANISM: Dependovirus adeno-associated virus

<400> SEQUENCE: 2747

Ile Thr Gly Asn Thr Thr
1               5

<210> SEQ ID NO 2748
<211> LENGTH: 10
<212> TYPE: PRT
<213> ORGANISM: Dependovirus adeno-associated virus

<400> SEQUENCE: 2748

Thr Thr Val Pro Thr Val Asp Asp Val Asp
1               5                   10

<210> SEQ ID NO 2749
<211> LENGTH: 2
<212> TYPE: PRT
<213> ORGANISM: Dependovirus adeno-associated virus

<400> SEQUENCE: 2749

Asp Ser
1

<210> SEQ ID NO 2750
<211> LENGTH: 7
<212> TYPE: PRT
<213> ORGANISM: Dependovirus adeno-associated virus

<400> SEQUENCE: 2750
```

Asp Asn Ala Gly Ala Tyr Lys
1               5

<210> SEQ ID NO 2751
<211> LENGTH: 8
<212> TYPE: PRT
<213> ORGANISM: Dependovirus adeno-associated virus

<400> SEQUENCE: 2751

Arg Ile Gln Gly Pro Ser Gly Gly
1               5

<210> SEQ ID NO 2752
<211> LENGTH: 10
<212> TYPE: PRT
<213> ORGANISM: Dependovirus adeno-associated virus

<400> SEQUENCE: 2752

Ile Tyr Thr Ile Pro Gln Tyr Gly Tyr Cys
1               5                   10

<210> SEQ ID NO 2753
<211> LENGTH: 9
<212> TYPE: PRT
<213> ORGANISM: Dependovirus adeno-associated virus

<400> SEQUENCE: 2753

Val Ser Gln Ala Gly Ser Ser Gly Arg
1               5

<210> SEQ ID NO 2754
<211> LENGTH: 2
<212> TYPE: PRT
<213> ORGANISM: Dependovirus adeno-associated virus

<400> SEQUENCE: 2754

Ala Ala
1

<210> SEQ ID NO 2755
<211> LENGTH: 12
<212> TYPE: PRT
<213> ORGANISM: Dependovirus adeno-associated virus

<400> SEQUENCE: 2755

Ala Ser Asn Ile Thr Lys Asn Asn Val Phe Ser Val
1               5                   10

<210> SEQ ID NO 2756
<211> LENGTH: 7
<212> TYPE: PRT
<213> ORGANISM: Dependovirus adeno-associated virus

<400> SEQUENCE: 2756

Phe Ser Gly Glu Pro Asp Arg
1               5

<210> SEQ ID NO 2757
<211> LENGTH: 8
<212> TYPE: PRT
<213> ORGANISM: Dependovirus adeno-associated virus

<400> SEQUENCE: 2757

Val Tyr Asp Gln Thr Thr Ala Thr
1               5

```
<210> SEQ ID NO 2758
<211> LENGTH: 10
<212> TYPE: PRT
<213> ORGANISM: Dependovirus adeno-associated virus

<400> SEQUENCE: 2758

Val Thr Pro Gly Thr Arg Ala Ala Val Asn
1               5                   10

<210> SEQ ID NO 2759
<211> LENGTH: 2
<212> TYPE: PRT
<213> ORGANISM: Dependovirus adeno-associated virus

<400> SEQUENCE: 2759

Ala Asp
1

<210> SEQ ID NO 2760
<211> LENGTH: 7
<212> TYPE: PRT
<213> ORGANISM: Dependovirus adeno-associated virus

<400> SEQUENCE: 2760

Ser Asp Thr Gly Ser Tyr Ser
1               5

<210> SEQ ID NO 2761

<400> SEQUENCE: 2761

000

<210> SEQ ID NO 2762

<400> SEQUENCE: 2762

000

<210> SEQ ID NO 2763

<400> SEQUENCE: 2763

000

<210> SEQ ID NO 2764

<400> SEQUENCE: 2764

000

<210> SEQ ID NO 2765

<400> SEQUENCE: 2765

000

<210> SEQ ID NO 2766

<400> SEQUENCE: 2766

000

<210> SEQ ID NO 2767
```

<400> SEQUENCE: 2767

000

<210> SEQ ID NO 2768

<400> SEQUENCE: 2768

000

<210> SEQ ID NO 2769

<400> SEQUENCE: 2769

000

<210> SEQ ID NO 2770

<400> SEQUENCE: 2770

000

<210> SEQ ID NO 2771

<400> SEQUENCE: 2771

000

<210> SEQ ID NO 2772

<400> SEQUENCE: 2772

000

<210> SEQ ID NO 2773

<400> SEQUENCE: 2773

000

<210> SEQ ID NO 2774

<400> SEQUENCE: 2774

000

<210> SEQ ID NO 2775

<400> SEQUENCE: 2775

000

<210> SEQ ID NO 2776

<400> SEQUENCE: 2776

000

<210> SEQ ID NO 2777

<400> SEQUENCE: 2777

000

<210> SEQ ID NO 2778

<400> SEQUENCE: 2778

000

<210> SEQ ID NO 2779

<400> SEQUENCE: 2779

000

<210> SEQ ID NO 2780

<400> SEQUENCE: 2780

000

<210> SEQ ID NO 2781

<400> SEQUENCE: 2781

000

<210> SEQ ID NO 2782

<400> SEQUENCE: 2782

000

<210> SEQ ID NO 2783

<400> SEQUENCE: 2783

000

<210> SEQ ID NO 2784

<400> SEQUENCE: 2784

000

<210> SEQ ID NO 2785

<400> SEQUENCE: 2785

000

<210> SEQ ID NO 2786

<400> SEQUENCE: 2786

000

<210> SEQ ID NO 2787

<400> SEQUENCE: 2787

000

<210> SEQ ID NO 2788

<400> SEQUENCE: 2788

000

<210> SEQ ID NO 2789

<400> SEQUENCE: 2789

000

<210> SEQ ID NO 2790

<400> SEQUENCE: 2790

000

<210> SEQ ID NO 2791

<400> SEQUENCE: 2791

000

<210> SEQ ID NO 2792

<400> SEQUENCE: 2792

000

<210> SEQ ID NO 2793

<400> SEQUENCE: 2793

000

<210> SEQ ID NO 2794

<400> SEQUENCE: 2794

000

<210> SEQ ID NO 2795

<400> SEQUENCE: 2795

000

<210> SEQ ID NO 2796

<400> SEQUENCE: 2796

000

<210> SEQ ID NO 2797

<400> SEQUENCE: 2797

000

<210> SEQ ID NO 2798

<400> SEQUENCE: 2798

000

<210> SEQ ID NO 2799

<400> SEQUENCE: 2799

000

<210> SEQ ID NO 2800

<400> SEQUENCE: 2800

000

<210> SEQ ID NO 2801

-continued

<400> SEQUENCE: 2801

000

<210> SEQ ID NO 2802

<400> SEQUENCE: 2802

000

<210> SEQ ID NO 2803

<400> SEQUENCE: 2803

000

<210> SEQ ID NO 2804

<400> SEQUENCE: 2804

000

<210> SEQ ID NO 2805

<400> SEQUENCE: 2805

000

<210> SEQ ID NO 2806

<400> SEQUENCE: 2806

000

<210> SEQ ID NO 2807

<400> SEQUENCE: 2807

000

<210> SEQ ID NO 2808

<400> SEQUENCE: 2808

000

<210> SEQ ID NO 2809

<400> SEQUENCE: 2809

000

<210> SEQ ID NO 2810

<400> SEQUENCE: 2810

000

<210> SEQ ID NO 2811

<400> SEQUENCE: 2811

000

<210> SEQ ID NO 2812

<400> SEQUENCE: 2812

000

<210> SEQ ID NO 2813

<400> SEQUENCE: 2813

000

<210> SEQ ID NO 2814

<400> SEQUENCE: 2814

000

<210> SEQ ID NO 2815

<400> SEQUENCE: 2815

000

<210> SEQ ID NO 2816

<400> SEQUENCE: 2816

000

<210> SEQ ID NO 2817

<400> SEQUENCE: 2817

000

<210> SEQ ID NO 2818

<400> SEQUENCE: 2818

000

<210> SEQ ID NO 2819

<400> SEQUENCE: 2819

000

<210> SEQ ID NO 2820

<400> SEQUENCE: 2820

000

<210> SEQ ID NO 2821

<400> SEQUENCE: 2821

000

<210> SEQ ID NO 2822

<400> SEQUENCE: 2822

000

<210> SEQ ID NO 2823

<400> SEQUENCE: 2823

000

<210> SEQ ID NO 2824

<400> SEQUENCE: 2824

000

<210> SEQ ID NO 2825

<400> SEQUENCE: 2825

000

<210> SEQ ID NO 2826

<400> SEQUENCE: 2826

000

<210> SEQ ID NO 2827

<400> SEQUENCE: 2827

000

<210> SEQ ID NO 2828

<400> SEQUENCE: 2828

000

<210> SEQ ID NO 2829

<400> SEQUENCE: 2829

000

<210> SEQ ID NO 2830

<400> SEQUENCE: 2830

000

<210> SEQ ID NO 2831

<400> SEQUENCE: 2831

000

<210> SEQ ID NO 2832

<400> SEQUENCE: 2832

000

<210> SEQ ID NO 2833

<400> SEQUENCE: 2833

000

<210> SEQ ID NO 2834

<400> SEQUENCE: 2834

000

<210> SEQ ID NO 2835

<400> SEQUENCE: 2835

000

<210> SEQ ID NO 2836

<400> SEQUENCE: 2836

000

<210> SEQ ID NO 2837

<400> SEQUENCE: 2837

000

<210> SEQ ID NO 2838

<400> SEQUENCE: 2838

000

<210> SEQ ID NO 2839

<400> SEQUENCE: 2839

000

<210> SEQ ID NO 2840

<400> SEQUENCE: 2840

000

<210> SEQ ID NO 2841

<400> SEQUENCE: 2841

000

<210> SEQ ID NO 2842

<400> SEQUENCE: 2842

000

<210> SEQ ID NO 2843

<400> SEQUENCE: 2843

000

<210> SEQ ID NO 2844

<400> SEQUENCE: 2844

000

<210> SEQ ID NO 2845

<400> SEQUENCE: 2845

000

<210> SEQ ID NO 2846

<400> SEQUENCE: 2846

000

<210> SEQ ID NO 2847

<400> SEQUENCE: 2847

000

<210> SEQ ID NO 2848

<400> SEQUENCE: 2848

000

<210> SEQ ID NO 2849

<400> SEQUENCE: 2849

000

<210> SEQ ID NO 2850

<400> SEQUENCE: 2850

000

<210> SEQ ID NO 2851

<400> SEQUENCE: 2851

000

<210> SEQ ID NO 2852

<400> SEQUENCE: 2852

000

<210> SEQ ID NO 2853

<400> SEQUENCE: 2853

000

<210> SEQ ID NO 2854

<400> SEQUENCE: 2854

000

<210> SEQ ID NO 2855

<400> SEQUENCE: 2855

000

<210> SEQ ID NO 2856

<400> SEQUENCE: 2856

000

<210> SEQ ID NO 2857

<400> SEQUENCE: 2857

000

<210> SEQ ID NO 2858

<400> SEQUENCE: 2858

000

<210> SEQ ID NO 2859

<400> SEQUENCE: 2859

000

<210> SEQ ID NO 2860

<400> SEQUENCE: 2860

000

<210> SEQ ID NO 2861

<400> SEQUENCE: 2861

000

<210> SEQ ID NO 2862

<400> SEQUENCE: 2862

000

<210> SEQ ID NO 2863

<400> SEQUENCE: 2863

000

<210> SEQ ID NO 2864

<400> SEQUENCE: 2864

000

<210> SEQ ID NO 2865

<400> SEQUENCE: 2865

000

<210> SEQ ID NO 2866

<400> SEQUENCE: 2866

000

<210> SEQ ID NO 2867

<400> SEQUENCE: 2867

000

<210> SEQ ID NO 2868

<400> SEQUENCE: 2868

000

<210> SEQ ID NO 2869
<400> SEQUENCE: 2869
000

<210> SEQ ID NO 2870
<400> SEQUENCE: 2870
000

<210> SEQ ID NO 2871
<400> SEQUENCE: 2871
000

<210> SEQ ID NO 2872
<400> SEQUENCE: 2872
000

<210> SEQ ID NO 2873
<400> SEQUENCE: 2873
000

<210> SEQ ID NO 2874
<400> SEQUENCE: 2874
000

<210> SEQ ID NO 2875
<400> SEQUENCE: 2875
000

<210> SEQ ID NO 2876
<400> SEQUENCE: 2876
000

<210> SEQ ID NO 2877
<400> SEQUENCE: 2877
000

<210> SEQ ID NO 2878
<400> SEQUENCE: 2878
000

<210> SEQ ID NO 2879
<400> SEQUENCE: 2879
000

<210> SEQ ID NO 2880

<400> SEQUENCE: 2880

000

<210> SEQ ID NO 2881

<400> SEQUENCE: 2881

000

<210> SEQ ID NO 2882

<400> SEQUENCE: 2882

000

<210> SEQ ID NO 2883

<400> SEQUENCE: 2883

000

<210> SEQ ID NO 2884

<400> SEQUENCE: 2884

000

<210> SEQ ID NO 2885

<400> SEQUENCE: 2885

000

<210> SEQ ID NO 2886

<400> SEQUENCE: 2886

000

<210> SEQ ID NO 2887

<400> SEQUENCE: 2887

000

<210> SEQ ID NO 2888

<400> SEQUENCE: 2888

000

<210> SEQ ID NO 2889

<400> SEQUENCE: 2889

000

<210> SEQ ID NO 2890

<400> SEQUENCE: 2890

000

<210> SEQ ID NO 2891

<400> SEQUENCE: 2891

000

<210> SEQ ID NO 2892

<400> SEQUENCE: 2892

000

<210> SEQ ID NO 2893

<400> SEQUENCE: 2893

000

<210> SEQ ID NO 2894

<400> SEQUENCE: 2894

000

<210> SEQ ID NO 2895

<400> SEQUENCE: 2895

000

<210> SEQ ID NO 2896

<400> SEQUENCE: 2896

000

<210> SEQ ID NO 2897

<400> SEQUENCE: 2897

000

<210> SEQ ID NO 2898

<400> SEQUENCE: 2898

000

<210> SEQ ID NO 2899

<400> SEQUENCE: 2899

000

<210> SEQ ID NO 2900

<400> SEQUENCE: 2900

000

<210> SEQ ID NO 2901

<400> SEQUENCE: 2901

000

<210> SEQ ID NO 2902

<400> SEQUENCE: 2902

000

<210> SEQ ID NO 2903

<400> SEQUENCE: 2903

000

<210> SEQ ID NO 2904

<400> SEQUENCE: 2904

000

<210> SEQ ID NO 2905

<400> SEQUENCE: 2905

000

<210> SEQ ID NO 2906

<400> SEQUENCE: 2906

000

<210> SEQ ID NO 2907

<400> SEQUENCE: 2907

000

<210> SEQ ID NO 2908

<400> SEQUENCE: 2908

000

<210> SEQ ID NO 2909

<400> SEQUENCE: 2909

000

<210> SEQ ID NO 2910

<400> SEQUENCE: 2910

000

<210> SEQ ID NO 2911

<400> SEQUENCE: 2911

000

<210> SEQ ID NO 2912

<400> SEQUENCE: 2912

000

<210> SEQ ID NO 2913

<400> SEQUENCE: 2913

000

<210> SEQ ID NO 2914

<400> SEQUENCE: 2914

000

<210> SEQ ID NO 2915

<400> SEQUENCE: 2915

000

<210> SEQ ID NO 2916

<400> SEQUENCE: 2916

000

<210> SEQ ID NO 2917

<400> SEQUENCE: 2917

000

<210> SEQ ID NO 2918

<400> SEQUENCE: 2918

000

<210> SEQ ID NO 2919

<400> SEQUENCE: 2919

000

<210> SEQ ID NO 2920

<400> SEQUENCE: 2920

000

<210> SEQ ID NO 2921

<400> SEQUENCE: 2921

000

<210> SEQ ID NO 2922

<400> SEQUENCE: 2922

000

<210> SEQ ID NO 2923

<400> SEQUENCE: 2923

000

<210> SEQ ID NO 2924

<400> SEQUENCE: 2924

000

<210> SEQ ID NO 2925

<400> SEQUENCE: 2925

000

<210> SEQ ID NO 2926

<400> SEQUENCE: 2926

000

<210> SEQ ID NO 2927

<400> SEQUENCE: 2927

000

<210> SEQ ID NO 2928

<400> SEQUENCE: 2928

000

<210> SEQ ID NO 2929

<400> SEQUENCE: 2929

000

<210> SEQ ID NO 2930

<400> SEQUENCE: 2930

000

<210> SEQ ID NO 2931

<400> SEQUENCE: 2931

000

<210> SEQ ID NO 2932

<400> SEQUENCE: 2932

000

<210> SEQ ID NO 2933

<400> SEQUENCE: 2933

000

<210> SEQ ID NO 2934

<400> SEQUENCE: 2934

000

<210> SEQ ID NO 2935

<400> SEQUENCE: 2935

000

<210> SEQ ID NO 2936

<400> SEQUENCE: 2936

000

<210> SEQ ID NO 2937

<400> SEQUENCE: 2937

000

<210> SEQ ID NO 2938

<400> SEQUENCE: 2938

000

<210> SEQ ID NO 2939

<400> SEQUENCE: 2939

000

<210> SEQ ID NO 2940

<400> SEQUENCE: 2940

000

<210> SEQ ID NO 2941

<400> SEQUENCE: 2941

000

<210> SEQ ID NO 2942

<400> SEQUENCE: 2942

000

<210> SEQ ID NO 2943

<400> SEQUENCE: 2943

000

<210> SEQ ID NO 2944

<400> SEQUENCE: 2944

000

<210> SEQ ID NO 2945

<400> SEQUENCE: 2945

000

<210> SEQ ID NO 2946

<400> SEQUENCE: 2946

000

<210> SEQ ID NO 2947

<400> SEQUENCE: 2947

000

<210> SEQ ID NO 2948
<400> SEQUENCE: 2948
000

<210> SEQ ID NO 2949
<400> SEQUENCE: 2949
000

<210> SEQ ID NO 2950
<400> SEQUENCE: 2950
000

<210> SEQ ID NO 2951
<400> SEQUENCE: 2951
000

<210> SEQ ID NO 2952
<400> SEQUENCE: 2952
000

<210> SEQ ID NO 2953
<400> SEQUENCE: 2953
000

<210> SEQ ID NO 2954
<400> SEQUENCE: 2954
000

<210> SEQ ID NO 2955
<400> SEQUENCE: 2955
000

<210> SEQ ID NO 2956
<400> SEQUENCE: 2956
000

<210> SEQ ID NO 2957
<400> SEQUENCE: 2957
000

<210> SEQ ID NO 2958
<400> SEQUENCE: 2958
000

<210> SEQ ID NO 2959

<400> SEQUENCE: 2959

000

<210> SEQ ID NO 2960

<400> SEQUENCE: 2960

000

<210> SEQ ID NO 2961

<400> SEQUENCE: 2961

000

<210> SEQ ID NO 2962

<400> SEQUENCE: 2962

000

<210> SEQ ID NO 2963

<400> SEQUENCE: 2963

000

<210> SEQ ID NO 2964

<400> SEQUENCE: 2964

000

<210> SEQ ID NO 2965

<400> SEQUENCE: 2965

000

<210> SEQ ID NO 2966

<400> SEQUENCE: 2966

000

<210> SEQ ID NO 2967

<400> SEQUENCE: 2967

000

<210> SEQ ID NO 2968

<400> SEQUENCE: 2968

000

<210> SEQ ID NO 2969

<400> SEQUENCE: 2969

000

<210> SEQ ID NO 2970

<400> SEQUENCE: 2970

000

<210> SEQ ID NO 2971

<400> SEQUENCE: 2971

000

<210> SEQ ID NO 2972

<400> SEQUENCE: 2972

000

<210> SEQ ID NO 2973

<400> SEQUENCE: 2973

000

<210> SEQ ID NO 2974

<400> SEQUENCE: 2974

000

<210> SEQ ID NO 2975

<400> SEQUENCE: 2975

000

<210> SEQ ID NO 2976

<400> SEQUENCE: 2976

000

<210> SEQ ID NO 2977

<400> SEQUENCE: 2977

000

<210> SEQ ID NO 2978

<400> SEQUENCE: 2978

000

<210> SEQ ID NO 2979

<400> SEQUENCE: 2979

000

<210> SEQ ID NO 2980

<400> SEQUENCE: 2980

000

<210> SEQ ID NO 2981

<400> SEQUENCE: 2981

000

<210> SEQ ID NO 2982

<400> SEQUENCE: 2982

000

<210> SEQ ID NO 2983

<400> SEQUENCE: 2983

000

<210> SEQ ID NO 2984

<400> SEQUENCE: 2984

000

<210> SEQ ID NO 2985

<400> SEQUENCE: 2985

000

<210> SEQ ID NO 2986

<400> SEQUENCE: 2986

000

<210> SEQ ID NO 2987

<400> SEQUENCE: 2987

000

<210> SEQ ID NO 2988

<400> SEQUENCE: 2988

000

<210> SEQ ID NO 2989

<400> SEQUENCE: 2989

000

<210> SEQ ID NO 2990

<400> SEQUENCE: 2990

000

<210> SEQ ID NO 2991

<400> SEQUENCE: 2991

000

<210> SEQ ID NO 2992

<400> SEQUENCE: 2992

000

<210> SEQ ID NO 2993

<400> SEQUENCE: 2993

000

<210> SEQ ID NO 2994

<400> SEQUENCE: 2994

000

<210> SEQ ID NO 2995

<400> SEQUENCE: 2995

000

<210> SEQ ID NO 2996

<400> SEQUENCE: 2996

000

<210> SEQ ID NO 2997

<400> SEQUENCE: 2997

000

<210> SEQ ID NO 2998

<400> SEQUENCE: 2998

000

<210> SEQ ID NO 2999

<400> SEQUENCE: 2999

000

<210> SEQ ID NO 3000

<400> SEQUENCE: 3000

000

<210> SEQ ID NO 3001
<211> LENGTH: 1278
<212> TYPE: PRT
<213> ORGANISM: Homo sapiens

<400> SEQUENCE: 3001

```
Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
                20                  25                  30

Ile Ala Tyr Gly Asp Lys Arg Tyr Asn Cys Glu Tyr Ser Gly Pro Pro
            35                  40                  45

Lys Pro Leu Pro Lys Asp Gly Tyr Asp Leu Val Gln Glu Leu Cys Pro
        50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
```

```
                    85                  90                  95
Cys Pro Ser Cys Phe Tyr Asn Leu Leu Asn Leu Phe Cys Glu Leu Thr
                100                 105                 110

Cys Ser Pro Arg Gln Ser Gln Phe Leu Asn Val Thr Ala Thr Glu Asp
                115                 120                 125

Tyr Val Asp Pro Val Thr Asn Gln Thr Lys Thr Asn Val Lys Glu Leu
130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
                180                 185                 190

Met Phe Asn Lys Asp Asn Gly Gln Ala Pro Phe Thr Ile Thr Pro Val
                195                 200                 205

Phe Ser Asp Phe Pro Val His Gly Met Glu Pro Met Asn Asn Ala Thr
210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
                260                 265                 270

Trp Ile Thr Tyr Met Ala Phe Leu Leu Val Phe Phe Gly Ala Phe Phe
                275                 280                 285

Ala Val Trp Cys Tyr Arg Lys Arg Tyr Phe Val Ser Glu Tyr Thr Pro
                290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
                340                 345                 350

Val Ile Phe Phe Ser Leu Val Phe Ile Thr Ala Cys Ser Ser Gly Leu
                355                 360                 365

Val Phe Val Arg Val Thr Thr Asn Pro Val Asp Leu Trp Ser Ala Pro
                370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
                420                 425                 430

Pro Pro Leu Asp Ile Gln Ile Leu His Gln Val Leu Asp Leu Gln Ile
                435                 440                 445

Ala Ile Glu Asn Ile Thr Ala Ser Tyr Asp Asn Glu Thr Val Thr Leu
                450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Phe Val Tyr Ala Asp Tyr His Thr His
                500                 505                 510
```

```
Phe Leu Tyr Cys Val Arg Ala Pro Ala Ser Leu Asn Asp Thr Ser Leu
            515                 520                 525

Leu His Asp Pro Cys Leu Gly Thr Phe Gly Gly Pro Val Phe Pro Trp
        530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
            580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
    610                 615                 620

Val Ile Ser Tyr Ala Ile Met Phe Leu Tyr Ile Ser Leu Ala Leu Gly
625                 630                 635                 640

His Ile Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
            660                 665                 670

Gly Val Phe Ser Tyr Ile Gly Leu Pro Leu Thr Leu Ile Val Ile Glu
        675                 680                 685

Val Ile Pro Phe Leu Val Leu Ala Val Gly Val Asp Asn Ile Phe Ile
    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
            740                 745                 750

Val Met Pro Ala Val His Thr Phe Ser Leu Phe Ala Gly Leu Ala Val
        755                 760                 765

Phe Ile Asp Phe Leu Leu Gln Ile Thr Cys Phe Val Ser Leu Leu Gly
    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
            820                 825                 830

Trp Met Arg Pro Ile Val Ile Ala Ile Phe Val Gly Val Leu Ser Phe
        835                 840                 845

Ser Ile Ala Val Leu Asn Lys Val Asp Ile Gly Leu Asp Gln Ser Leu
    850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
            900                 905                 910

Gly Cys Asn Asn Asp Ser Leu Val Gln Gln Ile Phe Asn Ala Ala Gln
        915                 920                 925
```

```
Leu Asp Asn Tyr Thr Arg Ile Gly Phe Ala Pro Ser Ser Trp Ile Asp
        930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
                965                 970                 975

Val Arg Cys Arg Pro Leu Thr Pro Glu Gly Lys Gln Arg Pro Gln Gly
                980                 985                 990

Gly Asp Phe Met Arg Phe Leu Pro Met Phe Leu Ser Asp Asn Pro Asn
            995                 1000                1005

Pro Lys Cys Gly Lys Gly Gly His Ala Ala Tyr Ser Ser Ala Val
    1010                1015                1020

Asn Ile Leu Leu Gly His Gly Thr Arg Val Gly Ala Thr Tyr Phe
    1025                1030                1035

Met Thr Tyr His Thr Val Leu Gln Thr Ser Ala Asp Phe Ile Asp
    1040                1045                1050

Ala Leu Lys Lys Ala Arg Leu Ile Ala Ser Asn Val Thr Glu Thr
    1055                1060                1065

Met Gly Ile Asn Gly Ser Ala Tyr Arg Val Phe Pro Tyr Ser Val
    1070                1075                1080

Phe Tyr Val Phe Tyr Glu Gln Tyr Leu Thr Ile Ile Asp Asp Thr
    1085                1090                1095

Ile Phe Asn Leu Gly Val Ser Leu Gly Ala Ile Phe Leu Val Thr
    1100                1105                1110

Met Val Leu Leu Gly Cys Glu Leu Trp Ser Ala Val Ile Met Cys
    1115                1120                1125

Ala Thr Ile Ala Met Val Leu Val Asn Met Phe Gly Val Met Trp
    1130                1135                1140

Leu Trp Gly Ile Ser Leu Asn Ala Val Ser Leu Val Asn Leu Val
    1145                1150                1155

Met Ser Cys Gly Ile Ser Val Glu Phe Cys Ser His Ile Thr Arg
    1160                1165                1170

Ala Phe Thr Val Ser Met Lys Gly Ser Arg Val Glu Arg Ala Glu
    1175                1180                1185

Glu Ala Leu Ala His Met Gly Ser Ser Val Phe Ser Gly Ile Thr
    1190                1195                1200

Leu Thr Lys Phe Gly Gly Ile Val Val Leu Ala Phe Ala Lys Ser
    1205                1210                1215

Gln Ile Phe Gln Ile Phe Tyr Phe Arg Met Tyr Leu Ala Met Val
    1220                1225                1230

Leu Leu Gly Ala Thr His Gly Leu Ile Phe Leu Pro Val Leu Leu
    1235                1240                1245

Ser Tyr Ile Gly Pro Ser Val Asn Lys Ala Lys Ser Cys Ala Thr
    1250                1255                1260

Glu Glu Arg Tyr Lys Gly Thr Glu Arg Glu Arg Leu Leu Asn Phe
    1265                1270                1275

<210> SEQ ID NO 3002
<211> LENGTH: 3834
<212> TYPE: DNA
<213> ORGANISM: Homo sapiens

<400> SEQUENCE: 3002
atgaccgctc gcggcctggc ccttggcctc ctcctgctgc tactgtgtcc agcgcaggtg      60
```

```
ttttcacagt cctgtgtttg gtatggagag tgtggaattg catatgggga caagaggtac    120
aattgcgaat attctggccc accaaaacca ttgccaaagg atggatatga cttagtgcag    180
gaactctgtc caggattctt ctttggcaat gtcagtctct gttgtgatgt tcggcagctt    240
cagacactaa aagacaacct gcagctgcct ctacagtttc tgtccagatg tccatcctgt    300
ttttataacc tactgaacct gttttgtgag ctgacatgta gccctcgaca gagtcagttt    360
ttgaatgtta cagctactga agattatgtt gatcctgtta caaaccagac gaaaacaaat    420
gtgaaagagt tacaatacta cgtcggacag agttttgcca atgcaatgta caatgcctgc    480
cgggatgtgg aggcccccte aagtaatgac aaggccctgg gactcctgtg tgggaaggac    540
gctgacgcct gtaatgccac caactggatt gaatacatgt tcaataagga caatggacag    600
gcacctttta ccatcactcc tgtgttttca gattttccag tccatgggat ggagcccatg    660
aacaatgcca ccaaaggctg tgacgagtct gtggatgagg tcacagcacc atgtagctgc    720
caagactgct ctattgtctg tggccccaag ccccagcccc cacctcctcc tgctccctgg    780
acgatccttg gcttggacgc catgtatgtc atcatgtgga tcacctacat ggcgttttg    840 cttgtgtttt ttggagcatt ttttgcagtg tggtgctaca gaaaacggta ttttgtctcc    900
gagtacactc ccatcgatag caatatagct ttttctgtta atgcaagtga caaggagag    960 gcgtcctgct gtgaccctgt cagcgcagca tttgagggct gcttgaggcg gctgttcaca   1020
cgctgggggt ctttctgcgt ccgaaaccct ggctgtgtca ttttcttctc gctggtcttc   1080
attactgcgt gttcgtcagg cctggtgttt gtccgggtca caaccaatcc agttgacctc   1140
tggtcagccc ccagcagcca ggctcgcctg gaaaaagagt actttgacca gcactttggg   1200
cctttcttcc ggacggagca gctcatcatc cgggcccctc tcactgacaa acacatttac   1260
cagccatacc cttcgggagc tgatgtaccc tttggacctc cgcttgacat acagatactg   1320
caccaggttc ttgacttaca aatagccatc gaaaacatta ctgcctctta tgacaatgag   1380
actgtgacac ttcaagacat ctgccttggcc cctctttcac cgtataacac gaactgcacc   1440
attttgagtg tgttaaatta cttccagaac agccattccg tgctggacca caagaaaggg   1500
gacgacttct ttgtgtatgc cgattaccac acgcactttc tgtactgcgt acgggctcct   1560
gcctctctga atgatacaag tttgctccat gacccttgtc tgggtacgtt tggtggacca   1620
gtgttcccgt ggcttgtgtt gggaggctat gatgatcaaa actacaataa cgccactgcc   1680
cttgtgatta ccttccctgt caataattac tataatgata cagagaagct ccagagggcc   1740
caggcctggg aaaaagagtt tattaatttt gtgaaaaact acaagaatcc caatctgacc   1800
atttccttca ctgctgaacg aagtattgaa gatgaactaa atcgtgaaag tgacagtgat   1860
gtcttcaccg ttgtaattag ctatgccatc atgtttctat atatttccct agccttgggg   1920
cacatcaaaa gctgtcgcag gcttctggtg gattcgaagg tctcactagg catcgcgggc   1980
atcttgatcg tgctgagctc ggtggcttgc ccttgggtg tcttcagcta cattgggttg   2040
cccttgaccc tcattgtgat tgaagtcatc ccgttcctgg tgctggctgt ggagtggac   2100 aacatcttca ttctggtgca ggcctaccag agagatgaac gtcttcaagg ggaaaccctg   2160
gatcagcagc tgggcagggt cctaggagaa gtggctccca gtatgttcct gtcatccttt   2220
tctgagactg tagcattttt cttaggagca ttgtccgtga tgccagccgt gcacaccttc   2280
tctctctttg cgggattggc agtcttcatt gactttcttc tgcagattac ctgtttcgtg   2340
agtctcttgg ggttagacat taaacgtcaa gagaaaaatc ggctagacat cttttgctgt   2400
gtcagaggtg ctgaagatgg aacaagcgtc caggcctcag agagctgttt gtttcgcttc   2460
```

```
ttcaaaaact cctattctcc acttctgcta aaggactgga tgagaccaat tgtgatagca    2520
atatttgtgg gtgttctgtc attcagcatc gcagtcctga acaaagtaga tattggattg    2580
gatcagtctc tttcgatgcc agatgactcc tacatggtgg attatttcaa atccatcagt    2640
cagtacctgc atgcgggtcc gcctgtgtac tttgtcctgg aggaagggca cgactacact    2700
tcttccaagg ggcagaacat ggtgtgcggc ggcatgggct gcaacaatga ttccctggtg    2760
cagcagatat ttaacgcggc gcagctggac aactataccc gaataggctt cgcccctcg     2820 tcctggatcg acgattattt cgactgggtg aagccacagt cgtcttgctg tcgagtggac    2880
aatatcactg accagttctg caatgcttca gtggttgacc ctgcctgcgt tcgctgcagg    2940
cctctgactc cggaaggcaa acagaggcct caggggggag acttcatgag attcctgccc    3000
atgttccttt cggataaccc taaccccaag tgtggcaaag gggacatgc tgcctatagt     3060 tctgcagtta acatcctcct tggccatggc accagggtcg agccacgta cttcatgacc     3120 taccacaccg tgctgcagac ctctgctgac tttattgacg ctctgaagaa agcccgactt    3180
atagccagta atgtcaccga aaccatgggc attaacggca gtgcctaccg agtatttcct    3240
tacagtgtgt tttatgtctt ctacgaacag tacctgacca tcattgacga cactatcttc    3300
aacctcggtg tgtccctggg cgcgatattt ctggtgacca tggtcctcct gggctgtgag    3360
ctctggtctg cagtcatcat gtgtgccacc atcgccatgg tcttggtcaa catgtttgga    3420
gttatgtggc tctgggcat cagtctgaac gctgtatcct tggtcaacct ggtgatgagc     3480
tgtggcatct ccgtggagtt ctgcagccac ataaccagag cgttcacggt gagcatgaaa    3540
ggcagccgcg tggagcgcgc ggaagaggca cttgcccaca tgggcagctc cgtgttcagt    3600
ggaatcacac ttacaaaatt tggagggatt gtggtgttgg cttttgccaa atctcaaatt    3660
ttccagatat tctacttcag gatgtatttg gccatggtct tactgggagc cactcacgga    3720
ttaatatttc tccctgtctt actcagttac ataggggccat cagtaaataa agccaaaagt    3780
tgtgccactg aagagcgata caaaggaaca gagcgcgaac ggcttctaaa tttc           3834
```

<210> SEQ ID NO 3003
<211> LENGTH: 141
<212> TYPE: DNA
<213> ORGANISM: Artificial Sequence
<220> FEATURE:
<223> OTHER INFORMATION: 5 prime Inverted Terminal Repeat

<400> SEQUENCE: 3003

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggttcc t                                                141
```

<210> SEQ ID NO 3004
<211> LENGTH: 141
<212> TYPE: DNA
<213> ORGANISM: Artificial Sequence
<220> FEATURE:
<223> OTHER INFORMATION: 3 prime Inverted Terminal Repeat

<400> SEQUENCE: 3004

```
aggaacccct agtgatggag ttggccactc cctctctgcg cgctcgctcg ctcactgagg      60
ccgggcgacc aaaggtcgcc cgacgcccgg gctttgcccg gcggcctcag tgagcgagc      120 gagcgcgcag ctgcctgcag g                                               141
```

<210> SEQ ID NO 3005
<211> LENGTH: 278
<212> TYPE: DNA
<213> ORGANISM: Gallus gallus

<400> SEQUENCE: 3005

| | | |
|---|---|---|
| tcgaggtgag ccccacgttc tgcttcactc tccccatctc cccccctcc ccaccccaa | 60 |
| ttttgtattt atttattttt taattatttt gtgcagcgat gggggcgggg ggggggggg | 120 |
| ggcgcgcgcc aggcggggcg gggcggggcg aggggcgggg cggggcgagg cggagaggtg | 180 |
| cggcggcagc caatcagagc ggcgcgctcc gaaagtttcc ttttatggcg aggcggcggc | 240 |
| ggcggcggcc ctataaaaag cgaagcgcgc ggcgggcg | 278 |

<210> SEQ ID NO 3006
<211> LENGTH: 240
<212> TYPE: DNA
<213> ORGANISM: Artificial Sequence
<220> FEATURE:
<223> OTHER INFORMATION: GUSB240 Promoter

<400> SEQUENCE: 3006

| | | |
|---|---|---|
| cggctggggc tgagggtgag ggtcccgttt ccccaaaggc ctagcctggg gttccagcca | 60 |
| caagccctac cgggcagcgc ccggccccgc ccctccaggc ctggcactcg tcctcaacca | 120 |
| agatggcgcg gatggcttca ggcgcatcac gacaccggcg cgtcacgcga cccgccctac | 180 |
| gggcacctcc cgcgcttttc ttagcgccgc agacggtggc cgagcggggg accgggaagc | 240 |

<210> SEQ ID NO 3007
<211> LENGTH: 379
<212> TYPE: DNA
<213> ORGANISM: Artificial Sequence
<220> FEATURE:
<223> OTHER INFORMATION: GUSB379 Promoter

<400> SEQUENCE: 3007

| | | |
|---|---|---|
| attcctgctg ggaaaagcaa gtggaggtgc tccttgaaga aacaggggga tcccaccgat | 60 |
| ctcaggggtt ctgttctggc ctgcggccct ggatcgtcca gcctgggtcg gggtggggag | 120 |
| cagacctcgc ccttatcggc tggggctgag ggtgagggtc ccgtttcccc aaaggcctag | 180 |
| cctggggttc cagccacaag ccctaccggg cagcgcccgg ccccgcccct ccaggcctgg | 240 |
| cactcgtcct caaccaagat ggcgcggatg gcttcaggcg catcacgaca ccggcgcgtc | 300 |
| acgcgacccg ccctacgggc acctcccgcg cttttcttag cgccgcagac ggtggtcgag | 360 |
| cgggggaccg ggaagctta | 379 |

<210> SEQ ID NO 3008
<211> LENGTH: 146
<212> TYPE: DNA
<213> ORGANISM: Unknown
<220> FEATURE:
<223> OTHER INFORMATION: Herpes simplex virus

<400> SEQUENCE: 3008

| | | |
|---|---|---|
| atgacacaaa ccccgcccag cgtcttgtca ttggcgaatt cgaacacgca gatgcagtcg | 60 |
| gggcggcgcg gtcccaggtc cacttcgcat attaaggtga cgcgtgtggc ctcgaacacc | 120 |
| gagcgaccct gcagcgaccc gcttaa | 146 |

<210> SEQ ID NO 3009
<211> LENGTH: 301

```
<212> TYPE: DNA
<213> ORGANISM: Unknown
<220> FEATURE:
<223> OTHER INFORMATION: Cytomegalovirus sp.

<400> SEQUENCE: 3009
tacataactt acggtaaatg ccccgcctgg ctgaccgccc aacgaccccc gcccattgac    60
gtcaataatg acgtatgttc ccatagtaac gccaataggg actttccatt gacgtcaatg   120
ggtggagtat ttacggtaaa ctgcccactt ggcagtacat caagtgtatc atatgccaag   180
tacgccccct attgacgtca atgacggtaa atggcccgcc tggcattatg cccagtacat   240
gaccttatgg gactttccta cttggcagta catctacgta ttagtcatcg ctattaccat   300
g                                                                  301

<210> SEQ ID NO 3010
<211> LENGTH: 97
<212> TYPE: DNA
<213> ORGANISM: Unknown
<220> FEATURE:
<223> OTHER INFORMATION: simian virus 40

<400> SEQUENCE: 3010
gtaagtttag tcttttttgtc ttttatttca ggtcccggat ccggtggtgg tgcaaatcaa    60
agaactgctc ctcagtggat gttgccttta cttctag                              97

<210> SEQ ID NO 3011
<211> LENGTH: 133
<212> TYPE: DNA
<213> ORGANISM: Artificial Sequence
<220> FEATURE:
<223> OTHER INFORMATION: chimeric Intron

<400> SEQUENCE: 3011
gtaagtatca aggttacaag acaggtttaa ggagaccaat agaaactggg cttgtcgaga    60
cagagaagac tcttgcgttt ctgataggca cctattggtc ttactgacat ccactttgcc   120
tttctctcca cag                                                      133

<210> SEQ ID NO 3012
<211> LENGTH: 122
<212> TYPE: DNA
<213> ORGANISM: Unknown
<220> FEATURE:
<223> OTHER INFORMATION: SV40 poly A signal

<400> SEQUENCE: 3012
taagatacat tgatgagttt ggacaaacca caactagaat gcagtgaaaa aaatgcttta    60
tttgtgaaat ttgtgatgct attgctttat ttgtaaccat tataagctgc aataaacaag   120
tt                                                                  122

<210> SEQ ID NO 3013
<211> LENGTH: 56
<212> TYPE: DNA
<213> ORGANISM: Oryctolagus cuniculus

<400> SEQUENCE: 3013
aataaaggaa atttattttc attgcaatag tgtgttggaa ttttttgtgt ctctca        56

<210> SEQ ID NO 3014
<211> LENGTH: 4685
<212> TYPE: DNA
```

<213> ORGANISM: Artificial Sequence
<220> FEATURE:
<223> OTHER INFORMATION: AAV transfer cassette 1

<400> SEQUENCE: 3014

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac tagggggttcc ttgcgtcgac tcgaggtgag ccccacgttc tgcttcactc     180
tccccatctc ccccccctcc ccacccccaa ttttgtattt atttattttt taattatttt     240
gtgcagcgat gggggcgggg gggggggggg ggcgcgcgcc aggcggggcg gggcggggcg     300
aggggcgggg cggggcgagg cggagaggtg cggcggcagc caatcagagc ggcgcgctcc     360
gaaagtttcc ttttatggcg aggcggcggc ggcggcggcc ctataaaaag cgaagcgcgc     420
ggcgggcgat gcatgtaagt ttagtctttt tgtcttttat ttcaggtccc ggatccggtg     480
gtggtgcaaa tcaaagaact gctcctcagt ggatgttgcc tttacttcta gcaccggtcg     540
ccaccatgac cgctcgcggc ctggcccttg cctcctcct gctgctactg tgtccagcgc      600
aggtgttttc acagtcctgt gtttggtatg gagagtgtgg aattgcatat ggggacaaga     660
ggtacaattg cgaatattct ggcccaccaa aaccattgcc aaaggatgga tatgacttag     720
tgcaggaact ctgtccagga ttcttctttg gcaatgtcag tctctgttgt gatgttcggc     780
agcttcagac actaaaagac aacctgcagc tgcctctaca gttctgtgcc agatgtccat     840
cctgtttttta taacctactg aacctgtttt gtgagctgac atgtagccct cgacagagtc     900
agttttttgaa tgttacagct actgaagatt atgttgatcc tgttacaaac cagacgaaaa     960
caaatgtgaa agagttacaa tactacgtcg acagagtttt tgccaatgca atgtacaatg    1020
cctgccggga tgtggaggcc ccctcaagta atgacaaggc cctgggactc tgtgtgggaa    1080
aggacgctga cgcctgtaat gccaccaact ggattgaata catgttcaat aaggacaatg    1140
gacaggcacc tttttaccatc actcctgtgt tttcagattt tccagtccat gggatggagc    1200
ccatgaacaa tgccaccaaa ggctgtgacg agtctgtgga tgaggtcaca gcaccatgta    1260
gctgccaaga ctgctctatt gtctgtggcc ccaagcccca gccccacct cctcctgctc     1320
cctggacgat ccttggcttg gacgccatgt atgtcatcat gtggatcacc tacatggcgt    1380
ttttgcttgt gttttttgga gcatttttg cagtgtggtg ctacagaaaa cggtattttg    1440
tctccgagta cactcccatc gatagcaata tagcttttt tgttaatgca agtgacaaag    1500
gagaggcgtc ctgctgtgac cctgtcagcg cagcatttga gggctgcttg aggcggctgt    1560
tcacacgctg ggggtctttc tgcgtccgaa acctggctg tgtcattttc ttctcgctgg    1620
tcttcattac tgcgtgttcg tcaggcctgg tgtttgtccg ggtcacaacc aatccagttg    1680
acctctggtc agcccccagc agccaggctc gcctggaaaa agagtacttt gaccagcact    1740
tgggcctttt cttccggacg gagcagctca tcatccgggc ccctctcact gacaaacaca    1800
tttaccagcc ataccccttcg ggagctgatg tacccttttgg acctccgctt gacatacaga    1860
tactgcacca ggttcttgac ttacaaatag ccatcgaaaa cattactgcc tcttatgaca    1920
atgagactgt gacacttcaa gacatctgct tggcccctct tcaccgtat aacacgaact    1980
gcaccatttt gagtgtgtta aattacttcc agaacagcca ttccgtgctg gaccacaaga    2040
aagggggacga cttctttgtg tatgccgatt accacacgca ctttctgtac tgcgtacggg    2100
ctcctgcctc tctgaatgat acaagttgc tccatgaccc ttgtctgggt acgttttggtg    2160
gaccagtgtt cccgtggctt gtgttgggag ctatgatga tcaaaactac aataacgcca    2220
```

```
ctgcccttgt gattaccttc cctgtcaata attactataa tgatacagag aagctccaga    2280
gggcccaggc ctgggaaaaa gagtttatta attttgtgaa aaactacaag aatcccaatc    2340
tgaccatttc cttcactgct gaacgaagta ttgaagatga actaaatcgt gaaagtgaca    2400
gtgatgtctt caccgttgta attagctatg ccatcatgtt tctatatatt tccctagcct    2460
tggggcacat caaaagctgt cgcaggcttc tggtggattc gaaggtctca ctaggcatcg    2520
cgggcatctt gatcgtgctg agctcggtgg cttgctcctt gggtgtcttc agctacattg    2580
ggttgccctt gaccctcatt gtgattgaag tcatcccgtt cctggtgctg gctgttggag    2640
tggacaacat cttcattctg gtgcaggcct accagagaga tgaacgtctt caaggggaaa    2700
ccctggatca gcagctgggc agggtcctag agaagtggc tcccagtatg ttcctgtcat    2760
ccttttctga gactgtagca tttttcttag gagcattgtc cgtgatgcca gccgtgcaca    2820
ccttctctct ctttgcggga ttggcagtct tcattgactt tcttctgcag attacctgtt    2880
tcgtgagtct cttggggtta gacattaaac gtcaagagaa aaatcggcta gacatctttt    2940
gctgtgtcag aggtgctgaa gatggaacaa gcgtccaggc ctcagagagc tgtttgtttc    3000
gcttcttcaa aaactcctat tctccacttc tgctaaagga ctggatgaga ccaattgtga    3060
tagcaatatt tgtgggtgtt ctgtcattca gcatcgcagt cctgaacaaa gtagatattg    3120
gattggatca gtctctttcg atgccagatg actcctacat ggtggattat ttcaaatcca    3180
tcagtcagta cctgcatgcg ggtccgcctg tgtactttgt cctggaggaa gggcacgact    3240
acacttcttc caaggggcag aacatggtgt gcggcggcat gggctgcaac aatgattccc    3300
tggtgcagca gatatttaac gcggcgcagc tggacaacta tacccgaata ggcttcgccc    3360
cctcgtcctg gatcgacgat tatttcgact gggtgaagcc acagtcgtct tgctgtcgag    3420
tggacaatat cactgaccag ttctgcaatg cttcagtggt tgaccctgcc tgcgttcgct    3480
gcaggcctct gactccggaa ggcaaacaga ggcctcaggg gggagacttc atgagattcc    3540
tgcccatgtt cctttcggat aaccctaacc ccaagtgtgg caaaggggga catgctgcct    3600
atagttctgc agttaacatc ctccttggcc atggcaccag ggtcggagcc acgtacttca    3660
tgacctacca caccgtgctg cagacctctg ctgactttat tgacgctctg aagaaagccc    3720
gacttatagc cagtaatgtc accgaaacca tgggcattaa cggcagtgcc taccgagtat    3780
ttcccttacag tgtgttttat gtcttctacg aacagtacct gaccatcatt gacgacacta    3840
tcttcaacct cggtgtgtcc ctgggcgcga tatttctggt gaccatggtc ctcctgggct    3900
gtgagctctg gtctgcagtc atcatgtgtg ccaccatcgc catggtcttg gtcaacatgt    3960
ttggagttat gtggctctgg ggcatcagtc tgaacgctgt atccttggtc aacctggtga    4020
tgagctgtgg catctccgtg gagttctgca gccacataac cagagcgttc acggtgagca    4080
tgaaaggcag ccgcgtggag cgcgcggaag aggcacttgc ccacatgggc agctccgtgt    4140
tcagtggaat cacacttaca aaatttggag ggattgtggt gttggctttt gccaaatctc    4200
aaattttcca gatattctac ttcaggatgt atttggccat ggtcttactg ggagccactc    4260
acgattaat atttctccct gtcttactca gttacatagg gccatcagta aataaagcca    4320
aaagttgtgc cactgaagag cgatacaaag gaacagagcg cgaacggctt ctaaatttct    4380
aggtttaaac aagctttaag atacattgat gagtttggac aaaccacaac tagaatgcag    4440
tgaaaaaaat gctttatttg tgaaatttgt gatgctattg ctttattttgt aaccattata    4500
agctgcaata aacaagttct cgagccatgg gcgcgccatc gatgaggaac ccctagtgat    4560
```

| | |
|---|---:|
| ggagttggcc actccctctc tgcgcgctcg ctcgctcact gaggccgggc gaccaaaggt | 4620 |
| cgcccgacgc ccgggctttg cccggcggc ctcagtgagc gagcgagcgc gcagctgcct | 4680 |
| gcagg | 4685 |

<210> SEQ ID NO 3015
<211> LENGTH: 4617
<212> TYPE: DNA
<213> ORGANISM: Artificial Sequence
<220> FEATURE:
<223> OTHER INFORMATION: AAV transfer cassette 2

<400> SEQUENCE: 3015

| | |
|---|---:|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac tagggggttcc ttgcgtcgac cggctggggc tgagggtgag ggtcccgttt | 180 |
| ccccaaaggc ctagcctggg gttccagcca caagccctac cgggcagcgc ccggccccgc | 240 |
| ccctccaggc ctggcactcg tcctcaacca agatggcgcg gatggcttca ggcgcatcac | 300 |
| gacaccggcg cgtcacgcga cccgccctac gggcacctcc cgcgcttttc ttagcgccgc | 360 |
| agacggtggc cgagcggggg accgggaagc atgcatgtaa gtatcaaggt tacaagacag | 420 |
| gtttaaggag accaatagaa actgggcttg tcgagacaga aagactctt gcgtttctga | 480 |
| taggcaccta ttggtcttac tgacatccac tttgcctttc tctccacagc accggtcgcc | 540 |
| accatgaccg ctcgcggcct ggccttggc ctcctcctgc tgctactgtg tccagcgcag | 600 |
| gtgttttcac agtcctgtgt ttggtatgga gagtgtggaa ttgcatatgg ggacaagagg | 660 |
| tacaattgcg aatattctgg cccaccaaaa ccattgccaa aggatggata tgacttagtg | 720 |
| caggaactct gtccaggatt cttctttggc aatgtcagtc tctgttgtga tgttcggcag | 780 |
| cttcagacac taaaagacaa cctgcagctg cctctacagt ttctgtccag atgtccatcc | 840 |
| tgtttttata acctactgaa cctgttttgt gagctgacat gtagccctcg acagagtcag | 900 |
| ttttttgaatg ttacagctac tgaagattat gttgatcctg ttacaaacca gacgaaaaca | 960 |
| aatgtgaaag agttacaata ctacgtcgga cagagttttg ccaatgcaat gtacaatgcc | 1020 |
| tgccgggatg tggaggcccc ctcaagtaat gacaaggccc tgggactcct gtgtgggaag | 1080 |
| gacgctgacg cctgtaatgc caccaactgg attgaataca tgttcaataa ggacaatgga | 1140 |
| caggcacctt ttaccatcac tcctgtgttt tcagattttc cagtccatgg gatggagccc | 1200 |
| atgaacaatg ccaccaaagg ctgtgacgag tctgtggatg aggtcacagc accatgtagc | 1260 |
| tgccaagact gctctattgt ctgtggcccc aagccccagc cccacctcc tcctgctccc | 1320 |
| tggacgatcc ttggcttgga cgccatgtat gtcatcatgt ggatcacctaa catggcgttt | 1380 |
| ttgcttgtgt ttttttggagc atttttttgca gtgtggtgct acagaaaacg gtattttgtc | 1440 |
| tccgagtaca ctcccatcga tagcaatata gcttttttctg ttaatgcaag tgacaaagga | 1500 |
| gaggcgtcct gctgtgaccc tgtcagcgca gcatttgagg gctgcttgag gcggctgttc | 1560 |
| acacgctggg ggtctttctg cgtccgaaac cctggctgtg tcattttctt ctcgctggtc | 1620 |
| ttcattactg cgtgttcgtc aggcctggtg tttgtccggg tcacaaccaa tccagttgac | 1680 |
| ctctggtcag ccccccagcag ccaggctcgc ctggaaaaag agtactttga ccagcacttt | 1740 |
| gggcctttct tccggacgga gcagctcatc atccgggccc ctctcactga caaacacatt | 1800 |
| taccagccat accccttcggg agctgatgta cccttttggac ctccgcttga catacagata | 1860 |
| ctgcaccagg ttcttgactt acaaatagcc atcgaaaaca ttactgcctc ttatgacaat | 1920 |

-continued

```
gagactgtga cacttcaaga catctgcttg gcccctcttt caccgtataa cacgaactgc   1980 accatttga gtgtgttaaa ttacttccag aacagccatt ccgtgctgga ccacaagaaa    2040
ggggacgact tctttgtgta tgccgattac cacacgcact ttctgtactg cgtacgggct   2100
cctgcctctc tgaatgatac aagtttgctc catgacccctt gtctgggtac gtttggtgga  2160
ccagtgttcc cgtggcttgt gttgggaggc tatgatgatc aaaactacaa taacgccact   2220
gcccttgtga ttaccttccc tgtcaataat tactataatg atacagagaa gctccagagg   2280
gcccaggcct gggaaaaaga gtttattaat tttgtgaaaa actacaagaa tcccaatctg   2340
accatttcct tcactgctga acgaagtatt gaagatgaac taaatcgtga aagtgacagt   2400
gatgtcttca ccgttgtaat tagctatgcc atcatgtttc tatatatttc cctagccttg   2460
gggcacatca aaagctgtcg caggcttctg gtggattcga aggtctcact aggcatcgcg   2520
ggcatcttga tcgtgctgag ctcggtggct tgctccttgg gtgtcttcag ctacattggg   2580
ttgcccttga ccctcattgt gattgaagtc atcccgttcc tggtgctggc tgttggagtg   2640
gacaacatct tcattctggt gcaggcctac cagagagatg aacgtcttca aggggaaacc   2700
ctggatcagc agctgggcag ggtcctagga gaagtggctc ccagtatgtt cctgtcatcc   2760
ttttctgaga ctgtagcatt tttcttagga gcattgtccg tgatgccagc cgtgcacacc   2820
ttctctctct tgcgggatt ggcagtcttc attgactttc ttctgcagat tacctgtttc    2880
gtgagtctct tggggttaga cattaaacgt caagagaaaa atcggctaga catcttttgc   2940
tgtgtcagag gtgctgaaga tggaacaagc gtccaggcct cagagagctg tttgtttcgc   3000
ttcttcaaaa actcctattc tccacttctg ctaaaggact ggatgagacc aattgtgata   3060
gcaatatttg tgggtgttct gtcattcagc atcgcagtcc tgaacaaagt agatattgga   3120
ttggatcagt ctctttcgat gccagatgac tcctacatgg tggattattt caaatccatc   3180
agtcagtacc tgcatgcggg tccgcctgtg tactttgtcc tggaggaagg gcacgactac   3240
acttcttcca aggggcagaa catggtgtgc ggcggcatgg gctgcaacaa tgattccctg   3300
gtgcagcaga tatttaacgc ggcgcagctg gacaactata cccgaatagg cttcgccccc   3360
tcgtcctgga tcgacgatta tttcgactgg gtgaagccac agtcgtcttg ctgtcgagtg   3420
gacaatatca ctgaccagtt ctgcaatgct tcagtggttg accctgcctg cgttcgctgc   3480
aggcctctga ctccggaagg caaacagagg cctcagggg gagacttcat gagattcctg    3540
cccatgttcc tttcggataa ccctaaccccc aagtgtggca aggggggaca tgctgcctat   3600
agttctgcag ttaacatcct ccttggccat ggcaccaggg tcggagccac gtacttcatg   3660
acctaccaca ccgtgctgca gacctctgct gactttattg acgctctgaa gaaagcccga   3720
cttatagcca gtaatgtcac cgaaaccatg ggcattaacg gcagtgccta ccgagtattt   3780
ccttacagtg tgttttatgt cttctacgaa cagtacctga ccatcattga cgacactatc   3840
ttcaacctcg gtgtgtccct gggcgcgata tttctggtga ccatggtcct cctgggctgt   3900
gagctctggt ctgcagtcat catgtgtgcc accatcgcca tggtcttggt caacatgttt   3960
ggagttatgt ggctctgggg catcagtctg aacgctgtat ccttggtcaa cctggtgatg   4020
agctgtggca tctccgtgga gttctgcagc cacataacca gagcgttcac ggtgagcatg   4080
aaaggcagcc gcgtggagcg cgcggaagag gcacttgccc acatgggcag ctccgtgttc   4140
agtggaatca cacttacaaa atttggaggg attgtggtgt tggcttttgc caaatctcaa   4200
attttccaga tattctactt caggatgtat ttggccatgg tcttactggg agccactcac   4260
```

-continued

| | |
|---|---|
| ggattaatat ttctccctgt cttactcagt tacatagggc catcagtaaa taaagccaaa | 4320 |
| agttgtgcca ctgaagagcg atacaaagga acagagcgcg aacggcttct aaatttctag | 4380 |
| gtttaaacaa gcttaataaa ggaaatttat tttcattgca atagtgtgtt ggaatttttt | 4440 |
| gtgtctctca ctcgagccat gggcgcgcca tcgatgagga acccctagtg atggagttgg | 4500 |
| ccactccctc tctgcgcgct cgctcgctca ctgaggccgg gcgaccaaag gtcgcccgac | 4560 |
| gcccgggctt tgcccgggcg gcctcagtga gcgagcgagc gcgcagctgc ctgcagg | 4617 |

<210> SEQ ID NO 3016
<211> LENGTH: 4720
<212> TYPE: DNA
<213> ORGANISM: Artificial Sequence
<220> FEATURE:
<223> OTHER INFORMATION: AAV Transfer Cassette 3

<400> SEQUENCE: 3016

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc ttgcgtcgac attcctgctg gaaaagcaa gtggaggtgc | 180 |
| tccttgaaga acaggggga tcccaccgat ctcaggggtt ctgttctggc ctgcggccct | 240 |
| ggatcgtcca gcctgggtcg gggtggggag cagacctcgc ccttatcggc tggggctgag | 300 |
| ggtgagggtc ccgtttcccc aaaggcctag cctgggttc cagccacaag ccctaccggg | 360 |
| cagcgcccgg ccccgcccct ccaggcctgg cactcgtcct caaccaagat ggcgcggatg | 420 |
| gcttcaggcg catcacgaca ccggcgcgtc acgcgacccg ccctacgggc acctcccgcg | 480 |
| cttttcttag cgccgcagac ggtggtcgag cgggggaccg ggaagcttaa tgcatgtaag | 540 |
| tttagtcttt ttgtctttta tttcaggtcc cggatccggt ggtggtgcaa atcaaagaac | 600 |
| tgctcctcag tggatgttgc ctttacttct agcaccggtc gccaccatga ccgctcgcgg | 660 |
| cctgccctt ggcctcctcc tgctgctact gtgtccagcg caggtgtttt cacagtcctg | 720 |
| tgtttggtat ggagagtgtg gaattgcata tggggacaag aggtacaatt gcgaatattc | 780 |
| tggcccacca aaaccattgc caaaggatgg atatgactta gtgcaggaac tctgtccagg | 840 |
| attcttcttt ggcaatgtca gtctctgttg tgatgttcgg cagcttcaga cactaaaaga | 900 |
| caacctgcag ctgcctctac agtttctgtc cagatgtcca tcctgttttt ataacctact | 960 |
| gaacctgttt tgtgagctga catgtagccc tcgacagagt cagttttga atgttacagc | 1020 |
| tactgaagat tatgttgatc ctgttacaaa ccagacgaaa acaaatgtga agagttaca | 1080 |
| atactacgtc ggacagagtt tgccaatgc aatgtacaat gcctgccggg atgtggaggc | 1140 |
| cccctcaagt aatgacaagg ccctgggact cctgtgtggg aaggacgctg acgcctgtaa | 1200 |
| tgccaccaac tggattgaat acatgttcaa taaggacaat ggacaggcac ttttaccat | 1260 |
| cactcctgtg ttttcagatt ttccagtcca tgggatggag cccatgaaca tgccaccaa | 1320 |
| aggctgtgac gagtctgtgg atgaggtcac agcaccatgt agctgccaag actgctctat | 1380 |
| tgtctgtggc cccaagcccc agcccccacc tcctcctgct ccctggacga tccttggctt | 1440 |
| ggacgccatg tatgtcatca tgtggatcac ctacatggcg ttttttgcttg tgttttttgg | 1500 |
| agcatttttt gcagtgtggt gctacagaaa acggtatttc gtctccgagt acactcccat | 1560 |
| cgatagcaat atagcttttt ctgttaatgc aagtgacaaa ggagaggcgt cctgctgtga | 1620 |
| ccctgtcagc gcagcatttg agggctgctt gaggcggctc ttcacacgct gggggtcttt | 1680 |
| ctgcgtccga aaccctggct gtgtcatttt cttctcgctg gtcttcatta ctgcgtgttc | 1740 |

-continued

```
gtcaggcctg gtgtttgtcc gggtcacaac caatccagtt gacctctggt cagcccccag   1800
cagccaggct cgcctggaaa aagagtactt tgaccagcac tttgggcctt tcttccggac   1860
ggagcagctc atcatccggg cccctctcac tgacaaacac atttaccagc atacccttc   1920 gggagctgat gtacccttg gacctccgct tgacatacag atactgcacc aggttcttga   1980
cttacaaata gccatcgaaa acattactgc ctcttatgac aatgagactg tgacacttca   2040
agacatctgc ttggcccctc tttcaccgta taacacgaac tgcaccattt tgagtgtgtt   2100
aaattacttc cagaacagcc attccgtgct ggaccacaag aaaggggacg acttctttgt   2160
gtatgccgat taccacacgc actttctgta ctgcgtacgg gctcctgcct ctctgaatga   2220
tacaagtttg ctccatgacc cttgtctggg tacgtttggt ggaccagtgt cccgtggct   2280 tgtgttggga ggctatgatg atcaaaacta caataacgcc actgcccttg tgattacctt   2340
ccctgtcaat aattactata atgatacaga aagctccag agggcccagg cctgggaaaa   2400
agagtttatt aattttgtga aaaactacaa gaatcccaat ctgaccattt ccttcactgc   2460
tgaacgaagt attgaagatg aactaaatcg tgaaagtgac agtgatgtct tcaccgttgt   2520
aattagctat gccatcatgt ttctatatat ttccctagcc ttggggcaca tcaaaagctg   2580
tcgcaggctt ctggtggatt cgaaggtctc actaggcatc gcgggcatct tgatcgtgct   2640
gagctcggtg gcttgctcct tgggtgtctt cagctacatt gggttgccct tgaccctcat   2700
tgtgattgaa gtcatcccgt tcctggtgct ggctgttgga gtggacaaca tcttcattct   2760
ggtgcaggcc taccagagag atgaacgtct tcaaggggaa accctggatc agcagctggg   2820
cagggtccta ggagaagtgg ctcccagtat gttcctgtca tccttttctg agactgtagc   2880
atttttctta ggagcattgt ccgtgatgcc agccgtgcac accttctctc tctttgcggg   2940
attggcagtc ttcattgact tcttctgca gattacctgt ttcgtgagtc tcttgggtt   3000 agacattaaa cgtcaagaga aaatcggctc agacatcttt tgctgtgtca gaggtgctga   3060
agatggaaca agcgtccagg cctcagagag ctgtttgttt cgcttcttca aaaactccta   3120
ttctccactt ctgctaaagg actggatgag accaattgtg atagcaatat ttgtgggtgt   3180
tctgtcattc agcatcgcag tcctgaacaa agtagatatt ggattggatc agtctctttc   3240
gatgccagat gactcctaca tggtggatta tttcaaatcc atcagtcagt acctgcatgc   3300
gggtccgcct gtgtactttg tcctggagga agggcacgac tacacttctt ccaagggggca   3360 gaacatggtg tgcggcggca tgggctgcaa caatgattcc ctggtgcagc agatatttaa   3420
cgcggcgcag ctggacaact atacccgaat aggcttcgcc ccctcgtcct ggatcgacga   3480
ttatttcgac tgggtgaagc cacagtcgtc ttgctgtcga gtggacaata tcactgacca   3540
gttctgcaat gcttcagtgg ttgaccctgc ctgcgttcgc tgcaggcctc tgactccgga   3600
aggcaaacag aggcctcagg ggggagactt catgagattc ctgcccatgt cctttcgga   3660 taaccctaac cccaagtgtg gcaaagggg acatgctgcc tatagttctg cagttaacat   3720
cctccttggc catggcacca gggtcggagc cacgtacttc atgacctacc acaccgtgct   3780
gcagacctct gctgactta ttgacgctct gaagaaagcc cgacttatag ccagtaatgt   3840
caccgaaacc atgggcatta acggcagtgc ctaccgagta tttccttaca gtgtgtttta   3900
tgtcttctac gaacagtacc tgaccatcat tgacgacact atcttcaacc tcggtgtgtc   3960
cctgggcgcg atatttctgg tgaccatggt cctcctgggc tgtgagctct ggtctgcagt   4020
catcatgtgt gccaccatcg ccatggtctt ggtcaacatg tttggagtta tgtggctctg   4080
```

| | |
|---|---|
| gggcatcagt ctgaacgctg tatccttggt caacctggtg atgagctgtg gcatctccgt | 4140 |
| ggagttctgc agccacataa ccagagcgtt cacggtgagc atgaaaggca gccgcgtgga | 4200 |
| gcgcgcggaa gaggcacttg cccacatggg cagctccgtg ttcagtggaa tcacacttac | 4260 |
| aaaatttgga gggattgtgg tgttggcttt tgccaaatct caaattttcc agatattcta | 4320 |
| cttcaggatg tatttggcca tggtcttact gggagccact cacggattaa tatttctccc | 4380 |
| tgtcttactc agttacatag gccatcagt aaataaagcc aaaagttgtg ccactgaaga | 4440 |
| gcgatacaaa ggaacagagc gcgaacggct tctaaatttc taggtttaaa caagcttaat | 4500 |
| aaaggaaatt tattttcatt gcaatagtgt gttggaattt tttgtgtctc tcactcgagc | 4560 |
| catgggcgcg ccatcgatga ggaaccccta gtgatggagt tggccactcc ctctctgcgc | 4620 |
| gctcgctcgc tcactgaggc cgggcgacca aggtcgccc gacgcccggg ctttgcccgg | 4680 |
| gcggcctcag tgagcgagcg agcgcgcagc tgcctgcagg | 4720 |

<210> SEQ ID NO 3017
<211> LENGTH: 4683
<212> TYPE: DNA
<213> ORGANISM: Artificial Sequence
<220> FEATURE:
<223> OTHER INFORMATION: AAV transfer casette 4

<400> SEQUENCE: 3017

| | |
|---|---|
| cctgcaggca gctgcgcgct cgctcgctca ctgaggccgc ccgggcaaag cccgggcgtc | 60 |
| gggcgacctt tggtcgcccg gcctcagtga gcgagcgagc gcgcagagag ggagtggcca | 120 |
| actccatcac taggggttcc ttgcgtcgac cggctgggc tgagggtgag ggtcccgttt | 180 |
| ccccaaaggc ctagcctggg gttccagcca caagccctac cgggcagcgc ccggccccgc | 240 |
| ccctccaggc ctggcactcg tcctcaacca agatggcgcg gatggcttca ggcgcatcac | 300 |
| gacaccggcg cgtcacgcga cccgccctac gggcacctcc cgcgcttttc ttagcgccgc | 360 |
| agacggtggc cgagcggggg accgggaagc atgcatgtaa gtatcaaggt tacaagacag | 420 |
| gtttaaggag accaatagaa actgggcttg tcgagacaga gaagactctt gcgtttctga | 480 |
| taggcaccta ttggtcttac tgacatccac tttgcctttc tctccacagc accggtcgcc | 540 |
| accatgaccg ctcgcggcct ggccttggc ctcctcctgc tgctactgtg tccagcgcag | 600 |
| gtgttttcac agtcctgtgt ttggtatgga gagtgtggaa ttgcatatgg gacaagagg | 660 |
| tacaattgcg aatattctgg cccaccaaaa ccattgccaa aggatggata tgacttagtg | 720 |
| caggaactct gtccaggatt cttctttggc aatgtcagtc tctgttgtga tgttcggcag | 780 |
| cttcagacac taaaagacaa cctgcagctg cctctacagt ttctgtccag atgtccatcc | 840 |
| tgttttttata acctactgaa cctgttttgt gagctgacat gtagccctcg acagagtcag | 900 |
| tttttgaatg ttacagctac tgaagattat gttgatcctg ttacaaacca gacgaaaaca | 960 |
| aatgtgaaag agttacaata ctacgtcgga cagagttttg ccaatgcaat gtacaatgcc | 1020 |
| tgccgggatg tggaggcccc ctcaagtaat gacaaggccc tgggactcct gtgtgggaag | 1080 |
| gacgctgacg cctgtaatgc caccaactgg attgaataca tgttcaataa ggacaatgga | 1140 |
| caggcacctt ttaccatcac tcctgtgttt tcagattttc cagtccatgg gatggagccc | 1200 |
| atgaacaatg ccaccaaagg ctgtgacgag tctgtggatg aggtcacagc accatgtagc | 1260 |
| tgccaagact gctctattgt ctgtggcccc aagcccagc ccccacctcc tcctgctccc | 1320 |
| tggacgatcc ttggcttgga cgccatgtat gtcatcatgt ggatcacctt catgcgcttt | 1380 |
| ttgcttgtgt tttttggagc attttttgca gtgtggtgct acagaaaacg gtattttgtc | 1440 |

-continued

```
tccgagtaca ctcccatcga tagcaatata gcttttctg ttaatgcaag tgacaaagga    1500
gaggcgtcct gctgtgaccc tgtcagcgca gcatttgagg gctgcttgag gcggctgttc    1560
acacgctggg ggtctttctg cgtccgaaac cctggctgtg tcattttctt ctcgctggtc    1620
ttcattactg cgtgttcgtc aggcctggtg tttgtccggg tcacaaccaa tccagttgac    1680
ctctggtcag cccccagcag ccaggctcgc ctggaaaaag agtactttga ccagcacttt    1740
gggcctttct tccggacgga gcagctcatc atccgggccc ctctcactga caaacacatt    1800
taccagccat acccttcggg agctgatgta ccctttggac ctccgcttga catacagata    1860
ctgcaccagg ttcttgactt acaaatagcc atcgaaaaca ttactgcctc ttatgacaat    1920
gagactgtga cacttcaaga catctgcttg gcccctcttt caccgtataa cacgaactgc    1980
accattttga gtgtgttaaa ttacttccag aacagccatt ccgtgctgga ccacaagaaa    2040
ggggacgact tctttgtgta tgccgattac cacacgcact ttctgtactg cgtacgggct    2100
cctgcctctc tgaatgatac aagtttgctc catgaccctt gtctgggtac gtttggtgga    2160
ccagtgttcc cgtggcttgt gttgggaggc tatgatgatc aaaactacaa taacgccact    2220
gcccttgtga ttaccttccc tgtcaataat tactataatg atacagagaa gctccagagg    2280
gcccaggcct gggaaaaaga gtttattaat tttgtgaaaa actacaagaa tcccaatctg    2340
accatttcct tcactgctga acgaagtatt gaagatgaac taaatcgtga agtgacagt    2400 gatgtcttca ccgttgtaat tagctatgcc atcatgtttc tatatatttc cctagccttg    2460
gggcacatca aaagctgtcg caggcttctg gtggattcga aggtctcact aggcatcgcg    2520
ggcatcttga tcgtgctgag ctcggtggct tgctccttgg gtgtcttcag ctacattggg    2580
ttgcccttga ccctcattgt gattgaagtc atcccgttcc tggtgctggc tgttggagtg    2640
gacaacatct tcattctggt gcaggcctac cagagagatg aacgtcttca aggggaaacc    2700
ctggatcagc agctgggcag ggtcctagga gaagtggctc ccagtatgtt cctgtcatcc    2760

тттттстgaga ctgtagcatt tttcttagga gcattgtccg tgatgccagc cgtgcacacc    2820

tctctctct tgcgggatt ggcagtcttc attgactttc ttctgcagat tacctgtttc    2880
gtgagtctct tggggttaga cattaaacgt caagagaaaa atcggctaga catcttttgc    2940

tgtgtcagag gtgctgaaga tggaacaagc gtccaggcct cagagagctg tttgtttcgc    3000

ttcttcaaaa actcctattc tccacttctg ctaaaggact ggatgagacc aattgtgata    3060
gcaatatttg tggtgttct gтcатттcagc atcgcagtcc tgaacaaagt agatatttga    3120

ttggatcagt ctctttcgat gccagatgac tcctacatgg tggatttatt caaatccatc    3180
agtcagtacc tgcatgcggg tccgcctgtg tactttgtcc tggaggaagg gcacgactac    3240
acttcttcca agggcagaa catggtgtgc ggcggcatgg gctgcaacaa тgатттcccтg    3300 gtgcagcaga tatttaacgc ggcgcagctg gacaactata cccgaatagg cttcgcccc    3360

tcgtcctgga tcgacgatta tttcgactgg gtgaagccac aгтcgтcттg ctgtcgagtg    3420 gacaatatca ctgaccagtt ctgcaatgct tcagtggttg accctgcctg cgttcgctgc    3480
aggcctctga ctccggaagg caaacagagg cctcaggggg gagacttcat gagatctctg    3540
cccatgttcc tttcggataa ccctaacccc aaгтgтggca aggggggaca tgctgcctat    3600
agttctgcag ttaacatcct ccttggccat ggcaccaggg tcggagccac gtacttcatg    3660
acctaccaca ccgtgctgca gacctctgct gactttattg acgctctgaa gaaagcccga    3720
cttatagcca gtaatgtcac cgaaaccatg ggcattaacg gcagtgccta ccgagтатттт    3780
```

```
ccttacagtg tgtttatgt cttctacgaa cagtacctga ccatcattga cgacactatc    3840
ttcaacctcg gtgtgtccct gggcgcgata tttctggtga ccatggtcct cctgggctgt    3900
gagctctggt ctgcagtcat catgtgtgcc accatcgcca tggtcttggt caacatgttt    3960
ggagttatgt ggctctgggg catcagtctg aacgctgtat ccttggtcaa cctggtgatg    4020
agctgtggca tctccgtgga gttctgcagc cacataacca gagcgttcac ggtgagcatg    4080
aaaggcagcc gcgtggagcg cgcggaagag gcacttgccc acatgggcag ctccgtgttc    4140
agtggaatca cacttacaaa atttggaggg attgtggtgt tggcttttgc caaatctcaa    4200
attttccaga tattctactt caggatgtat ttggccatgg tcttactggg agccactcac    4260
ggattaatat ttctccctgt cttactcagt tacatagggc catcagtaaa taaagccaaa    4320
agttgtgcca ctgaagagcg atacaaagga acagagcgcg aacggcttct aaatttctag    4380
gtttaaacaa gctttaagat acattgatga gtttggacaa accacaacta gaatgcagtg    4440
aaaaaaatgc tttatttgtg aaatttgtga tgctattgct ttatttgtaa ccattataag    4500
ctgcaataaa caagttctcg agccatgggc gcgccatcga tgaggaaccc ctagtgatgg    4560
agttggccac tccctctctg cgcgctcgct cgctcactga ggccgggcga ccaaaggtcg    4620
cccgacgccc gggctttgcc cgggcggcct cagtgagcga gcgagcgcgc agctgcctgc    4680
agg                                                                 4683
```

<210> SEQ ID NO 3018
<211> LENGTH: 4663
<212> TYPE: DNA
<213> ORGANISM: Artificial Sequence
<220> FEATURE:
<223> OTHER INFORMATION: AAV Transfer Casette 5

<400> SEQUENCE: 3018

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca     120
actccatcac taggggttcc ttgcgtcgac cggctggggc tgagggtgag gtcccgttt     180
ccccaaaggc ctagcctggg gttccagcca caagccctac cgggcagcgc ccggccccgc     240
ccctccaggc ctggcactcg tcctcaacca agatggcgcg gatggcttca ggcgcatcac     300
gacaccggcg cgtcacgcga cccgccctac gggcacctcc cgcgcttttc ttagcgccgc     360
agacggtggc cgagcggggg accgggaagc atgcatgtaa gtttagtctt tttgtctttt     420
atttcaggtc ccggatccgg tggtggtgca aatcaaagaa ctgctcctca gtggatgttg     480
cctttacttc tagcaccggt cgccaccatg accgctcgcg gcctggccct tatgaccgct     540
cgcggccggc ctcctcctgc tgctactgtg tccagcgcag gtgttttcac agtcctgtgt     600
ttggtatgga gagtgtggaa ttgcatatgg ggacaagagg tacaattgcg aatattctgg     660
cccaccaaaa ccattgccaa aggatggata tgacttagtg caggaactct gtccaggatt     720
cttctttggc aatgtcagtc tctgttgtga tgttcggcag cttcagacac taaaagacaa     780
cctgcagctg cctctacagt ttctgtccag atgtccatcc tgttttata acctactgaa     840
cctgttttgt gagctgacat gtagccctcg acagagtcag ttttgaatg ttacagctac     900
tgaagattat gttgatcctg ttacaaacca gacgaaaaca aatgtgaaag agttacaata     960
ctacgtcgga cagagttttg ccaatgcaat gtacaatgcc tgccgggatg tggaggcccc    1020
ctcaagtaat gacaagggcc ctgggactcc tgtgtgggaag gacgctgacg cctgtaatgc    1080
caccaactgg attgaataca tgttcaataa ggacaatgga caggcacctt ttaccatcac    1140
```

```
tcctgtgttt tcagattttc cagtccatgg gatggagccc atgaacaatg ccaccaaagg    1200
ctgtgacgag tctgtggatg aggtcacagc accatgtagc tgccaagact gctctattgt    1260
ctgtggcccc aagccccagc ccccacctcc tcctgctccc tggacgatcc ttggcttgga    1320
cgccatgtat gtcatcatgt ggatcaccta catggcgttt ttgcttgtgt tttttggagc    1380
attttttgca gtgtggtgct acagaaaacg gtattttgtc tccgagtaca ctcccatcga    1440
tagcaatata gcttttttctg ttaatgcaag tgacaaagga gaggcgtcct gctgtgaccc    1500
tgtcagcgca gcatttgagg gctgcttgag gcggctgttc acacgctggg ggtctttctg    1560
cgtccgaaac cctggctgtg tcattttctt ctcgctggtc ttcattactg cgtgttcgtc    1620
aggcctggtg tttgtccggg tcacaaccaa tccagttgac ctctggtcag cccccagcag    1680
ccaggctcgc ctggaaaaag tactttttga ccagcacttt gggcctttct ccgacggaa    1740 gcagctcatc atccgggccc ctctcactga caaacacatt taccagccat cccttcggg    1800 agctgatgta ccctttggac ctccgcttga catacagata ctgcaccagg ttcttgactt    1860
acaaatagcc atcgaaaaca ttactgcctc ttatgacaat gagactgtga cacttcaaga    1920
catctgcttg gcccctcttt caccgtataa acgaactgc accattttga gtgtgttaaa    1980
ttacttccag aacagccatt ccgtgctgga ccacaagaaa ggggacgact tctttgtgta    2040
tgccgattac cacacgcact ttctgtactg cgtacgggct cctgcctctc tgaatgatac    2100
aagtttgctc catgacccctt gtctgggtac gtttggtgga ccagtgttcc cgtggcttgt    2160
gttgggaggc tatgatgatc aaaactacaa taacgccact gccccttgtga ttaccttccc    2220 tgtcaataat tactataatg atacagagaa gctccagagg gcccaggcct gggaaaaaga    2280 gttttattaat tttgtgaaaa actacaagaa tcccaatctg accatttcct tcactgctga    2340
acgaagtatt gaagatgaac taaatcgtga aagtgacagt gatgtcttca ccgttgtaat    2400
tagctatgcc atcatgtttc tatatatttc cctagcttg gggcacatca aaagctgtcg    2460
caggcttctg gtggattcga aggtctcact aggcatcgcg ggcatcttga tcgtgctgag    2520
ctcggtggct tgctccttgg ggtgtcttcag ctacattggg ttgcccttga ccctcattgt    2580
gattgaagtc atcccgttcc tggtgctggc tgttggagtg gacaacatct tcattctggt    2640
gcaggcctac cagagagatg aacgtcttca aggggaaacc ctggatcagc agctgggcag    2700
ggtcctagga gaagtggctc ccagtatgtt cctgtcatcc ttttctgaga ctgtagcatt    2760
tttcttagga gcattgtccg tgatgccagc cgtgcacacc ttctctctct ttgcgggatt    2820
ggcagtcttc attgactttc ttctgcagat tacctgtttc gtgagtctct gggggttaga    2880
cattaaacgt caagagaaaa atcggctaga catcttttgc tgtgtcagag gtgctgaaga    2940
tggaacaagc gtccaggcct cagagagctg tttgtttcgc ttcttcaaaa actcctattc    3000
tccacttctg ctaaaggact ggatgagacc aattgtgata gcaatatttg tgggtgttct    3060
gtcattcagc atcgcagtcc tgaacaaagt agatattgga ttggatcagt ctctttcgat    3120
gccagatgac tcctacatgg tggattattt caaatccatc agtcagtacc tgcatgcggg    3180
tccgcctgtg tactttgtcc tggaggaagg gcacgactac acttcttcca agggggcagaa    3240 catggtgtgc ggcggcatgg gctgcaacaa tgattccctg gtgcagcaga tatttaacgc    3300
ggcgcagctg gacaactata cccgaatagg cttcgccccc tcgtcctgga tcgacgatta    3360
tttcgactgg gtgaagccac agtcgtcttg ctgtcgagtg gacaatatca ctgaccagtt    3420
ctgcaatgct tcagtggttg accctgcctg cgttcgctgc aggcctctga ctccggaagg    3480
```

```
caaacagagg cctcaggggg gagacttcat gagattcctg cccatgttcc tttcggataa      3540 ccctaaccc  aagtgtggca aaggggaca  tgctgcctat agttctgcag ttaacatcct      3600
ccttggccat ggcaccaggg tcggagccac gtacttcatg acctaccaca ccgtgctgca      3660
gacctctgct gactttattg acgctctgaa gaaagcccga cttatagcca gtaatgtcac      3720
cgaaaccatg ggcattaacg gcagtgccta ccgagtattt ccttacagtg tgttttatgt      3780
cttctacgaa cagtacctga ccatcattga cgacactatc ttcaacctcg gtgtgtccct      3840
gggcgcgata tttctggtga ccatggtcct cctgggctgt gagctctggt ctgcagtcat      3900
catgtgtgcc accatcgcca tggtcttggt caacatgttt ggagttatgt ggctctgggg      3960
catcagtctg aacgctgtat ccttggtcaa cctggtgatg agctgtggca tctccgtgga      4020
gttctgcagc cacataacca gagcgttcac ggtgagcatg aaaggcagcc gcgtggagcg      4080
cgcggaagag gcacttgccc acatgggcag ctccgtgttc agtggaatca cacttacaaa      4140
atttggaggg attgtggtgt tggcttttgc caaatctcaa attttccaga tattctactt      4200
caggatgtat ttggccatgg tcttactggg agccactcac ggattaatat ttctccctgt      4260
cttactcagt tacataggc  catcagtaaa taaagccaaa agttgtgcca ctgaagagcg      4320
atacaaagga acagagcgcg aacggcttct aaatttctag gtttaaacaa gctttaagat      4380
acattgatga gtttggacaa accacaacta gaatgcagtg aaaaaaatgc tttatttgtg      4440
aaatttgtga tgctattgct ttatttgtaa ccattataag ctgcaataaa caagttctcg      4500
agccatgggc gcgccatcga tgaggaaccc ctagtgatgg agttggccac tccctctctg      4560
cgcgctcgct cgctcactga ggccgggcga ccaaaggtcg cccgacgccc gggctttgcc      4620
cgggcggcct cagtgagcga gcgagcgcgc agctgcctgc agg                       4663
```

<210> SEQ ID NO 3019
<211> LENGTH: 4691
<212> TYPE: DNA
<213> ORGANISM: Artificial Sequence
<220> FEATURE:
<223> OTHER INFORMATION: AAV Transfer Casette 6

<400> SEQUENCE: 3019

```
cctgcaggca gctgcgcgct cgctcgctca ctgaggccgc ccgggcaaag cccgggcgtc        60
gggcgacctt tggtcgcccg gcctcagtga gcgagcgagc gcgcagagag ggagtggcca       120
actccatcac tagggttcc  ttgcgtcgac tacataactt acggtaaatg gcccgcctgg       180
ctgaccgccc aacgacccc  gcccattgac gtcaataatg acgtatgttc ccatagtaac       240
gccaataggg actttccatt gacgtcaatg ggtggagtat ttacggtaaa ctgcccactt       300
ggcagtacat caagtgtatc atatgccaag tacgccccct attgacgtca atgacggtaa       360
atggcccgcc tggcattatg cccagtacat gaccttatgg gactttccta cttggcagta       420
catctacgta ttagtcatcg ctattaccat ggatgacaca aacccccgcc agcgtcttgt       480
cattggcgaa ttcgaacacg cagatgcagt cggggcggcg cggtcccagg tccacttcgc       540
atattaaggt gacgcgtgtg gcctcgaaca ccgagcgacc ctgcagcgac ccgcttaaat       600
gcataccggt cgccaccatg accgctcgcg gcctggcccc tggcctcctc ctgctgctac       660
tgtgtccagc gcaggtgttt tcacagtcct gtgtttggta tggagagtgt ggaattgcat       720 atgggacaa gaggtacaat tgcgaatatt ctggcccacc aaaaccattg ccaaaggatg        780
gatatgactt agtgcaggaa ctctgtccag gattcttctt tggcaatgtc agtctctgtt       840
gtgatgttcg gcagcttcag acactaaaag acaacctgca gctgcctcta cagtttctgt       900
```

-continued

```
ccagatgtcc atcctgtttt tataacctac tgaacctgtt ttgtgagctg acatgtagcc      960
ctcgacagag tcagtttttg aatgttacag ctactgaaga ttatgttgat cctgttacaa     1020
accagacgaa acaaatgtg aaagagttac aatactacgt cggacagagt tttgccaatg     1080
caatgtacaa tgcctgccgg gatgtggagg cccctcaag taatgacaag ccctgggac      1140
tcctgtgtgg gaaggacgct gacgcctgta atgccaccaa ctggattgaa tacatgttca     1200
ataaggacaa tggacaggca ccttttacca tcactcctgt gttttcagat tttccagtcc     1260
atgggatgga gcccatgaac aatgccacca aaggctgtga cgagtctgtg gatgaggtca     1320
cagcaccatg tagctgccaa gactgctcta ttgtctgtgg ccccaagccc cagcccccac     1380
ctcctcctgc tccctggacg atccttggct tggacgccat gtatgtcatc atgtggatca     1440
cctacatggc gttttgctt gtgttttttg gagcattttt tgcagtgtgg tgctacagaa      1500
aacggtattt tgtctccgag tacactccca tcgatagcaa tatagctttt tctgttaatg     1560
caagtgacaa aggagaggcg tcctgctgtg accctgtcag cgcagcattt gagggctgct     1620
tgaggcggct gttcacacgc tgggggtctt tctgcgtccg aaaccctggc tgtgtcattt     1680
tcttctcgct ggtcttcatt actgcgtgtt cgtcaggcct ggtgtttgtc cgggtcacaa     1740
ccaatccagt tgacctctgg tcagccccca gcagccaggc tcgcctggaa aaagagtact     1800
ttgaccagca ctttgggcct ttcttccgga cggagcagct catcatccgg gcccctctca     1860
ctgacaaaca catttaccag ccatacccctt cgggagctga tgtacccttt ggacctccgc    1920
ttgcataca gatactgcac caggttcttg acttacaaat agccatcgaa acattactg      1980
cctcttatga caatgagact gtgacacttc aagacatctg cttggcccct ctttcaccgt     2040
ataacacgaa ctgcaccatt ttgagtgtgt taaattactt ccagaacagc cattccgtgc     2100
tggaccacaa gaaaggggac gacttctttg tgtatgccga ttaccacacg cactttctgt     2160
actgcgtacg ggctcctgcc tctctgaatg atacaagttt gctccatgac ccttgtctgg     2220
gtacgtttgg tggaccagtg ttcccgtggc ttgtgttggg aggctatgat gatcaaaact     2280
acaataacgc cactgccctt gtgattacct ccctgtcaa taattactat aatgatacag     2340
agaagctcca gagggcccag gcctgggaaa aagagtttat taattttgtg aaaaactaca     2400
agaatcccaa tctgaccatt tccttcactg ctgaacgaag tattgaagat gaactaaatc     2460
gtgaaagtga cagtgatgtc ttcaccgttg taattagcta tgccatcatg tttctatata     2520
tttccctagc cttggggcac atcaaaagct gtcgcaggct tctggtggat tcgaaggtct     2580
cactaggcat cgcgggcatc ttgatcgtgc tgagctcggt ggcttgctcc ttgggtgtct     2640
tcagctacat tgggttgccc ttgaccctca ttgtgattga agtcatcccg ttcctggtgc     2700
tggctgttgg agtggacaac atcttcattc tggtgcaggc ctaccagaga gatgaacgtc     2760
ttcaagggga aaccctggat cagcagctgg gcagggtcct aggagaagtg gctcccagta     2820
tgttcctgtc atccttttct gagactgtag cattttttctt aggagcattg tccgtgatgc     2880
cagccgtgca caccttctct ctctttgcgg gattggcagt cttcattgac tttcttctgc     2940
agattacctg tttcgtgagt ctcttggggt tagacattaa acgtcaagag aaaaatcggc     3000
tagacatctt ttgctgtgtc agaggtgctg aagatgaac aagcgtccag gcctcagaga      3060
gctgtttgtt tcgcttcttc aaaaactcct attctccact tctgctaaag gactggatga     3120
gaccaattgt gatagcaata tttgggggtg ttctgtcatt cagcatcgca gtcctgaaca     3180
aagtagatat tggattggat cagtctcttt cgatgccaga tgactcctac atggtggatt     3240
```

|                                                                                       |      |
| ------------------------------------------------------------------------------------- | ---- |
| atttcaaatc catcagtcag tacctgcatg cgggtccgcc tgtgtacttt gtcctggagg                      | 3300 |
| aagggcacga ctacacttct tccaaggggc agaacatggt gtgcggcggc atgggctgca                      | 3360 |
| acaatgattc cctggtgcag cagatattta acgcggcgca gctggacaac tatacccgaa                      | 3420 |
| taggcttcgc cccctcgtcc tggatcgacg attatttcga ctgggtgaag ccacagtcgt                      | 3480 |
| cttgctgtcg agtggacaat atcactgacc agttctgcaa tgcttcagtg gttgaccctg                      | 3540 |
| cctgcgttcg ctgcaggcct ctgactccgg aaggcaaaca gaggcctcag ggggagact                       | 3600 |
| tcatgagatt cctgcccatg ttcctttcgg ataaccctaa ccccaagtgt ggcaaagggg                      | 3660 |
| gacatgctgc ctatagttct gcagttaaca tcctccttgg ccatggcacc agggtcggag                      | 3720 |
| ccacgtactt catgacctac cacaccgtgc tgcagacctc tgctgacttt attgacgctc                      | 3780 |
| tgaagaaagc ccgacttata gccagtaatg tcaccgaaac catgggcatt aacggcagtg                      | 3840 |
| cctaccgagt atttccttac agtgtgtttt atgtcttcta cgaacagtac ctgaccatca                      | 3900 |
| ttgacgacac tatcttcaac ctcggtgtgt ccctgggcgc gatatttctg gtgaccatgg                      | 3960 |
| tcctcctggg ctgtgagctc tggtctgcag tcatcatgtg tgccaccatc gccatggtct                      | 4020 |
| tggtcaacat gtttggagtt atgtggctct ggggcatcag tctgaacgct gtatccttgg                      | 4080 |
| tcaacctggt gatgagctgt ggcatctccg tggagttctg cagccacata accagagcgt                      | 4140 |
| tcacggtgag catgaaaggc agccgcgtgg agcgcgcgga agaggcactt gcccacatgg                      | 4200 |
| gcagctccgt gttcagtgga atcacactta caaaatttgg agggattgtg gtgttggctt                      | 4260 |
| ttgccaaatc tcaaattttc cagatattct acttcaggat gtatttggcc atggtcttac                      | 4320 |
| tgggagccac tcacggatta atatttctcc ctgtcttact cagttacata gggccatcag                      | 4380 |
| taaataaagc caaaagttgt gccactgaag agcgatacaa aggaacagag cgcgaacggc                      | 4440 |
| ttctaaattt ctaggtttaa acaagcttaa taaaggaaat ttattttcat tgcaatagtg                      | 4500 |
| tgttggaatt ttttgtgtct ctcactcgag ccatgggcgc gccatcgatg aggaacccct                      | 4560 |
| agtgatggag ttggccactc cctctctgcg cgctcgctcg ctcactgagg ccgggcgacc                      | 4620 |
| aaaggtcgcc cgacgcccgg gctttgcccg ggcggcctca gtgagcgagc gagcgcgcag                      | 4680 |
| ctgcctgcag g                                                                          | 4691 |

<210> SEQ ID NO 3020
<211> LENGTH: 1278
<212> TYPE: PRT
<213> ORGANISM: Homo sapiens

<400> SEQUENCE: 3020

Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg
                85                  90                  95

Cys Pro Ser Cys Phe Tyr Asn Leu Leu Asn Leu Phe Cys Glu Leu Thr
            100                 105                 110

-continued

```
Cys Ser Pro Arg Gln Ser Gln Phe Leu Asn Val Thr Ala Thr Glu Asp
            115                 120                 125

Tyr Val Asp Pro Val Thr Asn Gln Thr Lys Thr Asn Val Lys Glu Leu
130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
                165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
            195                 200                 205

Phe Ser Asp Phe Pro Val His Gly Met Glu Pro Met Asn Asn Ala Thr
210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
                245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
            275                 280                 285

Ala Val Trp Cys Tyr Arg Lys Arg Tyr Phe Val Ser Glu Tyr Thr Pro
            290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
                325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
            355                 360                 365

Val Phe Val Arg Val Thr Thr Asn Pro Val Asp Leu Trp Ser Ala Pro
370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
                405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
            435                 440                 445

Ala Ile Glu Asn Ile Thr Ala Ser Tyr Asp Asn Glu Thr Val Thr Leu
450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
                485                 490                 495

His Lys Lys Gly Asp Asp Phe Val Tyr Ala Asp Tyr His Thr His
            500                 505                 510

Phe Leu Tyr Cys Val Arg Ala Pro Ala Ser Leu Asn Asp Thr Ser Leu
            515                 520                 525

Leu His Asp Pro Cys Leu Gly Thr Phe Gly Gly Pro Val Phe Pro Trp
```

```
              530                 535                 540
Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
                565                 570                 575

Leu Gln Arg Ala Gln Ala Trp Glu Lys Glu Phe Ile Asn Phe Val Lys
                580                 585                 590

Asn Tyr Lys Asn Pro Asn Leu Thr Ile Ser Phe Thr Ala Glu Arg Ser
                595                 600                 605

Ile Glu Asp Glu Leu Asn Arg Glu Ser Asp Ser Asp Val Phe Thr Val
                610                 615                 620

Val Ile Ser Tyr Ala Ile Met Phe Leu Tyr Ile Ser Leu Ala Leu Gly
625                 630                 635                 640

His Met Lys Ser Cys Arg Arg Leu Leu Val Asp Ser Lys Val Ser Leu
                645                 650                 655

Gly Ile Ala Gly Ile Leu Ile Val Leu Ser Ser Val Ala Cys Ser Leu
                660                 665                 670

Gly Val Phe Ser Tyr Ile Gly Leu Pro Leu Thr Leu Ile Val Ile Glu
                675                 680                 685

Val Ile Pro Phe Leu Val Leu Ala Val Gly Val Asp Asn Ile Phe Ile
                690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                725                 730                 735

Leu Ser Ser Phe Ser Glu Thr Val Ala Phe Phe Leu Gly Ala Leu Ser
                740                 745                 750

Val Met Pro Ala Val His Thr Phe Ser Leu Phe Ala Gly Leu Ala Val
                755                 760                 765

Phe Ile Asp Phe Leu Leu Gln Ile Thr Cys Phe Val Ser Leu Leu Gly
                770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                805                 810                 815

Leu Phe Arg Phe Phe Lys Asn Ser Tyr Ser Pro Leu Leu Leu Lys Asp
                820                 825                 830

Trp Met Arg Pro Ile Val Ile Ala Ile Phe Val Gly Val Leu Ser Phe
                835                 840                 845

Ser Ile Ala Val Leu Asn Lys Val Asp Ile Gly Leu Asp Gln Ser Leu
850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                885                 890                 895

His Asp Tyr Thr Ser Ser Lys Gly Gln Asn Met Val Cys Gly Gly Met
                900                 905                 910

Gly Cys Asn Asn Asp Ser Leu Val Gln Gln Ile Phe Asn Ala Ala Gln
                915                 920                 925

Leu Asp Asn Tyr Thr Arg Ile Gly Phe Ala Pro Ser Ser Trp Ile Asp
                930                 935                 940

Asp Tyr Phe Asp Trp Val Lys Pro Gln Ser Ser Cys Cys Arg Val Asp
945                 950                 955                 960
```

```
Asn Ile Thr Asp Gln Phe Cys Asn Ala Ser Val Val Asp Pro Ala Cys
            965                 970                 975

Val Arg Cys Arg Pro Leu Thr Pro Glu Gly Lys Gln Arg Pro Gln Gly
            980                 985                 990

Gly Asp Phe Met Arg Phe Leu Pro Met Phe Leu Ser Asp Asn Pro Asn
            995                 1000                1005

Pro Lys Cys Gly Lys Gly Gly His Ala Ala Tyr Ser Ser Ala Val
        1010                1015                1020

Asn Ile Leu Leu Gly His Gly Thr Arg Val Gly Ala Thr Tyr Phe
        1025                1030                1035

Met Thr Tyr His Thr Val Leu Gln Thr Ser Ala Asp Phe Ile Asp
        1040                1045                1050

Ala Leu Lys Lys Ala Arg Leu Ile Ala Ser Asn Val Thr Glu Thr
        1055                1060                1065

Met Gly Ile Asn Gly Ser Ala Tyr Arg Val Phe Pro Tyr Ser Val
        1070                1075                1080

Phe Tyr Val Phe Tyr Glu Gln Tyr Leu Thr Ile Ile Asp Asp Thr
        1085                1090                1095

Ile Phe Asn Leu Gly Val Ser Leu Gly Ala Ile Phe Leu Val Thr
        1100                1105                1110

Met Val Leu Leu Gly Cys Glu Leu Trp Ser Ala Val Ile Met Cys
        1115                1120                1125

Ala Thr Ile Ala Met Val Leu Val Asn Met Phe Gly Val Met Trp
        1130                1135                1140

Leu Trp Gly Ile Ser Leu Asn Ala Val Ser Leu Val Asn Leu Val
        1145                1150                1155

Met Ser Cys Gly Ile Ser Val Glu Phe Cys Ser His Ile Thr Arg
        1160                1165                1170

Ala Phe Thr Val Ser Met Lys Gly Ser Arg Val Glu Arg Ala Glu
        1175                1180                1185

Glu Ala Leu Ala His Met Gly Ser Ser Val Phe Ser Gly Ile Thr
        1190                1195                1200

Leu Thr Lys Phe Gly Gly Ile Val Val Leu Ala Phe Ala Lys Ser
        1205                1210                1215

Gln Ile Phe Gln Ile Phe Tyr Phe Arg Met Tyr Leu Ala Met Val
        1220                1225                1230

Leu Leu Gly Ala Thr His Gly Leu Ile Phe Leu Pro Val Leu Leu
        1235                1240                1245

Ser Tyr Ile Gly Pro Ser Val Asn Lys Ala Lys Ser Cys Ala Thr
        1250                1255                1260

Glu Glu Arg Tyr Lys Gly Thr Glu Arg Glu Arg Leu Leu Asn Phe
        1265                1270                1275
```